(12) United States Patent
Andersen et al.

(10) Patent No.: US 9,365,510 B2
(45) Date of Patent: Jun. 14, 2016

(54) AZIRIDINE BISPHENOL ETHERS AND RELATED COMPOUNDS AND METHODS FOR THEIR USE

(71) Applicants: British Columbia Cancer Agency Branch, Vancouver (CA); The University of British Columbia, Vancouver (CA)

(72) Inventors: Raymond John Andersen, Vancouver (CA); Marianne Dorothy Sadar, Vancouver (CA)

(73) Assignees: British Columbia Cancer Agency Branch (CA); The University of British Columbia (CA)

( * ) Notice: Subject to any disclaimer, the term of this patent is extended or adjusted under 35 U.S.C. 154(b) by 0 days.

(21) Appl. No.: 13/863,849

(22) Filed: Apr. 16, 2013

(65) Prior Publication Data

US 2013/0336962 A1 Dec. 19, 2013

Related U.S. Application Data

(60) Provisional application No. 61/624,826, filed on Apr. 16, 2012.

(51) Int. Cl.
| | |
|---|---|
| C07C 41/00 | (2006.01) |
| C07C 43/02 | (2006.01) |
| A61K 31/075 | (2006.01) |
| C07D 203/10 | (2006.01) |
| A61K 31/396 | (2006.01) |
| A61K 45/06 | (2006.01) |

(52) U.S. Cl.
CPC ............ *C07D 203/10* (2013.01); *A61K 31/396* (2013.01); *A61K 45/06* (2013.01)

(58) Field of Classification Search
USPC ....................................................... 568/641
See application file for complete search history.

(56) References Cited

U.S. PATENT DOCUMENTS

| | | | |
|---|---|---|---|
| 2,571,217 A | 10/1951 | Davis et al. | |
| 2,890,189 A | 6/1959 | Greenlee | |
| 4,284,574 A | 8/1981 | Bagga | |
| 4,369,298 A | 1/1983 | Kida et al. | |
| 4,855,184 A | 8/1989 | Klun et al. | |
| 4,904,760 A | 2/1990 | Gaku et al. | |
| 5,043,375 A | 8/1991 | Henning et al. | |
| 5,155,196 A | 10/1992 | Kolb et al. | |
| 5,362,615 A | 11/1994 | Hagemann et al. | |
| 5,403,697 A | 4/1995 | Doessel et al. | |
| 5,753,730 A | 5/1998 | Nagata et al. | |
| 5,998,674 A | 12/1999 | Taketani et al. | |
| 6,218,430 B1 | 4/2001 | Allegretto et al. | |
| 6,245,117 B1 | 6/2001 | Nishikawa et al. | |
| 7,183,323 B2 | 2/2007 | Chinn et al. | |
| 7,674,795 B2 | 3/2010 | Mailliet et al. | |
| 8,686,050 B2 | 4/2014 | Sadar et al. | |
| 9,173,939 B2 | 11/2015 | Andersen et al. | |
| 2003/0092724 A1 | 5/2003 | Kao et al. | |
| 2003/0105268 A1 | 6/2003 | Boriack et al. | |
| 2004/0049004 A1 | 3/2004 | Boriak et al. | |
| 2004/0243316 A1 | 12/2004 | Weinmann et al. | |
| 2008/0153837 A1 | 6/2008 | Mailliet et al. | |
| 2008/0193380 A1 | 8/2008 | Dalton et al. | |
| 2008/0255395 A1 | 10/2008 | Dai et al. | |
| 2009/0105349 A1 | 4/2009 | Barvian et al. | |
| 2011/0230556 A1 | 9/2011 | Sadar et al. | |
| 2013/0045204 A1 | 2/2013 | Sadar et al. | |
| 2013/0109758 A1 | 5/2013 | Sadar et al. | |
| 2013/0131167 A1 | 5/2013 | Sadar et al. | |
| 2013/0245129 A1 | 9/2013 | Sadar et al. | |
| 2014/0248263 A1 | 9/2014 | Andersen et al. | |
| 2014/0335080 A1 | 11/2014 | Andersen et al. | |
| 2015/0010469 A1 | 1/2015 | Andersen et al. | |
| 2015/0125389 A1 | 5/2015 | Andersen et al. | |

FOREIGN PATENT DOCUMENTS

| | | |
|---|---|---|
| CA | 2 339 775 A1 | 3/2000 |
| CA | 2 606 262 A1 | 11/2006 |

(Continued)

OTHER PUBLICATIONS

Garuti, L., et al., Current Medicinal Chemistry vol. 18, pp. 2981-2994. Published 2011.*

(Continued)

*Primary Examiner* — Paul Zarek
*Assistant Examiner* — George W Kosturko
(74) *Attorney, Agent, or Firm* — Cooley LLP

(57) ABSTRACT

Compounds having a structure of Formula I:

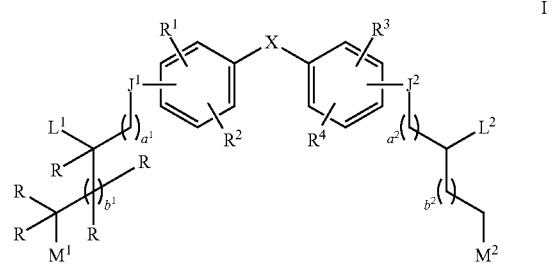

or a pharmaceutically acceptable salt, tautomer or stereoisomer thereof, wherein R, $R^1$, $R^2$, $R^3$, $R^4$, $M^1$, $M^2$, X, $L^1$, $L^2$, $J^1$, $J^2$, $a^1$, $a^2$, $b^1$ and $b^2$ are as defined herein, and wherein at least one of $M^2$ or $L^2$ is a moiety comprising an aziridine, acrylamide or sulfonate functional group, are provided. Uses of such compounds for treatment of various indications, including prostate cancer as well as methods of treatment involving such compounds are also provided.

46 Claims, No Drawings

(56) References Cited

FOREIGN PATENT DOCUMENTS

| | | | |
|---|---|---|---|
| EP | 0056175 A1 | 7/1982 |
| EP | 0 293 768 A1 | 12/1988 |
| EP | 0515128 A1 | 11/1992 |
| FR | 1389005 | 2/1965 |
| JP | B-S45-008432 | 3/1970 |
| JP | 63-196675 | 8/1988 |
| JP | H01-503541 | 11/1989 |
| JP | H02-4815 | 1/1990 |
| JP | 6-049473 A2 | 4/1994 |
| JP | 9-176240 A | 7/1997 |
| JP | A-H10-316803 | 12/1998 |
| JP | 11-166087 A2 | 6/1999 |
| JP | 2000-072705 A2 | 3/2000 |
| JP | 2005-325301 A | 11/2005 |
| JP | 2006-208607 A | 8/2006 |
| JP | 2006-265351 A2 | 10/2006 |
| JP | 2007-290980 | 11/2007 |
| PL | 135932 | 9/1984 |
| PL | 141793 B1 | 8/1987 |
| WO | WO 88/09782 | 12/1988 |
| WO | WO 98/34930 A1 | 8/1998 |
| WO | 00/01813 A2 | 1/2000 |
| WO | WO 00/01813 A2 | 1/2000 |
| WO | 00/10958 A1 | 3/2000 |
| WO | WO 00/10958 A1 | 3/2000 |
| WO | 01/88013 A2 | 11/2001 |
| WO | WO 01/88013 A2 | 11/2001 |
| WO | WO 02/05813 A2 | 1/2002 |
| WO | 03/004481 A1 | 1/2003 |
| WO | WO 03/004481 A1 | 1/2003 |
| WO | WO 2005/042464 A1 | 5/2005 |
| WO | 2005/077967 A1 | 8/2005 |
| WO | WO 2005/077967 A1 | 8/2005 |
| WO | WO 2008/101806 A2 | 8/2008 |
| WO | 2010/000066 A1 | 1/2010 |
| WO | WO 2010000066 A1 * | 1/2010 |
| WO | 2011/082487 A1 | 7/2011 |
| WO | 2011/082488 A1 | 7/2011 |
| WO | WO 2011/082487 A1 | 7/2011 |
| WO | WO 2011/082488 A1 | 7/2011 |
| WO | 2012/139039 A2 | 10/2012 |
| WO | 2012/145328 A1 | 10/2012 |
| WO | 2012/145330 A1 | 10/2012 |
| WO | WO 2012/139039 A2 | 10/2012 |
| WO | WO 2012/145328 A1 | 10/2012 |
| WO | WO 2012/145330 A1 | 10/2012 |
| WO | 2013/028791 A1 | 2/2013 |
| WO | WO 2013/028572 A1 | 2/2013 |
| WO | WO 2013/028791 A1 | 2/2013 |
| WO | WO 2014/179867 A1 | 11/2014 |

OTHER PUBLICATIONS

Xu, X. et al, Journal of Polymer Science: Part A Polymer Chemistry vol. 45 pp. 99-110. Published 2007.*
Danquah, M. et al., Pharmaceutical Research vol. 26, pp. 2081-2092. Published 2009.*
Garuti et al (Current Medicinal Chemistry vol. 18 pp. 2981-2994, published 2011).*
Danquah et al (Pharmaceutical Research vol. 26 pp. 2081-2092 published 2009).*
Xu et al (Journal of Polymer Science Part A: Polymer Chemistry vol. 46 pp. 99-110. Published 2007).*
Andersen et al., "Bisphenol Compounds and Methods for Their Use," U.S. Appl. No. 14/110,615, filed Oct. 8, 2013, 157 pages.
Bao et al., "Androgen signaling is required for the vitamin D-mediated growth inhibition in human prostate cancer cells," *Nature Publishing Group* 23:3350-3360, 2004.
Biles et al., "Determination of the Diglycidyl Ether of Bisphenol A and Its Derivatives in Canned Foods," *Journal. Agric. Food Chem.* 47:1965-1969, 1999.
Bisson et al., "Discovery of antiandrogen activity of nonsteroidal scaffolds of marketed drugs," *PNAS* 104(29):11927-11932, Jul. 17, 2007.

Blaszczyk et al., "Osteoblast-Derived Factors Induce Androgen-Independent Proliferation and Expression of Prostate-Specific Antigen in Human Prostate Cancer Cells," *Clinical Cancer Research* 10:1860-1869, Mar. 1, 2004.
Chang et al., "Development of Peptide Antagonists for the Androgen Receptor Using Combinatorial Peptide Phage Display," *Molecular Endocrinology* 19(10):2478-2490, 2005.
Dehm et al., "Ligand-independent Androgen Receptor Activity is Activation Function-2-independent and Resistant to Antiandrogens in Androgen Refractory Prostate Cancer Cells," *The Journal of Biological Chemistry* 281(38):27882-27893, Sep. 22, 2006.
Dehm et al., "Splicing of a Novel *Androgen Receptor* Exon Generates a Constitutively Active Androgen Receptor that Mediates Prostate Cancer Therapy Resistance," *Cancer Res* 68(13):5469-5477, Jul. 1, 2008.
Estébanez-Perpiñá et al., "A surface on the androgen receptor that allosterically regulates coactivator binding," *PNAS* 104:15224-15229, Sep. 19, 2007.
Estébanez-Perpiñá et al., "The Molecular Mechanisms of Coactivator Utilization in Ligand-dependent Transactivation by the Androgen Receptor," *The Journal of Biological Chemistry* 280(9):8060-8068, 2005.
Fehlberg et al., "Bisphenol A diglycidyl ether induces apoptosis in tumor cells independently of peroxisome proliferator-activated receptor-γ, in caspase-dependent and - independent manners," *Biochem. J.* 362:573-578, 2002.
Gregory et al., "Epidermal Growth Factor Increases Coactivation of the Androgen Receptor in Recurrent Prostate Cancer," *The Journal of Biological Chemistry* 279(8):7119-7130, 2004.
Guo et al., "A Novel Androgen Receptor Splice Variant is Up-regulated during Prostate Cancer Progression and Promotes Androgen Depletion-Resistant Growth," *Cancer Res* 69(6):2305-2313, Mar. 15, 2009.
He et al., "Structural Basis for Androgen Receptor Interdomain and Coactivator Interactions Suggests a Transition in Nuclear Receptor Activation Function Dominance," *Molecular Cell* 16: 425-438, Nov. 5, 2004.
Hur et al., "Recognition and Accommodation at the Androgen Receptor Coactivator Binding Interface," $PL^0$ *S Biology* 2(9):1303-1312, Sep. 2004.
Kolbel et al., "Design of Liquid Crystalline Block Molecules with Nonconventional Mesophase Morphologies: Calamitic Bolaamphiphiles with Lateral Alkyl Chains," *J. Am. Chem. Soc.* 123:6809-6818, 2001.
Kumar et al., "Synthesis of new crown analogs derived from bisphenol," *Indian Journal Chemistry* 36B:656-661, Aug. 1997.
Loren et al., "Synthesis of achiral and racemic catenanes based on terpyridine and a directionalized terpyridine mimic, pyridylphenanthroline," *Org. Biomol. Chem.* 3(17):3105-3116, 2005.
Martin et al., "A new precursor for the radiosynthesis of [$^{18}$F]FLT," *Nuclear Medicine and Biology* 29:263-273, 2002.
Paris et al., "Phenylphenols, biphenols, bisphenol-A and 4-*tert*-octylphenol exhibit α and β estrogen activities and antiandrogen activity in reporter cell lines," *Molecular and Cellular Endocrinology* 193:43-49, 2002.
Quayle et al., "Androgen receptor decoy molecules block the growth of prostate cancer," *PNAS* 104(4):1331-1336, Jan. 23, 2007.
Reid et al., "Conformational Analysis of the Androgen Receptor Amino-terminal Domain Involved in Transactivation," *The Journal of Biological Chemistry* 277(22):20079-20086, 2002.
Sadar et al., "Prostate cancer: molecular biology of early progression to androgen independence," *Endocrine-Related Cancer* 6:487-502, 1999.
Sadar, "Androgen-independent Induction of Prostate-specific Antigen Gene Expression via Cross-talk between the Androgen Receptor and Protein Kinase A Signal Transduction Pathways," *The Journal of Biological Chemistry* 274(12):7777-7783, 1999.
Satoh et al., "Study on anti-androgenic effects of bisphenol a diglycidyl ether (BADGE), bisphenol F diglycidyl ether (BFDGE) and their derivatives using cells stably transfected with human androgen receptor, AR-EcoScreen," *Food and Chemical Toxicology* 42(6):983-993, Jun. 2004.

(56) References Cited

OTHER PUBLICATIONS

Schafer et al., "Migration from can coatings: Part 3. Synthesis, identification and quantification of migrating epoxy-based substances below 1000 Da," *Food Additives Contaminants* 21(4):390-405, Apr. 2004.

Taplin et al., "Selection for Androgen Receptor Mutations in Prostate Cancers Treated with Androgen Antagonist[1]," *Cancer Research* 59:2511-2515, Jun. 1, 1999.

Ueda et al., "Activation of the Androgen Receptor N-terminal Domain by Interleukin-6 via MAPK and STAT3 Signal Transduction Pathways," *The Journal of Biological Chemistry* 277(9):7076-7085, 2002.

Ueda et al., "Ligand-independent Activation of the Androgen Receptor by Interleukin-6 and the Role of Steroid Receptor Coactivator-1 in Prostate Cancer Cells," *The Journal of Biological Chemistry* 277(41):38087-38094, Oct. 11, 2002.

Uematsu et al., "Chlorohydrins of bisphenol a diglycidyl ether (BADGE) and of bisphenol F diglycidyl ether (BFDGE) in canned foods and ready-to-drink coffees from the Japanese market," *Food Additives and Contaminants* 18(2):177-185, 2001.

van Scherpenzeel et al., "Nanomolar affinity, iminosugar-based chemical probes for specific labeling of lysosomal glucocerebrosidase," *Bioorg. Med. Chem.* 18(1):267-273, 2010.

Anderson, R. et al., "Regression of Castrate-Recurrent Prostate Cancer by a Small-Molecule Inhibitor of the Amino-Terminus Domain of the Androgen Receptor", *Cancer Cell*, 17:535-546 (2010).

Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), Ref. No. 13510 and 39700 (EFSA-Q-2003-178), *The EFSA Journal*, 86:1-40 (2004).

Auzou et al., *European Journal of Medicinal Chemistry*, 9(5):548-554 (1974) (with English Abstract).

Balbay, M.D. et al., "Highly Metastatic Human Prostate Cancer Growing within the Prostate of Athymic Mice Overexpresses Vascular Endothelial Growth Factor", *Clinical Cancer Research*, 5:783-789 (1999).

Bao, B. et al., "Androgen signaling is required for the vitamin D-mediated growth inhibition in human prostate cancer cells", *Oncogene*, 23:3350-3360 (2004).

Berge, S.M. et al., "Pharmaceutical Salts", *Pharmaceutical Sciences*, 66(1):1-19 (1977).

Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, *Food Chemical Contaminants*, 83(6):1367-1376 (2000).

Biles, J.E. et al., "Determination of the Diglycidyl Ether of Bisphenol A and its Derivatives in Canned Foods", *J. Agric. Food Chem.*, 47:1965-1969 (1999).

Bisson, W.H. et al., "Discovery of antiandrogen activity of nonsteroidal scaffolds of marketed drugs", *PNAS*, 104(29):11927-11932 (2007).

Blaszczyk, N. et al., "Osteoblast-Derived factors Induce Androgen-Independent Proliferation and Expression of Prostate-Specific Antigen in Human Prostate Cancer Cells", *Clin. Cancer Res.*, 10:1860-1869 (2004).

Bohler, Paul et al., "Identification of Migrants from Coatings of Food Cans and Tubes: Reaction Products of Bisphenol-A-Diglycidyl Ether (BADGE) with Phenols and Solvents", *Mitt. Gebiete Lebensm. Hyg.*, 89:529-547 (1998).

Bruckheimer, E.M. et al., "Apoptosis in prostate carcinogenesis A growth regulator and a therapeutic target", *Cell Tissue Res*, 301:153-162 (2000).

Chang, C. et al., "Development of Peptide Antagonists for the Androgen Receptor Using Combinatorial Peptide Phage Display", *Molecular Endocrinology*, 19(10):2478-2490 (2005).

Clinton, G.M. et al., "Estrogen action in human ovarian cancer", *Critical Reviews in Oncology/Hematology*, 25:1-9 (1997).

Culig, Zoran et al., "Androgen Receptor Activation in Prostatic Tumor Cell Lines by Insulin-like Growth Factor-I, Keratinocyte Growth Factor, and Epidermal Growth Factor", *Cancer Research*, 54:5474-5478 (1994).

Das, Debasish et al., "Sulfonic acid functionalized mesoporous MCM-41 silica as a convenient catalyst for Bisphenol-A synthesis", *Chemical Communications*, pp. 2178-2179 (2001).

Dehm, S. et al., "Ligand-independent Androgen Receptor Activity is Activation Function-2-independent and Resistant to Antiandrogens in Androgen Refractory Prostate Cancer Cells", *The Journal of Biological Chemistry*, 281(38):27882-27893 (2006).

Dehm, S. et al., "Splicing of a Novel Androgen Receptor Exon Generates a Constitutively Active Androgen Receptor that Mediates Prostate Cancer Therapy Resistance", *Cancer Research*, 68:5469-5477 (2008).

Edmondson, J. M. et al., "The human ovarian surface epithelium is an androgen responsive tissue", *British Journal of Cancer*, 86:879-885 (2002).

Estebanez-Perpiãá, E. et al., "A surface on the androgen receptor that allosterically regulates coactivator binding," *PNAS*, 104 (41):16074-16079 (2007).

Estebanez-Perpiñá, E. et al., "The Molecular Mechanisms of Coactivator Utilization in Ligand-dependent Transactivation by the Androgen Receptor," *The Journal of Biological Chemistry*, 280(9):8060-8068 (2005).

Fehlberg S. et al., "Bisphenol A diglycidyl ether induces apoptosis in tumor cells independently of peroxisome proliferator-activated receptor-y, in caspase-dependent and -independent manners," *Biochem. J.*, 362:573-578 (2002).

Gallart-Ayala, H. et al., "The analysis of bisphenol A-diglycidyl ether (BADGE), bisphenol F-diglycidyl ether (BFDGE) and their derivatives in canned food and beverages by LC-MS/MS", *Thermo Fisher Scientific Inc.*, 4 pages (2011).

Gleave, Martin et al., "Acceleration of Human Prostate Cancer Growth in Vivo by Factors Produced by Prostate and Bone Fibroblasts", *Cancer Research*, 51:3753-3761 (1991).

Gregory, Christopher et al., "Epidermal Growth Factor Increases Coactivation of the Androgen Receptor in Recurrent Prostate Cancer", *The Journal of Biological Chemistry*, 279(8):7119-7130 (2004).

Guinan, P.D. et al., "Impotence Therapy and Cancer of the Prostate", *The American Journal of Surgery*, 131:599-600 (1976).

Guo, Zhiyong et al., "A Novel Androgen Receptor Splice Variant is Up-regulated during Prostate Cancer Progression and Promotes Androgen Depletion—Resistant Growth", *Cancer Research*, 69:2305-13 (2009).

Haggstrom, Stina et al., "Testosterone Induces Vascular Endothelial Growth Factor Synthesis in the Ventral Prostate in Castrated Rats", *The Journal of Urology*, 161:1620-1625 (1999).

Harper et al., "Expression of Androgen Receptor and Growth Factors in Premalignant Lesions of the Prostate", *Journal of Pathology*, 186:169-177 (1998).

He, B. et al., "Activation Function 2 in the Human Androgen Receptor Ligand Binding Domain Mediates Interdomain Communication with the $NH_2$-terminal Domain", *The Journal of Biological Chemistry*, 274(52):37219-37225 (1999).

He, B. et al., "Structural Basis for Androgen Receptor Interdomain and Coactivator Interactions Suggests a Transition in Nuclear Receptor Activation Function Dominance", *Molecular Cell*, 16:425-438 (2004).

Heinlein, Cynthia A., et al., "Androgen Receptor in Prostate Cancer", *Endocrine Reviews*, 25(2):276-308 (2004).

Helzlsouer, Kathy J., et al., "Serum Gonadotropins and Steroid Hormones and the Development of Ovarian Cancer", *JAMA*, 274(24):1926-1930 (1995).

Horoszewicz, J.S. et al., "LNCaP Model of Human Prostatic Carcinoma", *Cancer Research*, 43:1809-1818 (1983).

Hu, R. et al., "Ligand-Independent Androgen Receptor Variants Derived from Splicing of Cryptic Exons Signify Hormone-Refractory Prostate Cancer", *Cancer Research*, 69:16-22 (2009).

Huber, P.R. et al., "Prostate Specific Antigen. Experimental and Clinical Observations", *Scand. J. Urol Nephrol.*, 104:33-39 (1987).

(56) References Cited

OTHER PUBLICATIONS

Hur, E. et al., "Recognition and Accommodation at the Androgen Receptor Coactivator Binding Interface", *PLoS Biology*, 2(9): 1303-131 (2004).

Isaacs, J.T., et al., "New Biochemical Methods to Determine Androgen Sensitivity of Prostatic Cancer: The Relative Enzymatic Index (REI)", *Prostate Cancer and Hormone Receptors*, pp. 133-144 (1979).

Isaacs, J.T., "Antagonistic Effect of Androgen on Prostatic Cell Death", *The Prostate*, 5:545-557 (1984).

Jackson, J. A. et al., "Prostatic Complications of Testosterone Replacement Therapy", *Arch Intern Med.*, 149:2365-2366 (1989).

Jenster, G. et al., "Domains of the Human Androgen Receptor Involved in Steroid Binding, Transcriptional Activation, and Subcellular Localization", *Molecular Endocrinology*, 5:1396-404 (1991).

Jia, L. et al., "Androgen Receptor Signaling: Mechanism of Interleukin-6 Inhibition", *Cancer Research*, 64:2619-2626 (2004).

Jia, L. et al., "Androgen Receptor-Dependent PSA Expression in Androgen-Independent Prostate Cancer Cells Does Not Involve Androgen Receptor Occupancy of the PSA Locus", *Cancer Research*, 65:8003-8008 (2005).

Kaighn, M.E. et al., "Prostate Carcinoma: Tissue Culture Cell Lines", *National Cancer Institute Monograph* No. 49, pp. 17-21 (1978).

Kemppainen, J. A. et al., "Distinguishing ANDROGEN Receptor Agonists and Antagonists: Distinct Mechanisms of Activation by Medroxyprogesterone Acetate and Dihydrotestosterone", *Mol. Endocrinol.*, 13:440-454 (1999).

Kim, D. et al., "Androgen Receptor Expression and Cellular Proliferation During Transition from Androgen-Dependent to Recurrent Growth after Castration in the CWR22 Prostate Cancer Xenograft", *American Journal of Pathology*, 160(1):219-226 (2002).

Kolbel, M. et al., "Design of Liquid Crystalline Block Molecules with Nonconventional Mesophase Morphologies: Calamitic Bolaamphiphiles with Lateral Alkyl Chains", *J. Am. Chem. Soc.*,123:6809-6818 (2001).

Kumar, S. et al., "Synthesis of new crown analogs derived from bisphenol," *Indian Journal Chemistry*, 36B:656-661 (1997).

L'Heureux, A. et al., "Aminodifluorosulfinium Salts: Selective Fluorination Reagents with Enhanced Thermal Stability and Ease of Handling", *J. Org. Chem*, 75:3401-3411 (2010).

Langley, E. et al., "Evidence for an Anti-parallel Orientation of the Ligand-activated Human Androgen Receptor Dimer", *The Journal of Biological Chemistry*, 270(50):29983-29990 (1995).

Lannoye, G.S. et al., "N-Fluoroalkylated and N-alkylated analogs of the dopaminergic D-2 receptor antagonist raclopride", *J. Med. Chem.*, 33(9):2430-2437 (1990).

Loren, J.C. et al., "Synthesis of achiral and racemic catenanes based on terpyridine and a directionalized terpyridine mimic, pyridyl-phenanthroline", *Org. Biomol. Chem.*, 3(17):3105-3116 (2005).

Louie, M.C. et al., "Androgen-induced recruitment of RNA polymerase II to a nuclear receptor—p160 coactivator complex", *PNAS*, 100(5)2226-2230 (2003).

Martin, S.J. et al., "A new precursor for the radiosynthesis of [$^{18}$F]FLT", *Nuclear Medicine and Biology*, 29:263-273 (2002).

Masiello, D. et al., "Bicalutamide Functions as an Androgen Receptor Antagonist by Assembly of a Transcriptionally Inactive Receptor", *The Journal of Biological Chemistry*, 277(29):26321-26326 (2002).

Melnyk, O. et al., "Neutralizing Ant-Vascular Endothelial Growth Factor Antibody Inhibits Further Growth of Established Prostate Cancer and Metastases in a Pre-Clinical Model", *The Journal of Urology*, 161:960-963 (1999).

Miller, J.I. et al., "The Clinical Usefulness of Serum Prostate Specific Antigen After Hormonal Therapy of Metastatic Prostate Cancer", *The Journal of Urology*, 147:956-961 (1992).

Mitsiades, C.S. et al., "Molecular biology and cellular physiology of refractoriness to androgen ablation therapy in advanced prostate cancer", *Expert Opin. Investig. Drugs*,10(6):1099-1115 (2001).

Nakazawa, H. et al., "In vitro assay of hydrolysis and chlorohydroxy derivatives of bisphenol A diglycidyl ether for estrogenic activity", *Food and Chemical Toxicology*, 40:1827-1832 (2002).

Nazareth, L.V. et al, "Activation of the Human Androgen Receptor through a Protein Kinase A Signaling Pathway", *The Journal of Biological Chemistry*, 271(33):19900-19907 (1996).

Noble, R. L., "The development of prostatic adenocarcinoma in Nb Rats following prolonged sex hormone administration", *Cancer Research*, 37:1929-1933 (1977).

Noble, R. L., "Sex steroids as a cause of adenocarcinoma of the dorsal prostate in Nb Rats, and their influence on the growth of transplants", *Oncology*, 34:138-141 (1977).

Ogawa, Y. et al., "Estrogenic activities of chemicals related to food contact plastics and rubbers tested by the yeast two-hybrid assay," *Food Additives and Contaminants*, 23:4, 422-430 (2006).

Paris, F. et al., "Phenylphenols, biphenols, bisphenol-A and 4-tert-octyphenol exhibit $\alpha$ and $\beta$ estrogen activities and antiandrogen activity in reporter cell lines," *Molecular and Cellular Endocrinology*, 193:43-49 (2002).

Poustka, J. et al., "Determination and occurrence of bisphenol A, bisphenol A diglycidyl ether, and bisphenol F diglycidyl ether, including their derivatives, in canned foodstuffs' from the Czech retail market," *Czech J. Food Sci.*, 25(4):221-229 (2006).

Quayle, S. et al., "Androgen receptor decoy molecules block the growth of prostate cancer", *PNAS*, 104(4): 1331-1336 (2007).

Rao, B.R. et al., "Endocrine Factors in Common Epithelial Ovarian Cancer", *Endocrine Reviews*, 12(1):14-26 (1991).

Reid, J. et al., "Conformational Analysis of the Androgen Receptor Amino-terminal Domain Involved in Transactivation", *The Journal of Biological Chemistry*, 277:20079-20086 (2002).

Risch, H.A., "Hormonal Etiology of Epithelial Ovarian Cancer, With a Hypothesis Concerning the Role of Androgens and Progesterone", *Journal of the National Cancer Institute*, 90(23):1774-1786 (1998).

Roberts, J. T. et al., "Adenocarcinoma of Prostate in 40-Year-Old Body-Builder", *Lancet*, 2:742 (1986).

Rokicki, G. et al., "Reactions of 4-chloromethyl-1,3-dioxolan-2-one with phenols as a new route to polyols and cyclic carbonates", *Journal f. prakt. Chemie.*, 327:718-722 (1985).

Ross, R.K. et al., "Androgen Metabolism and Prostate Cancer: Establishing a Model of Genetic Susceptibility", *European Urology*, 35:355-361 (1999).

Sadar, M., "Androgen-independent Induction of Prostate-specific Antigen Gene Expression via Cross-talk between the Androgen Receptor and Protein Kinase A signal Transduction Pathways," *The Journal of Biological Chemistry*, 274(12):7777-7783 (1999).

Sadar, M. et al., "Prostate cancer: molecular biology of early progression to androgen independence", *Endocrine-Related Cancer*, 6:487-502 (1999).

Sadar, M.D. et al., "Characterization of a New in Vivo Hollow Fiber Model for the Study of Progression of Prostate Cancer to Androgen Independence", *Molecular Cancer Therapeutics*, 1:629-637 (2002).

Sato, N. et al., "Intermittent Androgen Suppression Delays Progression to Androgen-independent Regulation of Prostate-specific Antigen Gene in the LNCaP Prostate Tumour Model", *J. Steroid Biochem. Mol. Biol.*, 58:139-146 (1996).

Sato, N. et al., "A Metastatic and Androgen-sensitive Human Prostate Cancer Model Using Intraprostatic Inoculation of LNCaP Cells in SCID Mice", *Cancer Research*, 57:1584-1589 (1997).

Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", *Food and Chemical Toxicology*, 42:983-993 (2004).

Schaefer, A. et al, "Migration from can coatings: Part 3. Synthesis, identification and quantification of migrating epoxy-based substances below 1000 Da", *Food Additives and Contaminants*, 21(4):390-405 (2004).

Snoek, R. et al., "Induction of Cell-free, In Vitro Transcription by Recombinant Androgen Receptor Peptides", *J. Steroid Biochem. Mol. Biol.*, 59:243-250 (1996).

Still, W. C. et al., "Rapid Chromatographic Technique for Preparative Separations with Moderate Resolution", *J. Org. Chem.*, 43(14):2923-2925 (1978).

(56) References Cited

OTHER PUBLICATIONS

Sun, S. et al., "Castration resistance in human prostate cancer is conferred by a frequently occurring androgen receptor splice variant", *The Journal of Clinical Investigation*, 120(8):2715-30 (2010).
Tanji, N. et al., "Growth Factors: Rules in Andrology", *Archives of Andrology*, 47:1-7 (2001).
Taplin, M.E. et al., "Selection for Androgen Receptor Mutations in Prostate cancers Treated with Androgen Antagonist", *Cancer Research*, 59:2511-2515 (1999).
Taskeen, A. et al., "Analysis of bisphenol A in canned food: A mini review", *Asian Journal of Chemistry*, 22(5):4133-4135 (2010).
Thomson, A.A., "Role of androgens and fibroblast growth factors in prostatic development", *Reproduction*, 121:187-195 (2001).
Ueda, T. et al., "Activation of the Androgen Receptor N-terminal Domain by Interleukin-6 via MAPK and STAT3 Signal Transduction Pathways", *The Journal of Biological Chemistry*, 277(9):7076-7085 (2002).
Ueda, T. et al., "Ligand-independent Activation of the Androgen Receptor by Interleukin-6 and the Role of Steroid Receptor Coactivator-1 in Prostate cancer Cells", *The Journal of Biological Chemistry*, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese market", *Food Additives and Contaminants*, 18(2):177-185 (2001).
Van Der Kwast, T.H. et al., "Androgen Receptors in Endocrine-Therapy-Resistant Human Prostate Cancer", *Inter. J. Cancer*, 48:189-193 (1991).
Wang, G. et al., "Identification of genes targeted by the androgen and PKA signaling pathways in prostate cancer cells", *Oncogene*, 25:7311-7323 (2006).
Wang, Q. et al., "Spatial and Temporal Recruitment of Androgen Receptor and Its Coactivators Involves Chromosomal Looping and Polymerase Tracking", *Molecular Cell*, 19:631-642 (2005).
Wetherill, Y. B. et al., "In vitro molecular mechanisms of bisphenol A action," *Reproductive Toxicology*, 24:178-198 (2007).
Wilding, G., "The Importance of Steroid Hormones in Prostate Cancer", *Cancer Surveys*, 14:113-130 (1992).
Wilson, J.D. et al., "Long-Term Consequences of Castration in Men: Lessons from the Skoptzy and the Eunuchs of the Chinese and Ottoman Courts", *The Journal of Clinical Endocrinology & Metabolism*, 84:4324-4331 (1999).
Wong, C. et al., "Steroid Requirement for Androgen Receptor Dimerization and DNA Binding", *J. Biol. Chem.*, 268(25):19004-19012 (1993).
Ye, Deyong, "An Introduction to Computer-Aided Drug Design", 3 pages, Jan. 31, 2004.
Zuhayra, M. et al., "New approach for the synthesis of [$^{18}$F]fluoroethyltyrosine for cancer imaging: Simple, fast, and high yielding automated synthesis", *Bioorganic & Medicinal Chemistry*, 17:7441-7448 (2009).
Brzozowski, Z. et al., "Precursors for bisphenolic resins", CAPLUS Database Accession No. 1990:36690, Document No. 112:33690, (1987), 1 page (Abstract).
Choi, K. M. et al., "New Families of Photocurable Oligomeric Fluoromonomers for Use in Dental Composites", *Chemistry of Materials*, 8(12):2704-2707 (1996).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", *Journal of Macromolecular Science, Pure and Applied Chemistry*, A31(9):1105-1119 (1994).
Cook, W. D., "Fracture and Structure of Highly Crosslinked Polymer Composites", *Journal of Applied Polymer Science*, 42:1259-1269 (1991).

Myung, J-K et al., "An androgen receptor N-terminal domain antagonist for treating prostate cancer", *The Journal of Clinical Investigation*, 123(7):2948-2960 (2013).
Nedolya, N. A. et al., Zhurnal Organicheskoi Khimii, 30(8):1163-1166 (1994).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," *Polimery*, (Warsaw), 40(5):274-2777 (1995).
Reader, C. E. L., "Epoxy Resin Derivatives for Stoving Systems", *Surface Coatings Australia*, 25(10):6-9 (1988).
Rusu, E. et al.: "Photosensitive compounds with chloromethyl groups", *Revue Roumaine de Chimie*, 45(5):451-456 (2000).
Silverman, R. B., The Organic Chemistry of Drug Design and Drug Action, Academic Press, Inc., Harcourt Brace Jovanovich, pp. 15-20, 9 pages (1992).
Van Scherpenzeel, M. et al., "Nanomolar affinity, iminosugar-based chemical probes for specific labeling of lysosomal glucocerebrosidase", *Bioorganic & Medicinal Chemistry*, 18:267-273 (2010).
Supplementary European Search Report in EP Application No. 09771876.1 dated Jun. 20, 2011, 5 pages.
Supplementary European Search Report in EP Application No. 11731645.5 dated mailed Jun. 2, 2013, 11 pages.
Decision of Refusal for Japanese Application No. 2011-515039, mailed Dec. 2, 2014, 18 pages (English translation).
International Preliminary Report on Patentability for PCT/CA2009/000902 issued Jan. 5, 2011, 7 pages.
International Search Report for PCT/CA2009/000902 mailed Sep. 1, 2009, 4 pages.
Written Opinion for PCT/CA2009/000902 mailed Sep. 1, 2009, 6 pages.
International Preliminary Report on Patentability for PCT/US2012/032584 issued Oct. 8, 2013, 6 pages.
International Search Report for PCT/US2012/032584 mailed Jul. 31, 2012, 3 pages.
Written Opinion for PCT/US2012/032584 mailed Jul. 31, 2012, 5 pages.
International Preliminary Report on Patentability for PCT/US2012/033959 dated Oct. 22, 2013, 8 pages.
International Search Report for PCT/US2012/033959 mailed Jul. 18, 2012, 3 pages.
Written Opinion for PCT/US2012/033959 mailed Jul. 18, 2012, 7 pages.
International Preliminary Report on Patentability for PCT/US2012/033957 dated Oct. 22, 2013, 6 pages.
International Search Report for PCT/US2012/033957 mailed Jul. 18, 2012, 3 pages.
Written Opinion for PCT/US2012/033957 mailed Jul. 18, 2012, 5 pages.
International Preliminary Report on Patentability for PCT/CA2011/000019 dated Jul. 10, 2012, 8 pages.
International Search Report for PCT/CA2011/000019 mailed Mar. 21, 2011, 7 pages.
Written Opinion for PCT/CA2011/000019 mailed Mar. 21, 2011, 7 pages.
International Preliminary Report on Patentability for PCT/CA2011/000021 dated Jul. 10, 2012, 8 pages.
International Search Report for PCT/CA2011/000021 mailed Apr. 11, 2011, 8 pages.
Written Opinion for PCT/CA2011/000021 mailed Apr. 11, 2011, 7 pages.
International Preliminary Report on Patentability for PCT/US2012/051481 dated Feb. 25, 2014, 8 pages.
International Search Report for PCT/US2012/051481 mailed Nov. 26, 2012, 4 pages.
Written Opinion for PCT/US2012/051481 mailed Nov. 26, 2012, 7 pages.
International Preliminary Report on Patentability for PCT/US2012/051923 dated Feb. 25, 2014, 9 pages.

(56) References Cited

OTHER PUBLICATIONS

International Search Report for PCT/US2012/051923 mailed Jan. 28, 2013, 4 pages.
Written Opinion for PCT/US2012/051923 mailed Jan. 28, 2013, 8 pages.
Extended European Search Report in Application No. EP 12768410.8 dated Sep. 22, 2014, 10 pages.
International Search Report and Written Opinion for PCT/CA2014/000414 mailed Dec. 4, 2014, 6 pages.
International Search Report and Written Opinion for PCT/CA2014/000685 mailed Dec. 4, 2014, 13 pages.
Petersen, H. et al., "Determination of bisphenol A diglycidyl ether (BADGE) and its derivatives in food: identification and quantification by internal Standard", *Eur. Food Res. Technol.*, 216:355-364 (2003).
Poouthree, K. et al., "Comparison of resolution in microemulsion EKC and MEKC employing suppressed electroosmosis: Application to bisphenol-A-diglycidyl ether and its derivatives", *Electrophoresis*, 28(20):3705-3711 (2007).
Patani and LaVoie, "Bioisosterism: A Rational Approach in Drug Design", Chem. Rev., 96: 3147-3176 (1996).
Strub and McKim, "Dimethyl Sulfoxide USP, PhEur in Approved Pharmaceutical Products and Medical Devices", PharmaTech.com, 6 pages (2008). http://www.pharmtech.com/print/224268 ?page=full &rel=canonical.
Alvarez, C. et al., "Confirmational and Experimental Studies on the Dipole Moments of Models of Comblike Polymers", Macromolecules, 30(20): 6369-6375 (1997).
Henke, H., "Selektive präparative gelchromatographische Trennung niedermolekularer Verbindungen an Sephadex LH-20", Journal of Chromatography, 254: 296-308 (1983).
Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
International Preliminary Report on Patentability for PCT/CA2014/000414 mailed Nov. 10, 2015, 7 pages.

\* cited by examiner

AZIRIDINE BISPHENOL ETHERS AND RELATED COMPOUNDS AND METHODS FOR THEIR USE

CROSS-REFERENCE TO RELATED APPLICATIONS

This application claims priority to U.S. Provisional Application No. 61/624,826 filed Apr. 16, 2012, the disclosure of which is herein incorporated by reference in its entirety for all purposes.

BACKGROUND

1. Technical Field

This invention generally relates to bisphenol-related compounds and their use for treatment of various indications. In particular the invention relates to bisphenol-related compounds and their use for treatment of various cancers, for example all stages of prostate cancer, including androgen dependent, androgen-sensitive and castration-resistant prostate cancers.

2. Description of the Related Art

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (androgen ablation).

Androgens also play a role in female cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 *Scand J. Urol Nephrol.* 104, 33-39). Castration-resistant prostate cancer is biochemically characterized before the onset of symptoms by a rising titre of serum PSA (Miller et al 1992 *J. Urol.* 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR may be activated in the absence of testicular androgens by alternative signal transduction pathways in castration-resistant disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the AR include nonsteroidal antiandrogens such as bicalutamide (Casodex™), nilutamide, flutamide, investigational drugs MDV3100 and ARN-509, and the steroidal antiandrogen, cyproterone acetate. These antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.,* 59, 2511-2515 (1999)). These antiandrogens would also have no effect on the recently discovered AR splice variants that lack the ligand-binding domain (LBD) to result in a constitutively active receptor which promotes progression of androgen-independent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 Cancer Res. 69, 16-22; Sun et al 2010 J Clin Invest. 2010 120, 2715-30).

Conventional therapy has concentrated on androgen-dependent activation of the AR through its C-terminal domain. Recent studies developing antagonists to the AR have concentrated on the C-terminus and specifically: 1) the allosteric pocket and AF-2 activity (Estébanez-Perpiñá et al 2007, *PNAS* 104, 16074-16079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñá et al 2005, *JBC* 280, 8060-8068; He et al 2004, *Mol Cell* 16, 425-438).

The AR-NTD is also a target for drug development (e.g. WO 2000/001813), since the NTD contains Activation-Function-1 (AF_1) which is the essential region required for AR transcriptional activity (Jenster et al 1991. Mol Endocrinol. 5, 1396-404). The AR-NTD importantly plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR C-terminus LBD, this has not been the case for the NTD due to its high flexibility and intrinisic disorder in solution (Reid et al 2002 *J. Biol. Chem.* 277, 20079-20086) thereby hampering virtual docking drug discovery approaches.

Recent advances in the development of compounds that modulate AR include the bis-phenol compounds disclosed in published PCT WO 2010/000066 to the British Columbia Cancer Agency Branch and The University of British Columbia. While such compounds appear promising, there remains a need in the art for additional and/or improved compounds that modulate the AR, and which provide treatment for conditions that benefit from such modulation.

BRIEF SUMMARY

This invention is also based in part on the discovery that the compounds described herein, may be used to modulate Androgen Receptor (AR) activity either in vivo or in vitro for both research and therapeutic uses. While not wishing to be bound by theory, it is believed that the present compounds modulate AR, at least in part, due to their ability to form covalent bonds with the AR receptor. Such covalent binding is believed to increase the modulatory effect of the compounds (as opposed to non-covalent modulators) and thus make the compounds useful for therapeutic indications which benefit from modulation of AR. Example indications are provided below. Furthermore, due to their covalent binding properties, certain embodiments of the compounds are also useful as probes (e.g., radiolabled) to study the AR receptor.

In accordance with one embodiment, there is provided a compound having a structure of Formula I:

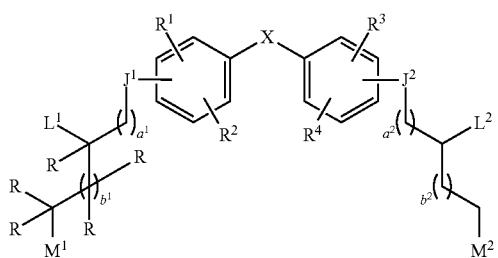

I or a pharmaceutically acceptable salt, tautomer or stereoisomer thereof, wherein R, $R^1$, $R^2$, $R^3$, $R^4$, M, X, $L^1$, $L^2$, $J^1$, $J^2$, $a^1$, $a^2$, $b^1$ and $b^2$ are as defined herein, and wherein at least one of $L^2$ of $M^2$ is a moiety comprising an aziridine, acrylamide or sulfonate functional group.

In other embodiments, the present disclosure provides the use of a compound of Formula I, for modulating androgen receptor (AR) activity. Methods for modulating AR, as well as pharmaceutical compositions comprising a compound of Formula I and a pharmaceutically acceptable excipient are also provided.

In addition, the present disclosure provides combination therapy treatments for any of the disease states disclosed herein, for example prostate cancer or Kennedy's disease. The disclosed therapies include use of a pharmaceutical composition comprising a compound of Formula I, an additional therapeutic agent and a pharmaceutically acceptable excipient. Methods and compositions related to the same are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

I. Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.

"Aziridine" or "aziridine functional group" refers to a moiety comprising a three-membered ring containing a nitrogen atom and two carbon atoms. Aziridines may be attached to the remainder of the molecule via the nitrogen atom or any of the carbon atoms. Aziridines may also be optionally substituted, that is either the nitrogen atom, or any of the carbon atoms may be substituted with a substituent. Representative substituents are described below.

"Acrylamide" or "acrylamide functional group" refers to a moiety comprising the following structure:

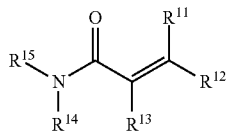

wherein $R^{11}$, $R^{12}$, $R^{13}$, $R^{14}$ and $R^{15}$ are each independently hydrogen, $C_1$-$C_{10}$ alkyl, aryl or aralkyl wherein at least one of the hydrogen atoms has been replaced with a bond to the remainder of the molecule. Acrylamides may be attached at any point to the remainder of the molecule and may be optionally substituted.

"Sulfonate" or "sulfonate functional group" refers to the —$OS(O)_2$—$R_a$ radical, wherein Ra is an alkyl, aryl or aralkyl moiety as defined below.

"Alkyl" refers to a straight, branched or non-aromatic cyclic hydrocarbon ("cycloalkyl") chain radical which is saturated or unsaturated (i.e., contains one or more double and/or triple bonds), having from one to twelve carbon atoms (e.g., one to ten, or one to six carbon atoms), and which is attached to the rest of the molecule by a single bond. Alkyls comprising any number of carbon atoms from 1 to 12 are included. An alkyl comprising up to 10 carbon atoms is a $C_1$-$C_{10}$ alkyl. A $C_1$-$C_{10}$ alkyl includes $C_{10}$ alkyls, $C_9$ alkyls, $C_8$ alkyls, $C_7$ alkyls, $C_6$ alkyls, $C_5$ alkyls, $C_4$ alkyls, $C_3$ alkyls, $C_2$ alkyls and $C_1$ alkyl (i.e., methyl) and includes, for example, and without limitation, saturated $C_1$-$C_{10}$ alkyl, $C_2$-$C_{10}$ alkenyl and $C_2$-$C_{10}$ alkynyl. Non-limiting examples of saturated $C_1$-$C_{10}$ alkyl include methyl, ethyl, n-propyl, i-propyl, sec-propyl, n-butyl, i-butyl, sec-butyl, t-butyl and n-penty, n-hexyl, n-heptane, and the like. Non-limiting examples of $C_2$-$C_{10}$ alkenyl include vinyl, allyl, isopropenyl, 1-propene-2-yl, 1-butene-1-yl, 1-butene-2-yl, 1-butene-3-yl, 2-butene-1-yl, 2-butene-2-yl, penteneyl, hexeneyl, and the like. Non-limiting examples of $C_2$-$C_{10}$ alkynyl include ethynyl, propynyl, butynyl, pentynyl, hexynyl, and the like. Unless stated otherwise specifically in the specification, an alkyl group may be optionally substituted (i.e., a hydrogen atom in the alkyl group may be replaced with an optional substituent). Alkyls include cycloalkyls as defined below.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$-$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Carbocycle" refers to a ring, wherein the atoms which form the ring consist solely of carbon atoms. Carbocycles include, without limitation, cycloalklys and aryls as defined herein.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halogen" or "halo" refers to fluoro (F), chloro (Cl), bromo (Br) and iodo (I) substituents. Halogen substitutents also include halogen radioisotopes.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group may be optionally substituted. Heterocycles include heteroaryls as defined below.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, cycloalkyl, aryl, carbocycle, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo (i.e., C=O), carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like. In certain embodiments, prodrugs of the present invention comprise one or more of the moieties in Table 1 below.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program and/or ChemDraw Version 11.0.1 software naming program (CambridgeSoft), wherein the compounds of the invention are named herein as derivatives of the central core structure. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

As used herein, the symbol "⊣" (hereinafter may be referred to as "a point of attachment bond") denotes a bond that is a point of attachment between two chemical entities, one of which is depicted as being attached to the point of attachment bond and the other of which is not depicted as being attached to the point of attachment bond. For example,

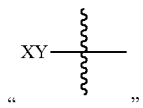

" "

indicates that the chemical entity "XY" is bonded to another chemical entity via the point of attachment bond. Furthermore, the specific point of attachment to the non-depicted chemical entity may be specified by inference. For example, the compound $CH_3$—$R^3$, wherein $R^3$ is H or


" "

infers that when $R^3$ is "XY", the point of attachment bond is the same bond as the bond by which $R^3$ is depicted as being bonded to $CH_3$.

II. Compounds and Compositions

As noted above, certain embodiments of the present invention are directed to compounds useful for treatment of various cancers, including various types of prostate cancers. While not wishing to be bound by theory, it is believed that binding of the compounds to the androgen receptor, in particular, covalent binding (for example at the N-terminal domain) may contribute to the activity of the disclosed compounds. In this regard, the present compounds are designed to include functional groups capable of forming covalent bonds with a nucleophile under certain in vivo conditions. For example, in some embodiments the reactivity of compounds of the present invention is such that they will not substantially react with various nucleophiles (e.g., glutathione) when the compounds are free in solution. However, when the free mobility of the compounds is restricted, and an appropriate nucleophile is brought into close proximity to the compound, for example when the compounds associate with, or bind to, the androgen receptor, the compounds are capable of forming covalent bonds with certain nucleophiles (e.g., thiols). Accordingly, one embodiment of the present disclosure includes compounds which form covalent bonds with the androgen receptor (e.g., at the N-terminal domain), thus resulting in irreversible (or substantially irreversible) inhibition of the same.

The present invention includes all compounds which have the above described properties (i.e., covalent binding to androgen receptor). Accordingly, the present compounds include a functional group having reactivity such that it can form a covalent bond with the androgen receptor, but will be substantially unreactive towards nucleophiles when not associated with or bound to the androgen receptor. In certain embodiments such functional groups include azirdine and/or acrylamide functional groups. Accordingly, one embodiment of the present invention is directed to a compound having a structure of Formula I:

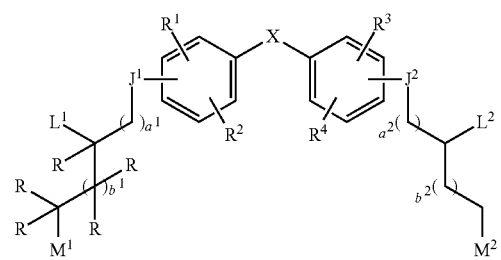

or a pharmaceutically acceptable salt, tautomer or stereoisomer thereof, wherein:

$M^1$ is halogen, —OH, —OY or —$OR^5$;

$M^2$ is halogen, —OH, —OY, —$OR^5$ or Z;

$L^1$ is H, halogen, —OH, —$OR^5$, —OY, —$SR^5$ or —$NR^5R^6R^7$;

$L^2$ is H, halogen, —OH, —$OR^5$, —OY, —$SR^5$, —$NR^5R^6R^7$ or Z;

Z is a moiety comprising an aziridine, acrylamide or sulfonate functional group;

$J^1$ and $J^2$ are each independently —O—, —$S(O)_{0-2}$—, —$NR^5$— or —$(CR^5R^6)$—;

X is a direct bond, —$C(R^8R^9)$—, —$C(=CR^8R^9)$—, —$C(R^8R^9)$-aryl-$C(R^8R^9)$—, —$C(=CR^8R^9)$-aryl-$C(=CR^8R^9)$—; —O—, —$S(O)_{0-2}$—, —$N(R^5)$—, —$C(=NOR^5)$—, —$C(=NR^5)$— or —$C(=O)$—;

Y is a moiety from Table I;

R is, at each occurrence, independently H or halogen;

$R^1$, $R^2$, $R^3$ and $R^4$ are each independently H, halogen or $C_1$-$C_{10}$ alkyl;

$R^5$ and $R^6$ are, at each occurrence, independently H, or $C_1$-$C_{10}$ alkyl;

$R^7$ is an electron pair, H, or $C_1$-$C_{10}$ alkyl;

$R^8$ and $R^9$ are each independently, H, halogen, $C_1$-$C_{10}$ alkyl, aryl, aralkyl or —$NR^5R^6$, or $R^8$ and $R^9$ may join to form a mono-, bi- or tri-cyclic carbocycle or heterocycle containing from 3 to 20 carbon atoms;

$a^1$, $a^2$, $b^1$ and $b^2$ are each independently 0, 1, 2, 3, 4 or 5;

wherein at least one of $M^2$ or $L^2$ is Z.

In certain embodiments, the compound has the following structure (Ia):

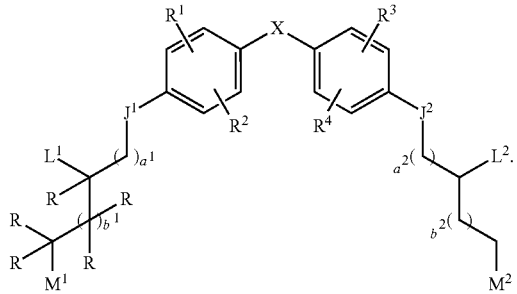

In some other embodiments, $R^8$ and $R^9$ are each independently H or $C_1$-$C_{10}$ alkyl. For example, in some embodiments $R^8$ and $R^9$ are each $C_1$-$C_{10}$ alkyl.

In still other embodiments, $R^8$ and $R^9$ join to form a mono-, bi- or tri-cyclic carbocycle or heterocycle containing from 3 to 20 carbon atoms.

In various other embodiments, X is —$[(CR^5R^6)$-aryl-$(CR^5R^6)]$—.

In yet more examples, X is —CH$_2$—, —C(CH$_3$)$_2$—, —S—, —(C=O)—,

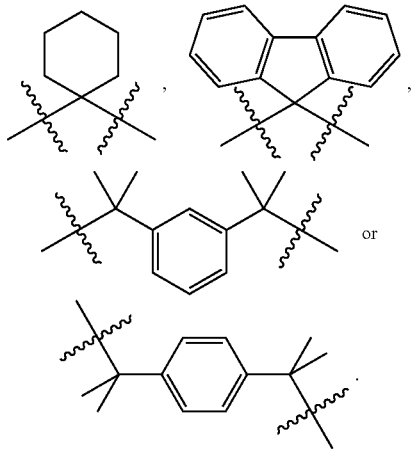

or

For example, in some examples X is —C(CH$_3$)$_2$—.

In various embodiments of any of the compounds of Formula I, at least one of R$^1$, R$^2$, R$^3$ or R$^4$ is H. For example, in some embodiments each of R$^1$, R$^2$, R$^3$ and R$^4$ is H.

In other embodiments, at least one of R$^1$, R$^2$, R$^3$ or R$^4$ is C$_1$-C$_{10}$ alkyl. For example, in some embodiments at least one of R$^1$, R$^2$, R$^3$ or R$^4$ is halogen.

In still other exemplary embodiments, at least one of J$^1$ or J$^2$ is —O—, and in other aspects each of J$^1$ and J$^2$ is —O—.

In some examples a$^1$ is 0 or 1. In other examples a$^2$ is 1. In still other embodiments b$^1$ is 0. Even other embodiments provide compounds of Formula I wherein b$^2$ is O.

In certain embodiments, each R is independently H or fluoro. For example, in some embodiments at least one R is fluoro, and in other embodiments each R is H.

Other examples include embodiments wherein L$^1$ is —OH, and other embodiments are directed to compound of Formula I wherein L$^2$ is —OH.

In some embodiments L$^1$ is halogen, for example fluoro. In other embodiments L$^2$ is halogen, for example fluoro.

In some embodiments L$^1$ is H, and in other embodiments L$^2$ is H.

In still other embodiments, L$^1$ is —OY. In other embodiments L$^2$ is —OY.

In certain embodiments of the foregoing Y is

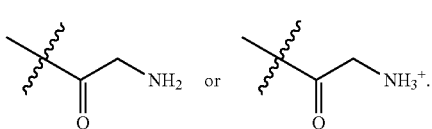

In some aspects M$^1$ is halogen, for example fluoro. In other embodiments, M$^1$ is —OH, and in other examples M$^1$ is —OR$^5$.

In some examples R$^5$ is an unsaturated alkyl. In other examples R$^5$ is a saturated alkyl. In certain embodiments of the foregoing, one or more carbon atoms of the C$_1$-C$_{20}$ alkyl are replaced with an oxygen atom. In other embodiments the alkyl is substituted with one or more —OH groups.

In some other embodiments M$^1$ Has one of the following structures:

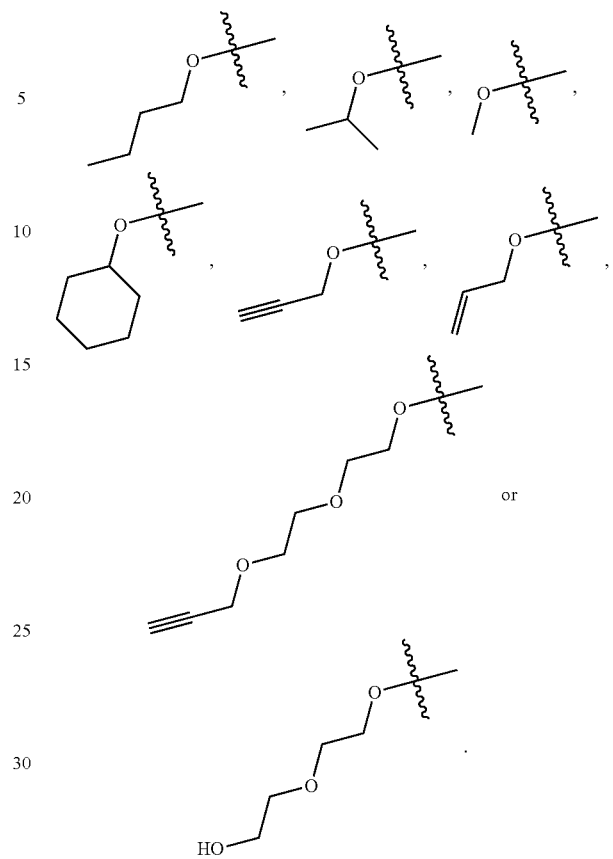

In certain embodiments of any of the preceding compounds M$^2$ is Z. In other embodiments of any of the preceding compounds L$^2$ is Z.

In some embodiments, L$^2$ is Z and M$^2$ is F, Cl, OH or —OR$^5$. In more specific embodiments, L$^2$ is Z, M$^2$ is F, Cl, OH or —OR$^5$ and Z has the following structure:

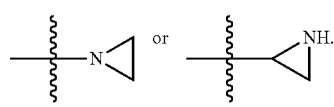

In other specific embodiments, L$^2$ is Z, M$^2$ is F, Cl, OH or —OR$^5$ and Z has the following structure:

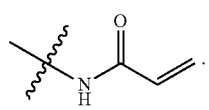 [SMILES: *NC(=O)C=C]

In still other embodiments, L$^2$ is Z, M$^2$ is F, Cl, OH or —OR$^5$ and Z has the following structure:

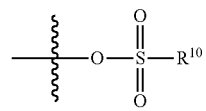

wherein $R^{10}$ is $C_1$-$C_{10}$ alkyl, aryl or aralkyl. For example, in some embodiments of the foregoing $R^{10}$ is methyl or 4-methylphenyl.

In yet other embodiments, $M^2$ is Z and $L^2$ is F, Cl, OH or —$OR^5$. In more specific embodiments, $M^2$ is Z, $L^2$ is F, Cl, OH or —$OR^5$ and Z has the following structure:

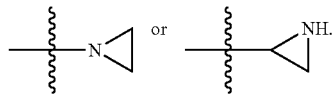

In other specific embodiments, $M^2$ is Z, $L^2$ is F, Cl, OH or —$OR^5$ and Z has the following structure:

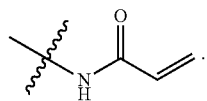 [SMILES: *NC(=O)C=C]

In still other embodiments, $M^2$ is Z, $L^2$ is F, Cl, OH or —$OR^5$ and Z has the following structure:

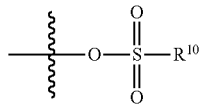

wherein $R^{10}$ is $C_1$-$C_{10}$ alkyl, aryl or aralkyl. For example, in some embodiments of the foregoing $R^{10}$ is methyl or 4-methylphenyl.

The compounds described herein are meant to include all racemic mixtures and all individual enantiomers or combinations thereof, whether or not they are specifically depicted herein. In certain embodiments, the compounds are provided in the form of a prodrug, Such prodrugs include compounds wherein of the OH groups are substituted to replace the H with a moiety selected from Table 1 (i.e., to form a OY moiety).

TABLE 1

Amino Acid, Polyethylene Glycol, and Phosphate Based Moieties

Amino Acid Based Moieties

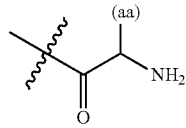

(aa) = any naturally occurring amino acid side chain

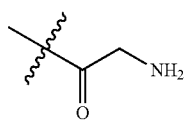 [SMILES: *C(=O)CN]

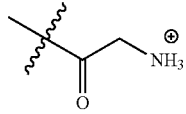 [SMILES: *C(=O)C[NH3+]]

TABLE 1-continued

Amino Acid, Polyethylene Glycol, and Phosphate Based Moieties

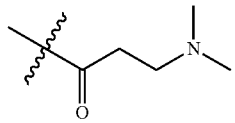 [SMILES: *C(=O)CCN(C)C]

Polyethylene Glycol Based Moieties

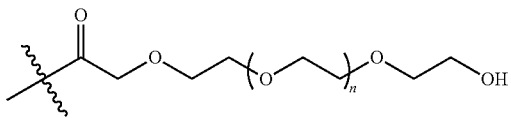

n = 1-200

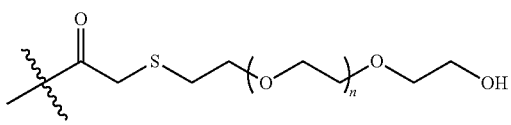

n = 1-200

Phosphate Based Moieties

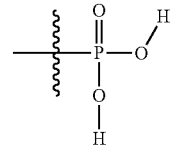 [SMILES: *P(=O)(O)O]

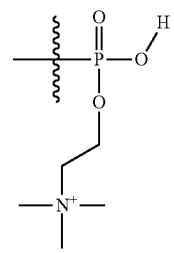

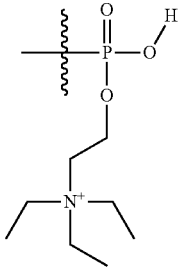 [SMILES: *P(=O)(O)OCC[N+](CC)(CC)CC]

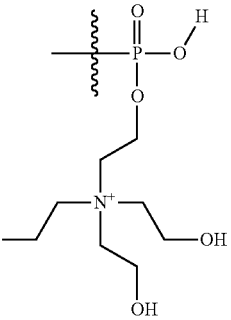

TABLE 1-continued
Amino Acid, Polyethylene Glycol, and Phosphate Based Moieties
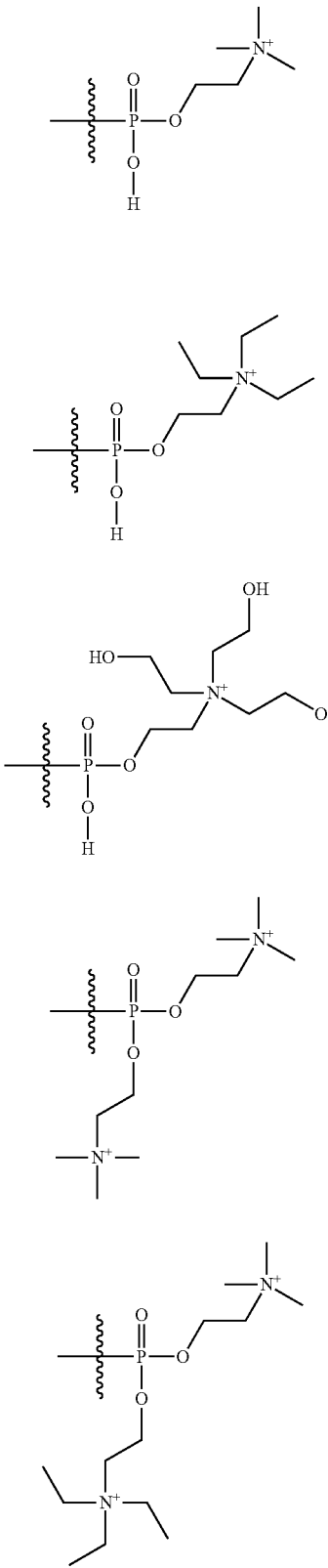
TABLE 1-continued
Amino Acid, Polyethylene Glycol, and Phosphate Based Moieties
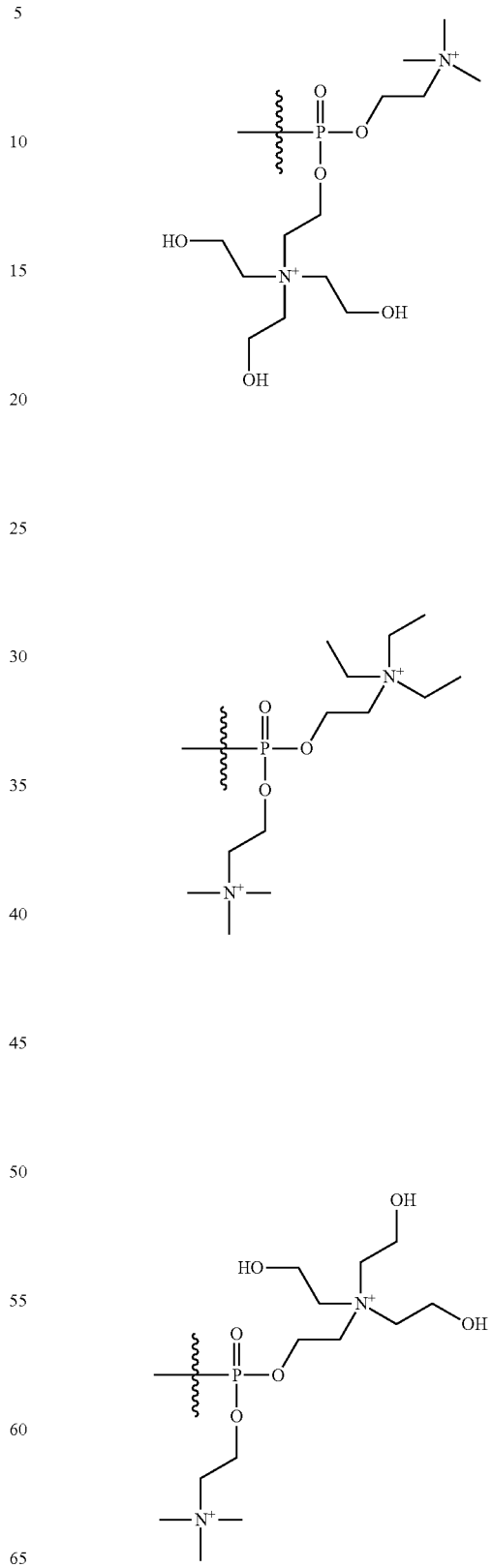

TABLE 1-continued

Amino Acid, Polyethylene Glycol, and Phosphate Based Moieties

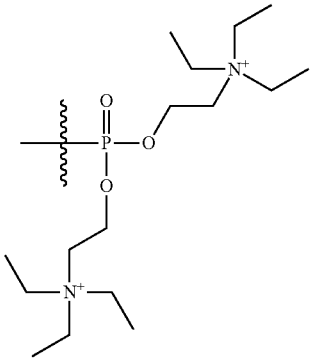 [SMILES: *P(=O)(OCC[N+](CC)(CC)CC)OCC[N+](CC)(CC)CC]

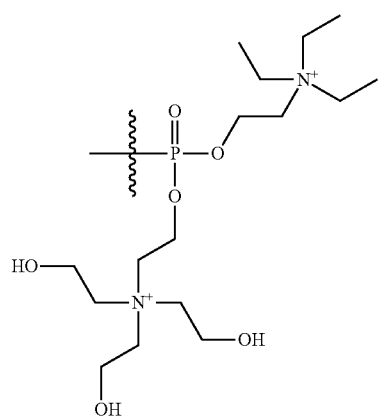 [SMILES: *P(=O)(OCC[N+](CC)(CC)CC)OCC[N+](CCO)(CCO)CCO]

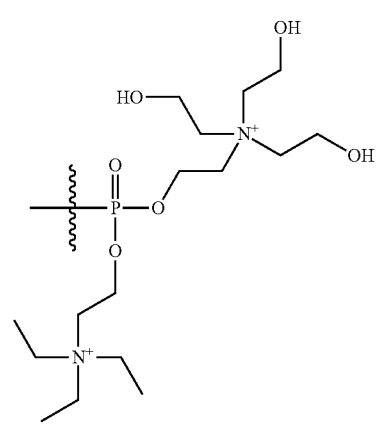 [SMILES: *P(=O)(OCC[N+](CC)(CC)CC)OCC[N+](CCO)(CCO)CCO]

TABLE 1-continued

Amino Acid, Polyethylene Glycol, and Phosphate Based Moieties

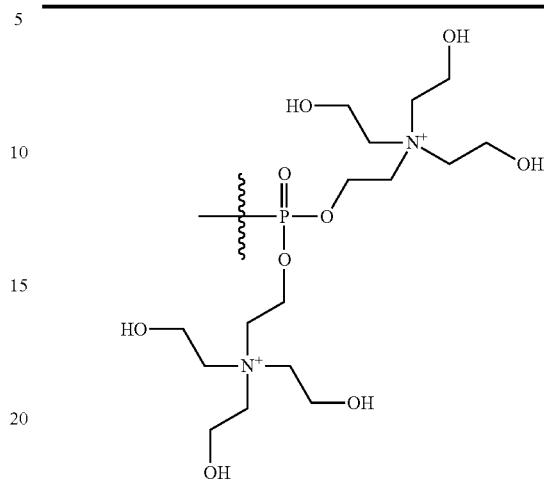

Moieties from TABLE 1 may be, for example, and without limitation, subdivided into three groups: 1) amino acid based moieties; 2) polyethylene glycol based moieties; and 3) phosphate based moieties. In the Moieties Table 1 above, the first four moieties are amino acid based moieties, the fifth and sixth are polyethylene glycol based moieties and the remaining moieties are phosphate based moieties.

The amino acid side chains of naturally occurring amino acids (as often denoted herein using "(aa)") are well known to a person of skill in the art and may be found in a variety of text books such as "Molecular Cell Biology" by James Darnell et al. Third Edition, published by Scientific American Books in 1995. Often the naturally occurring amino acids are represented by the formula $(NH_2)C(COOH)(H)(R)$, where the chemical groups in brackets are each bonded to the carbon not in brackets. R represents the side chains in this particular formula.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

Accordingly, prodrugs are also included within the scope of the present disclosure. For example, in one embodiment the hydrogen atom of one or more hydroxyl groups of any of the compounds of Formula I is replaced with a moiety from Table 1 (i.e., to form a —OY moiety). Non-limiting examples of such prodrugs include glycine esters and salts thereof as shown below.

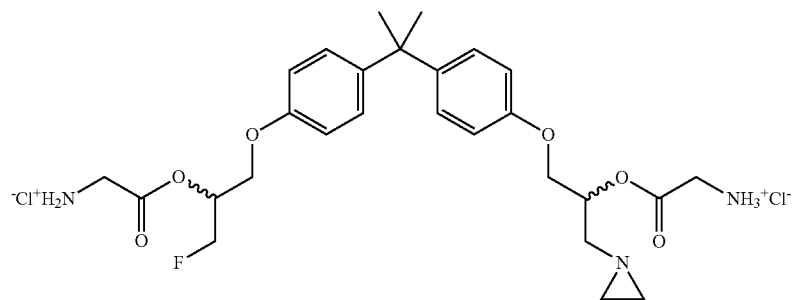

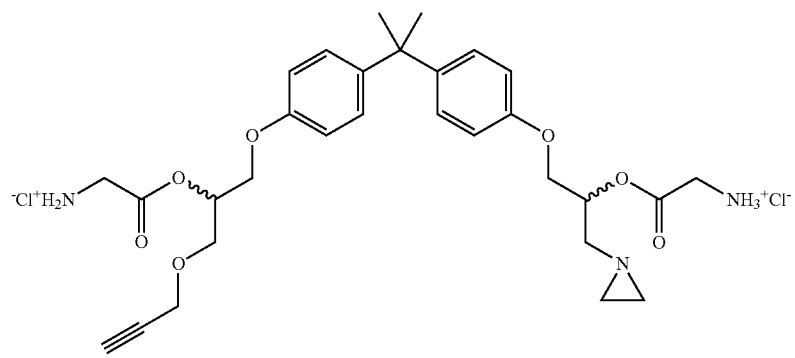

Compounds as described herein include all stereoisomers. Accordingly, the compounds include racemic mixtures, enantiomers and diastereomers of any of the compounds described herein. Tautomers of any of the compounds of formula I are also included within the scope of the invention.

As noted above, the compounds of the present invention (i.e., compounds of Formula I) may contain one or more asymmetric centers. Accordingly, in some embodiments the compounds are mixtures of different enantiomers (e.g., R and S) or different diastereomers. In other embodiments, the compounds are pure (or enriched) enantiomers or diastereomers. For purpose of clarity, the chiral carbons are not always depicted in the compounds; however, the present invention includes all stereoisomers (pure and mixtures) of all compounds of Formula I.

By way of example, compound Ia contains four stereocenters and is generally depicted as shown below:

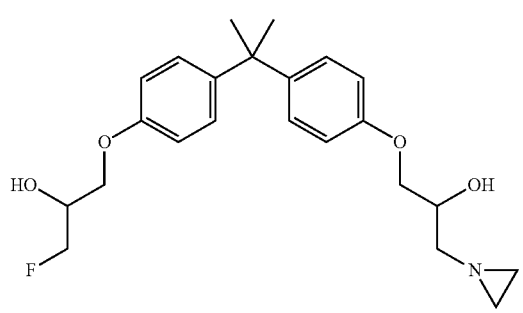

(Ia)

Although the compounds are generally depicted as above, the scope of the invention includes all possible stereoisomers. For example, with respect to compound Ia, the invention also includes the following stereoisomers:

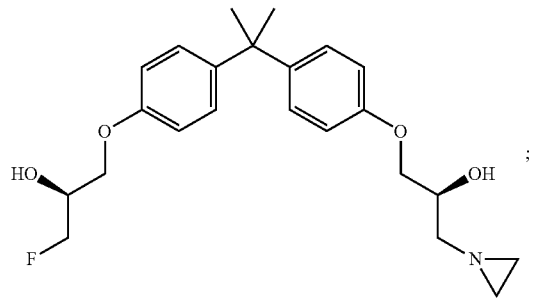

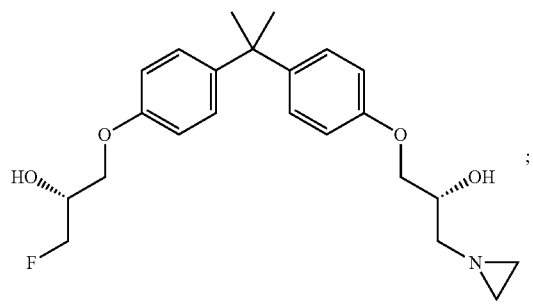

and

-continued

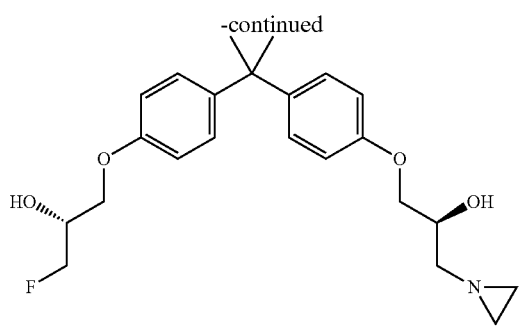

In an analagous fashion, the invention includes all possible stereoisomers of all compounds of Formula I, including the compounds provided in Table 2. One of ordinary skill in the art will readily understand how to derive all possible stereoisomers, especially in reference to the above example.

In other particular embodiments of the compounds as described anywhere herein, the following compounds (and all possible stereoisomers thereof) in Table 2 are provided.

TABLE 2

Representative Compounds

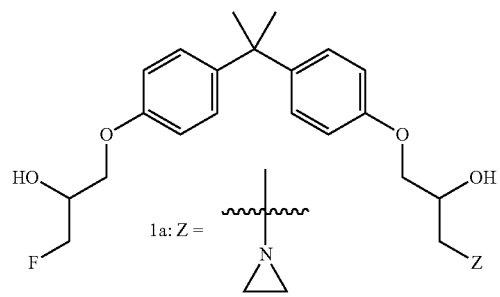

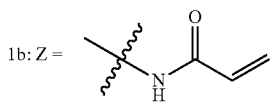

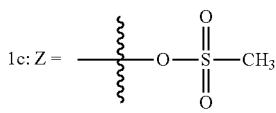

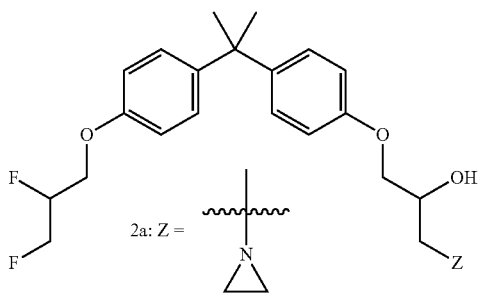

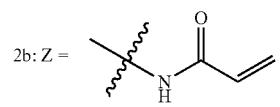

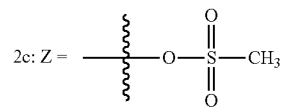

TABLE 2-continued
Representative Compounds
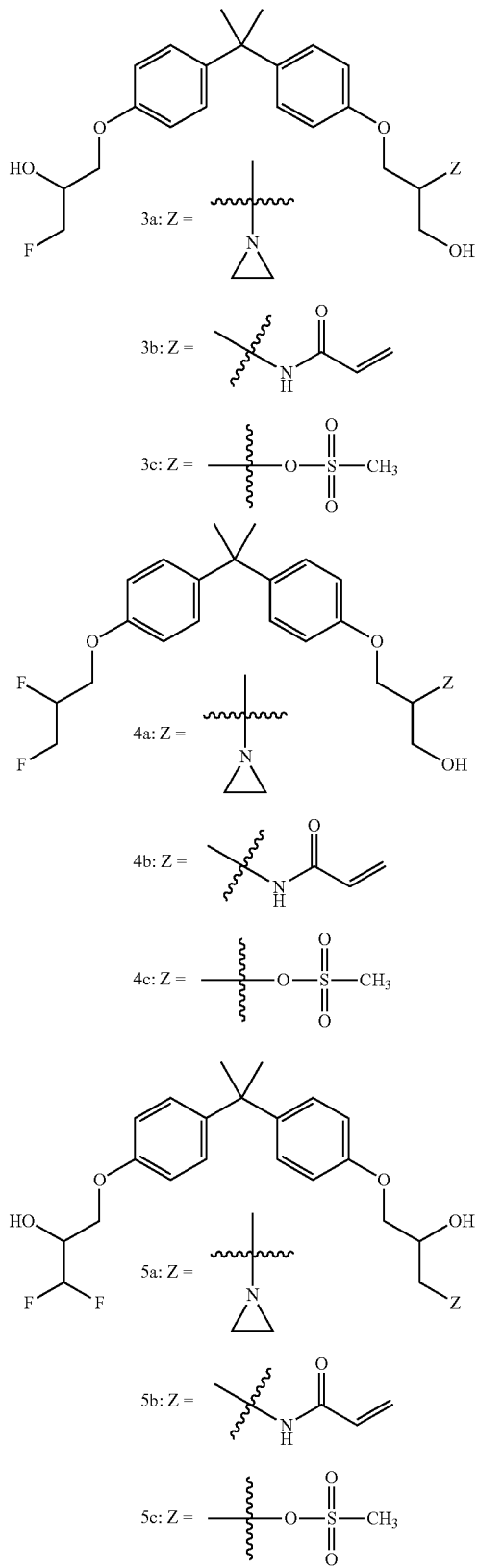

TABLE 2-continued
Representative Compounds
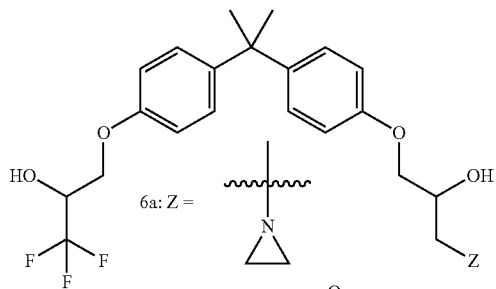
6a: Z = 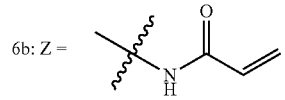
6b: Z = 
6c: Z = 
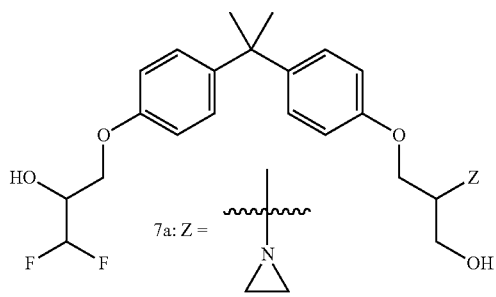
7a: Z = 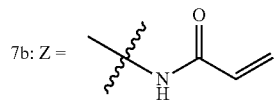
7b: Z = 
7c: Z = 
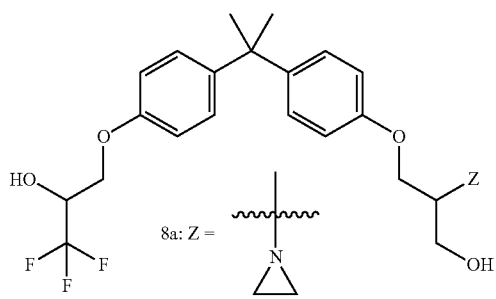
8a: Z = 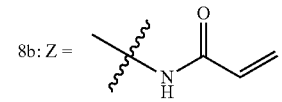
8b: Z = 
8c: Z =

TABLE 2-continued
Representative Compounds
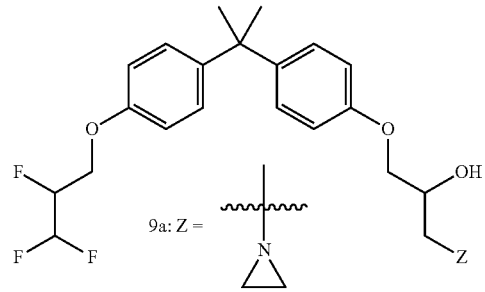
9a: Z = 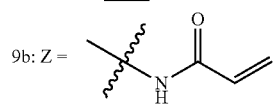
9b: Z = 
9c: Z = 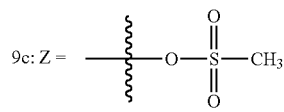
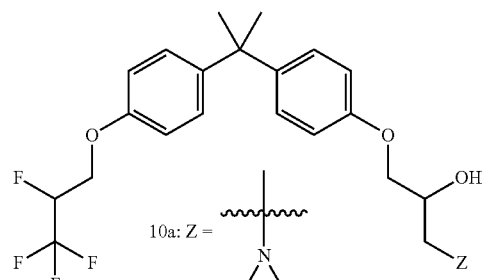
10a: Z = 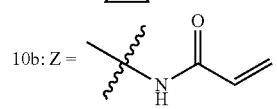
10b: Z = 
10c: Z = 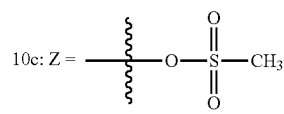
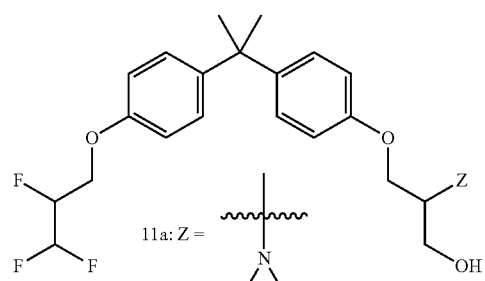
11a: Z = 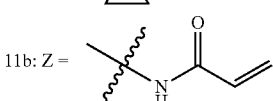
11b: Z = 
11c: Z = 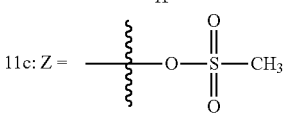

TABLE 2-continued
Representative Compounds
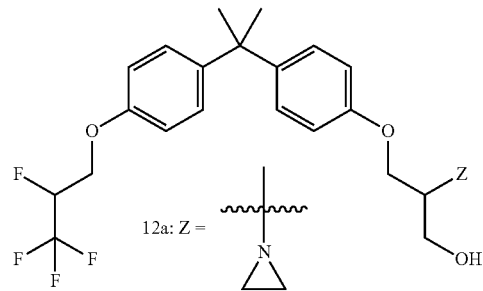
12a: Z = 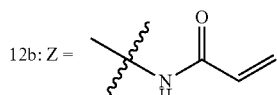
12b: Z = 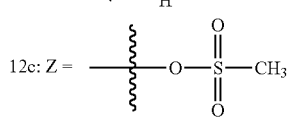
12c: Z =
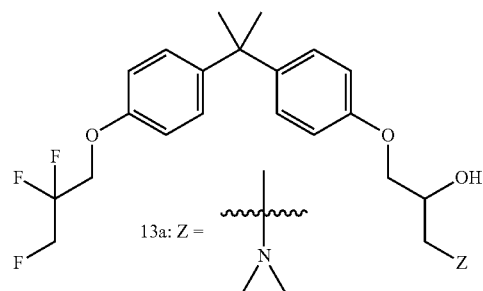
13a: Z = 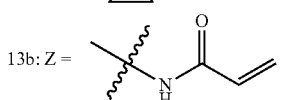
13b: Z = 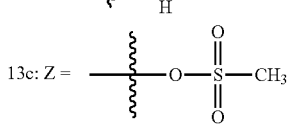
13c: Z =
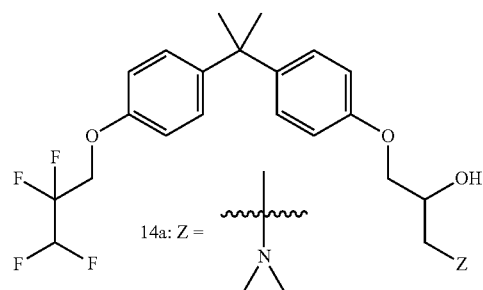
14a: Z = 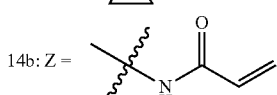
14b: Z = 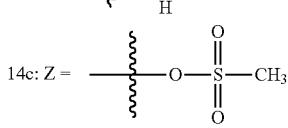
14c: Z =

TABLE 2-continued
Representative Compounds
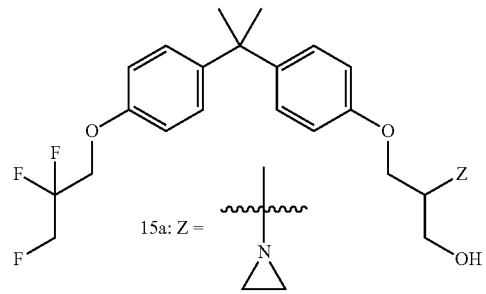
15a: Z = 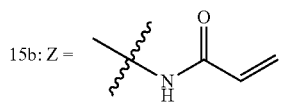
15b: Z = 
15c: Z = 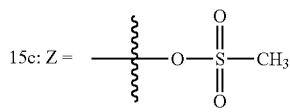
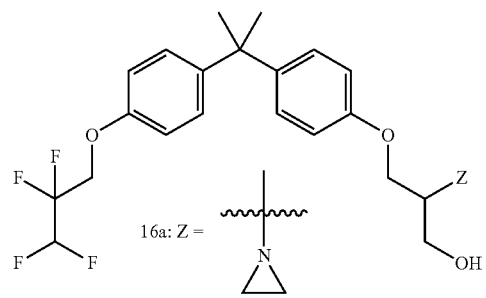
16a: Z = 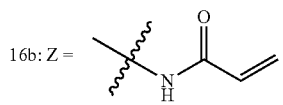
16b: Z = 
16c: Z = 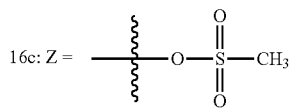
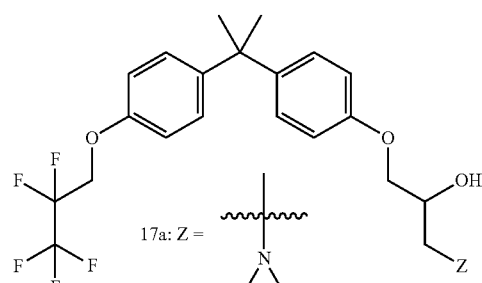
17a: Z = 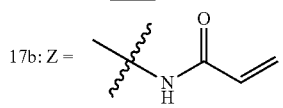
17b: Z = 
17c: Z = 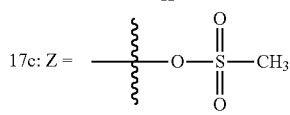

TABLE 2-continued
Representative Compounds
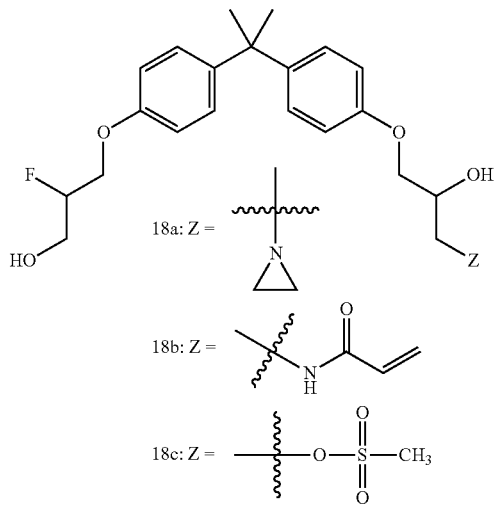
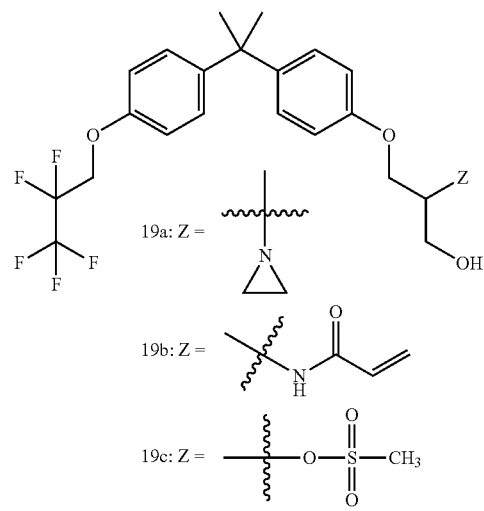
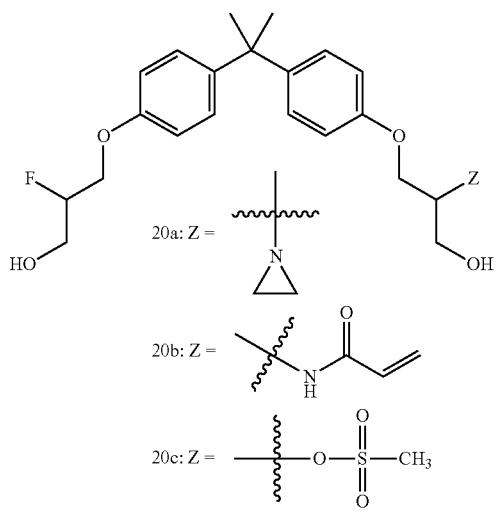

TABLE 2-continued
Representative Compounds
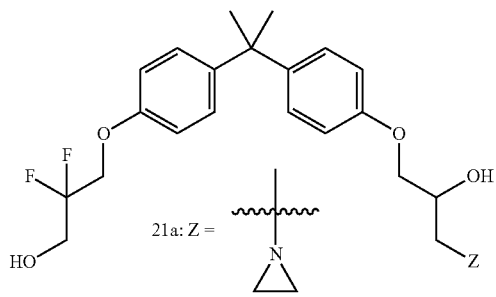
21a: Z = 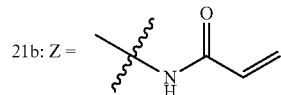
21b: Z = 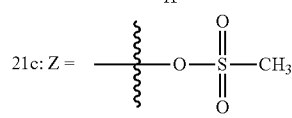
21c: Z =
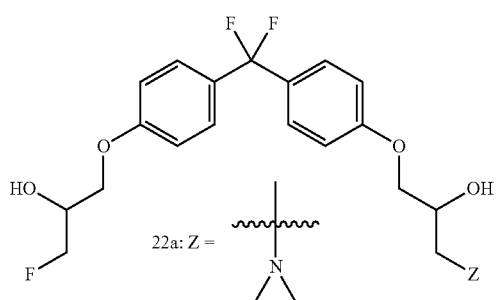
22a: Z = 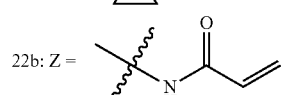
22b: Z = 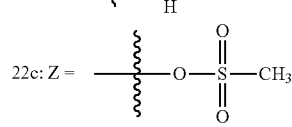
22c: Z =
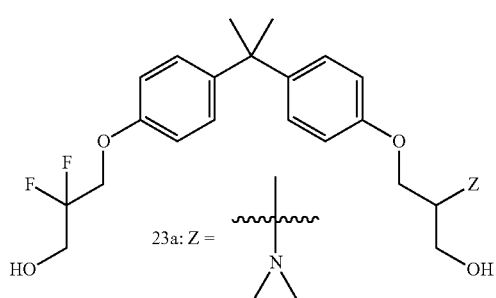
23a: Z = 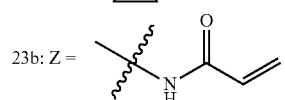
23b: Z = 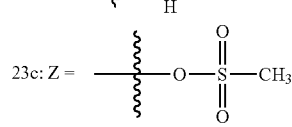
23c: Z =

TABLE 2-continued
Representative Compounds
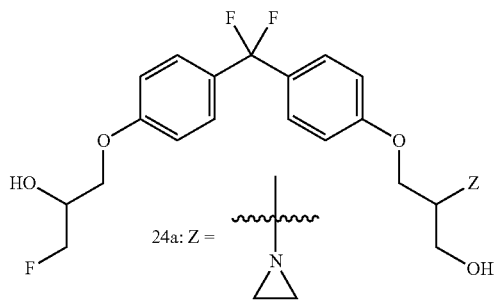
24a: Z = 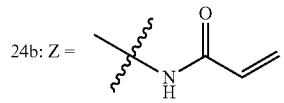
24b: Z = 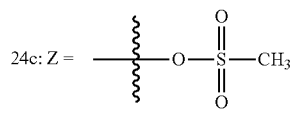
24c: Z = 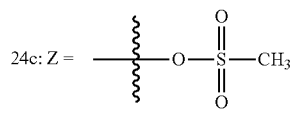
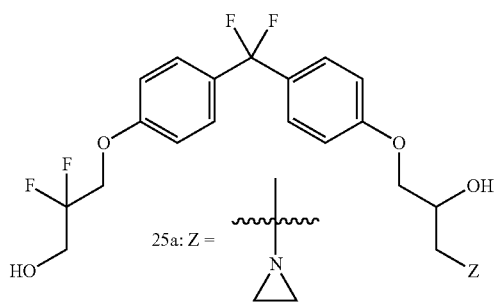
25a: Z = 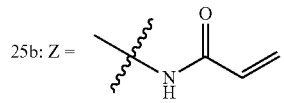
25b: Z = 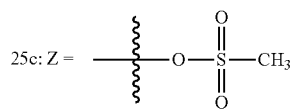
25c: Z = 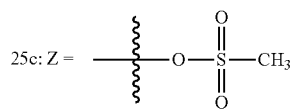
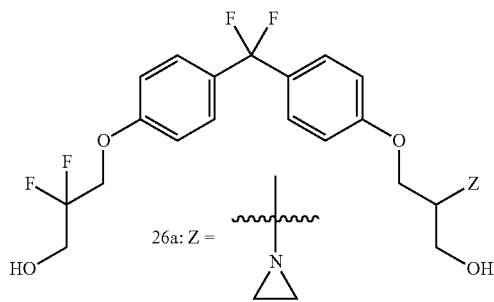
26a: Z = 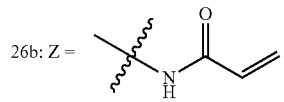
26b: Z = 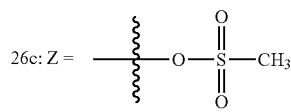
26c: Z = 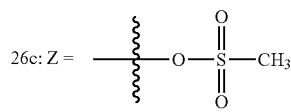

TABLE 2-continued
Representative Compounds
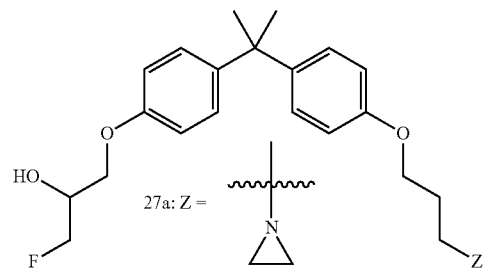
27a: Z = 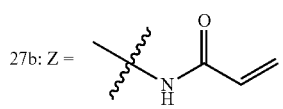
27b: Z = 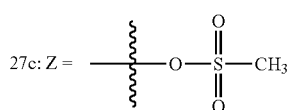
27c: Z = 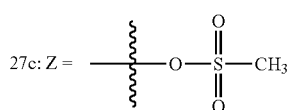
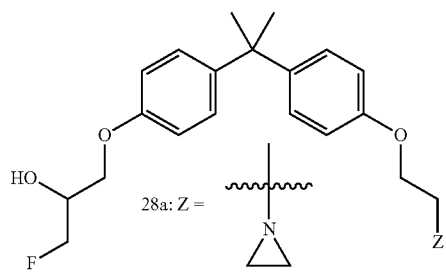
28a: Z = 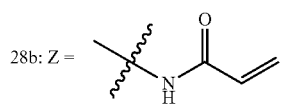
28b: Z = 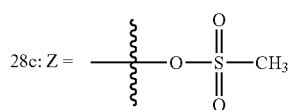
28c: Z = 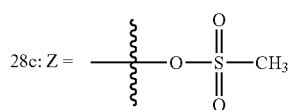
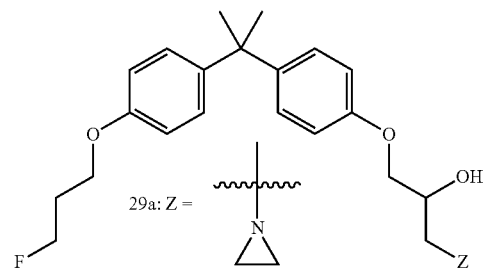
29a: Z = 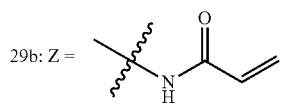
29b: Z = 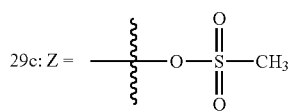
29c: Z = 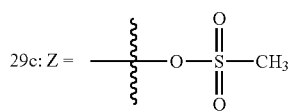

TABLE 2-continued
Representative Compounds
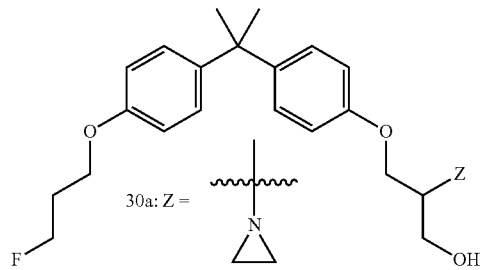
30a: Z = 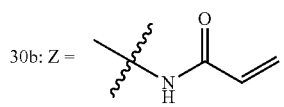
30b: Z = 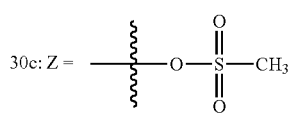
30c: Z = 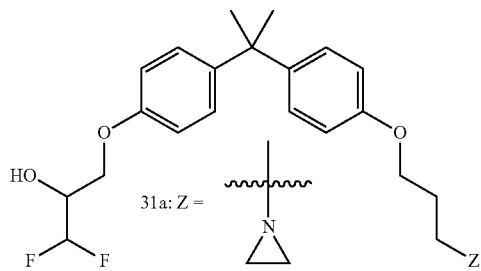
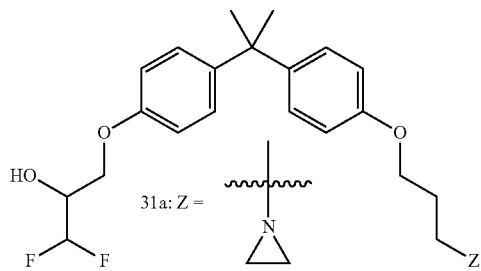
31a: Z = 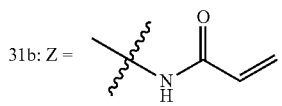
31b: Z = 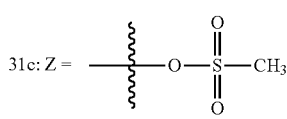
31c: Z =
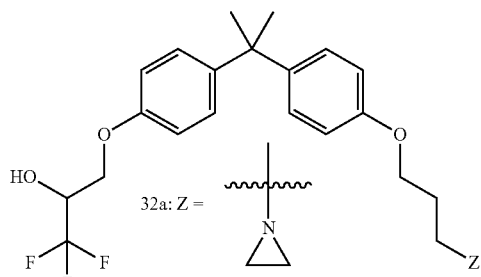
32a: Z = 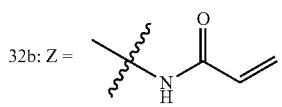
32b: Z = 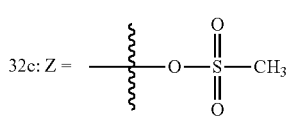
32c: Z =

TABLE 2-continued
Representative Compounds
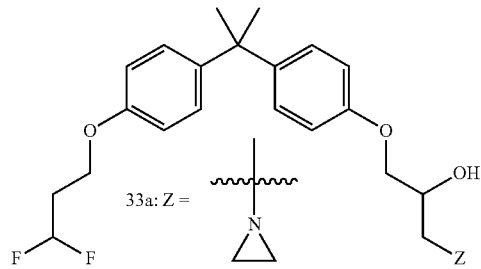
33a: Z =
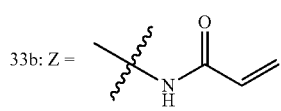
33b: Z =
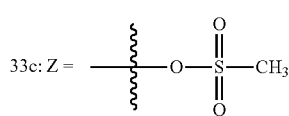
33c: Z =
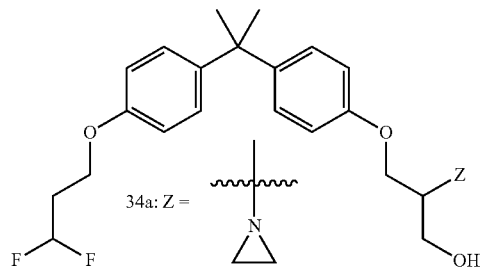
34a: Z =
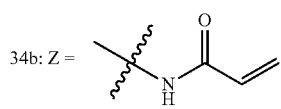
34b: Z =
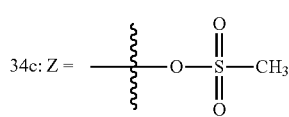
34c: Z =
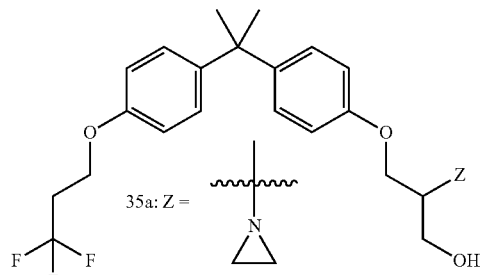
35a: Z =
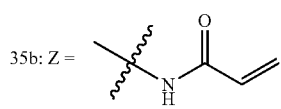
35b: Z =
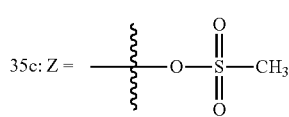
35c: Z =

TABLE 2-continued
Representative Compounds
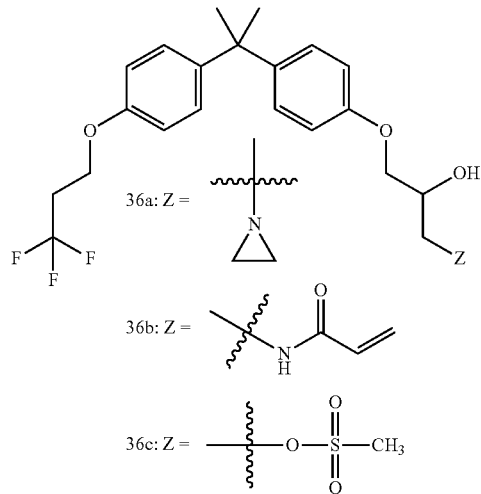
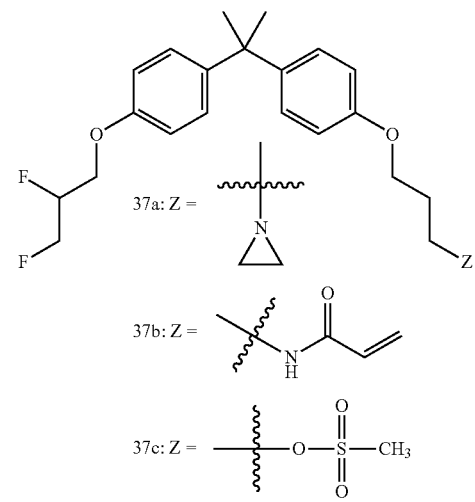
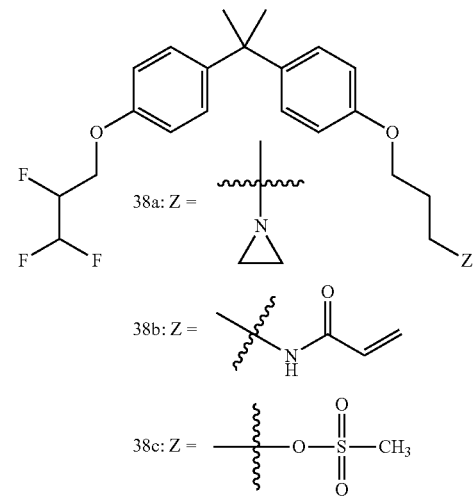

TABLE 2-continued
Representative Compounds
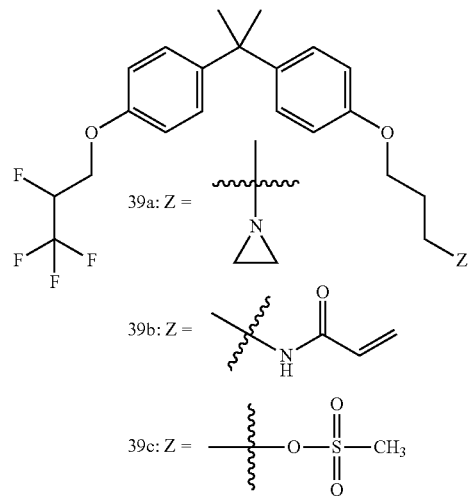
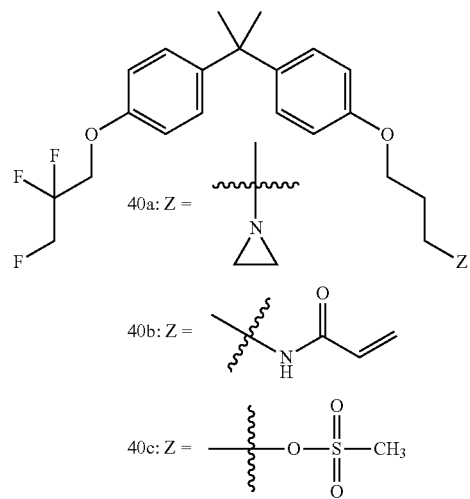
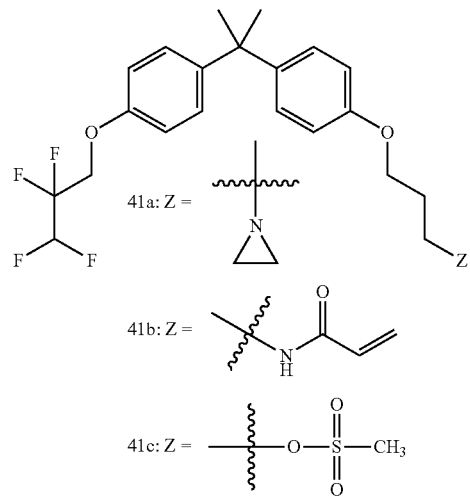

TABLE 2-continued
Representative Compounds
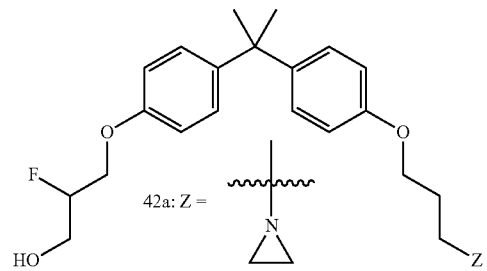
42a: Z = 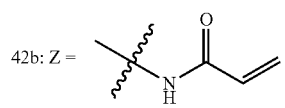
42b: Z = 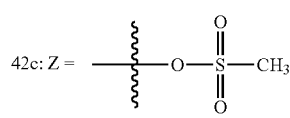
42c: Z =
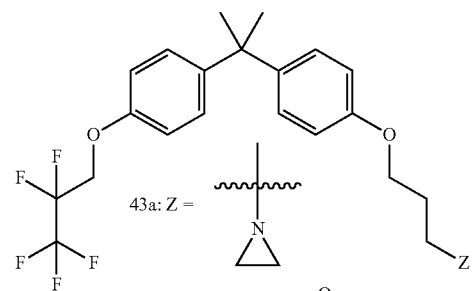
43a: Z = 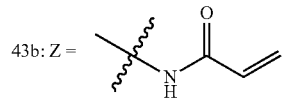
43b: Z = 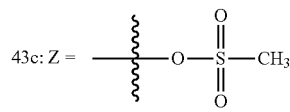
43c: Z =
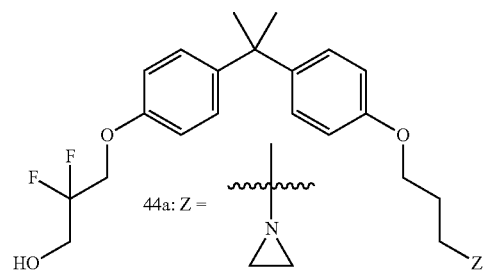
44a: Z = 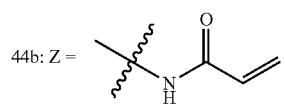
44b: Z = 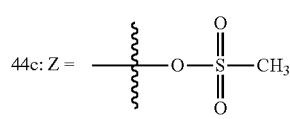
44c: Z =

TABLE 2-continued
Representative Compounds
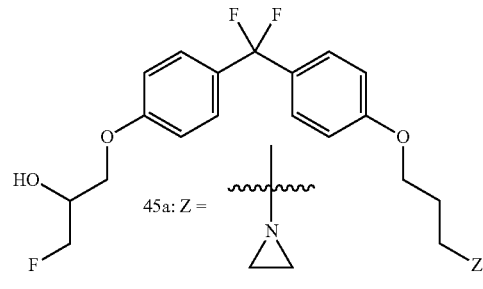
45a: Z = 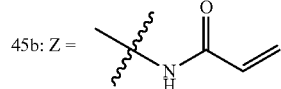
45b: Z = 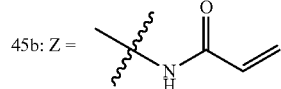
45c: Z = 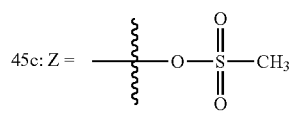
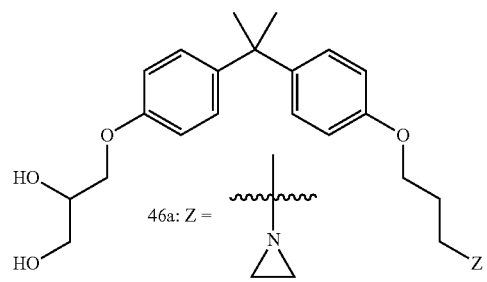
46a: Z = 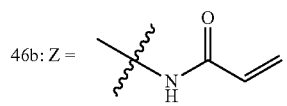
46b: Z = 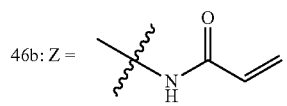
46c: Z = 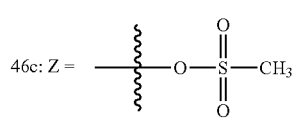
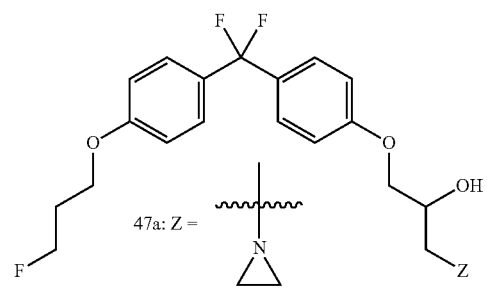
47a: Z = 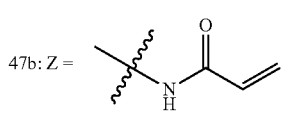
47b: Z = 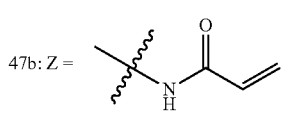
47c: Z = 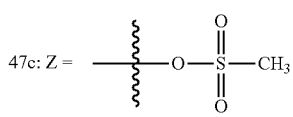

TABLE 2-continued
Representative Compounds
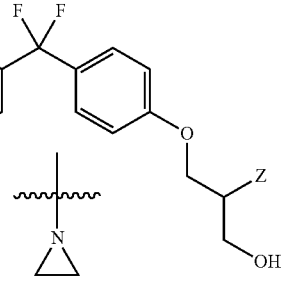

TABLE 2-continued
Representative Compounds
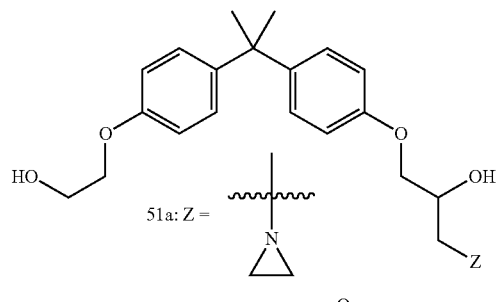
51a: Z =
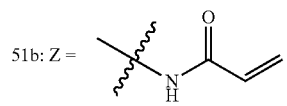
51b: Z =
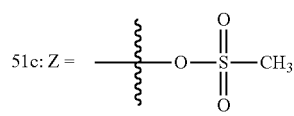
51c: Z =
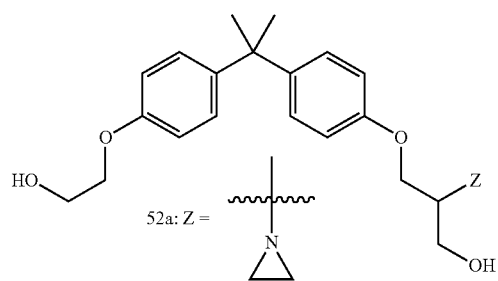
52a: Z =
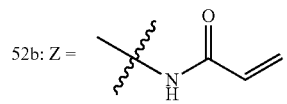
52b: Z =
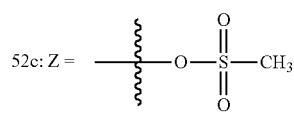
52c: Z =
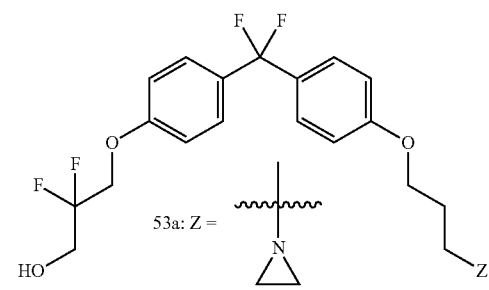
53a: Z =
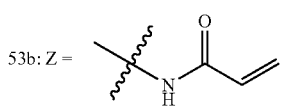
53b: Z =
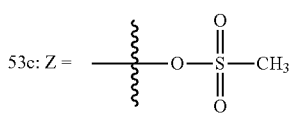
53c: Z =

TABLE 2-continued
Representative Compounds
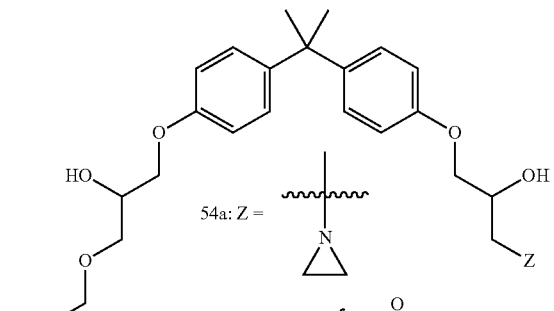
54a: Z = 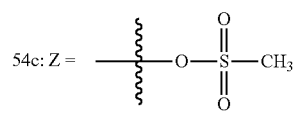
54b: Z = 
54c: Z = 
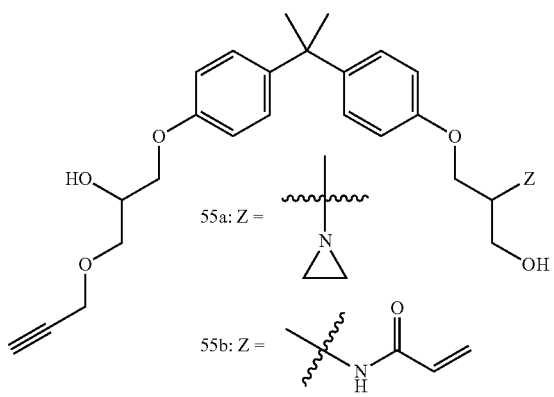
55a: Z = 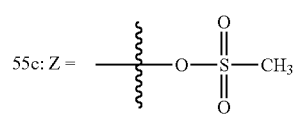
55b: Z = 
55c: Z = 
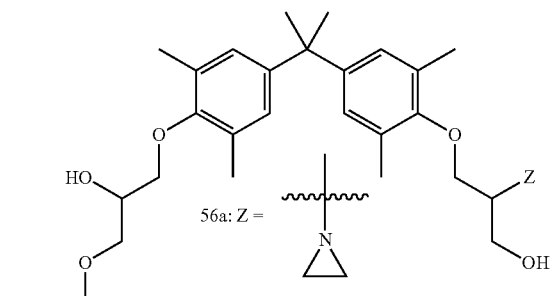
56a: Z = 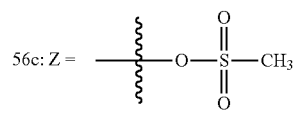
56b: Z = 
56c: Z =

TABLE 2-continued
Representative Compounds
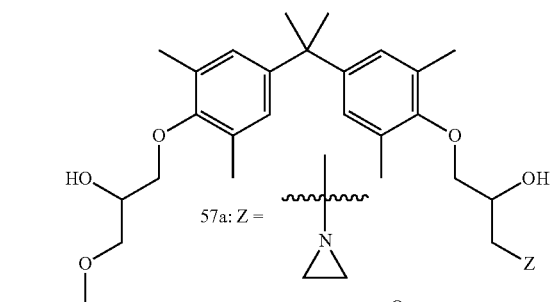
57a: Z =
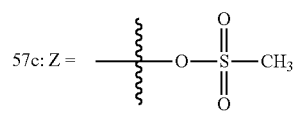
57b: Z =
57c: Z =
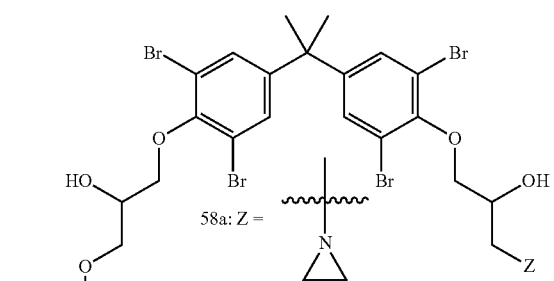
58a: Z =
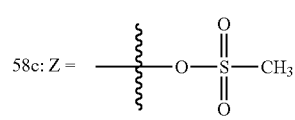
58b: Z =
58c: Z =
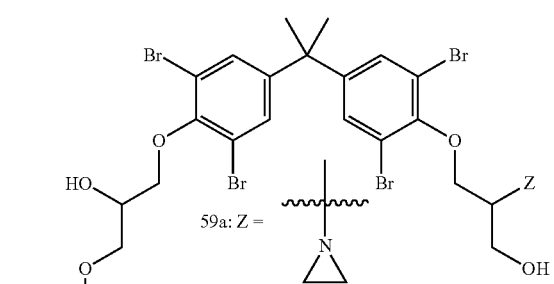
59a: Z =
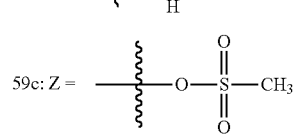
59b: Z =
59c: Z =

TABLE 2-continued
Representative Compounds
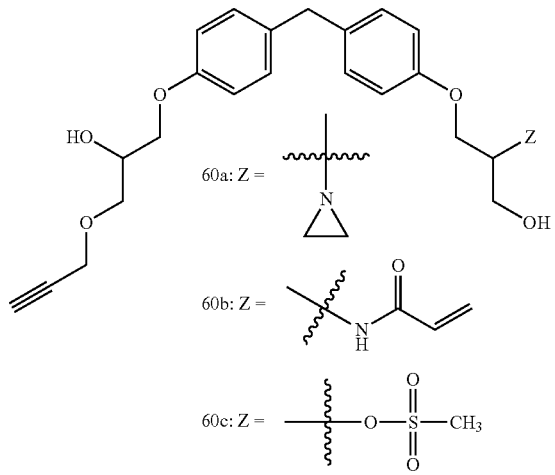
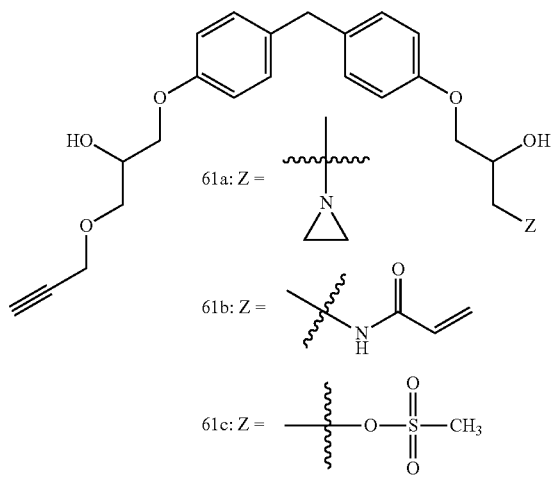
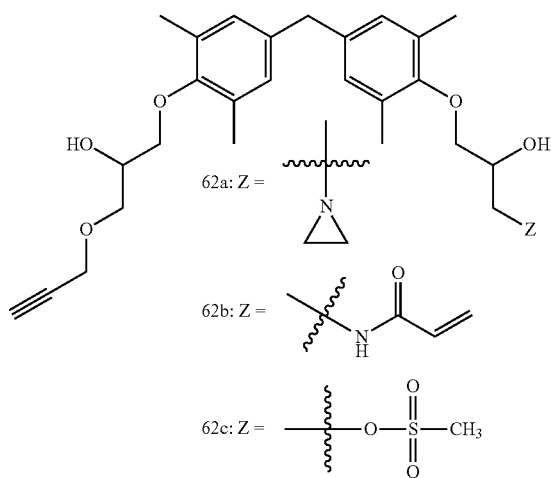

TABLE 2-continued
Representative Compounds
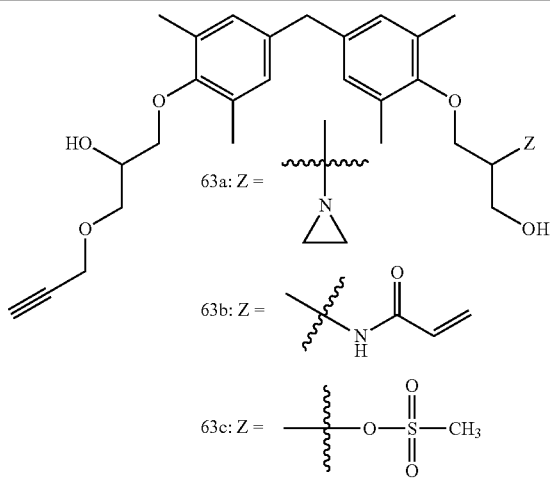
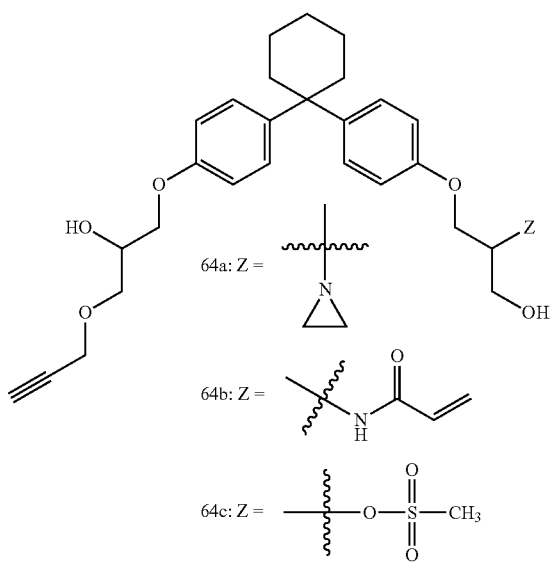
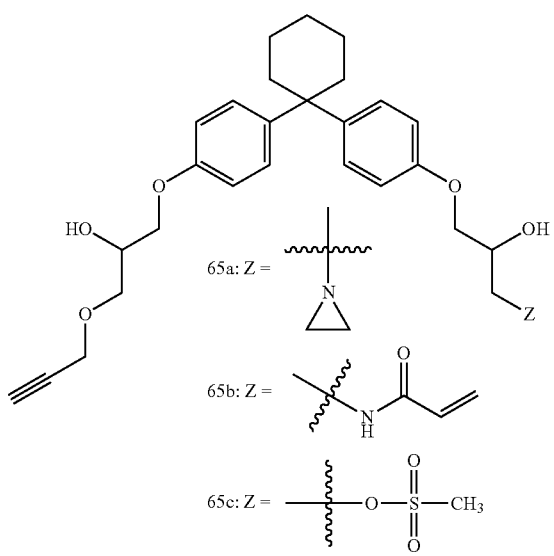

TABLE 2-continued
Representative Compounds
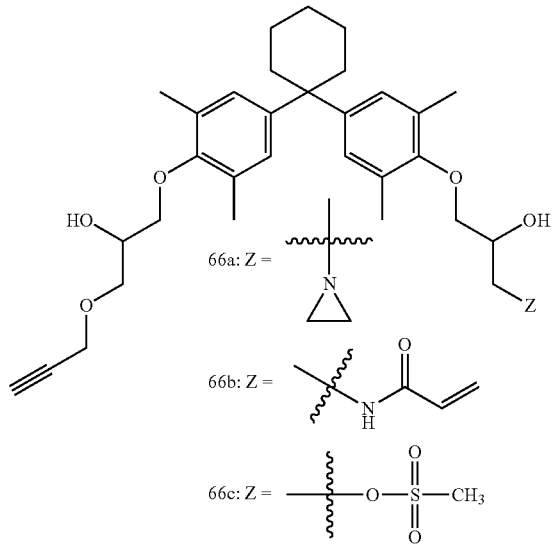
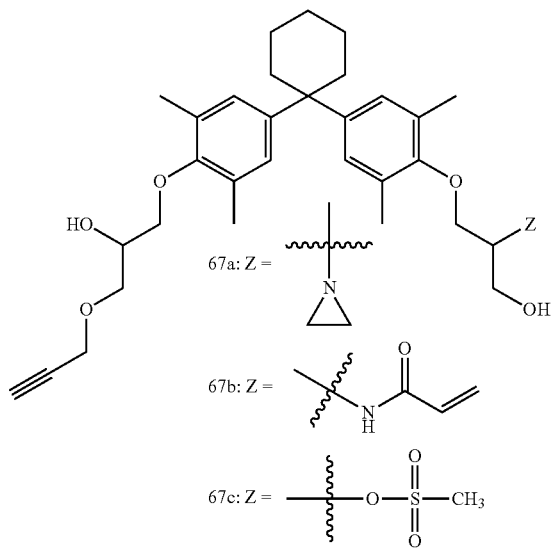

TABLE 2-continued
Representative Compounds
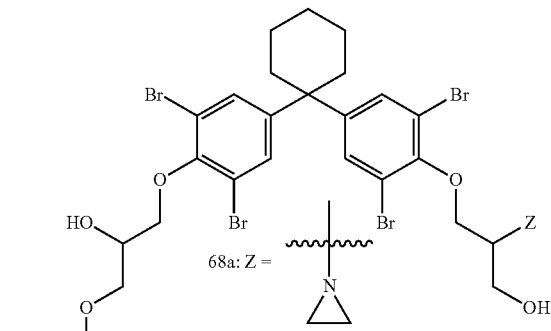
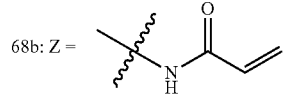
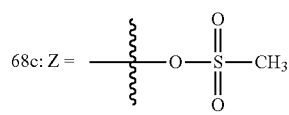
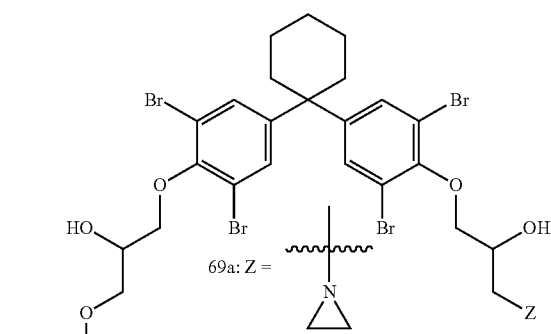
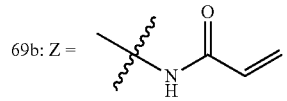
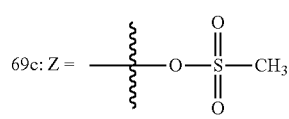
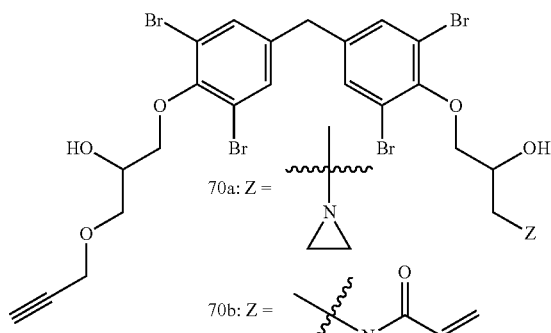
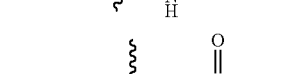
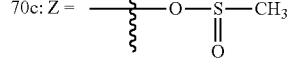

TABLE 2-continued
Representative Compounds
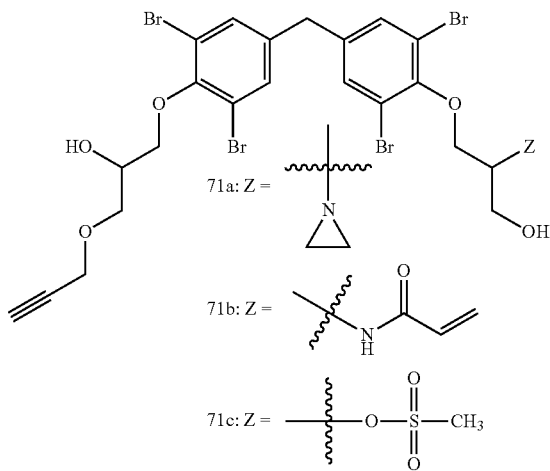
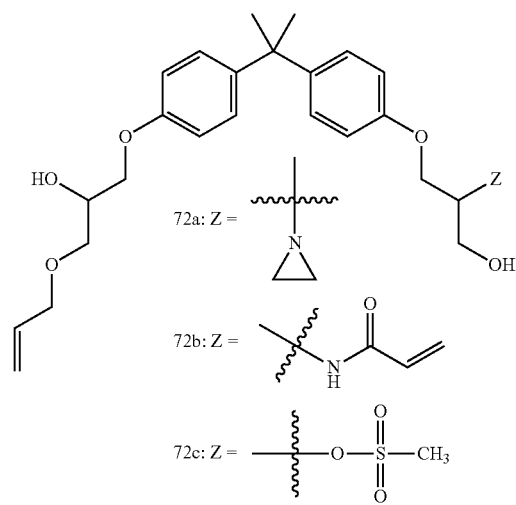
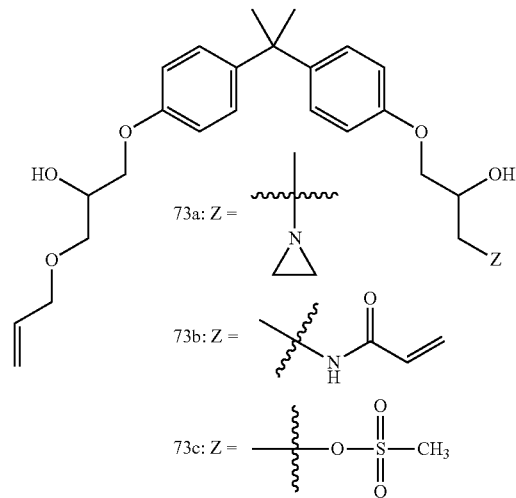

TABLE 2-continued
Representative Compounds
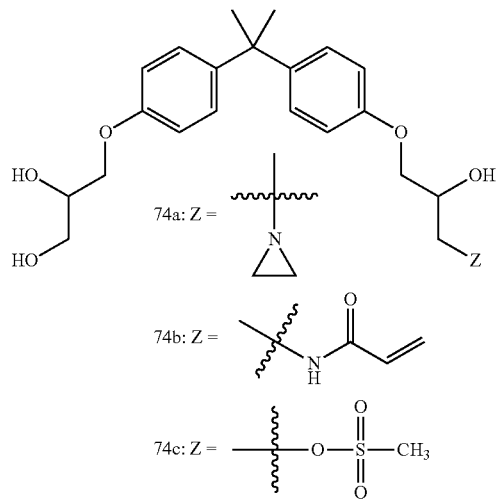
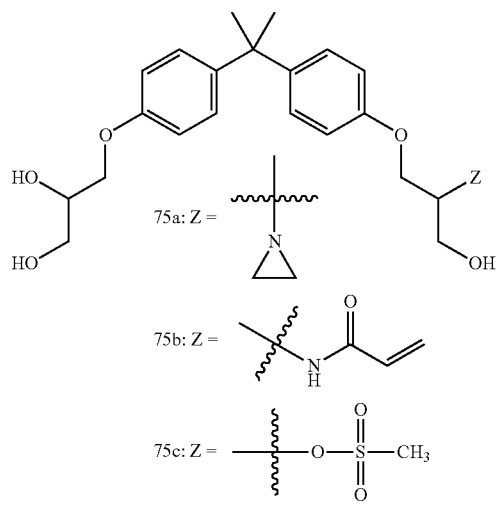
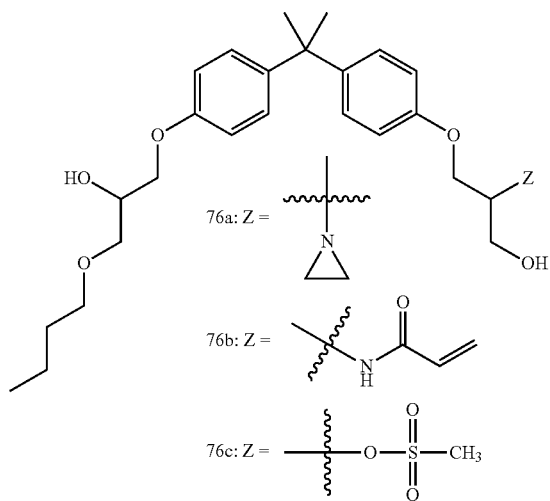

TABLE 2-continued
Representative Compounds
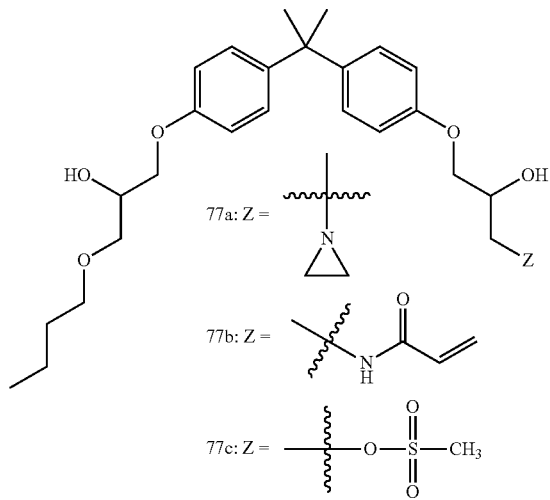
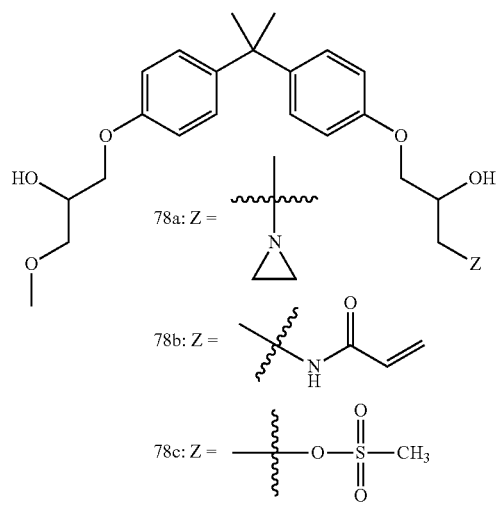
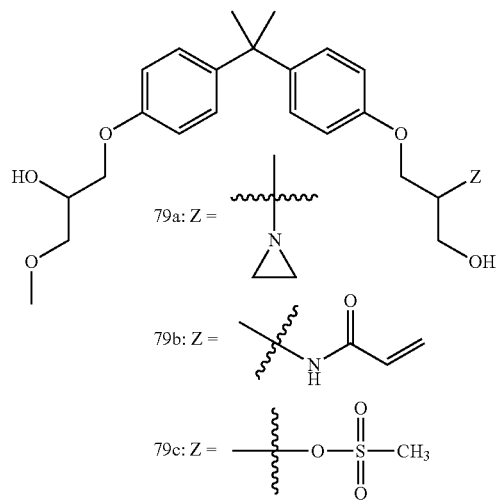

TABLE 2-continued
Representative Compounds
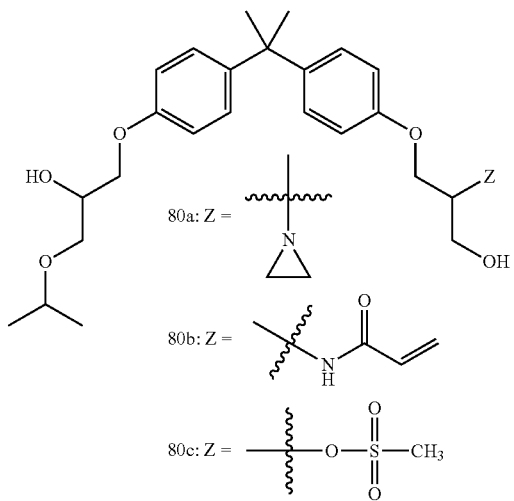
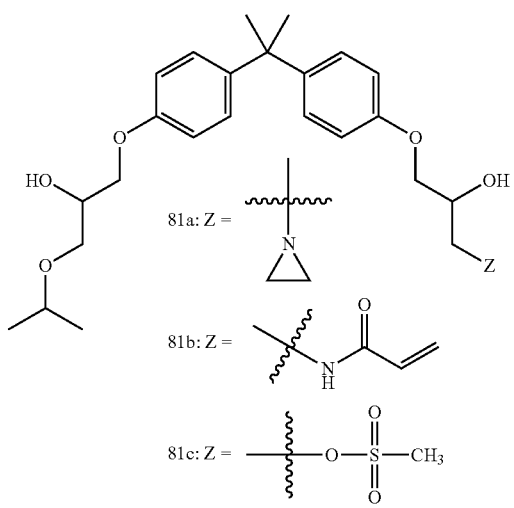
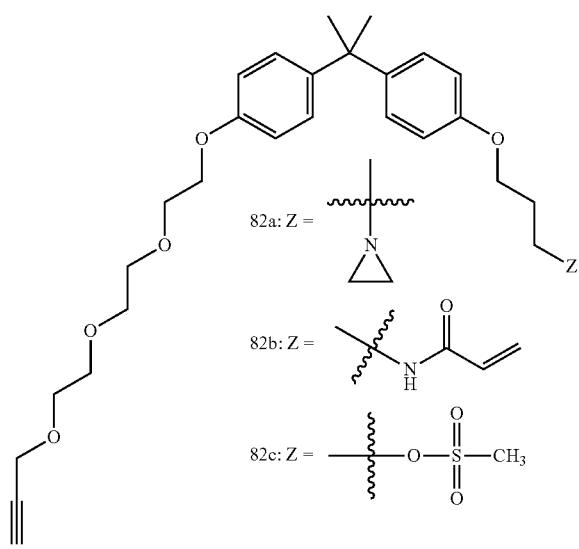

TABLE 2-continued
Representative Compounds
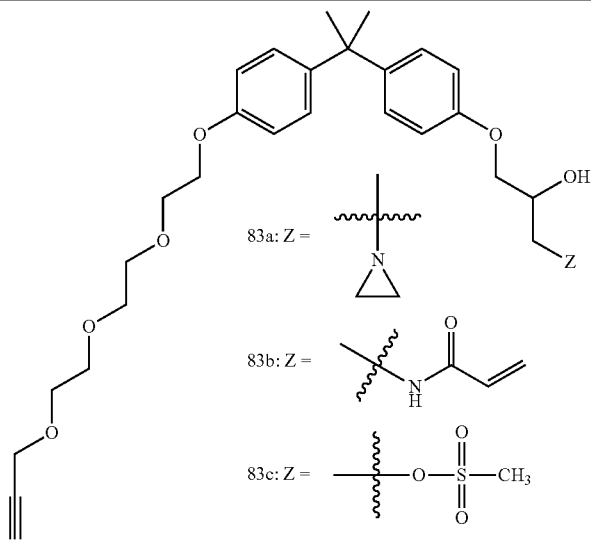
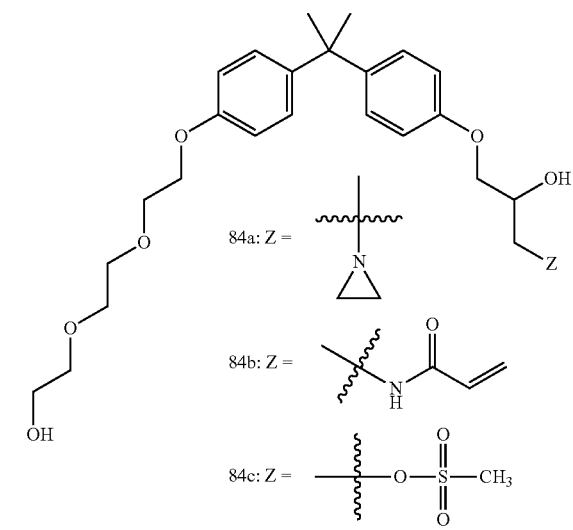
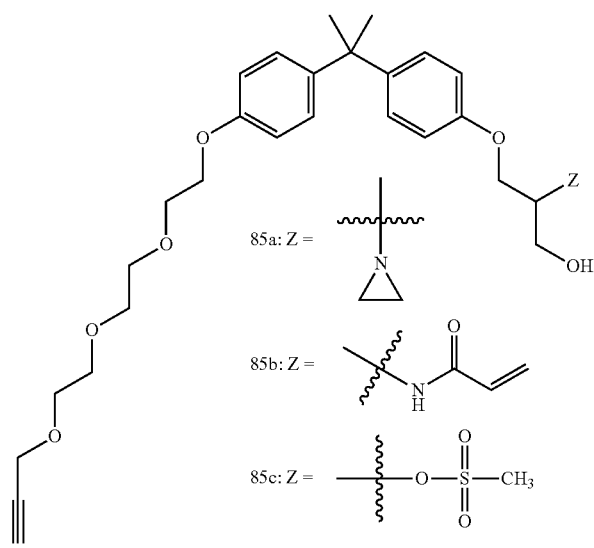

TABLE 2-continued
Representative Compounds
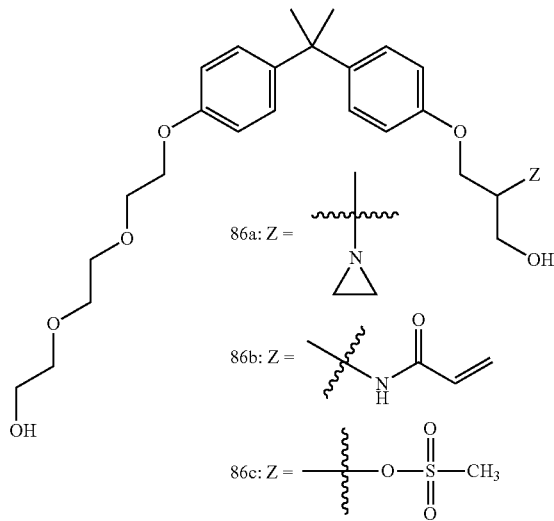
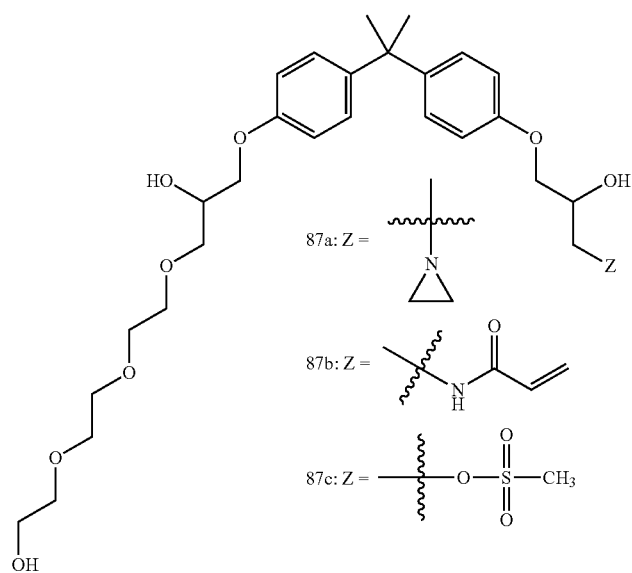

TABLE 2-continued
Representative Compounds
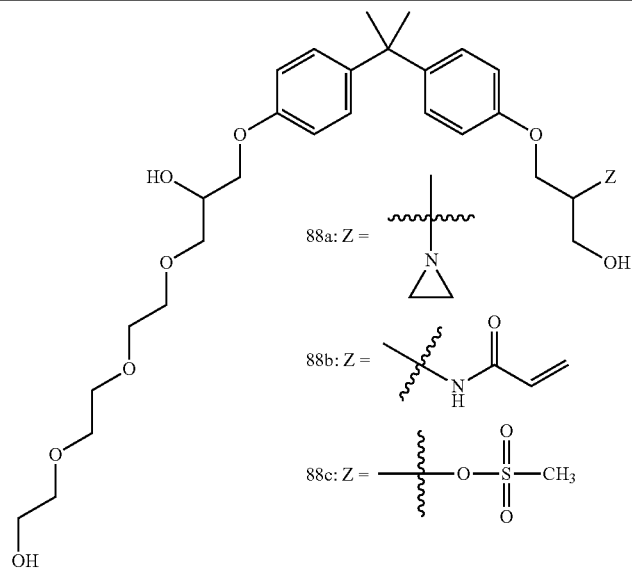
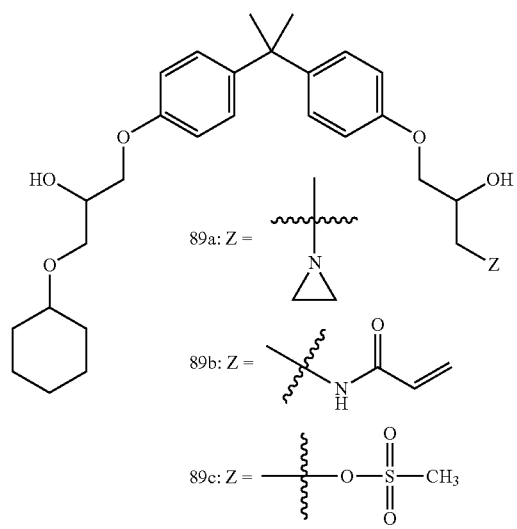
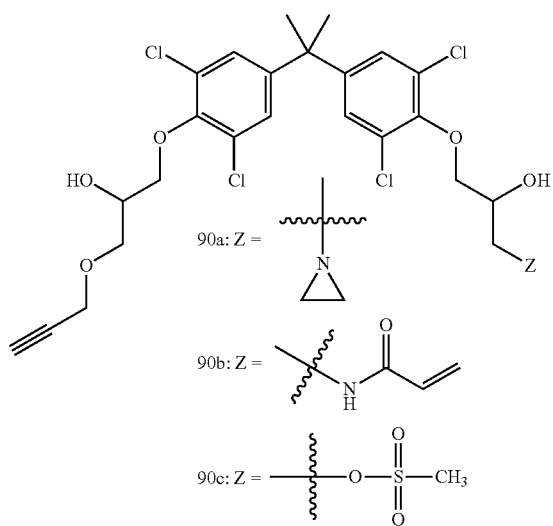

TABLE 2-continued
Representative Compounds
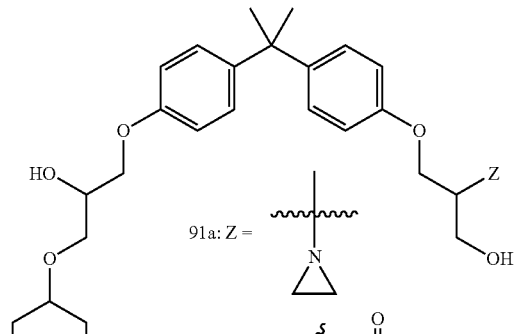
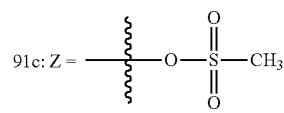
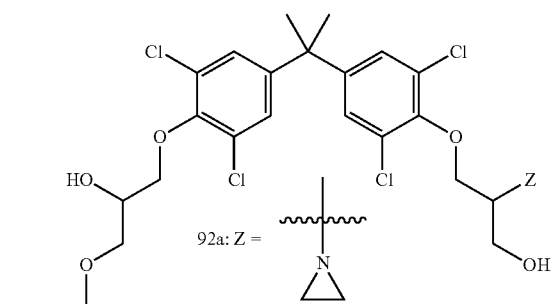
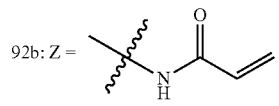
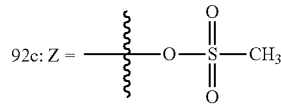
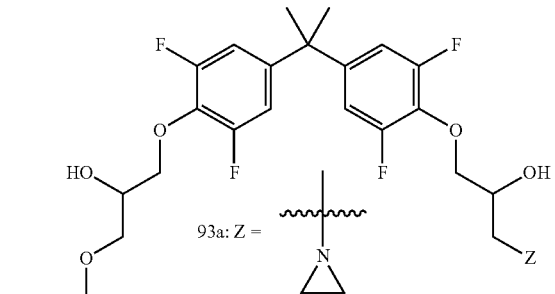
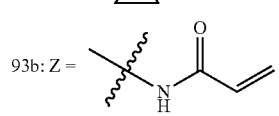
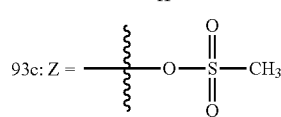

TABLE 2-continued
Representative Compounds
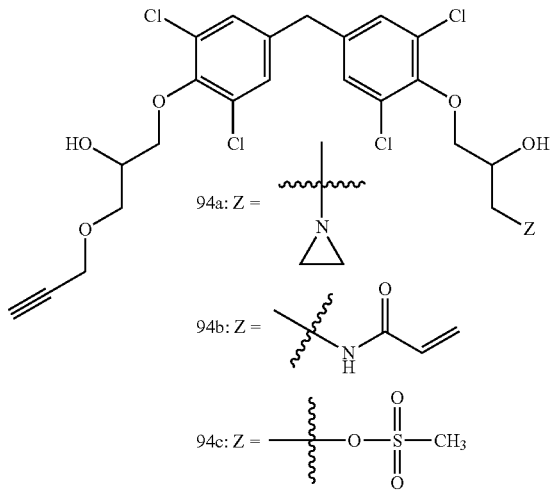
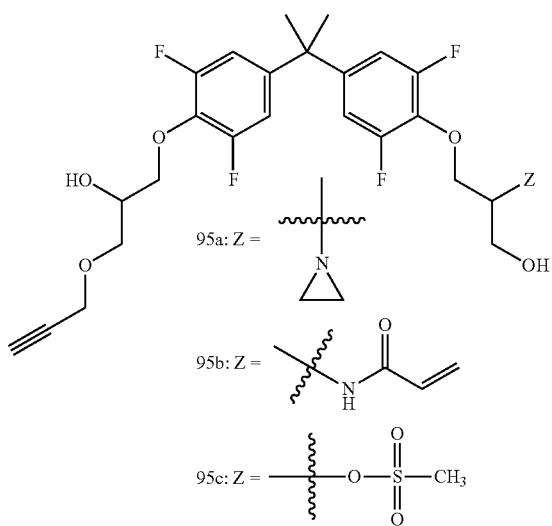
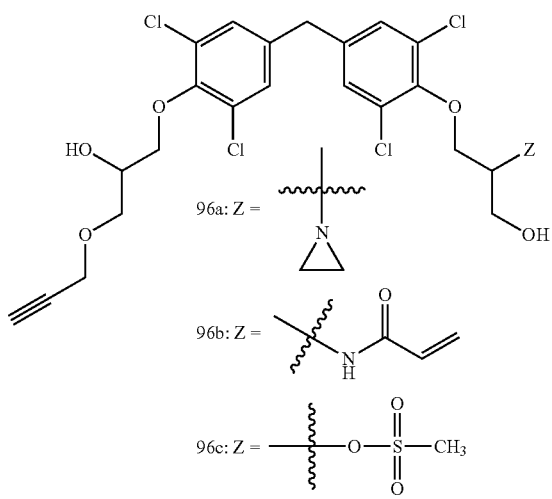

TABLE 2-continued
Representative Compounds
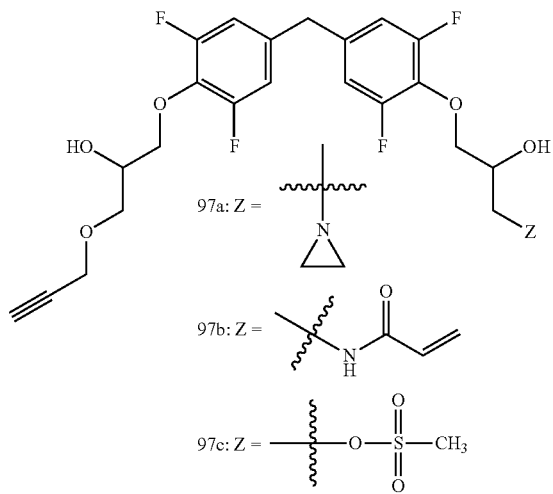
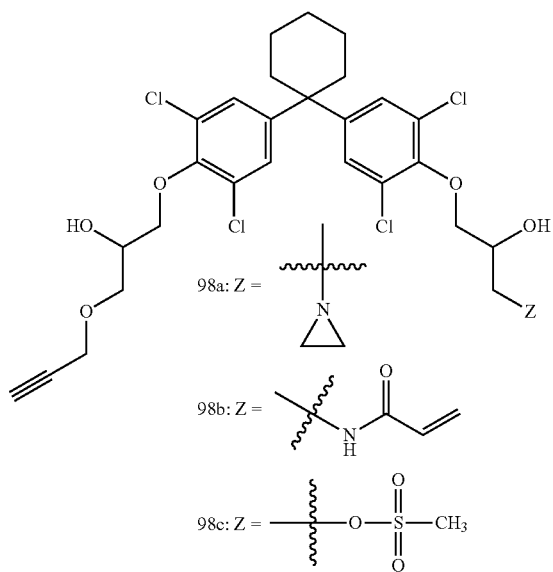
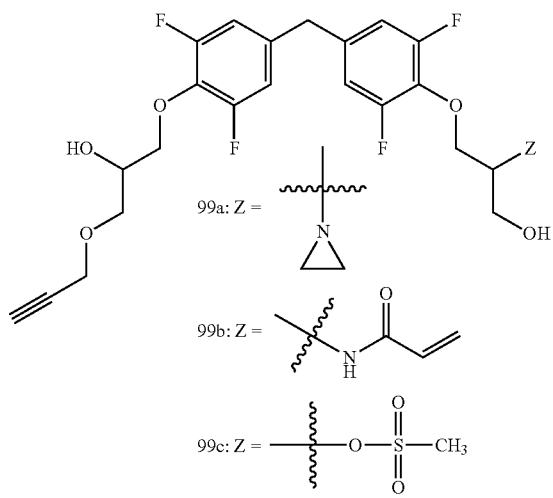

TABLE 2-continued
Representative Compounds
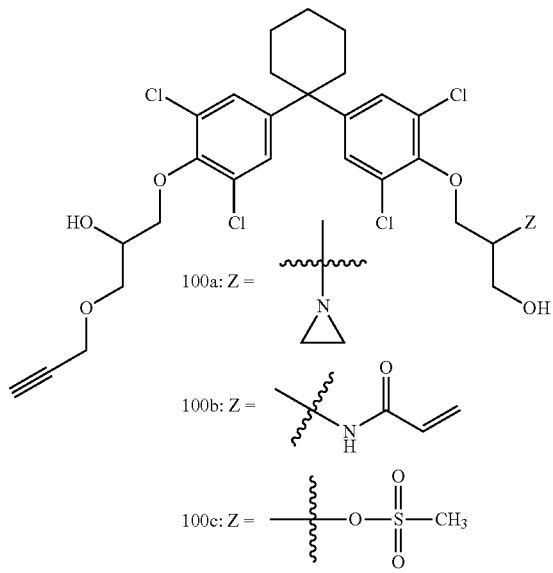
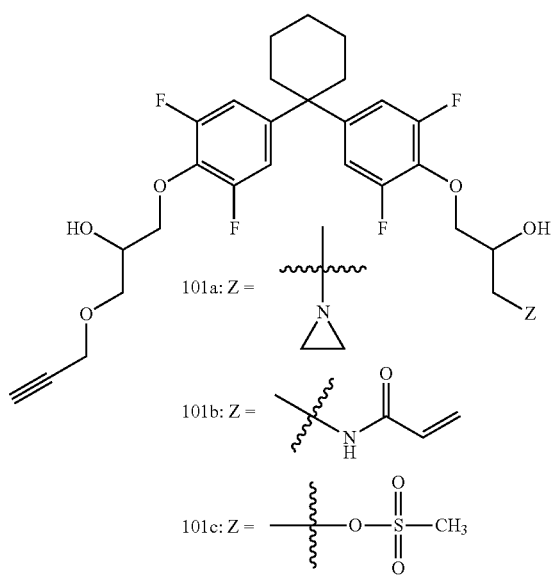

TABLE 2-continued
Representative Compounds
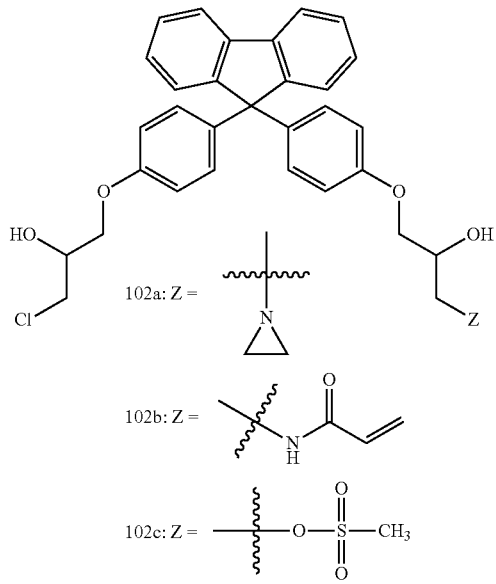
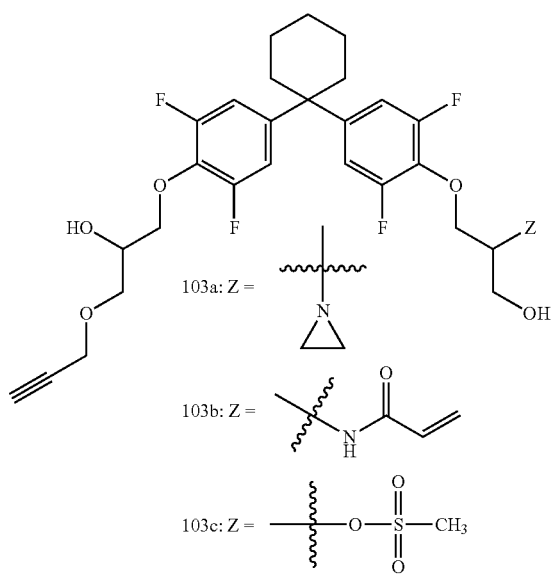

TABLE 2-continued
Representative Compounds
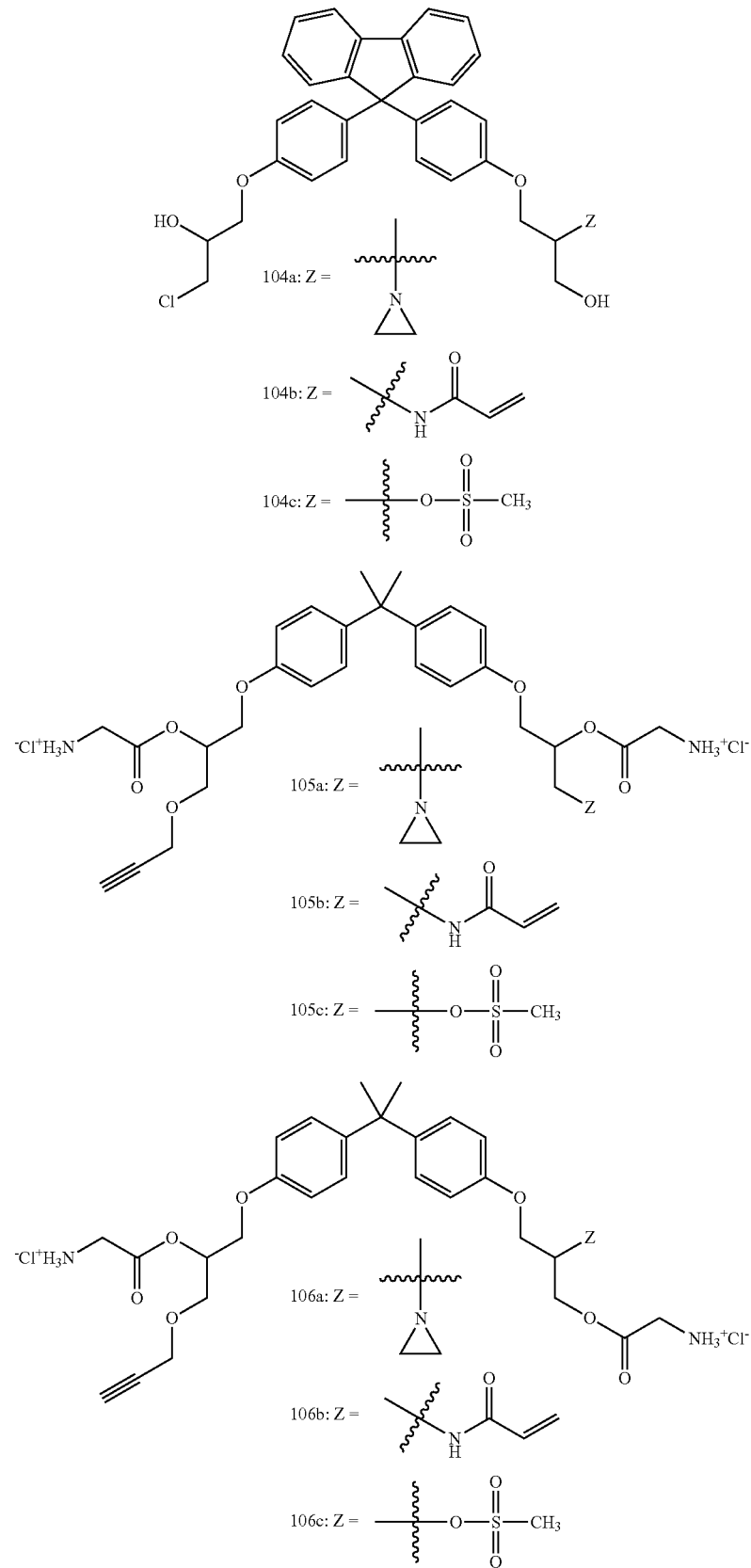

TABLE 2-continued
Representative Compounds
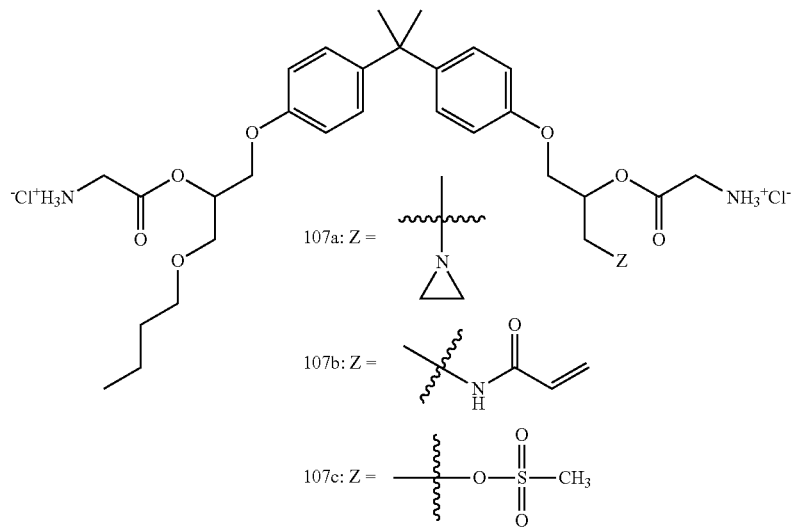
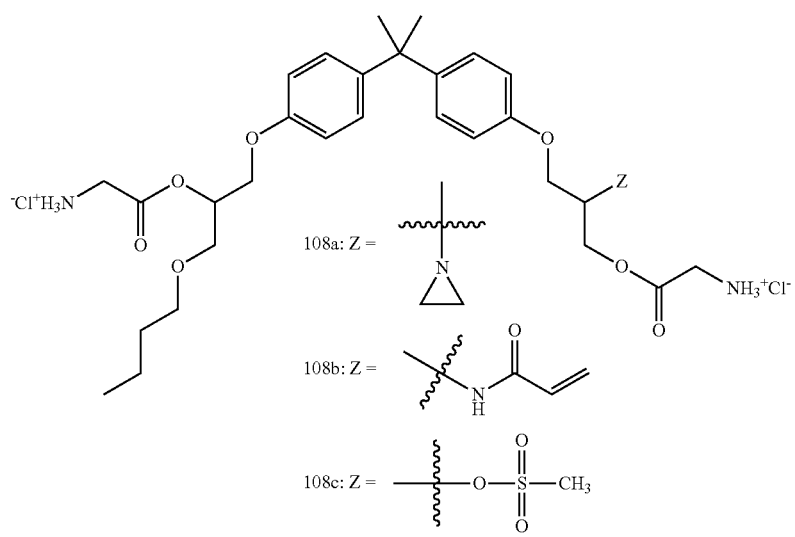

TABLE 2-continued
Representative Compounds
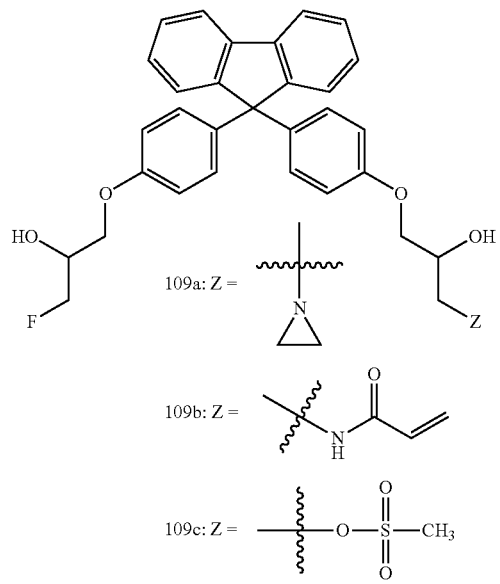
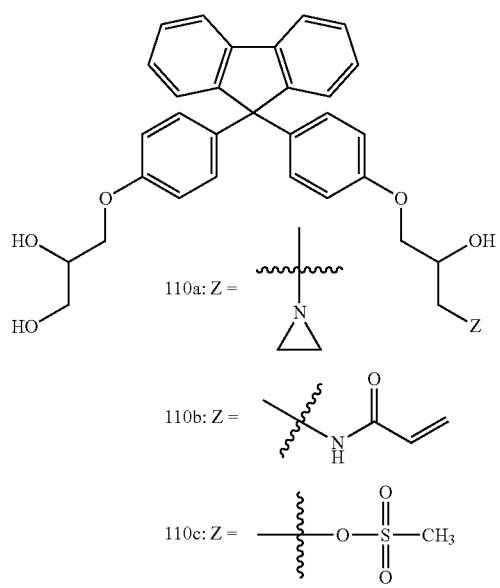

TABLE 2-continued
Representative Compounds
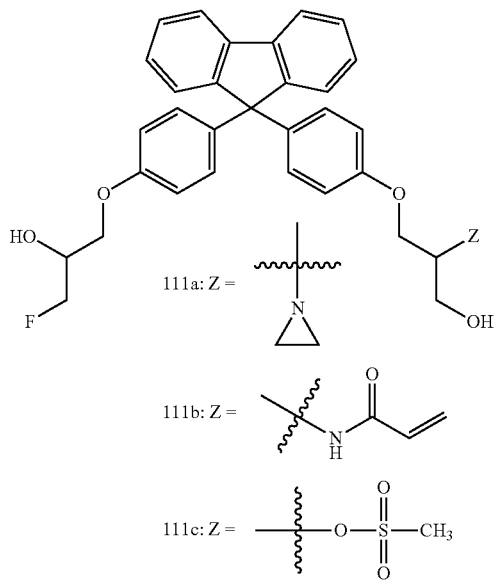
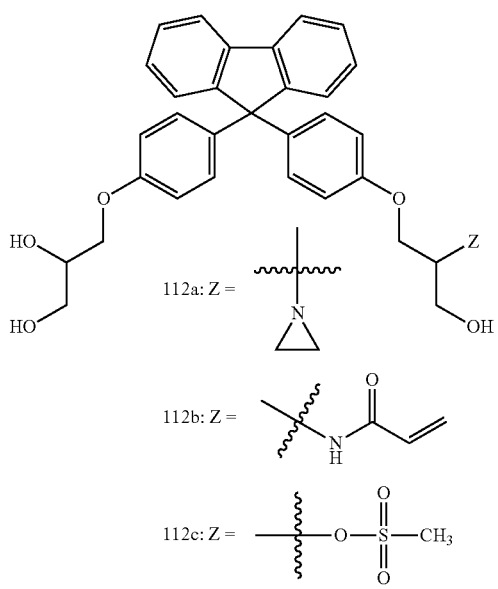

TABLE 2-continued
Representative Compounds
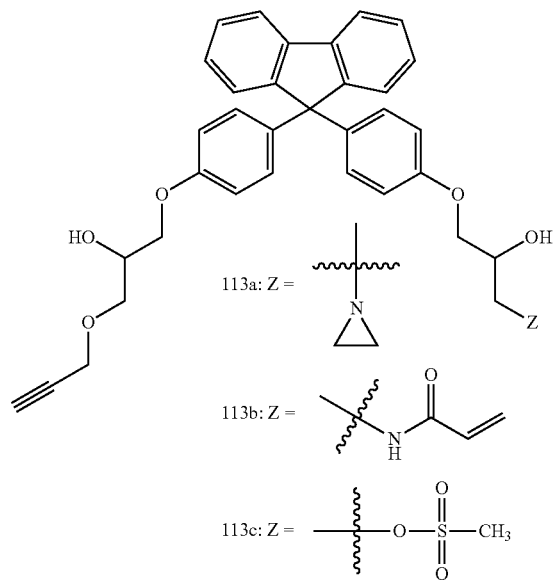
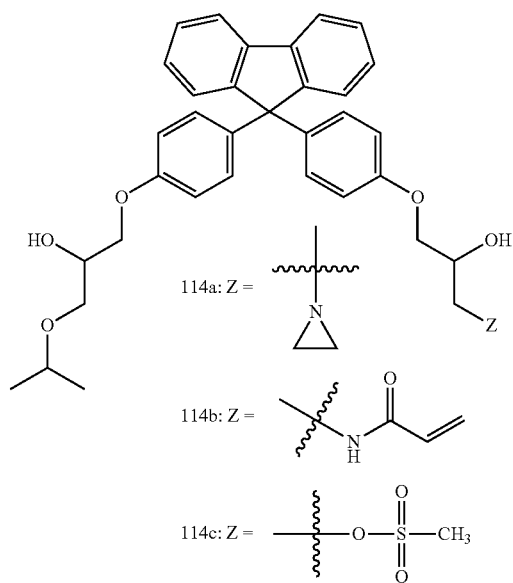

TABLE 2-continued
Representative Compounds
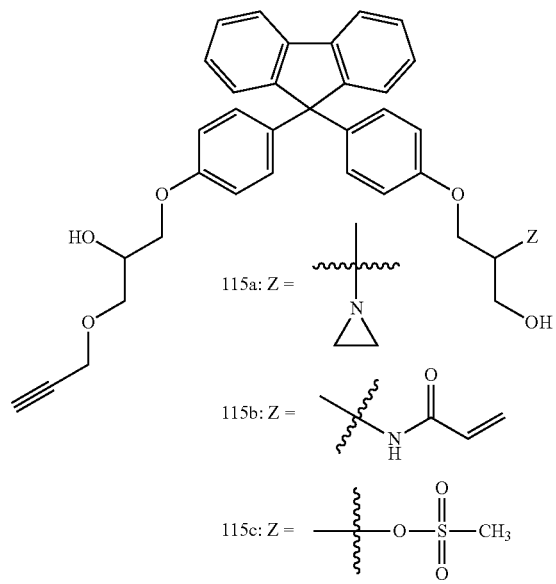
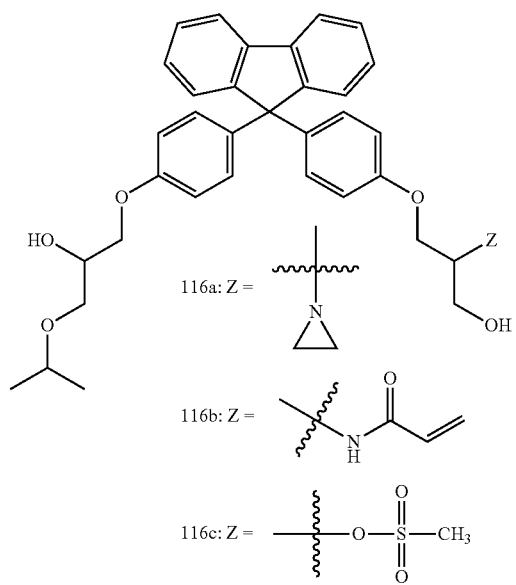

TABLE 2-continued
Representative Compounds
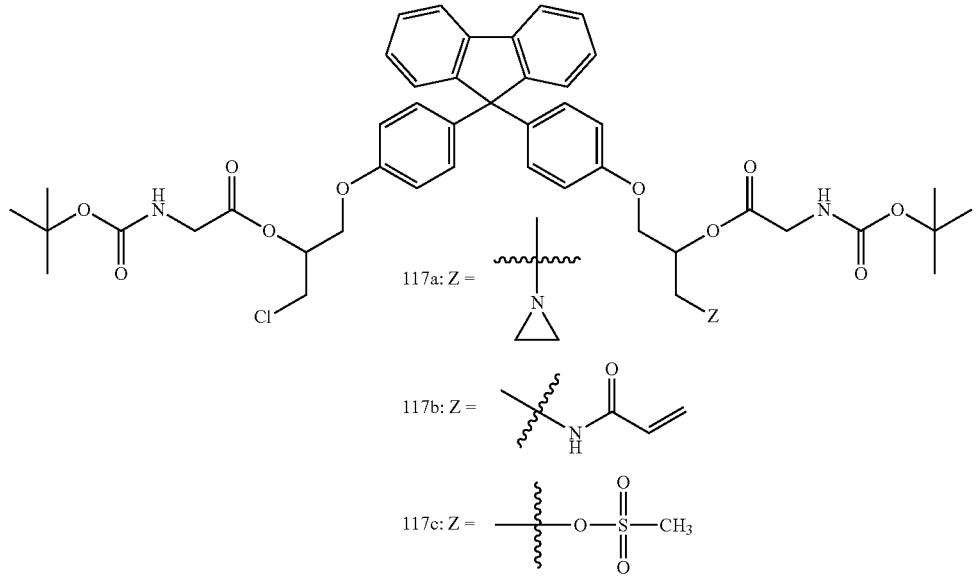
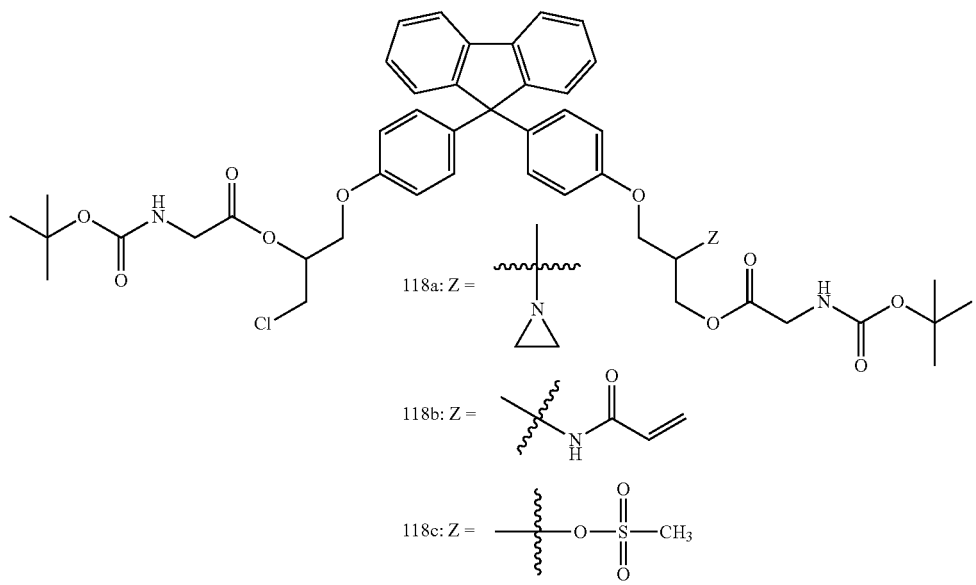

TABLE 2-continued
Representative Compounds
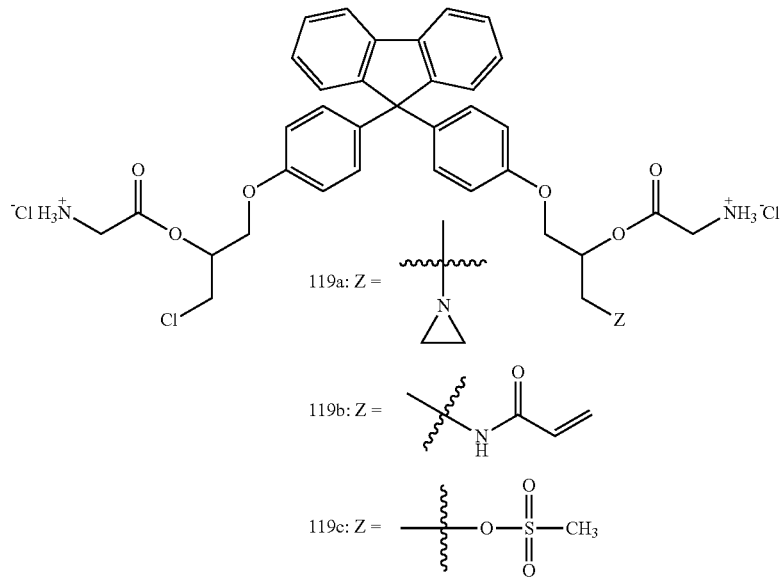

TABLE 2-continued
Representative Compounds
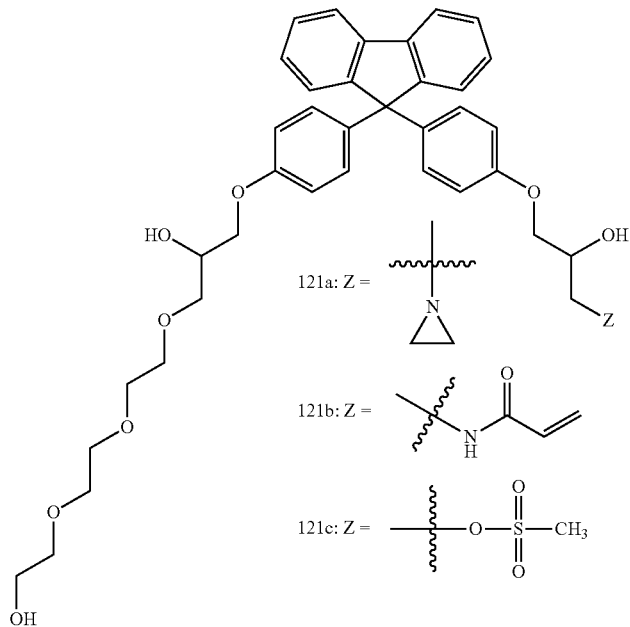
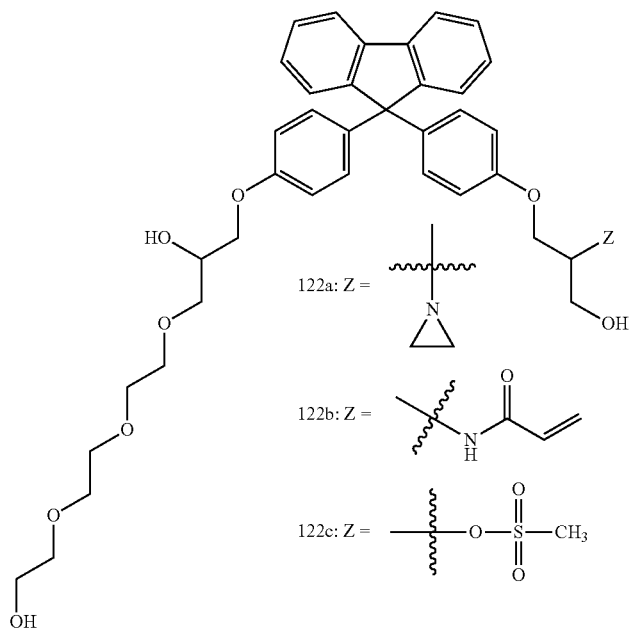

TABLE 2-continued
Representative Compounds
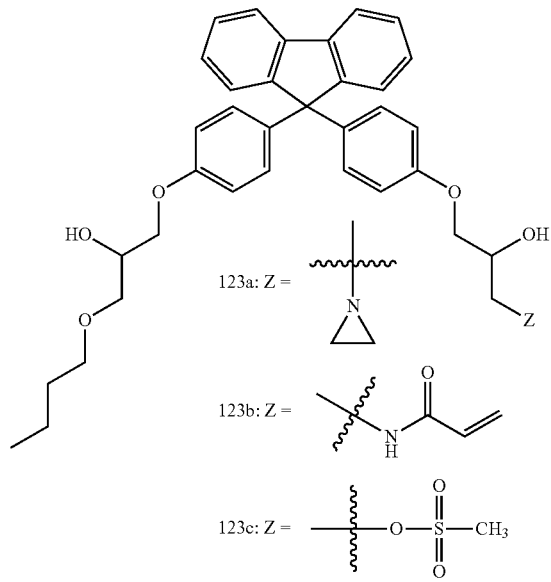
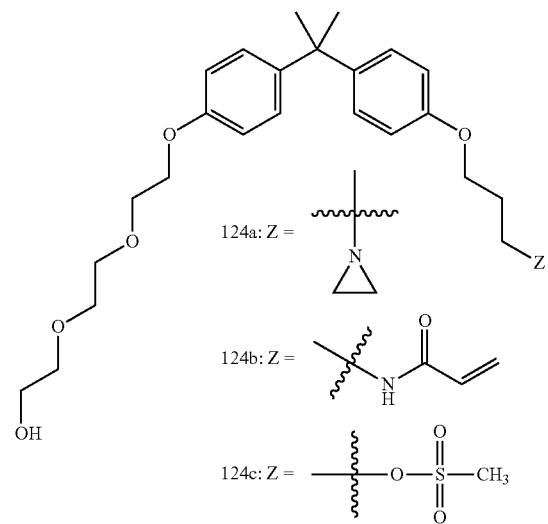

TABLE 2-continued
Representative Compounds
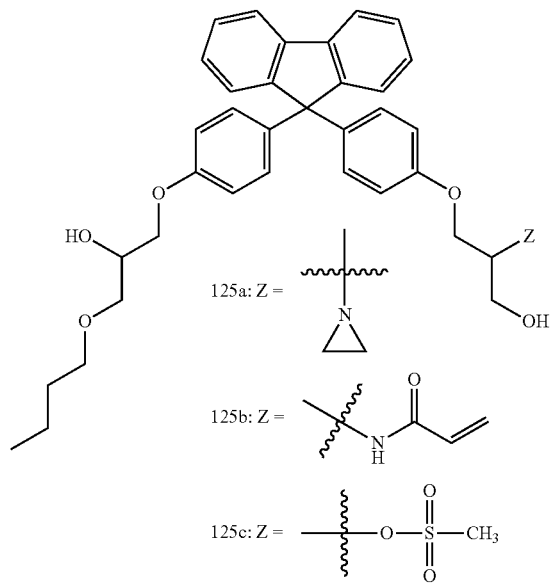
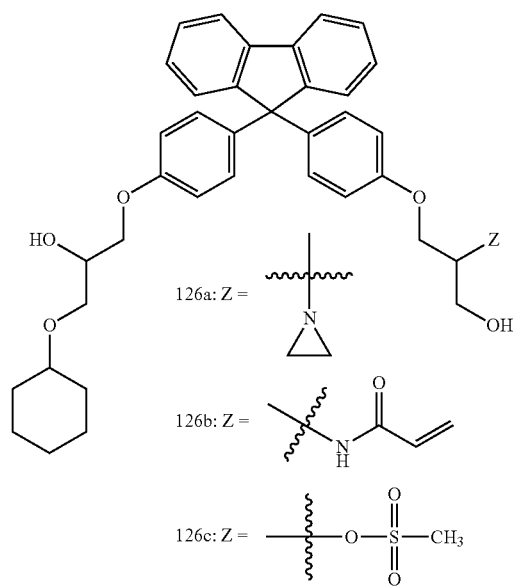

TABLE 2-continued
Representative Compounds
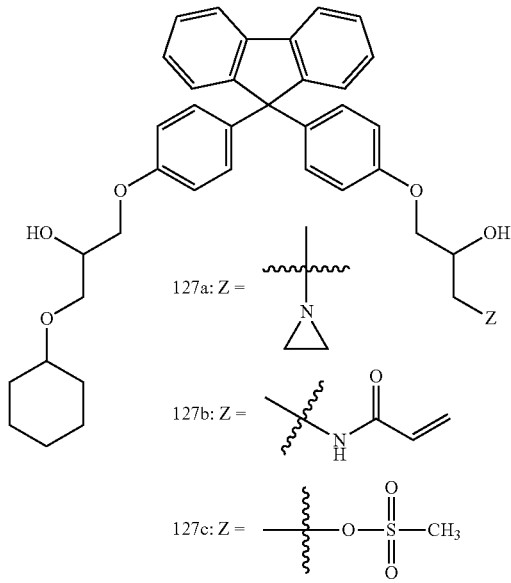
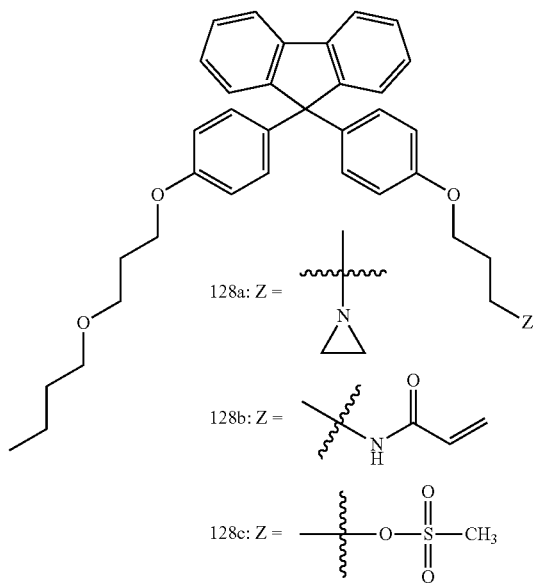

TABLE 2-continued
Representative Compounds
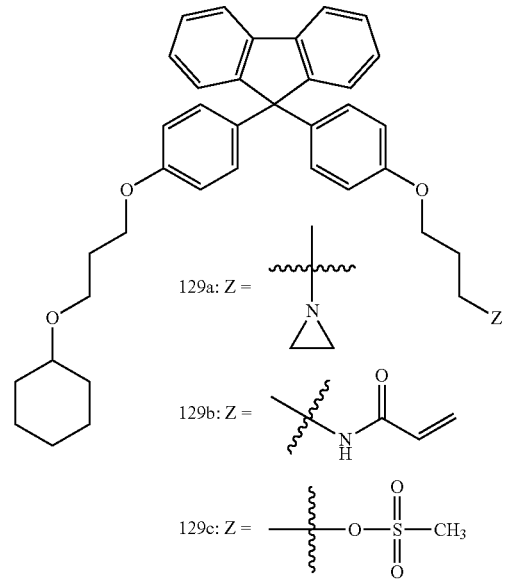
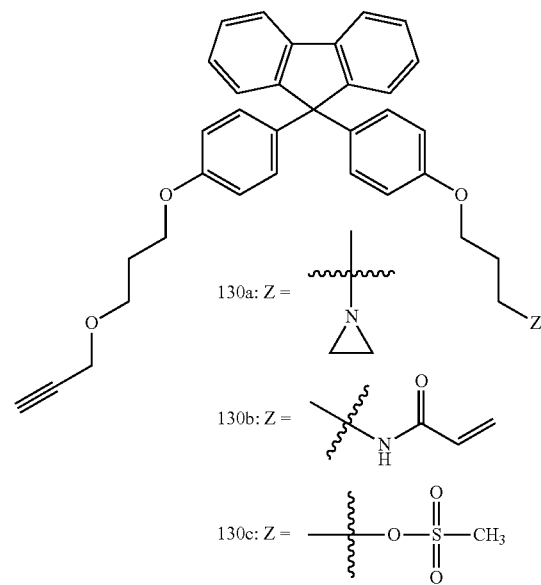

TABLE 2-continued
Representative Compounds
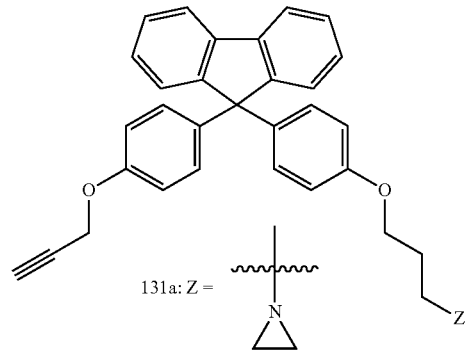
131a: Z = 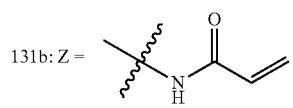
131b: Z = 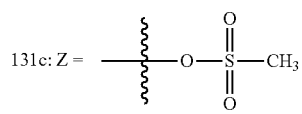
131c: Z = 
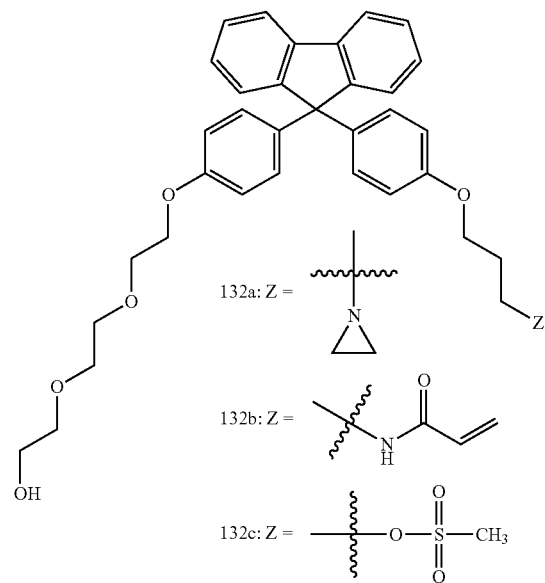
132a: Z = 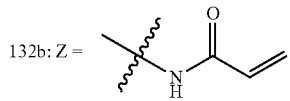
132b: Z = 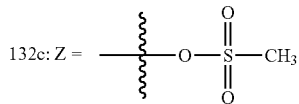
132c: Z =

TABLE 2-continued
Representative Compounds
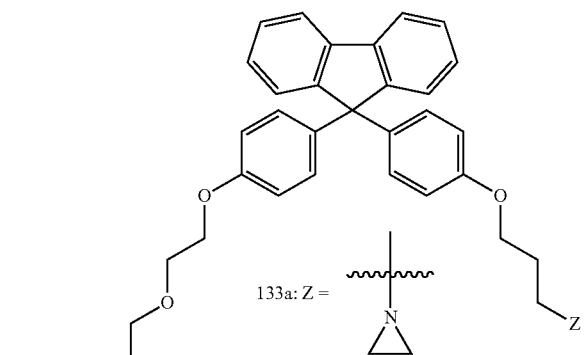
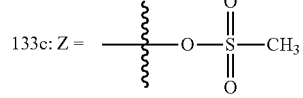
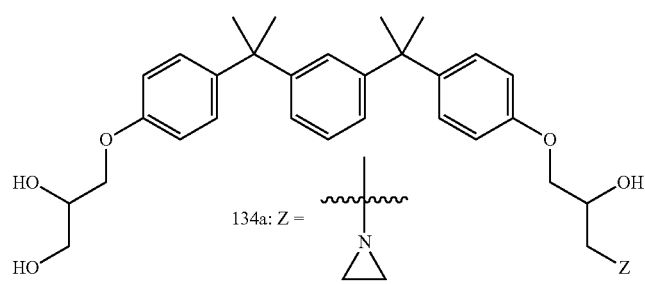
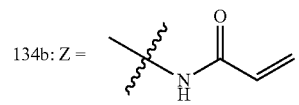
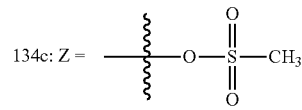
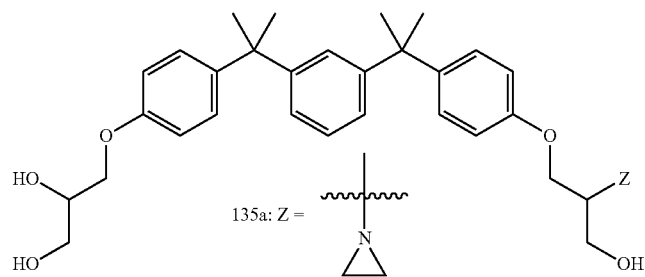
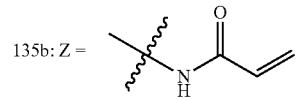
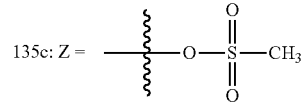

TABLE 2-continued
Representative Compounds
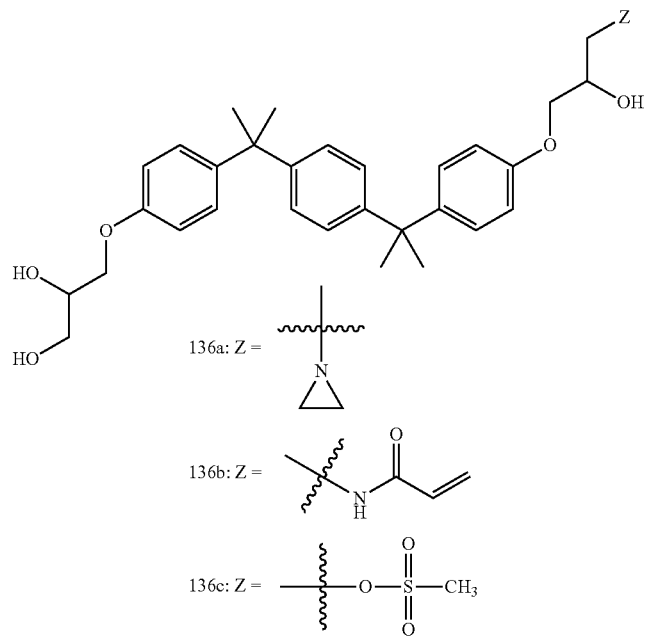
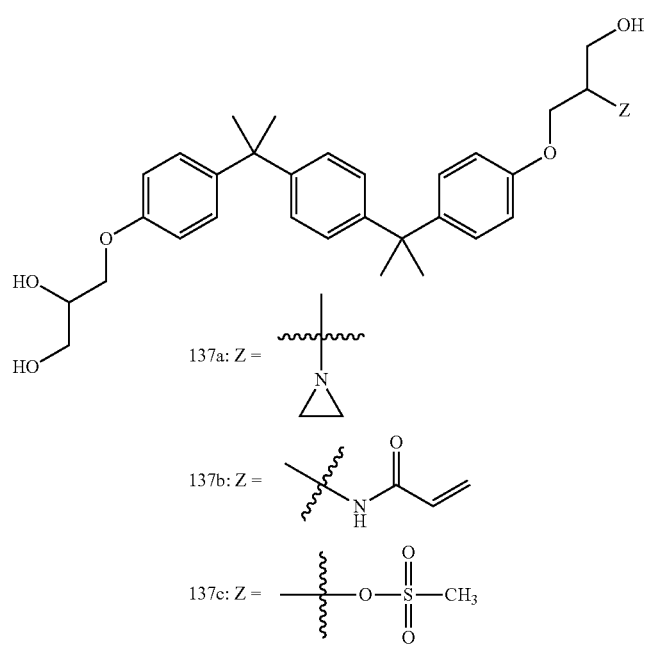

TABLE 2-continued
Representative Compounds
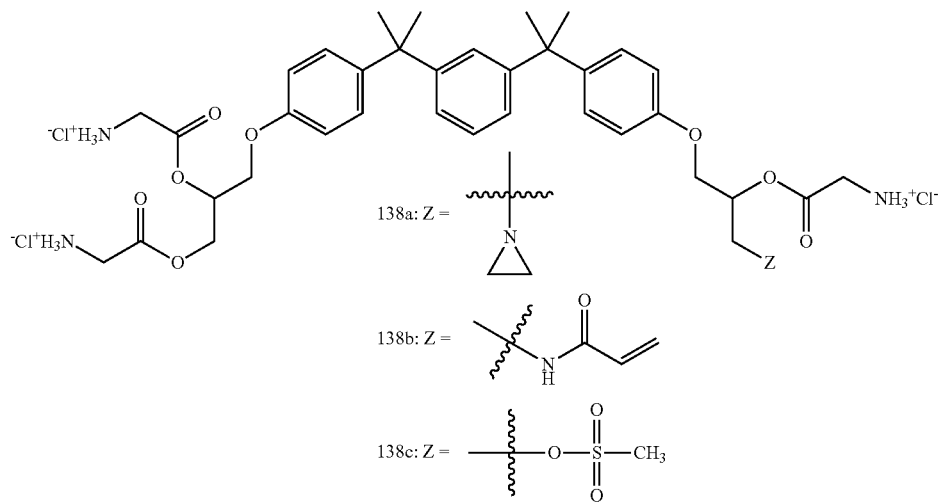
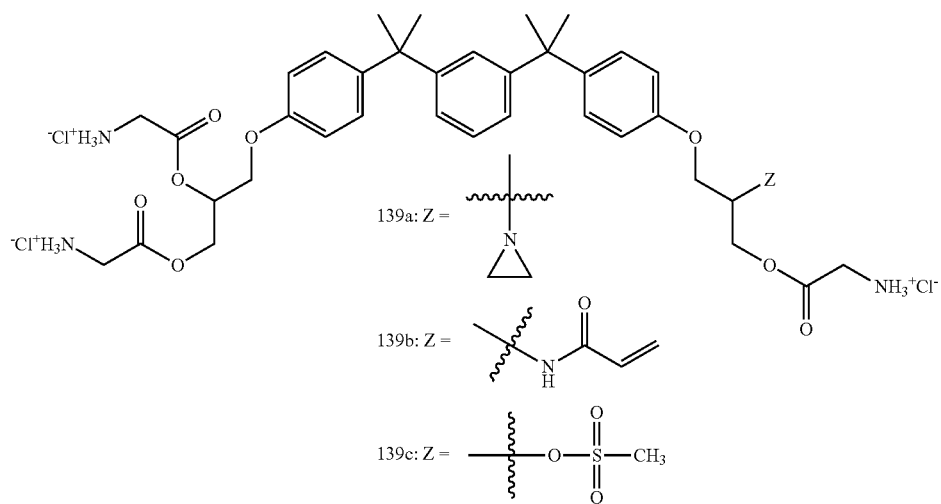

TABLE 2-continued
Representative Compounds
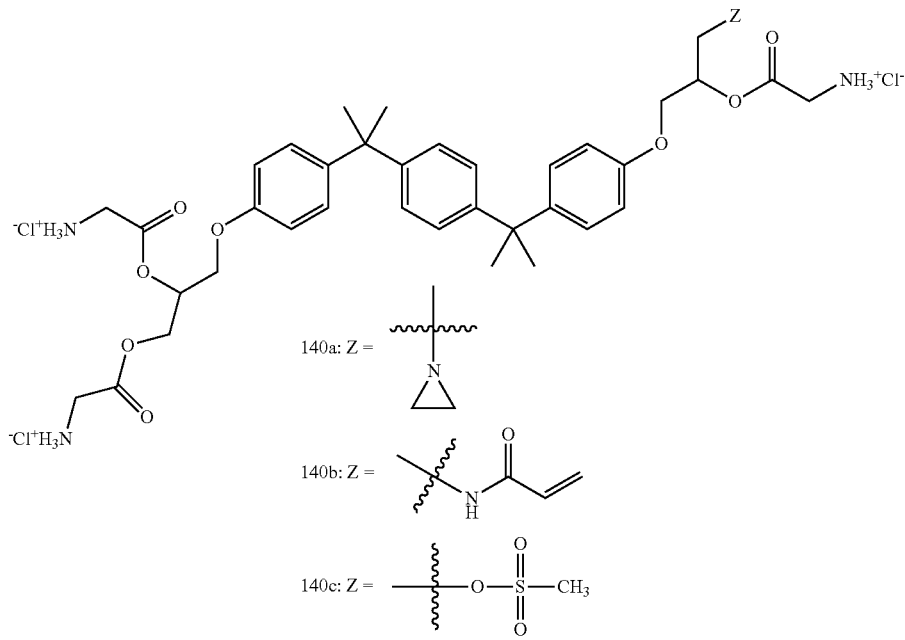
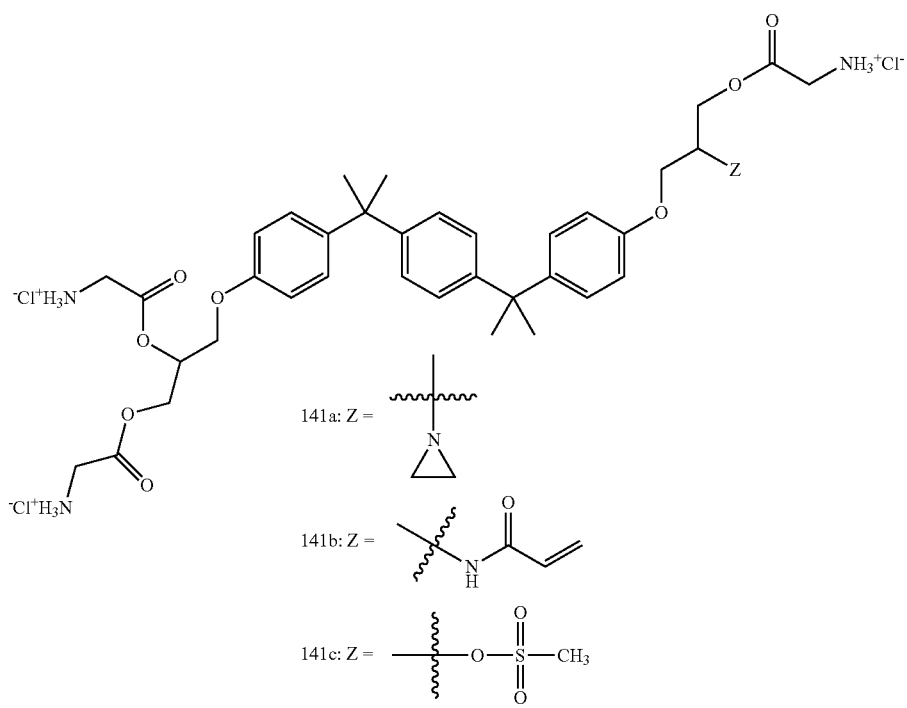

TABLE 2-continued
Representative Compounds
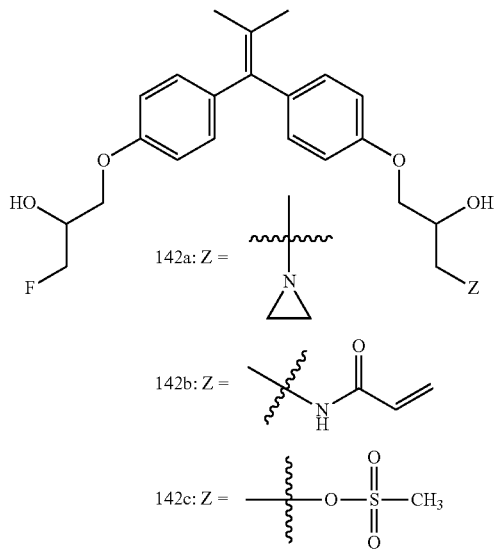
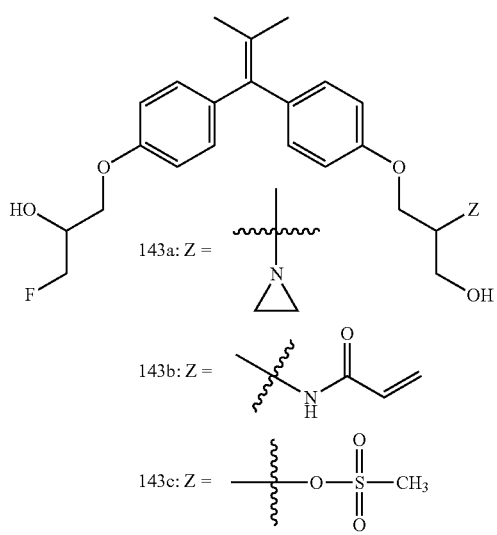

TABLE 2-continued
Representative Compounds
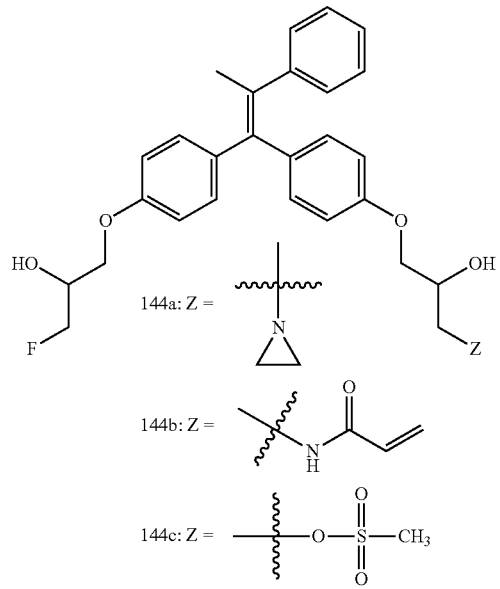
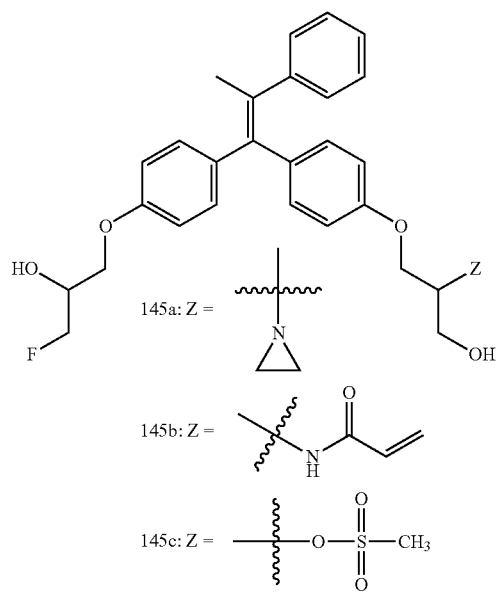

TABLE 2-continued
Representative Compounds
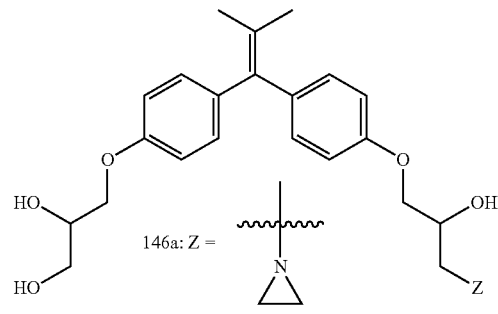
146a: Z = 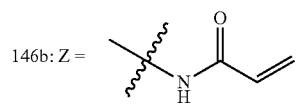
146b: Z = 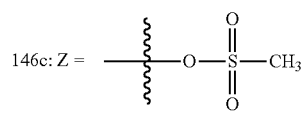
146c: Z =
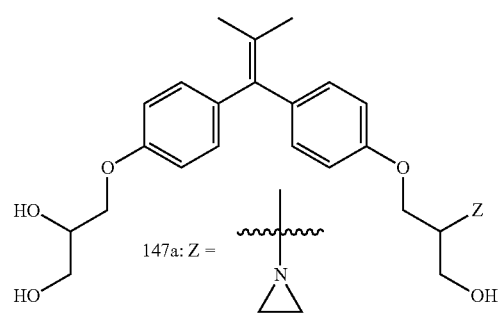
147a: Z = 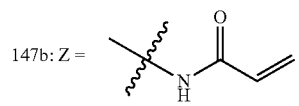
147b: Z = 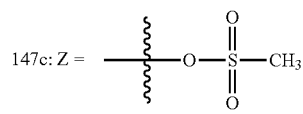
147c: Z =

TABLE 2-continued
Representative Compounds
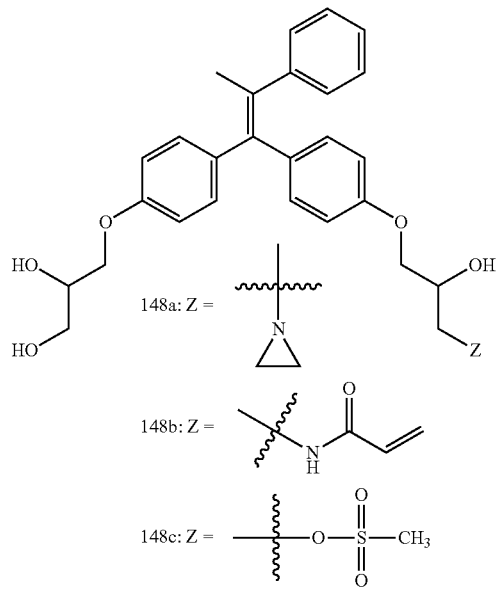
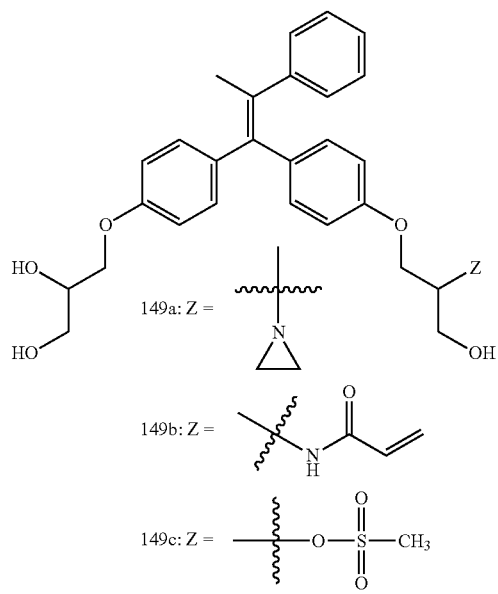

TABLE 2-continued
Representative Compounds
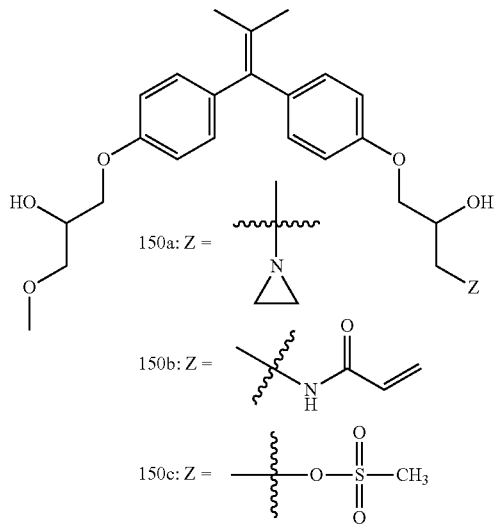
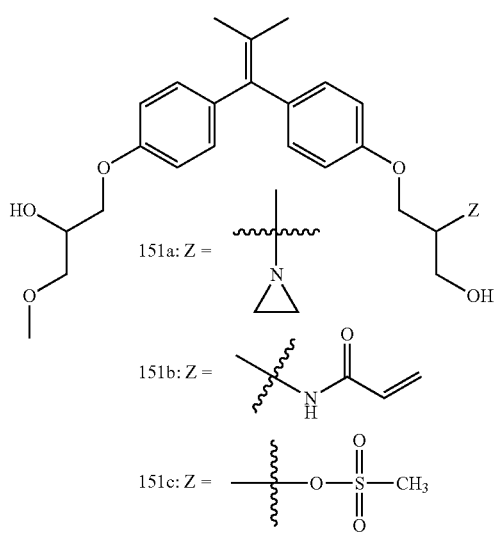

TABLE 2-continued
Representative Compounds
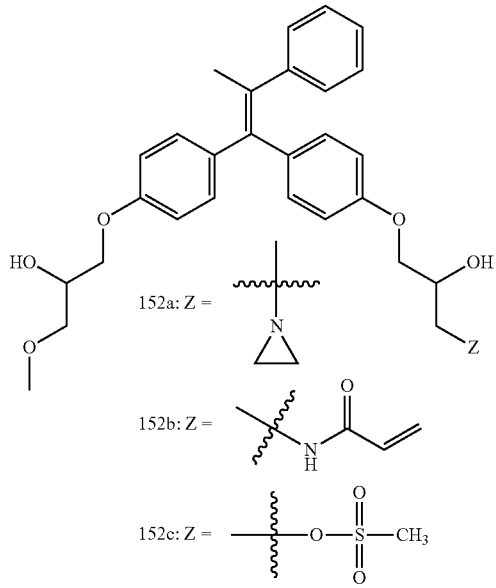
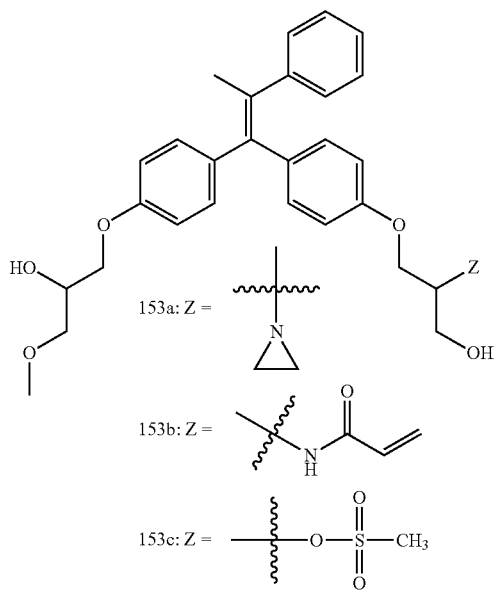

TABLE 2-continued
Representative Compounds
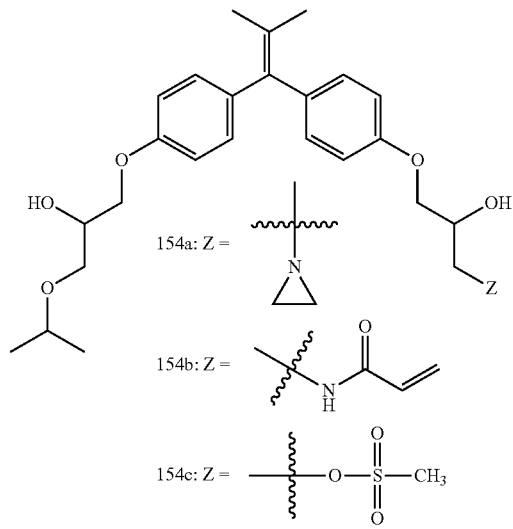
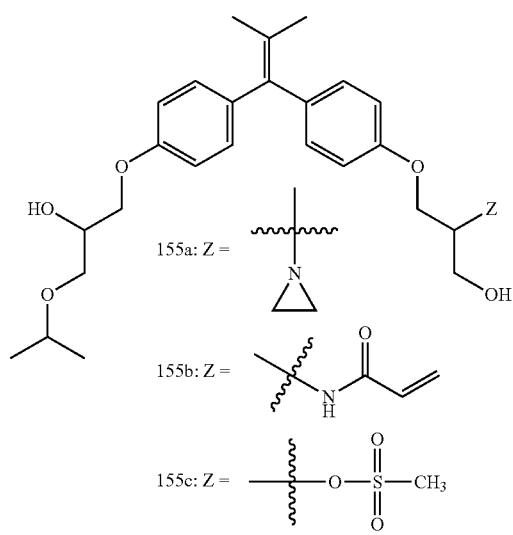

TABLE 2-continued
Representative Compounds
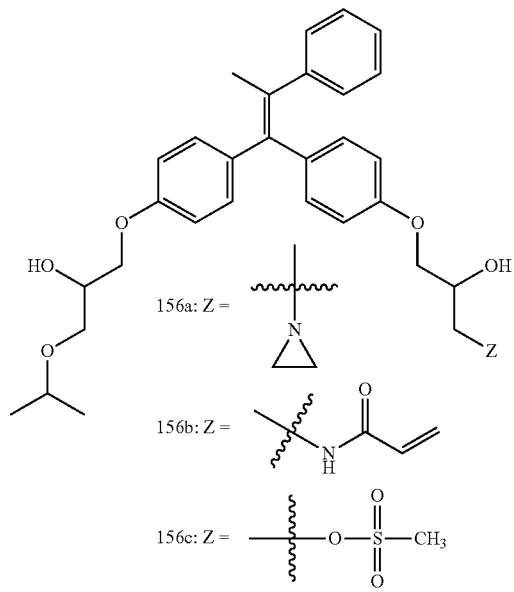
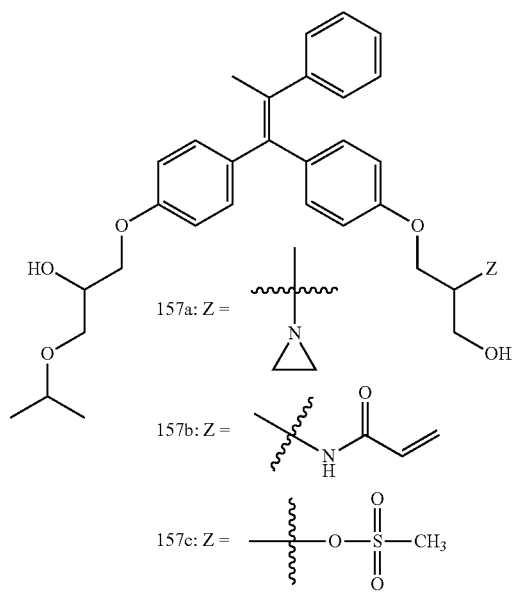

TABLE 2-continued
Representative Compounds
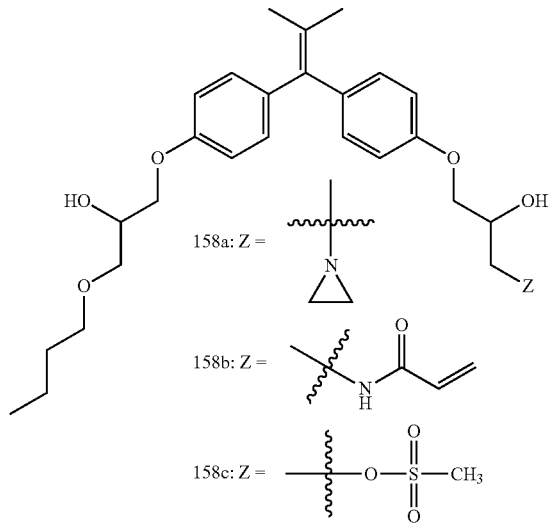
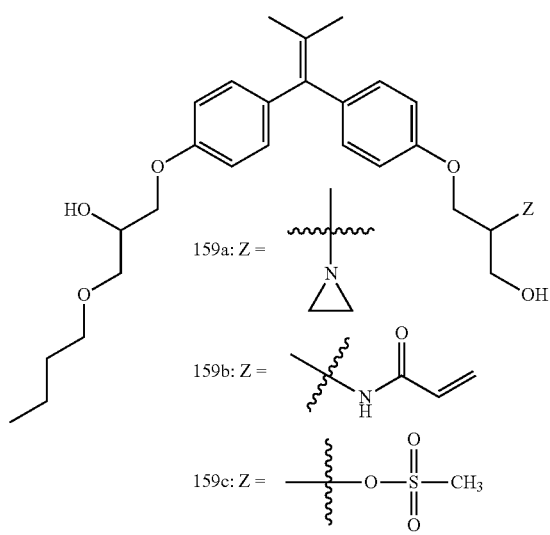

TABLE 2-continued
Representative Compounds
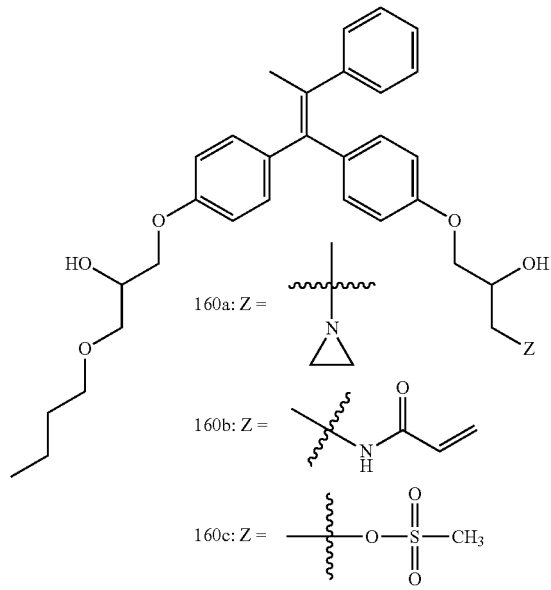
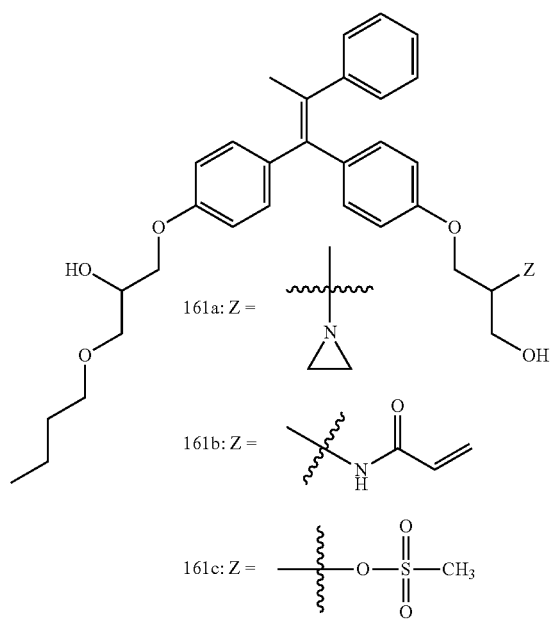

TABLE 2-continued
Representative Compounds
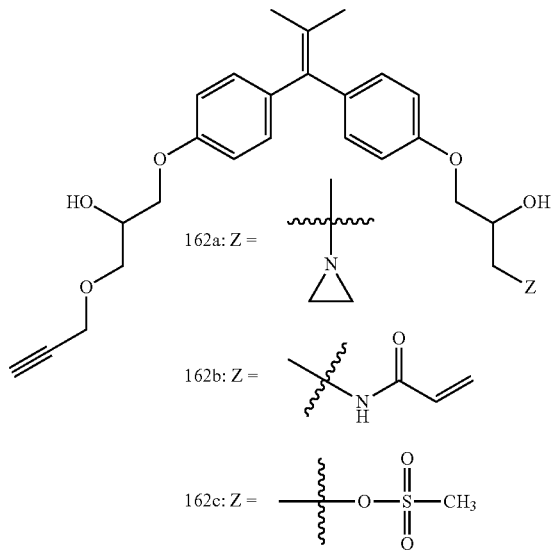
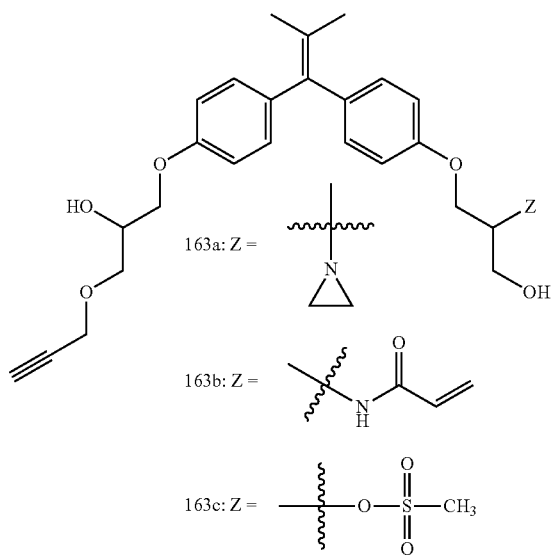

TABLE 2-continued
Representative Compounds
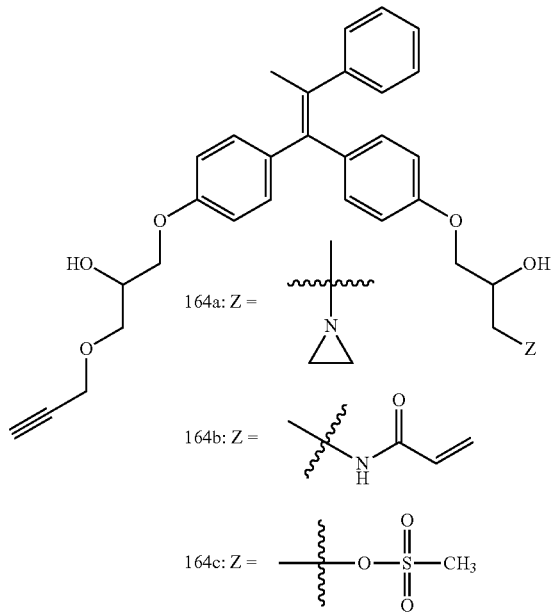
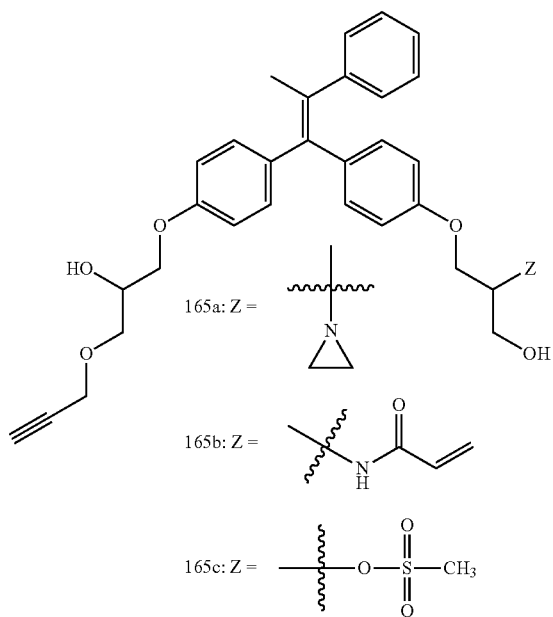

TABLE 2-continued
Representative Compounds
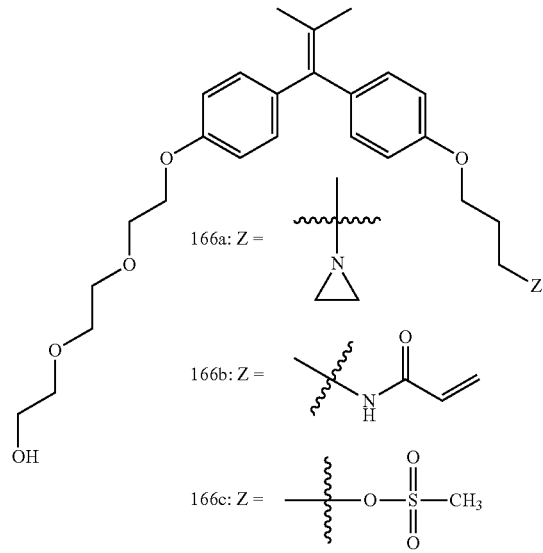
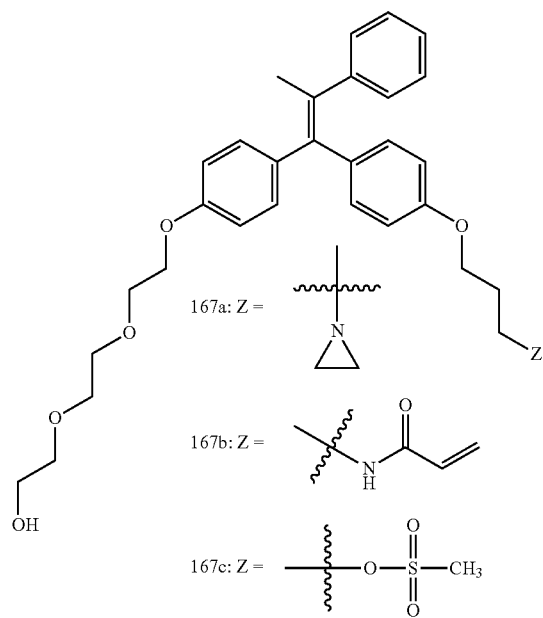

TABLE 2-continued
Representative Compounds
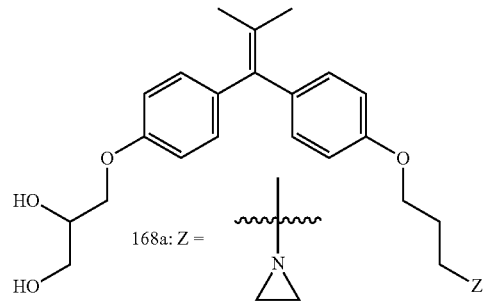
168a: Z =
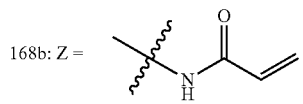
168b: Z =
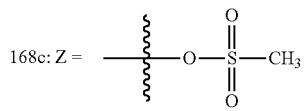
168c: Z =
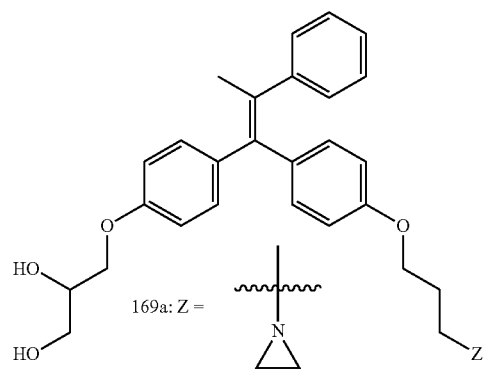
169a: Z =
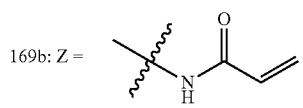
169b: Z =
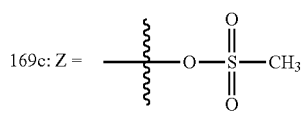
169c: Z =

TABLE 2-continued
Representative Compounds
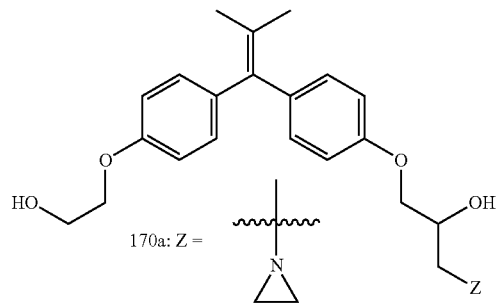
170a: Z =
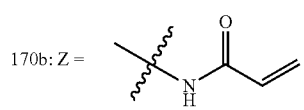
170b: Z =
170c: Z =
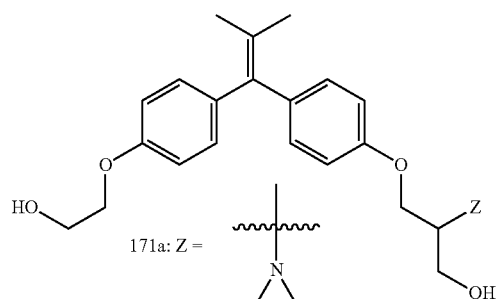
171a: Z =
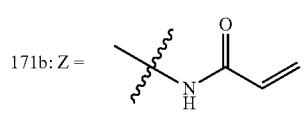
171b: Z =
171c: Z =

TABLE 2-continued

Representative Compounds

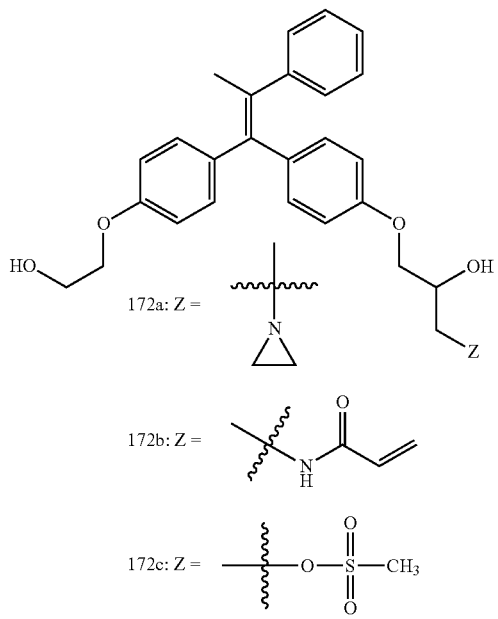

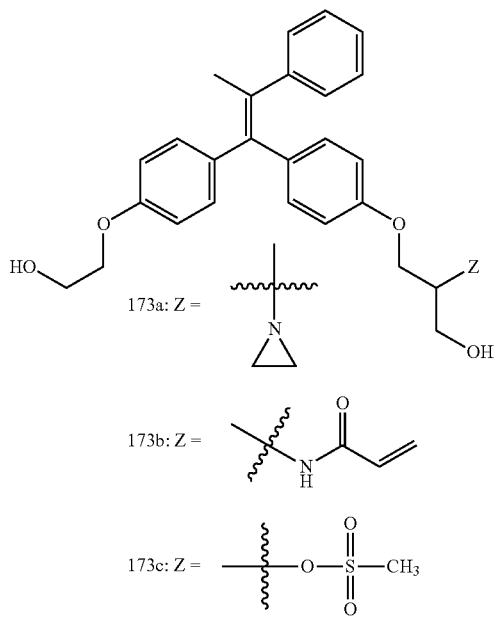

In certain embodiments, Z in any of the compounds in Table 2 is a moiety comprising an aziridine functional group. For example, in some embodiments Z in any of the compounds in Table 2 is

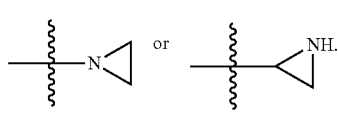

In certain other embodiments of any of the compounds in Table 2, Z is a moiety comprising an acrylamide functional group. For example, in some embodiments of any of the compounds in Table 2, Z has the following structure:

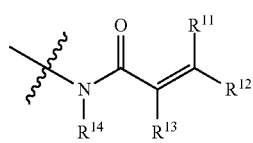

wherein $R^{11}$, $R^{12}$, $R^{13}$ and $R^{14}$ are each hydrogen, $C_{1-10}$ alkyl, aryl or aralkyl. In some other embodiments of any of the compounds in Table 2, Z has the following structure:

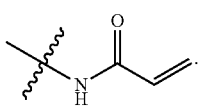 [SMILES: *NC(=O)C=C]

In certain other embodiments of any of the compounds in Table 2, Z is a moiety comprising a sulfonate functional group. For example, in some embodiments of any of any of the compounds in Table 2, Z has the following structure:

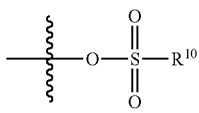

wherein $R^{10}$ is $C_1$-$C_{10}$ alkyl, aryl or aralkyl. For example, in some embodiments of the foregoing $R^{10}$ is methyl or 4-methylphenyl.

Compounds as described herein may be in the free form or in the form of a salt thereof. In some embodiments, compounds as described herein may be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

The present disclosure also provides a pharmaceutical composition comprising any one or more of the compounds (e.g., compounds of structure I) disclosed herein and a pharmaceutically acceptable carrier. In some embodiments, the pharmaceutical composition may be for treating one or more of the following: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration.

In some embodiments, pharmaceutical compositions in accordance with this invention may comprise a compound of formula I, or a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds for use in the present invention may be obtained from medical sources or modified using known methodologies from naturally occurring compounds. In addition, methods of preparing or synthesizing compounds of the present invention will be understood by a person of skill in the art having reference to known chemical synthesis principles, for example the synthetic procedures set forth in PCT Pub. Nos. WO 2010/000066; WO 2011/082487 and WO 2011/082488, in co-pending PCT Application No. US 2012/032584 and in co-pending U.S. Provisional Application Nos. 61/476,728; 61/476,729 and 61/525,643, which applications are hereby incorporated by reference in their entireties for all purposes.

Auzou et al 1974 *European Journal of Medicinal Chemistry* 9(5), 548-554 also describes suitable synthetic procedures that may be considered and suitably adapted for preparing compounds of Formula I as set out above. Other references that may be helpful include: Debasish Das, Jyh-Fu Lee and Soofin Cheng "Sulfonic acid functionalized mesoporous MCM-41 silica as a convenient catalyst for Bisphenol-A synthesis" *Chemical Communications*, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722. Each of the above references are hereby incorporated by reference in their entirety for all purposes.

For example, certain embodiments of the compounds of the present invention may be prepared with reference to the following General Reaction Scheme I:

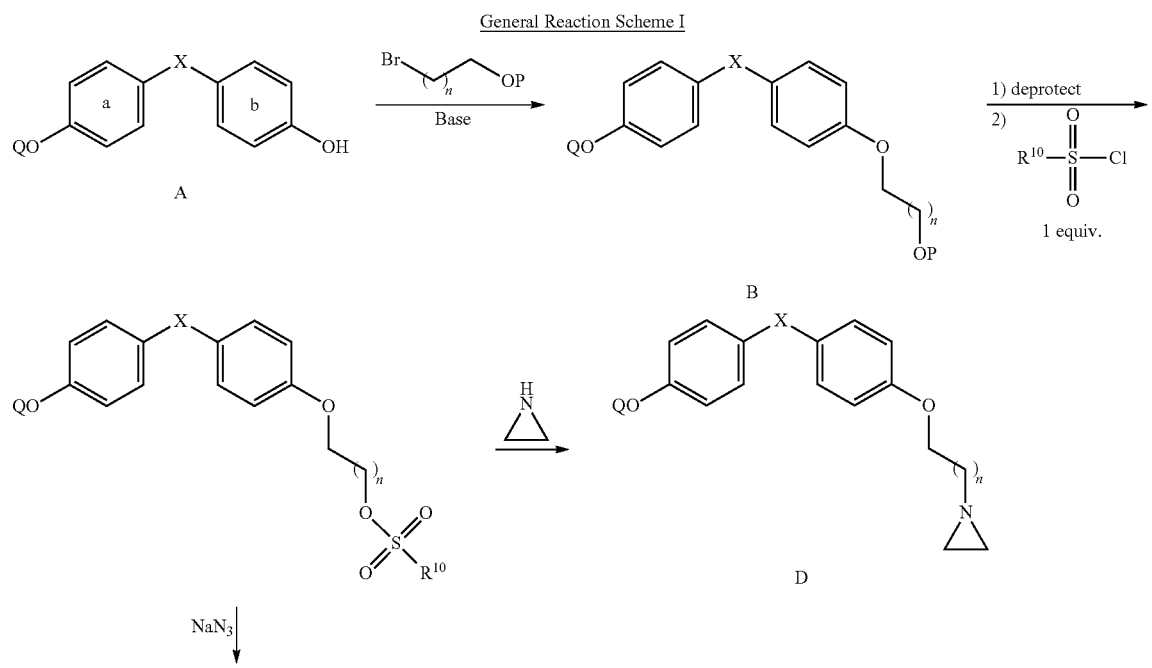

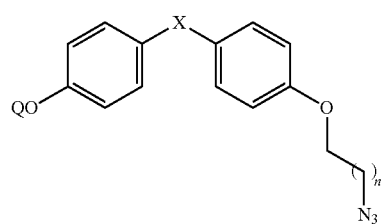 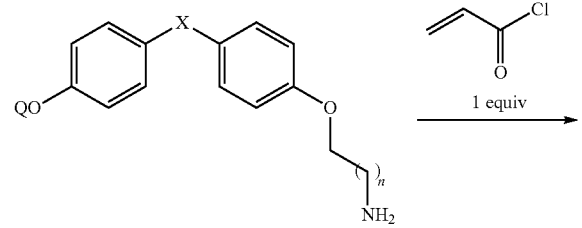

E  F

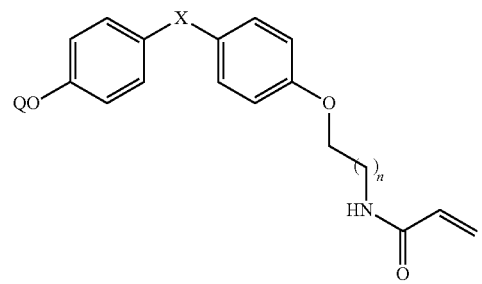

G

Referring to General Reaction Scheme I, bisphenol related compounds can be purchased from commercial sources or prepared according to methods known to those of ordinary skill in the art. The "a" ring of the bisphenol compounds can be functionalized according to known procedures to obtain compounds of structure A, wherein X is as defined herein and Q represents the following structure (which may be optionally protected according to known procedures):

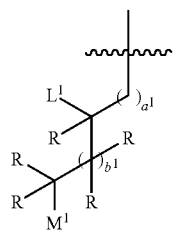

wherein $L^1$, R, M, $a^1$ and $b^1$ are as defined herein. Methods for functionalization of the "a" ring of compound A include those procedures described in PCT Pub. Nos. WO 2010/000066; WO 2011/082487 and WO 2011/082488. One of ordinary skill in the art will recognize that an appropriate protecting group strategy may be required. Compounds including fluorine moieties may be prepared according known methods. For example, in one embodiment a fluorine atom is introduced by treatment with diethylaminosulfurtrifluoride (DAST) or Xtalfluor-E or M (see *J. Org. Chem.* 2010, 75, 3401-3411, which is hereby incorporated by reference in its entirety). In other embodiments, a hydroxyl moiety may be converted to an appropriate leaving group, for example by reaction with tosyl chloride or mesyl anhydride, followed by reaction with [$K^+$/2,2,2-cryptand]$F^-$ or tetrabutylammonium fluoride. For descriptions of fluorination procedures see *J. Org. Chem.* 2010, 75, 3401-3411, *Bioorg. Med. Chem.* 2009, 17, 7441-7448, and *J. Med. Chem.* 1990, 33, 2430-2437, each of which is hereby incorporated by reference in its entirety.

Referring again to General reaction Scheme 1, reaction of compound A with an appropriately protected bromo alcohol (n is an integer from 0 to 6 and P represents an appropriate protecting group) results in compounds of structure B. Deprotection of B followed by treatment with an appropriate sulfonyl chloride ($R^{10}$ is $C_1$-$C_{10}$ alkyl, aryl or aralkyl) produces compounds of structure C, which comprise a sulfonate moiety. Reaction of C with an appropriate azide produces E, which can be subsequently reduced (e.g., with LiAlH$_4$ or other appropriate reducing agent) to the corresponding amine F. Amine F can be treated with acryloyl chloride to produce compounds comprising an acrylamide moiety. Alternatively, compound C can be treated with aziridine to produce compounds comprising an aziridine moiety (i.e., compound D).

Other various embodiments of the compounds of the present invention may be prepared with reference to the following General Reaction Scheme II:

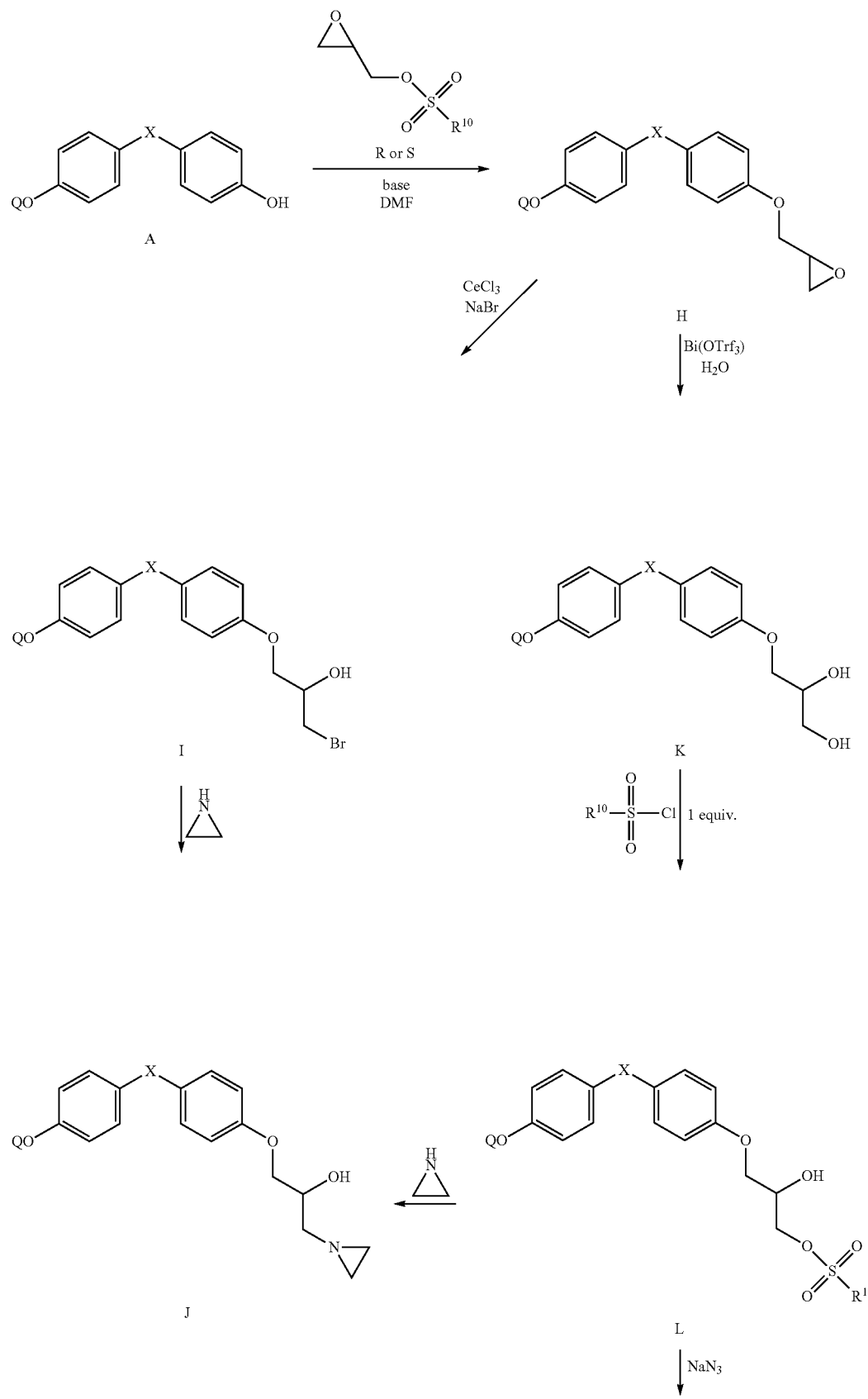

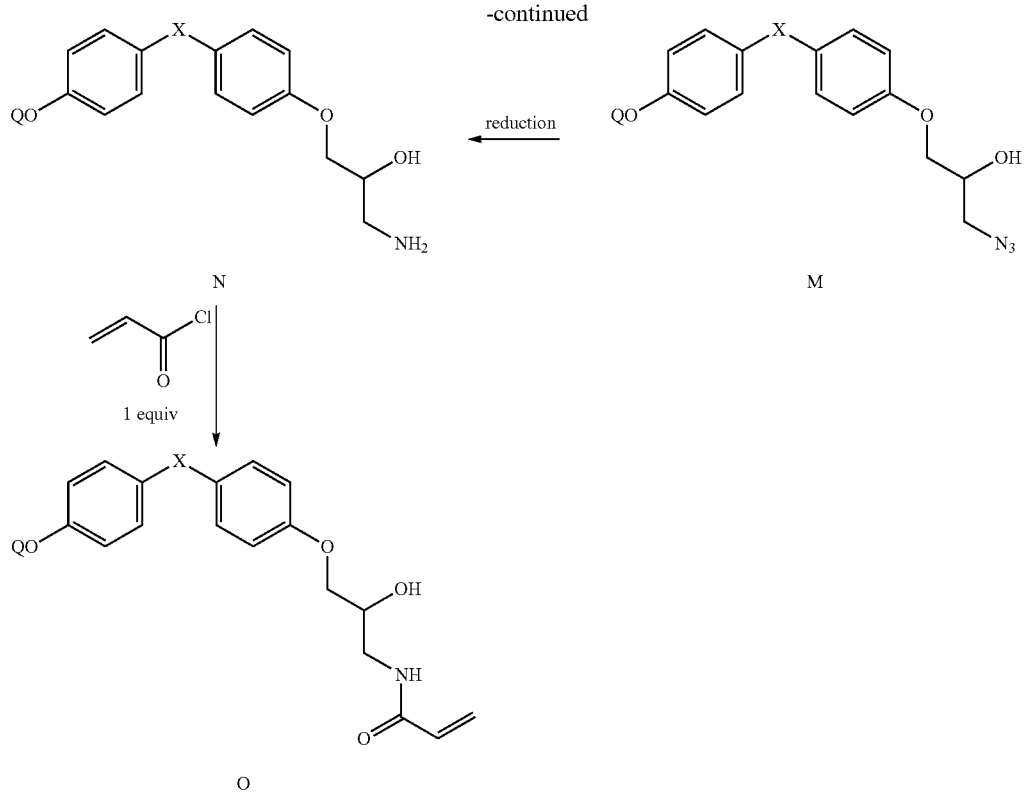

Referring to General Reaction Scheme II, compounds of structure A may be prepared as discussed above with reference to General Reaction Scheme I. Treatment of A with an appropriate epoxide provides H. Epoxide H can be opened to bromo alcohol (compound I) or diol (compound K) by treatment with CeCl$_3$/NaBr or Bi(OTrf)$_3$, respectively. Compounds comprising an aziridine moiety (i.e., compound J), can then be prepared by treatment of compound I with J.

Compound L, which comprises a sulfonate functional group, can be prepared by treatment of compound K with an appropriate sulfonyl chloride. Compound L can be used to prepare aziridine containing compounds (i.e., compound J) by treatment with aziridine, or can be converted to azide M. Azide M is then reduced (e.g., with LiAlH$_4$) to amine N and reacted with acryloyl chloride to produce compounds comprising an acrylamide moiety O.

One skilled in the art will recognize that variations to the order of the steps and reagents discussed in reference to to the above synthetic schemes are possible. Furthermore, an appropriate protecting group strategy, such as those described in, *Greene's Protective Groups in Organic Synthesis*, 4$^{th}$ Ed., Peter G. M. Wuts and Theodora W. Greene, John Wiley and Sons, Inc., 2007, which is hereby incorporated by reference in its entirety, may also be employed. In addition, compounds of structure I having various substitutions (e.g., different values for R$^1$, R$^2$, R$^3$, R$^4$, J$^1$, J$^2$, etc.) and different positional isomers can be prepared by modifications to the above starting materials and/or procedures. Such modifications are well within the ability of one of ordinary skill in the art. Finally, prodrugs of Formula I can be prepared by functionalizing a free hydroxyl in compounds of Formula I. Methods for such functionalization are well-known in the art, for example reaction with an acid chloride analogue of a moiety from Table 1 or any other suitable reagent.

III. Methods

The present compounds find use in any number of methods. For example, in some embodiments the compounds are useful in methods for modulating androgen receptor, Accordingly, in one embodiment, the present disclosure provides the use of any one of the foregoing compounds of Formula (I) for modulating androgen receptor (AR) activity. For example in some embodiments, modulating androgen receptor (AR) activity is in a mammalian cell. Modulating androgen receptor may be in a subject in need thereof (e.g., a mammalian subject) and for treatment of any of the described conditions or diseases.

In other embodiments, modulating androgen receptor (AR) activity is for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the indication is prostate cancer. In other embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). While in other embodiments, the prostate cancer is androgen-dependent prostate cancer. In other embodiments, the spinal and bulbar muscular atrophy is Kennedy's disease.

In other embodiments, the present disclosure provides a method of modulating androgen receptor (AR) activity, the method comprising administering any one of the foregoing compounds of Formula (I), or pharmaceutically acceptable salt thereof to a subject (e.g., mammal) in need thereof.

In other further embodiments of the foregoing method, modulating androgen receptor (AR) activity is for the treatment of one or more of the following: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). In other embodiments, the prostate cancer is androgen-dependent prostate cancer, and in other embodiments, the spinal and bulbar muscular atrophy is Kennedy's disease.

In yet other embodiments, the present disclosure provide the use of any of the compounds disclosed herein for modulating androgen receptor (AR) activity. For example, in certain embodiments modulating androgen receptor (AR) activity is in a mammalian cell.

In other examples, modulating androgen receptor (AR) activity is for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example, in certain embodiments the indication is prostate cancer, for example, castration resistant prostate cancer. In other examples, the prostate cancer is androgen-dependent prostate cancer. In other further embodiments, the spinal and bulbar muscular atrophy is Kennedy's disease.

The present disclosure also provides a method of modulating androgen receptor (AR) activity, the method comprising administering any of the compounds disclosed herein, or pharmaceutically acceptable salt thereof, to a subject in need thereof. For example, in certain specific embodiments modulating androgen receptor (AR) activity is for the treatment of one or more of the following: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. In certain embodiments, the spinal and bulbar muscular atrophy is Kennedy's disease.

In accordance with another embodiment, there is provided a use of the compounds of Formula (I) as described anywhere herein for preparation of a medicament for modulating androgen receptor (AR).

In accordance with a further embodiment, there is provided a method of screening for androgen receptor modulating compounds, wherein the compounds screened are selected from the compounds as described anywhere herein.

The modulating of the androgen receptor (AR) activity may be in a mammalian cell. The modulating of the androgen receptor (AR) activity may be in a mammal. The mammal may be a human.

Alternatively, the administering may be to a mammal. The administering may be to a mammal in need thereof and in an effective amount for the treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), and age-related macular degeneration.

The mammalian cell may be a human cell. The modulating AR activity may be for inhibiting AR N-terminal domain activity. The modulating AR activity may be for inhibiting AR activity. The modulating may be in vivo. The modulating AR activity may be for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), and age-related macular degeneration. The indication may be prostate cancer. The prostate cancer may be castration-resistant prostate cancer. The prostate cancer may be androgen-dependent prostate cancer.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (eg. HIFU), and in combination with chemotherapies, androgen ablation, antiandrogens or any other therapeutic approach.

With respect to combination therapies, one embodiment of the present disclosure provides a combination of any one or more of a compound of Formula I with one or more currently-used or experimental pharmacological therapies which are or may be utilized to treat any of the above disease states (e.g., androgen-independent prostate cancer or Kennedy's disease). Methods, uses and pharmaceutical compositions comprising the above combination are also provided.

In some embodiments, the present invention is directed to a method for modulating androgen receptor (e.g., for treatment of any of the above conditions) by administering to a subject in need thereof a pharmaceutical composition comprising a compound of structure I and an additional therapeutic agent. Pharmaceutical compositions (and uses thereof) comprising any one of the foregoing compounds of Formula (I), an additional therapeutic agent and a pharmaceutically acceptable carrier are also provided. For example, in some embodiments, the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy or age-related macular degeneration.

The disclosed compounds, which are thought to interfere with the AR principally through binding to the N-terminus of the AR, are expected to demonstrate beneficial synergistic therapeutic effects when used in concert with existing approved and in-development agents. That is, the biological impact of using the agents in concert with one another produces a biological and therapeutic effect which is greater than the simple additive effect of each of them separately.

Accordingly, one embodiment comprises the use of the disclosed compounds in combination therapy with one or more currently-used or experimental pharmacological therapies which are utilized for treating the above disease states irrespective of the biological mechanism of action of such pharmacological therapies, including without limitation pharmacological therapies which directly or indirectly inhibit the androgen receptor, pharmacological therapies which are cyto-toxic in nature, and pharmacological therapies which interfere with the biological production or function of androgen (hereinafter, the "Other Therapeutic Agents"). By "combination therapy" is meant the administration of any one or more of a compound of Formula I with one or more of another therapeutic agent to the same patient such that their pharmacological effects are contemporaneous with one another, or if not contemporaneous, that their effects are synergistic with one another even though dosed sequentially rather than contemporaneously.

Such administration includes without limitation dosing of one or more of a compound of Formula I and one or more of the Other Therapeutic Agent(s) as separate agents without any commingling prior to dosing, as well as formulations which include one or more Other Androgen-Blocking Therapeutic Agents mixed with one or more compound of Formula I as a pre-mixed formulation. Administration of the compound(s) of Formula I in combination with Other Therapeutic Agents for treatment of the above disease states also includes dosing by any dosing method including without limitation, intravenous delivery, oral delivery, intra-peritoneal delivery, intra-muscular delivery, or intra-tumoral delivery.

In another aspect of the present disclosure, the one or more of the Other Therapeutic Agent may be administered to the patient before administration of the compound(s) of Formula I. In another embodiment, the compound(s) of Formula I may be co-administered with one or more of the Other Therapeutic Agents. In yet another aspect, the one or more Other Therapeutic Agent may be administered to the patient after administration of the compound(s) of Formula I.

It is fully within the scope of the disclosure that the ratio of the doses of compound(s) of Formula I to that of the one or more Other Therapeutic Agents may or may not equal to one and may be varied accordingly to achieve the optimal therapeutic benefit.

For greater clarity the compound(s) of Formula I that are combined with the one or more Other Therapeutic Agents for improved treatment of the above disease states may comprise, but are not limited to any compound having a structure of Formula I, including those compounds shown in Table 2.

The Other Therapeutic Agents include without limitation any pharmacological agent which is currently approved by the FDA in the U.S. (or elsewhere by any other regulatory body) for use as pharmacological treatment of any of the above disease states, or which is currently being used experimentally as part of a clinical trial program that relates to the above disease states. Non-limiting examples of the Other Pharmacological Agents comprise, without limitation: the chemical entity known as MDV3100 (4-(3-(4-cyano-3-(trifluoromethyl)phenyl)-5,5-dimethyl-4-oxo-2-thioxoimidazolidin-1-yl)-2-fluoro-N-methylbenzamide) and related compounds, which appears to be a blocker of the AR LBD and is currently in development as a treatment for prostate cancer; the chemical entity known as TOK 001 and related compounds which appears to be a blocker of the AR LBD, and a CYP17 lyase inhibitor, and also appears to decrease overall androgen receptor levels in prostate cancer cells. TOK 001 is currently in development as a treatment for prostate cancer; the chemical entity known as ARN-509 and related compounds which appears to be a blocker of the AR LBD and is currently in development as a treatment for prostate cancer; the chemical entity known as abiraterone (or CB-7630; (3S, 8R,9S,10R,13S,14S)-10,13-dimethyl-17-(pyridin-3-yl) 2,3, 4,7,8,9,10,11,12,13,14,15-dodecahydro-1H-cyclopenta[a] phenanthren-3-ol), and related molecules, which appears to block the production of androgen and is currently in development for the treatment of prostate cancer; the chemical entity known as bicalutamide(N-[4-cyano-3-(trifluoromethyl)phenyl]-3-[(4-fluorophenyl)sulfonyl]-2-hydroxy-2-methylpropanamide) and related compounds, which appears to be a blocker of the AR LBD and which is currently used to treat prostate cancer, the chemical entity known as nilutamide (5,5-dimethyl-3-[4-nitro-3-(trifluoromethyl)phenyl]imidazolidine-2,4-dione) and related compounds, which appears to be a blocker of the AR LBD and which is currently used to treat prostate cancer, the chemical entity known as flutamide (2-methyl-N-[4-nitro-3-(trifluoromethyl)phenyl]-propanamide) and related compounds, which appears to be a blocker of the AR LBD and which is currently used to treat prostate cancer, the chemical entities know as cyproterone acetate (6-chloro-1β,2β-dihydro-17-hydroxy-3'H-cyclopropa[1,2] pregna-4,6-diene-3,20-dione) and related compounds, which appears to be a blocker of the AR LBD and which is currently used to treat prostate cancer, the chemical entity known as docetaxel (Taxotere; 1,7β,10β-trihydroxy-9-oxo-5β,20-epoxytax-11-ene-2α,4,13α-triyl 4-acetate 2-benzoate 13-{ (2R,3 S)-3-[(tert-butoxycarbonyl)amino]-2-hydroxy-3-phenylpropanoate}) and related compounds, which appears to be a cytotoxic antimicrotubule agent and is currently used in combination with prednisone to treat prostate cancer, the chemical entity known as Bevacizumab (Avastin), a monoclonal antibody that recognizes and blocks vascular endothelial growth factor A (VEGF-A) and may be used to treat prostate cancer, the chemical entity known as OSU-HDAC42 ((S)-(+)-N-hydroxy-4-(3-methyl-2-phenylbutyrylamino)-benzamide), and related compounds, which appears to act as a histone deacetylase inhibitor, and is currently being developed as a treatment for prostate cancer, the chemical entity known as VITAXIN which appears to be a monoclonal antibody against the vascular integrin αvβ3 to prevent angiogenesis, and which may be used to treat prostate cancer, the chemical entity known as sunitumib (N-(2-diethylaminoethyl)-5-[(Z)-(5-fluoro-2-oxo-1H-indol-3-ylidene)methyl]-2, 4-dimethyl-1H-pyrrole-3-carboxamide) and related compounds, which appears to inhibit multiple receptor tyrosine kinases (RTKs) and may be used for treatment of prostate cancer, the chemical entity known as ZD-4054 (N-(3-Methoxy-5-methylpyrazin-2-yl)-2-[4-(1,3,4-oxadiazol-2-yl)phenyl]pyridin-3-sulfonamid) and related compounds, which appears to block the edta receptor and which may be used for treatment of prostate cancer, the chemical entity known as VN/124-1 (3β-Hydroxy-17-(1H-benzimidazol-1-yl)androsta-5,16-diene), and related compounds which appears to block the production of androgen (via inhibition of -hydroxylase/17,20 lyase) and is currently in development for the treatment of prostate cancer; the chemical entity known as Cabazitaxel (XRP-6258), and related compounds, which appears to be a cytotoxic microtubule inhibitor, and which is currently used to treat prostate cancer; the chemical entity known as MDX-010 (Ipilimumab), a fully human monoclonai antibody that binds to and blocks the activity of CTLA-4 which is currently in development as an immunotherapeutic agent for treatment of prostate cancer; the chemical entity known as OGX 427 which appears to target HSP27 as an antisense agent, and which is currently in development for treatment of prostate cancer; the chemical entity known as OGX 011 which appears to target clusterin as an antisense agent, and which is currently in development as a treatment for prostate cancer; the chemical entity known as finasteride (Proscar, Propecia; N-(1,1-dimethylethyl)-3-oxo-(5α,17β)-4-azaandrost-1-ene-17-carboxamide), and related compounds, which appears to be a 5-alpha reductase inhibitor that reduces levels of dihydrotestosterone, and may be used to treat prostate cancer; the chemical entity known as dutasteride (Avodart; 5α,17β)-N-{2,5 bis(trifluoromethyl)phenyl}-3-oxo-4-azaandrost-1-ene-17-carboxamide) and related molecules, which appears to be a 5-alpha reductase inhibitor that reduces levels of dihydrotestosterone, and may be used in the treatment of prostate cancer; the chemical entity known as turosteride ((4aR,4bS,6aS,7S,9aS,9bS,11aR)-1,4a,6a-trimethyl-2-oxo-N-(propan-2-yl)-N-(propan-2 ylcarbamoyl)hexadecahydro-1H-indeno[5,4-f]quinoline-7-carboxamide), and related molecules, which appears to be a 5-alpha reductase inhibitor that reduces levels of dihydrotestosterone and may be used in the treatment of prostate cancer; the chemical entity known as bexlosteride (LY-191,704; (4aS,10bR)-8-chloro-4-methyl-1,2,4a,5,6,10b-hexahydrobenzo[f]quinolin-3-one), and related compounds, which appears to be a 5-alpha reductase inhibitor that reduces levels of dihydrotestosterone and may be used in the treatment of prostate cancer; the chemical entity known as izonsteride (LY-320,236; (4aR,10bR)-8-[(4-ethyl-1,3-benzothiazol-2-yl)sulfanyl]-4,10b-dimethyl-1,4,4a,5,6,10b-hexahydrobenzo[f]quinolin-3(2H)-one) and related compounds, which appears to be a 5-alpha reductase inhibitor that reduces levels of dihydrotestosterone and may be used for the treatment of prostate cancer; the chemical entity known as FCE 28260 and related compounds, which appears to be a 5-alpha reductase inhibitor that reduces levels of dihydrotestosterone and may be used for the treatment of prostate cancer; the chemical entity known as SKF105,111, and related compounds, which appears to be a 5-alpha reductase inhibitor that reduces levels of dihydrotestosterone and may be used for treatment of prostate cancer.

Accordingly, in certain embodiments the additional therapeutic agent is MDV3100, TOK 001, TOK 001; ARN-509; abiraterone, bicalutamide, nilutamide, flutamide, cyproterone acetate, docetaxel, Bevacizumab (Avastin), OSU-HDAC42, VITAXIN, sunitumib, ZD-4054, VN/124-, Cabazitaxel (XRP-6258), MDX-010 (Ipilimumab), OCX 427, OGX 011, finasteride, dutasteride, turosteride, bexlosteride, izonsteride, FCE 28260, SKF 105,111 or a related compound thereof.

In another embodiment, the present disclosure provides the use of any one of the foregoing pharmaceutical compositions (including compositions comprising a compound of formula I and an additional therapeutic agent) for modulating androgen receptor (AR) activity. For example in some embodiments, modulating androgen receptor (AR) activity is in a mammalian cell.

In other embodiments, modulating androgen receptor (AR) activity is for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the indication is prostate cancer. For example, in some embodiments, the prostate cancer is castration resistant prostate cancer, and in other embodiments the prostate cancer is androgen-dependent prostate cancer. In still other embodiments, the spinal and bulbar muscular atrophy is Kennedy's disease.

In yet another embodiment, the present disclosure provides a method of modulating androgen receptor (AR) activity, the method comprising administering any one of the foregoing pharmaceutical compositions (including compositions comprising a compound of formula I and an additional therapeutic agent) to a subject in need thereof. For example in some embodiments, modulating androgen receptor (AR) activity is for the treatment of one or more of the following: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. In other embodiments, the spinal and bulbar muscular atrophy is Kennedy's disease. In still other embodiments, the indication is prostate cancer. For example, in some embodiments, the prostate cancer is castration resistant prostate cancer, while in other embodiments, the prostate cancer is androgen-dependent prostate cancer.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions. Some compounds of this invention may be toxic at some concentrations. Titration studies may be used to determine toxic and non-toxic concentrations. Toxicity may be evaluated by examining a particular compound's or composition's specificity across cell lines using PC3 cells as a negative control that do not express functional AR. Animal studies may be used to provide an indication if the compound has any effects on other tissues. Systemic therapy that targets the AR will not likely cause major problems to other tissues since antiandrogens and androgen insensitivity syndrome are not fatal.

Compounds as described herein may be administered to a subject. As used herein, a "subject" may be a human, non-human primate, mammal, rat, mouse, cow, horse, pig, sheep, goat, dog, cat and the like. The subject may be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

Compounds described herein may also be used in assays and for research purposes. Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PKA) pathway with forskolin (FSK). Some compounds and compositions of this invention may inhibit both FSK and androgen (e.g. R1881, a synthetic androgen) induction of ARE-luciferase (ARE-luc). Constituative activity of the AR refers to splice variants lacking the AR ligand-binding domain. Such compounds may block a mechanism that is common to both ligand-dependent and ligand-independent activation of the AR, as well as constitutively active splice variants of the AR that lack ligand-binding domain. This could involve any step in activation of the AR including dissociation of heat-shock proteins, essential posttranslational modifications (e.g., acetylation, phosphorylation), nuclear translocation, protein-protein interactions, formation of the transcriptional complex, release of co-repressors, and/or increased degradation. Some compounds and compositions of this invention may inhibit ligand-only activity and may interfere with a mechanism specific to ligand-dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism may be used to treat such conditions. Some compounds and compositions of this invention may only inhibit FSK induction and may be specific inhibitors to ligand-independent activation of the AR. These compounds and compositions may interfere with the cascade of events that normally occur with FSK and/or PKA activity or any downstream effects that may play a role on the AR (e.g. FSK increases MAPK activity which has a potent effect on AR activity). Examples may include an inhibitor of cAMP and or PKA or other kinases. Some compounds and compositions of this invention may induce basal levels of activity of the AR (no androgen or stimulation of the PKA pathway). Some compounds and compositions of this invention may increase induction by R1881 or FSK. Such compounds and compositions may stimulate transcription or transactivation of the AR. Some compounds and compositions of this invention may inhibit activity of the androgen receptor. Interleukin-6 (IL-6) also causes ligand-independent activation of the AR in LNCaP cells and can be used in addition to FSK.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

The compounds described herein may be used for in vivo or in vitro research uses (i.e. non-clinical) to investigate the mechanisms of orphan and nuclear receptors (including steroid receptors such as the androgen receptor). Furthermore, these compounds may be used individually or as part of a kit for in vivo or in vitro research to investigate signal transduction pathways and/or the activation of orphan and nuclear receptors using recombinant proteins, cells maintained in culture, and/or animal models.

Various alternative embodiments and examples of the invention are described herein. These embodiments and examples are illustrative and should not be construed as limiting the scope of the invention. The following examples are provided for purposes of illustration, not limitation.

EXAMPLES

All non-aqueous reactions are performed in flame-dried round bottomed flasks. The flasks are fitted with rubber septa and reactions are conducted under a positive pressure of argon unless otherwise specified. Stainless steel syringes are used to transfer air- and moisture-sensitive liquids. Flash column chromatography is performed as described by Still et al. (Still, W. C.; Kahn, M.; Mitra, A. *J. Org. Chem.* 1978, 43, 2923) using 230-400 mesh silica gel. Thin-layer chromatography is performed using aluminium plates pre-coated with 0.25 mm 230-400 mesh silica gel impregnated with a fluorescent indicator (254 nm). Thin-layer chromatography plates are visualized by exposure to ultraviolet light and a "Seebach" staining solution (700 mL water, 10.5 g Cerium (IV) sulphate tetrahydrate, 15.0 g molybdato phosphoric acid, 17.5 g sulphuric acid) followed by heating (~1 min) with a heating gun (~250° C.). Organic solutions are concentrated on Büchi R-114 rotatory evaporators at reduced pressure (15-30 torr, house vacuum) at 25-40° C.

Commercial regents and solvents are used as received. All solvents used for extraction and chromatography are HPLC grade. Normal-phase Si gel Sep Paks™ are purchased from waters, Inc. Thin-layer chromatography plates are Kieselgel $60F_{254}$. All synthetic reagents are purchased from Sigma Aldrich and Fisher Scientific Canada.

Proton nuclear magnetic resonance ($^1$H NMR) spectra are recorded at 25° C. using a Bruker 400 with inverse probe and Bruker 400 spectrometers, are reported in parts per million on the δ scale, and are referenced from the residual protium in the NMR solvent (DMSO-$d_6$: δ 2.50 (DMSO-$d_5$), CDCl$_3$: δ 7.24 (CHCl$_3$)). Carbon-13 nuclear magnetic resonance ($^{13}$C NMR) spectra are recorded with a Bruker 400 spectrometer, are reported in parts per million on the δ scale, and are referenced from the carbon resonances of the solvent (DMSO-$d_6$: δ 39.51, CDCl$_3$: δ 77.00). Spectral features are tabulated in the following order: chemical shift (δ, ppm); multiplicity (s=singlet, d=doublet, t=triplet, m=multiplet, br=broad); coupling constant (J, Hz, number of protons).

LNCaP cells are employed initially for all experiments because they are well-differentiated human prostate cancer cells in which ligand-independent activation of the AR by FSK has been characterized (Nazareth et al 1996 *J. Biol. Chem.* 271, 19900-19907; and Sadar 1999 *J. Biol. Chem.* 274, 7777-7783). LNCaP cells express endogenous AR and secrete prostate-specific antigen (PSA) (Horoszewicz et al 1983 *Cancer Res.* 43, 1809-1818). LNCaP cells can be grown either as monolayers in cell culture or as tumors in the well-characterized xenograft model that progresses to androgen independence in castrated hosts (Sato et al 1996 *J. Steroid Biochem. Mol. Biol.* 58, 139-146; Gleave et al 1991 *Cancer Res.* 51, 3753-3761; Sato et al 1997 *Cancer Res.* 57, 1584-1589; and Sadar et al 2002 *Mol. Cancer Ther.* 1(8), 629-637). R1881 (a synthetic androgen) is employed since it is stable and avoids problems associated with the labile physiological ligand dihydrotestosterone (DHT). Reporter specificity may be determined using several alternative reporter gene constructs. Some well characterized ARE-driven reporter gene constructs that have been used extensively are the PSA (6.1 kb) enhance/promoter which contains several AREs and is highly inducible by androgens as well as by FSK (Ueda et al 2002 A *J. Biol. Chem.* 277, 7076-7085) and the ARR3-thymidine kinase (tk)-luciferase, which is an artificial reporter construct that contains three tandem repeats of the rat probasin ARE1 and ARE2 regions upstream of a luciferase reporter (Snoek et al 1996 *J. Steroid Biochem. Mol. Biol.* 59, 243-250).

Example 1

Synthesis of 1-(Aziridin-1-yl)-3-(4-(2-(4-(3-Fluoro-2-Hydroxypropoxy)Phenyl)Propan-2-yl)Phenoxy)Propan-2-ol (1A)

Compound 1a is prepared according to the above scheme. Compound i (where p represents a protecting group) is prepared according to procedures described in PCT Pub. No. WO 2010/000066 and co-pending U.S. Provisional Application No. 61/525,643 using appropriate protecting group strategies. Compound i is treated with oxiran-2-ylmethyl methanesulfonate in a basic DMF solution to prepare epoxide ii. Epoxide ii is then treated with Bi(OTrf)$_3$ in water to obtain diol iii. Diol iii is mesylated by reaction with mesylchloride and compound iv is isolated. Compound v is reacted with aziridine and deprotected to produce compound 1a.

The analagous compound having an acrylamide functional group (i.e., Compound 1b) instead of an aziridine is prepared

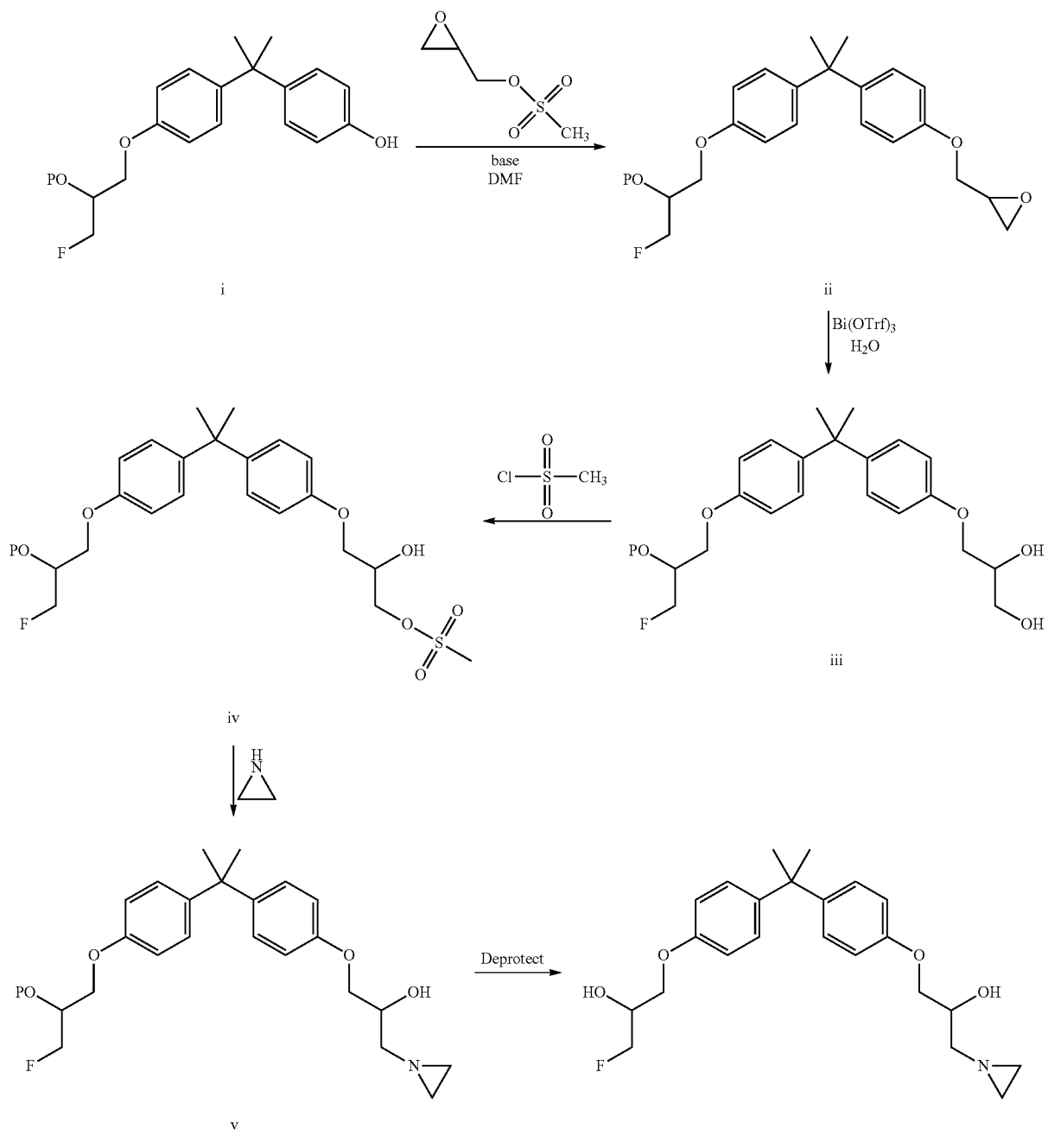

by treatment of compound v with LiAlH$_4$ to obtain the corresponding amine which is treated with acryloyl chloride to obtain Compound 1b.

Further, the analagous compound having sulfonate functional group (i.e., Compound 1c) instead of an aziridine is prepared by deprotection of iv. Sulfonates having different alkyl, aryl or aralkyl groups are prepared from the corresponding sulfonyl chloride reagent.

Other compounds of Formula 1 are prepared in an analogous fashion.

Example 2

In Vitro Activity of Compounds

LNCaP cells are transiently cotransfected with PSA (6.1 kb)-luciferase (0.25 µg/well) in 24-well plates for 24 h prior to pre-treatment with compounds of the invention for 1 hour before the addition of synthetic androgen, R1881 (1 nM) to induce PSA production or vehicle. The total amount of plasmid DNA transfected is normalized to 0.75 µg/well by the addition of the empty vector. After 48 h of incubation with R1881, the cells are harvested, and relative luciferase activity is determined. Test compounds are added to the cells at various concentrations and activity for each treatment is normalized to the predicted maximal activity induction (in the absence of test compounds, vehicle only). Plotting of sigmoidal curves (Boltzmann Function) and IC50 calculations are done using OriginPro 8.1 Sofware (Northampton, Mass., USA).

Furthermore, toxicity is assessed by both microscopic examination and reduction of protein levels. Solubility is assessed both macroscopically (cloudy media) and microscopically (formation of granules or crystals).

Example 3

In Vivo Dose Response of Compounds

In vivo dose response of compounds of the invention is determined according to the following procedure: Male athymic SCID-NOD mice, 6- to 8-weeks old, are inoculated subcutaneously with LNCaP cells (1×10$^6$) suspended in 75 µl of RPMI 1640 (5% FBS) and 75 µl of Matrigel (Becton Dickinson Labware) in the flank region via a 27-gauge needle under isofluorane anesthesia. Mice bearing LNCaP subcutaneous tumors are castrated when tumor volumes are approximately 100 mm$^3$. Seven days after castration, mice are injected intravenously by tail vein every other day for a total of 7 doses with compounds of the invention in 15% DMSO and 25.5% PEG. The experiment is complete 2 days after the last injection. Tumours are measured with calipers and their volumes calculated by the formula L×W×H×0.5236. Tumor volume as a function of compound dose is plotted.

Dose response of comparative compounds are also determined according to the above procedure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having a structure of Formula I:

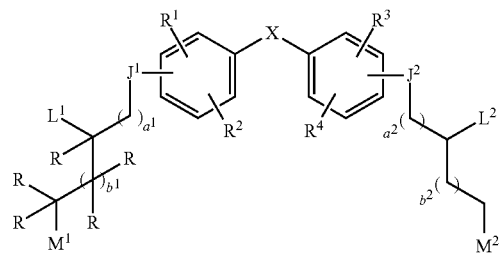

or a pharmaceutically acceptable salt, tautomer or stereoisomer thereof, wherein:

$M^1$ is halogen, —OH, —OY or —OR$^5$;

$M^2$ is halogen, —OH, —OY, —OR$^5$ or Z;

$L^1$ is H, halogen, —OH, —OR$^5$, —OY, —SR$^5$ or —NR$^5$R$^6$R$^7$;

$L^2$ is H, halogen, —OH, —OR$^5$, —OY, —SR$^5$, —NR$^5$R$^6$R$^7$ or Z;

Z is a moiety comprising an aziridine, acrylamide or sulfonate functional group;

$J^1$ and $J^2$ are each independently —O—, —S(O)$_{0-2}$—, —NR$^5$— or —(CR$^5$R$^6$)—;

X is a direct bond, —C(R$^8$R$^9$)—, —C(=CR$^8$R$^9$)—, —C(R$^8$R$^9$)-aryl-C(R$^8$R$^9$)—, —C(=CR$^8$R$^9$)-aryl-C(=CR$^8$R$^9$)—; —O—, —S(O)$_{0-2}$—, —N(R$^5$)—, —C(=NOR$^5$)—, —C(=NR$^5$)— or —C(=O)—;

Y is a moiety from Table I;

R is, at each occurrence, independently H or halogen;

$R^1$, $R^2$, $R^3$ and $R^4$ are each independently H, halogen or C$_1$-C$_{10}$ alkyl;

$R^5$ and $R^6$ are, at each occurrence, independently H, or C$_1$-C$_{10}$ alkyl;

$R^7$ is an electron pair, H, or C$_1$-C$_{10}$ alkyl;

$R^8$ and $R^9$ are each independently, H, halogen, C$_1$-C$_{10}$ alkyl, aryl, aralkyl or —NR$^5$R$^6$, or R$^8$ and R$^9$ may join to form a structure selected from the group consisting of:

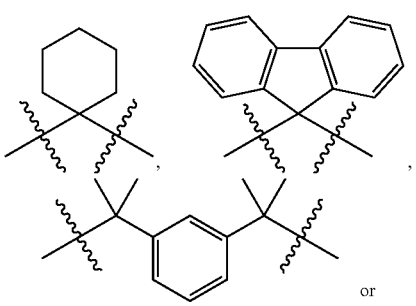

or

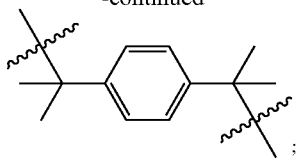

$a^1$, $a^2$, $b^1$ and $b^2$ are each independently 0, 1, 2, 3, 4 or 5; wherein at least one of $M^2$ or $L^2$ is Z.

2. The compound of claim 1, wherein the compound has the following structure (Ia):

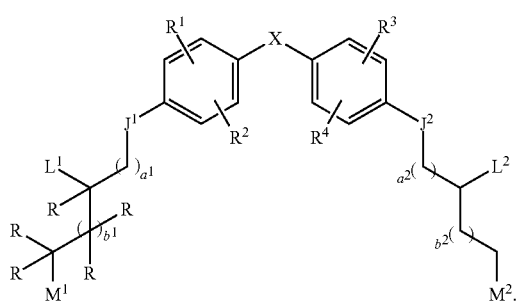

3. The compound of claim 1, wherein $R^8$ and $R^9$ are each independently H or $C_1$-$C_{10}$ alkyl.

4. The compound of claim 1, wherein $R^8$ and $R^9$ are each $C_1$-$C_{10}$ alkyl.

5. The compound of claim 1, wherein X is —$CH_2$—, —$C(CH_3)_2$—, —S—, —(C=O)—,

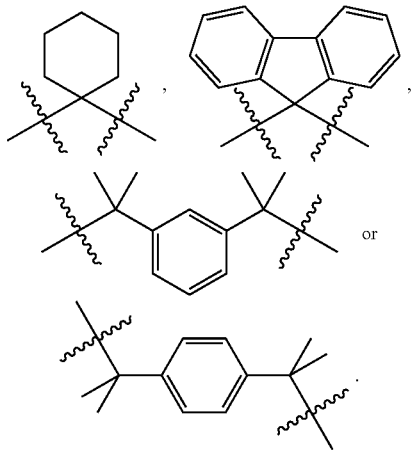

6. The compound of claim 5, wherein X is —$C(CH_3)_2$—.
7. The compound of claim 1, wherein at least one of $R^1$, $R^2$, $R^3$ or $R^4$ is H.
8. The compound of claim 1, wherein each of $R^1$, $R^2$, $R^3$ and $R^4$ is H.
9. The compound of claim 1, wherein at least one of $R^1$, $R^2$, $R^3$ or $R^4$ is $C_1$-$C_{10}$ alkyl.
10. The compound of claim 1, wherein at least one of $R^1$, $R^2$, $R^3$ or $R^4$ is halogen.
11. The compound of claim 1, wherein at least one of $J^1$ or $J^2$ is —O—.
12. The compound of claim 1, wherein each of $J^1$ and $J^2$ is —O—.

13. The compound of claim 1, wherein $a^1$ is 0 or 1.
14. The compound of claim 1, wherein $a^2$ is 1.
15. The compound of claim 1, wherein $b^1$ is 0.
16. The compound of claim 1, wherein $b^2$ is 0.
17. The compound of claim 1, wherein each R is independently H or fluoro.
18. The compound of claim 1, wherein at least one R is fluoro.
19. The compound of claim 1, wherein each R is H.
20. The compound of claim 1, wherein $L^1$ is —OH.
21. The compound of any of the preceding claims wherein $L^2$ is —OH.
22. The compound of claim 1, wherein $L^1$ is H.
23. The compound of claim 1, wherein $L^2$ is H.
24. The compound of claim 1, wherein $L^1$ is —OY.
25. The compound of claim 1, wherein $L^2$ is —OY.
26. The compound of claim 24, wherein Y is

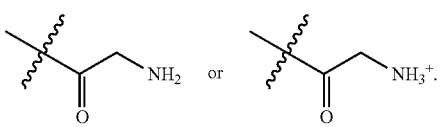

27. The compound of claim 1, wherein $M^1$ is halogen.
28. The compound of claim 27, wherein $M^1$ is fluoro.
29. The compound of claim 1, wherein $M^1$ is —OH.
30. The compound of claim 1, wherein $M^1$ is —$OR^5$.
31. The compound of claim 30, wherein $R^5$ is an unsaturated alkyl.
32. The compound of claim 30, wherein $R^5$ is a saturated alkyl.
33. The compound of claim 31, wherein one or more carbon atoms of the $C_1$-$C_{20}$ alkyl are replaced with an oxygen atom.
34. The compound of claim 31, wherein the alkyl is substituted with one or more —OH groups.
35. The compound of claim 1, wherein $M^1$ has one of the following structures:

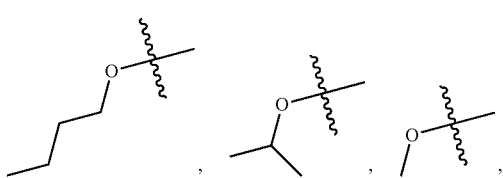

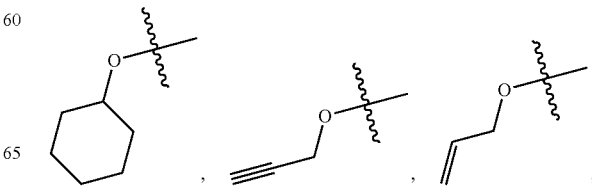

-continued
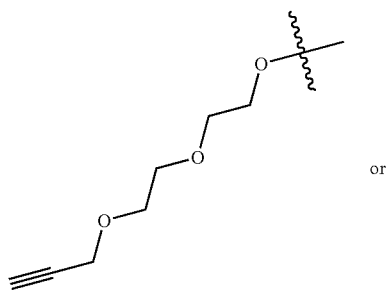
or
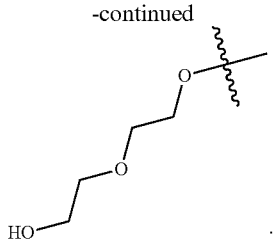
36. The compound of claim 1, wherein $M^2$ is Z.
37. The compound of claim 1, wherein $L^2$ is Z.
38. The compound of claim 1, wherein the compound has one of the following structures:
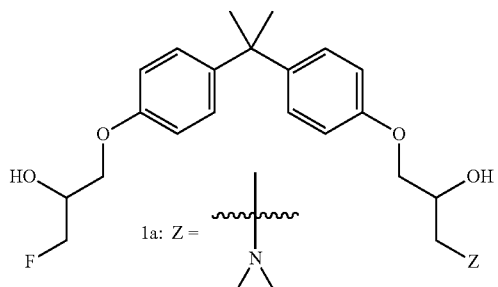
1a: Z = 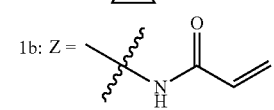
1b: Z = 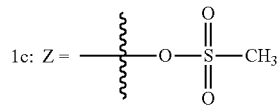
1c: Z = 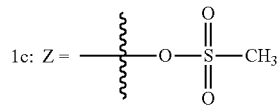
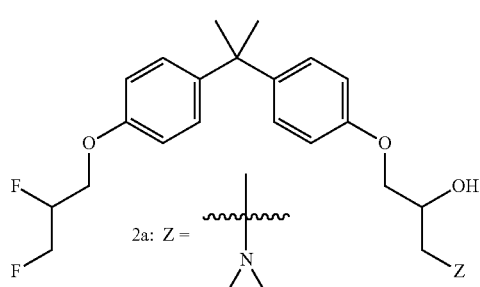
2a: Z = 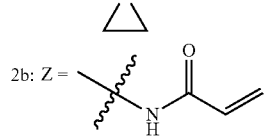
2b: Z = 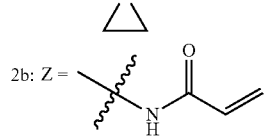
2c: Z = 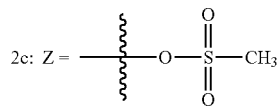
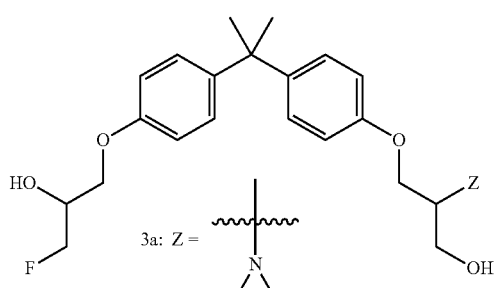
3a: Z = 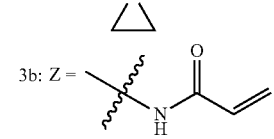
3b: Z = 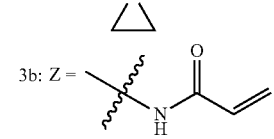
3c: Z = 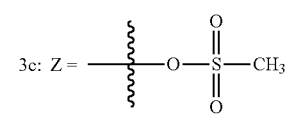
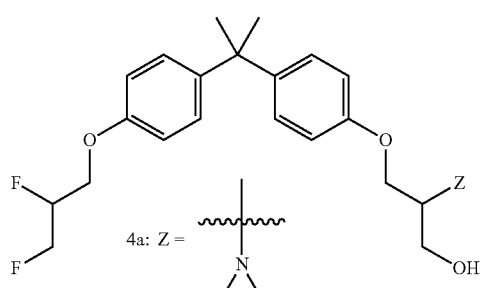
4a: Z = 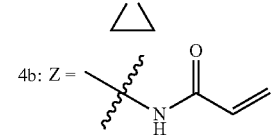
4b: Z = 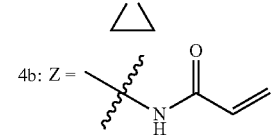
4c: Z = 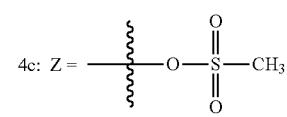

-continued
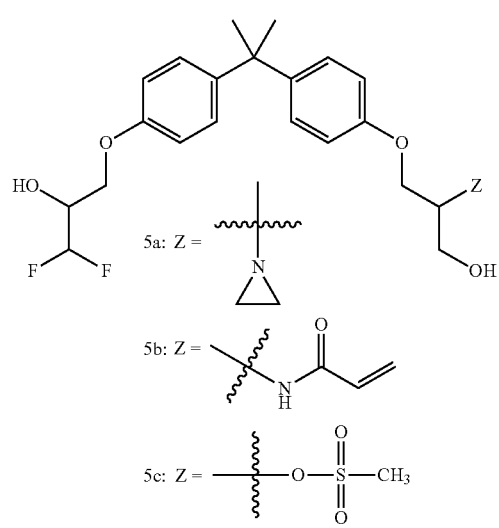
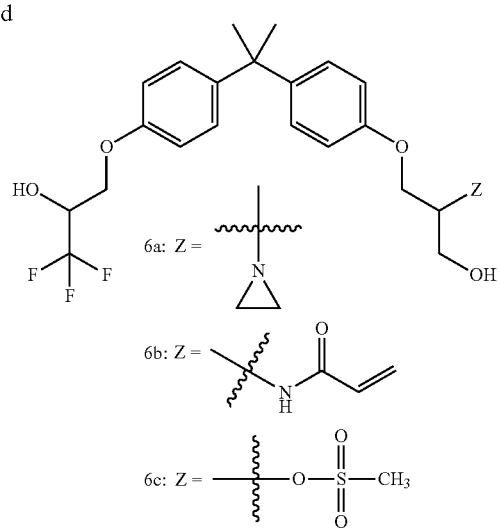
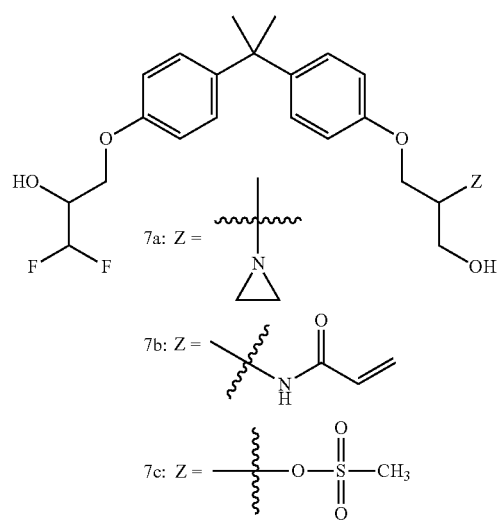
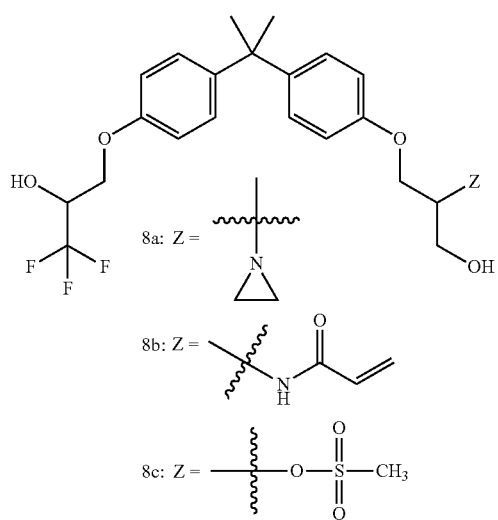
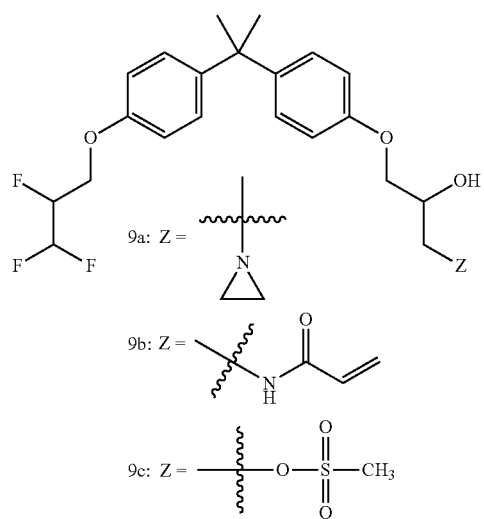
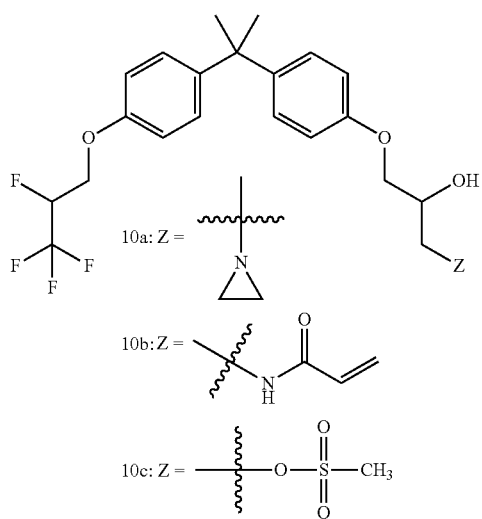

-continued
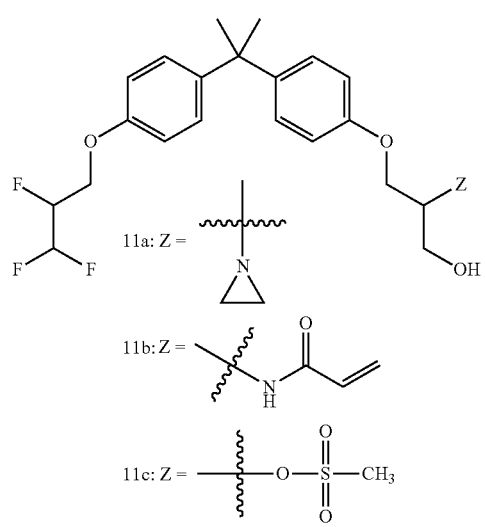
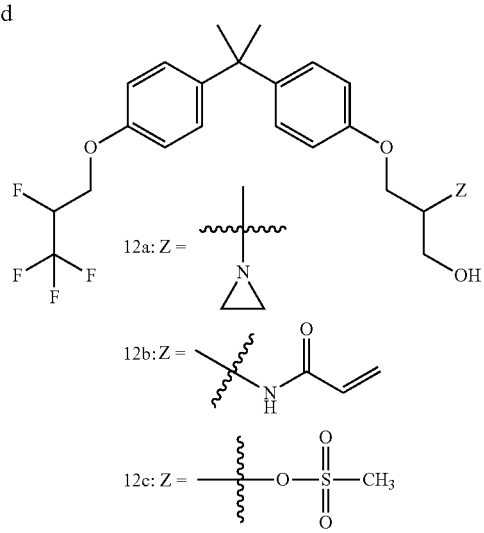
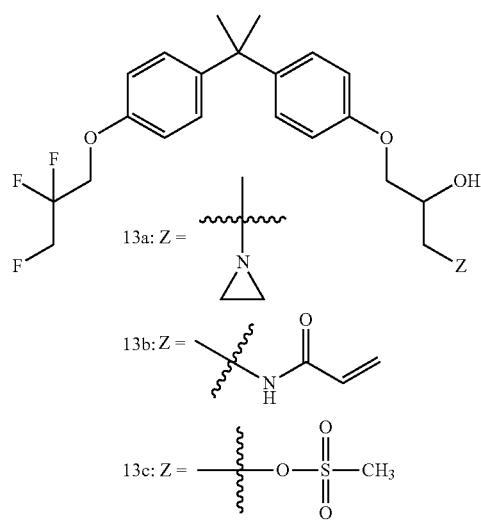
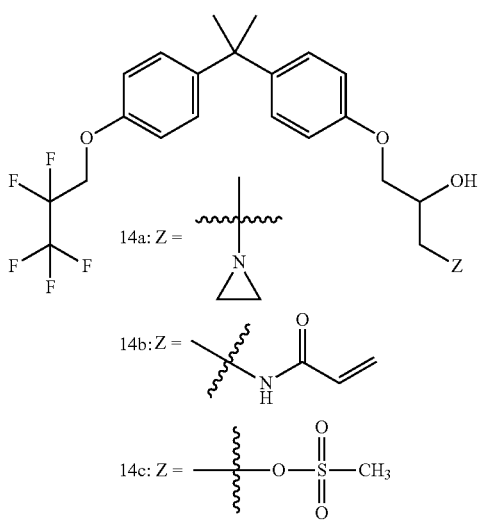
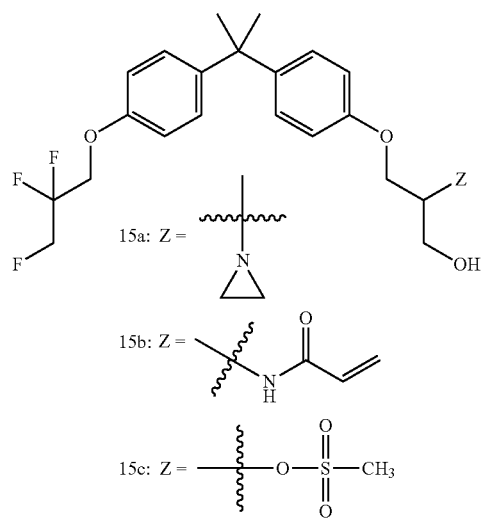
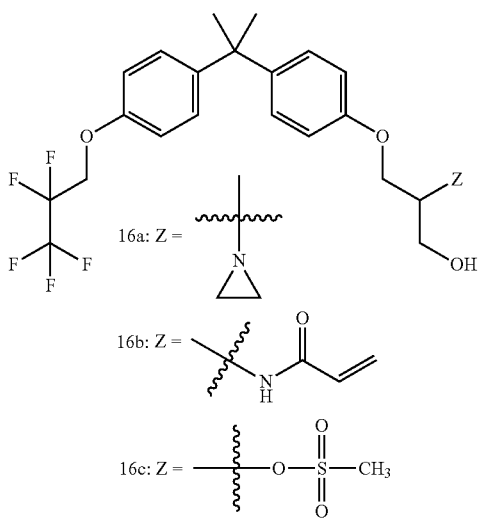

195
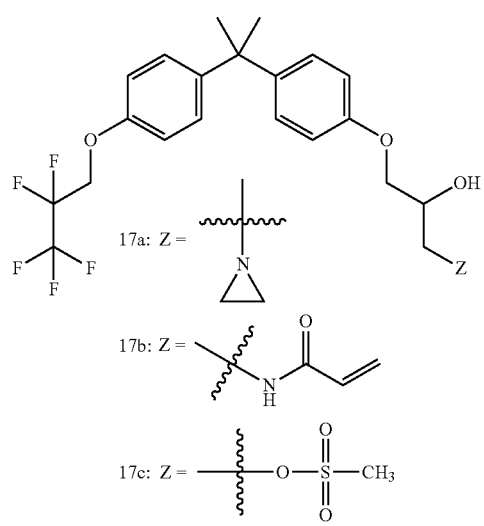
196
-continued
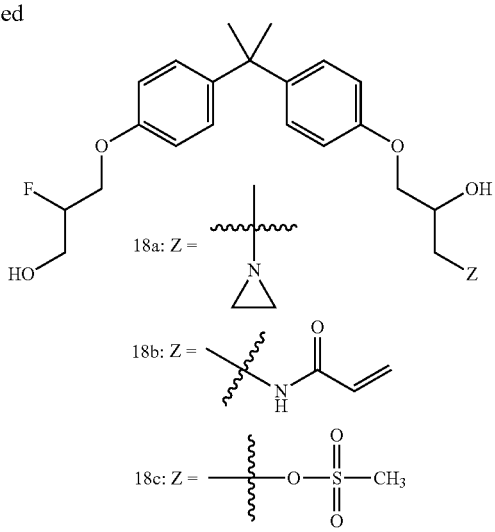
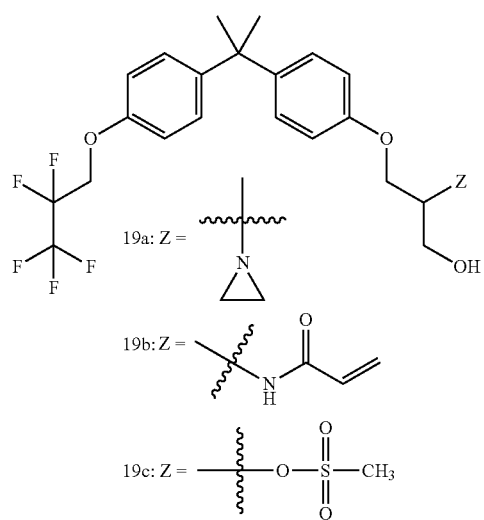
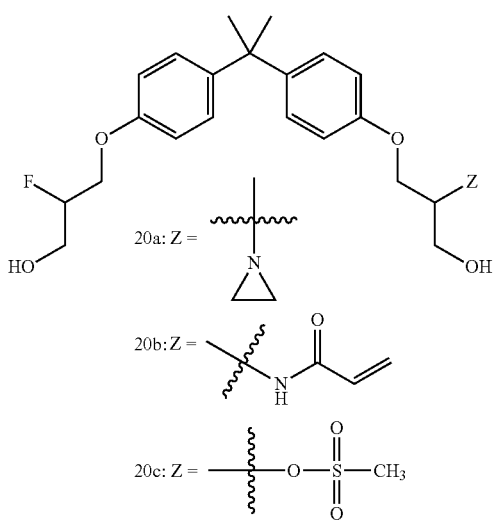
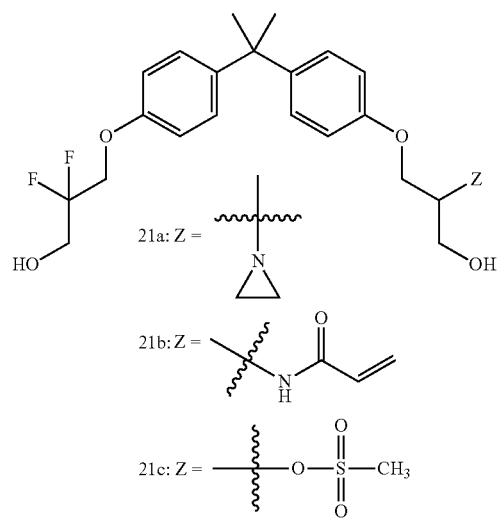
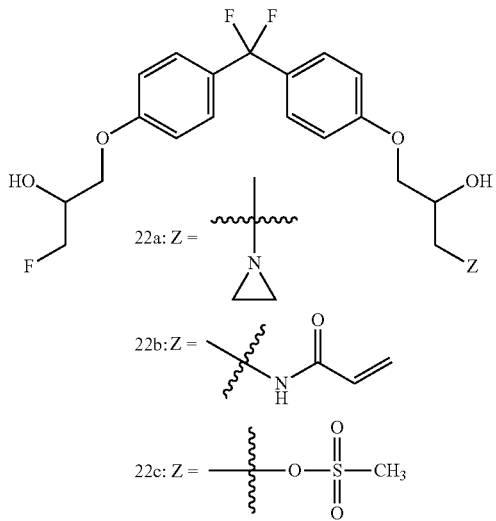

-continued
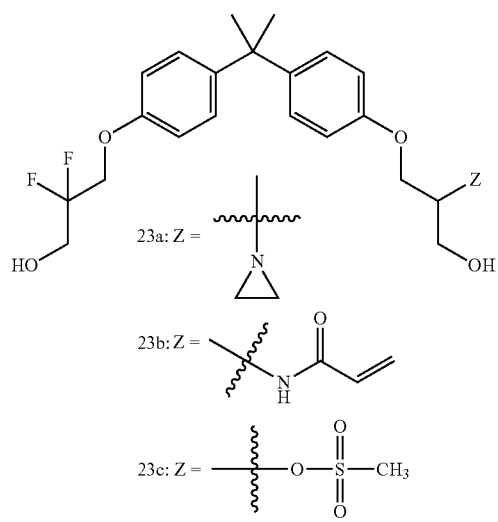
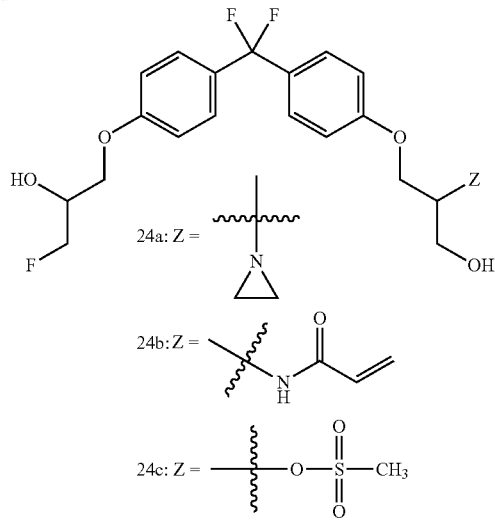
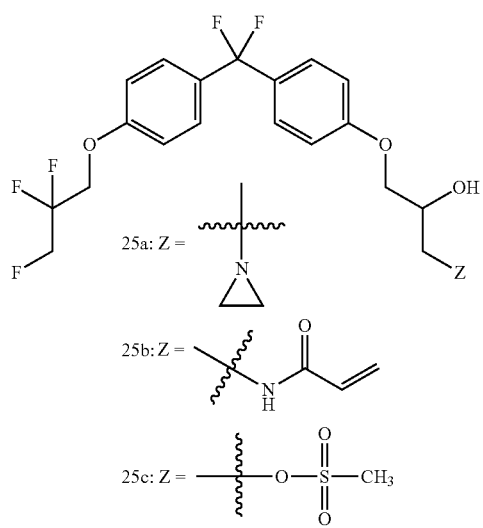
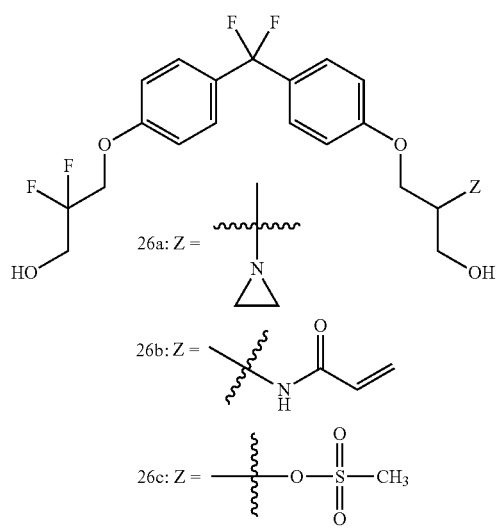
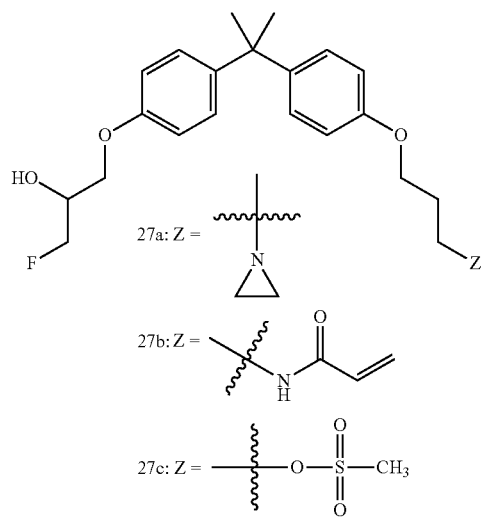
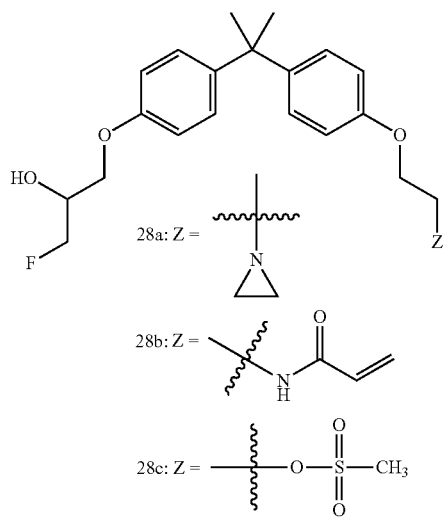

199
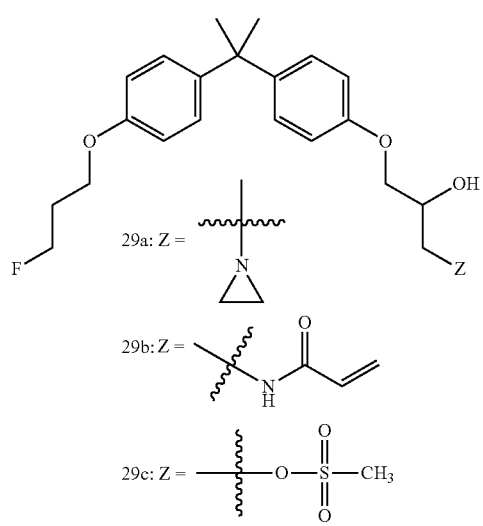
200
-continued
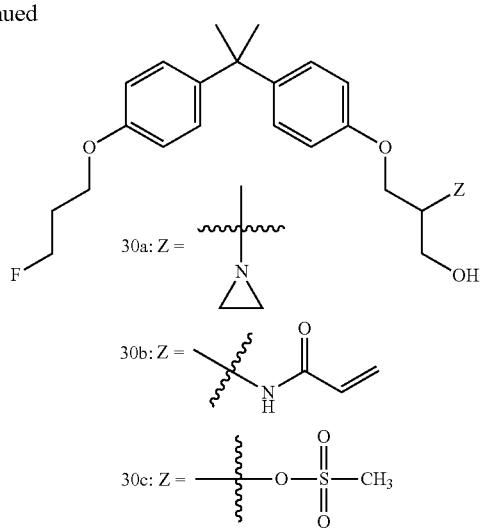
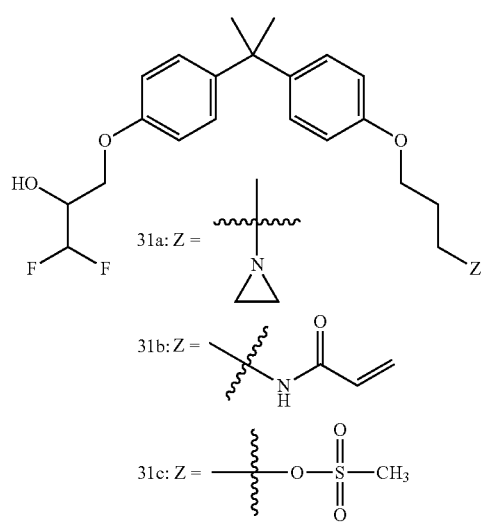
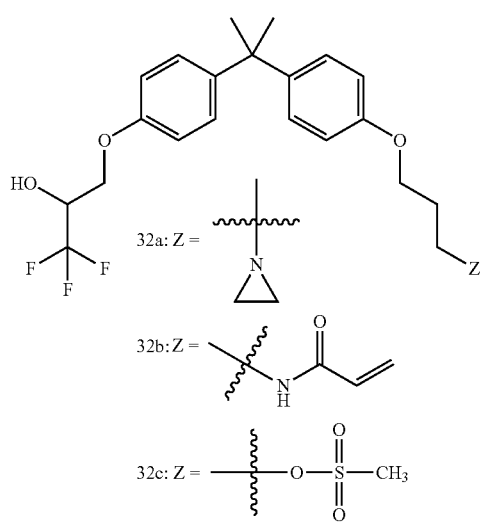
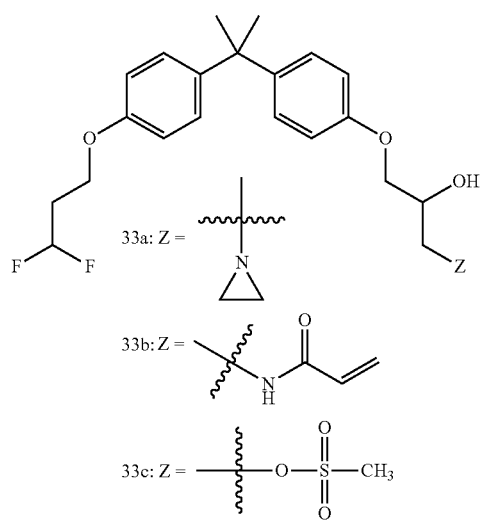
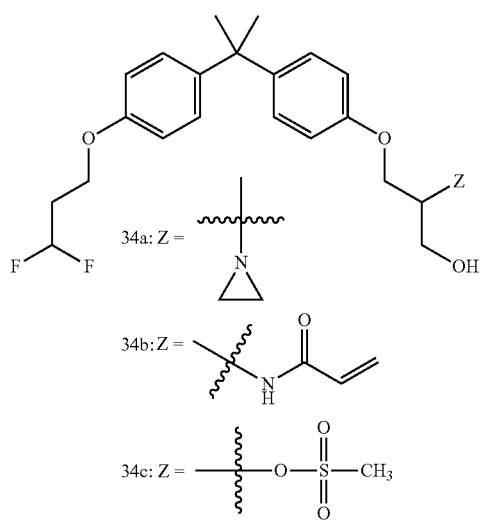

201 202
-continued
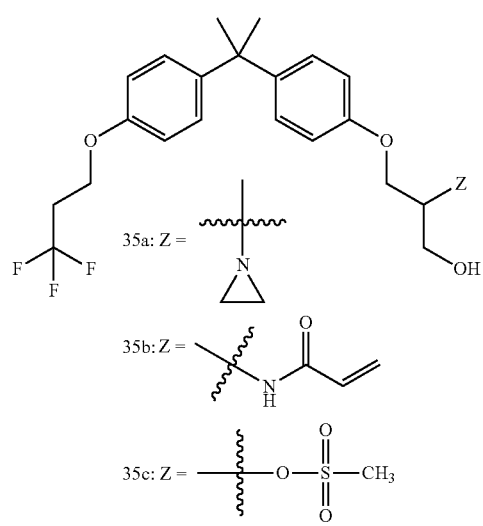
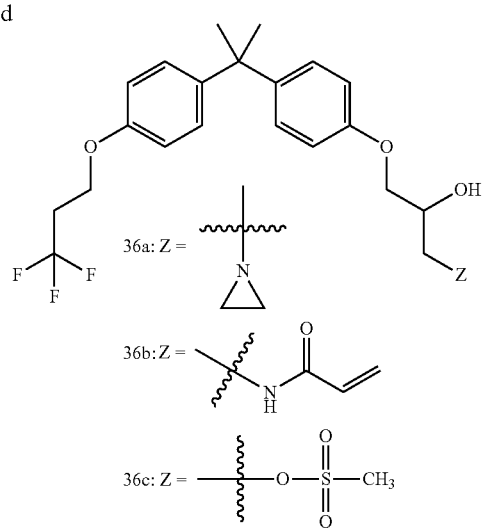
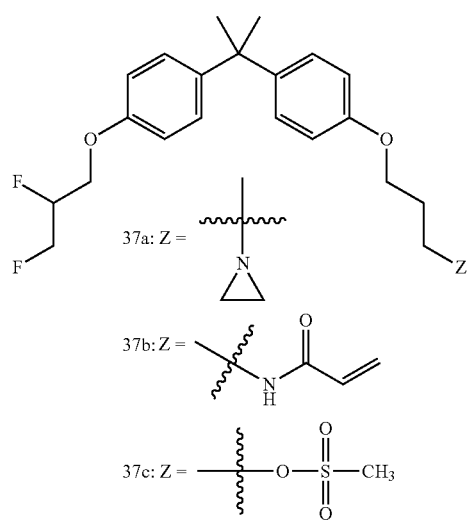
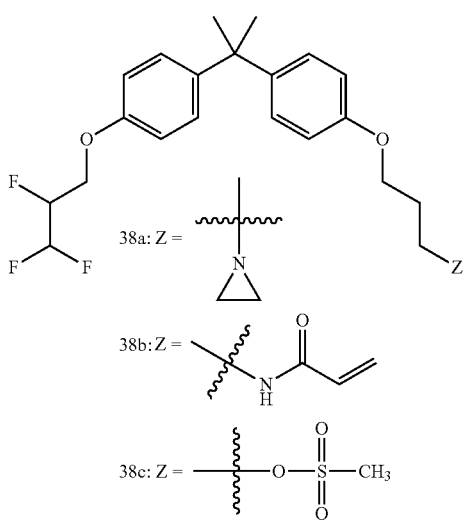
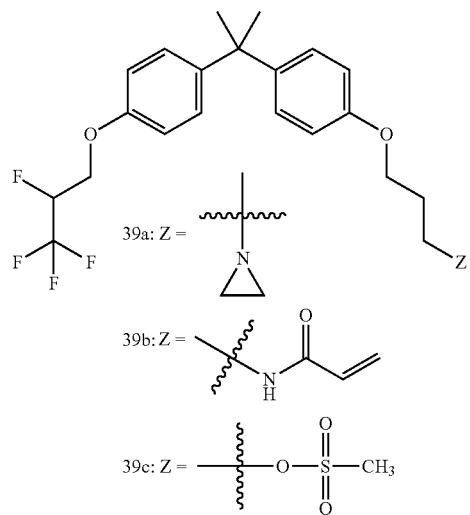
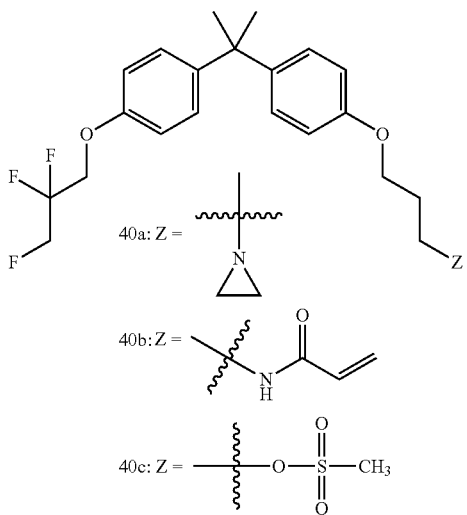

-continued
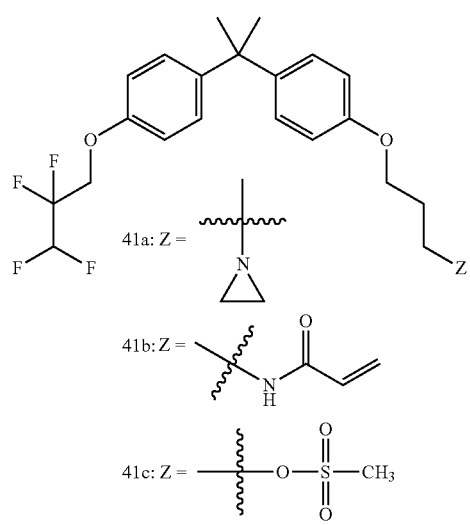
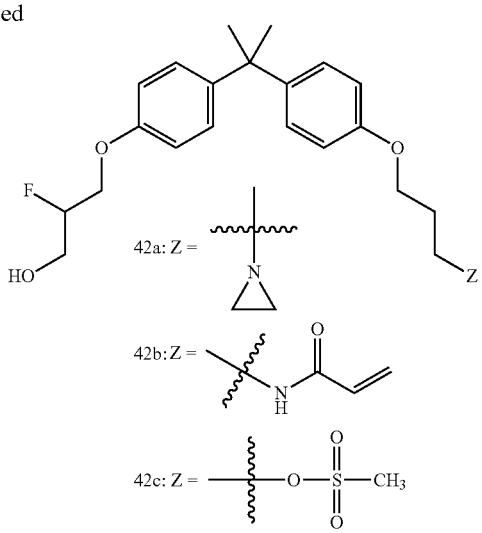
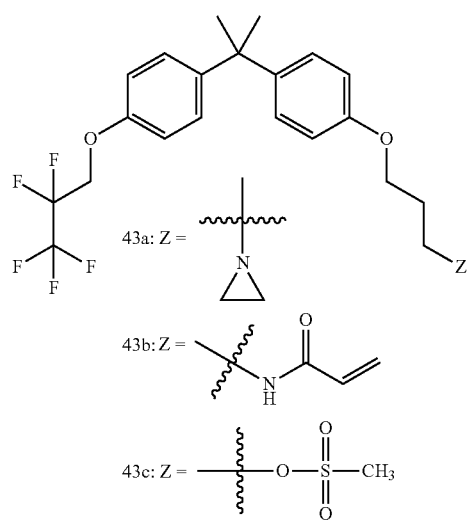
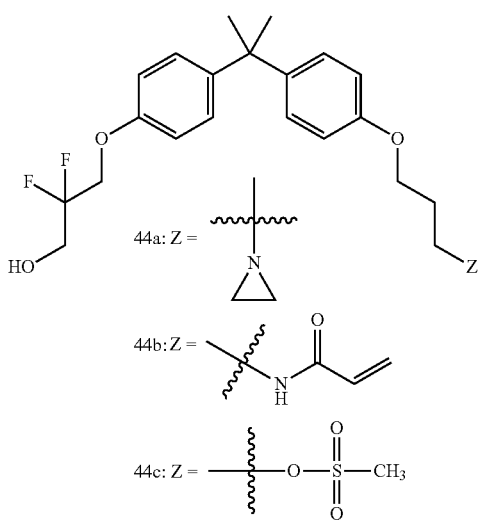
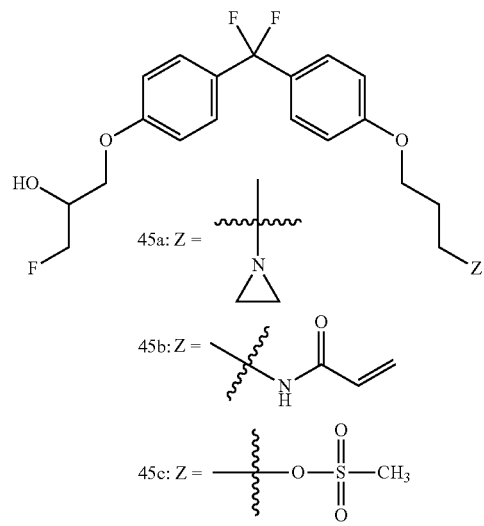
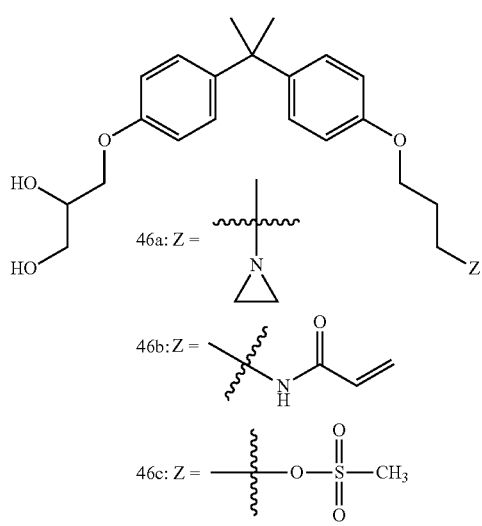

205 206
-continued
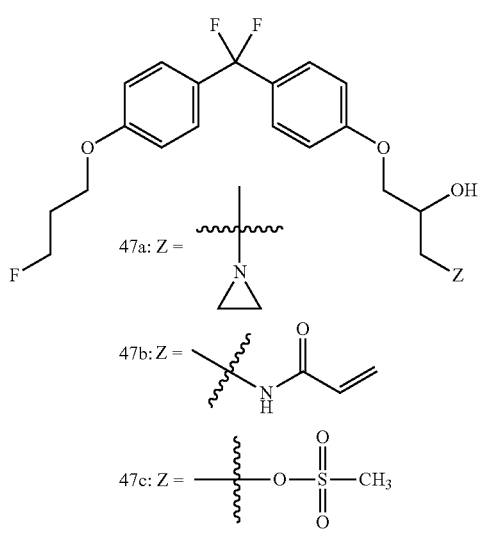
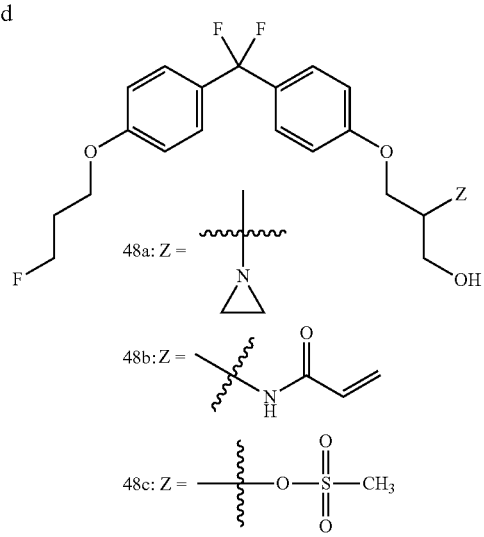
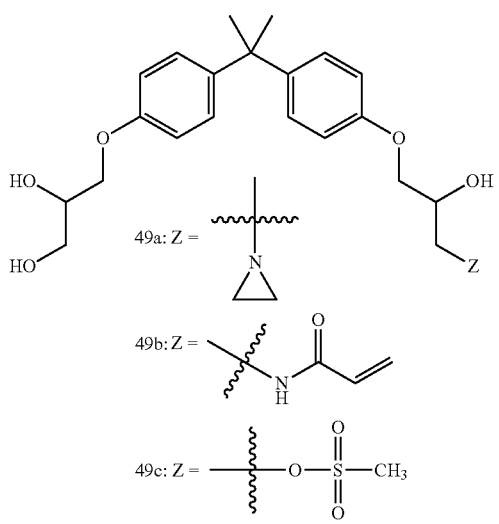
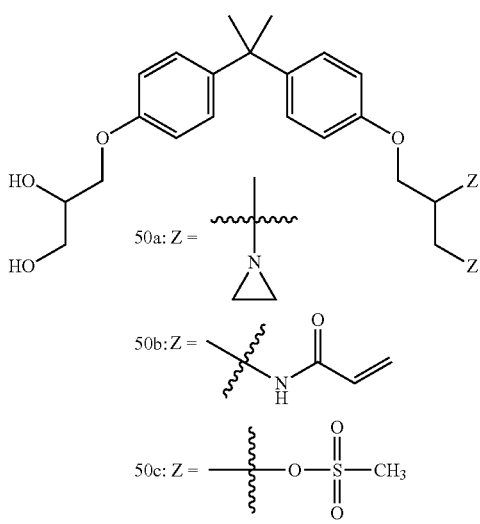
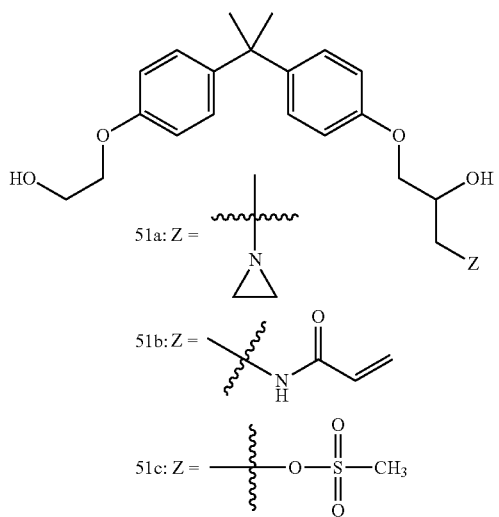
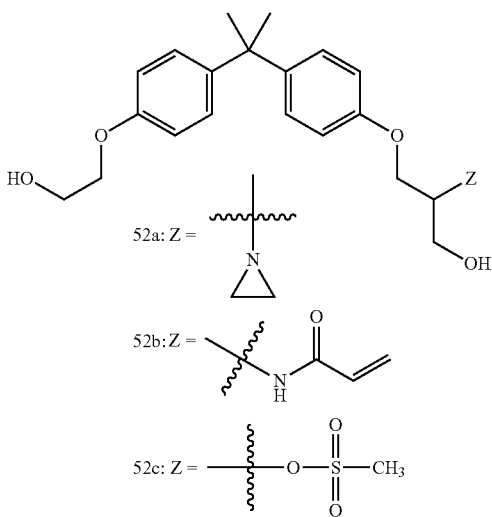

-continued
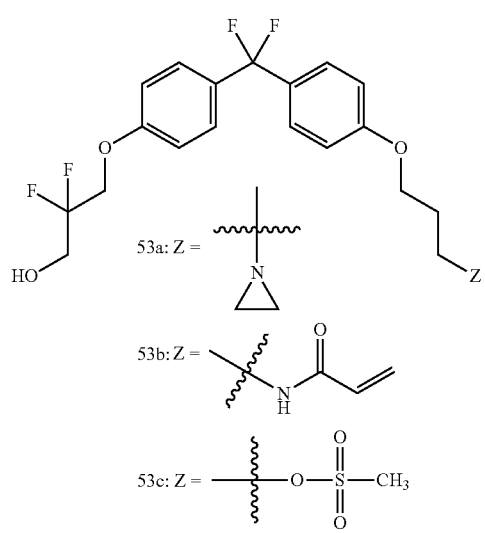
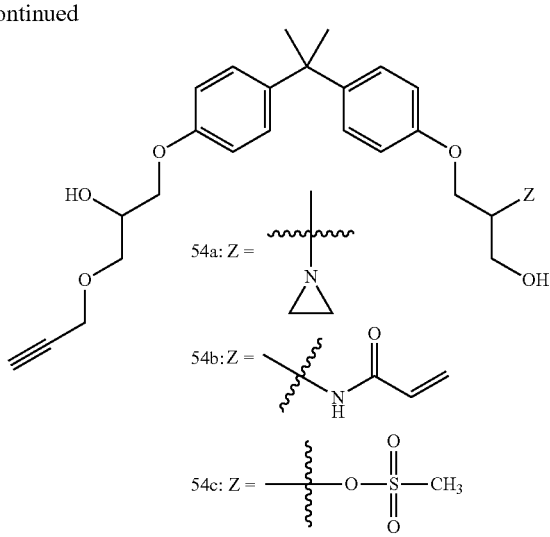
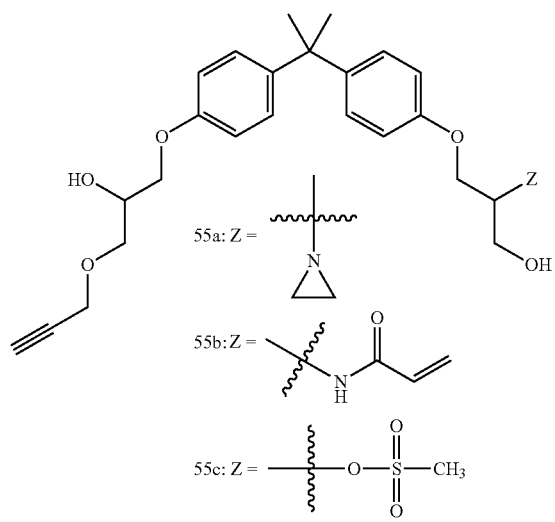
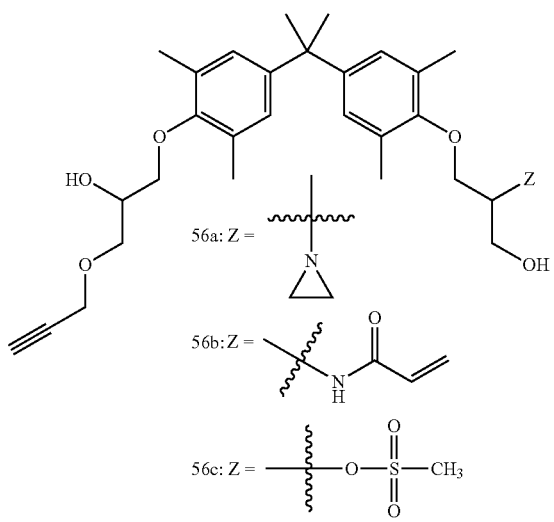
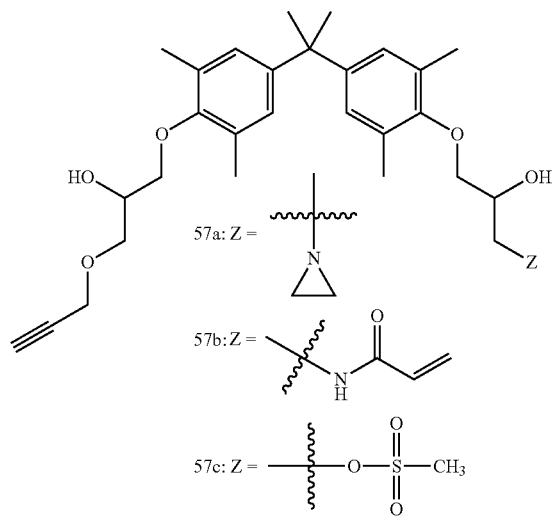
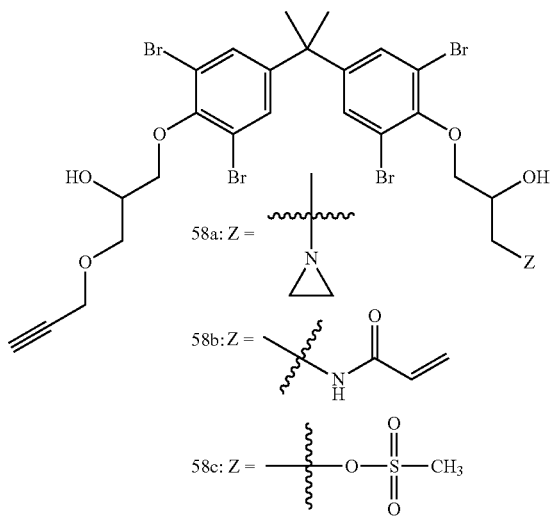

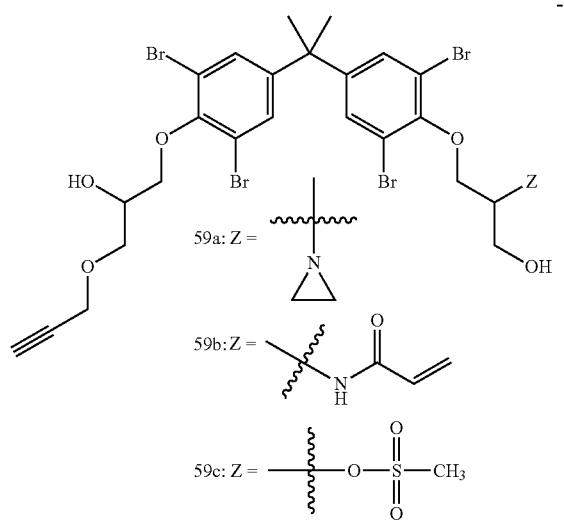
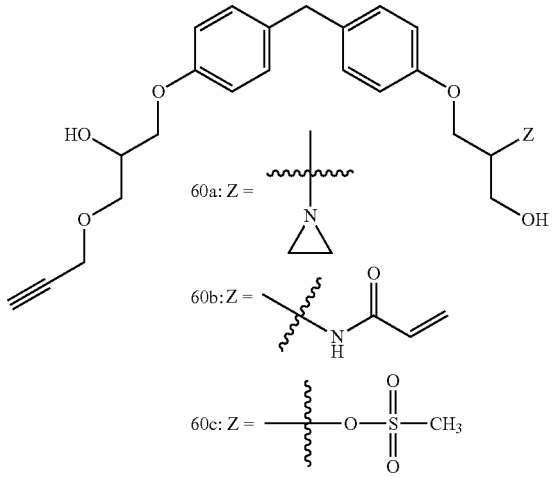
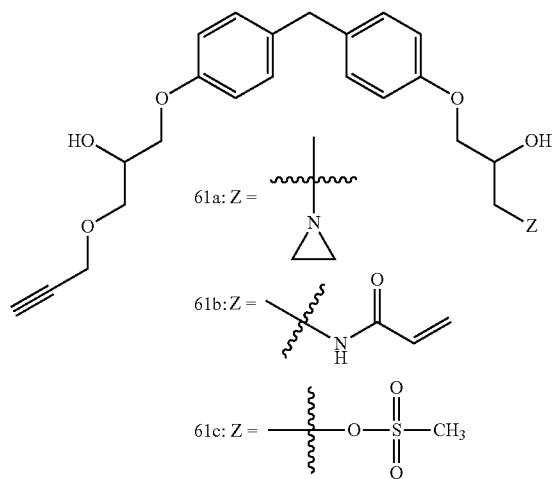
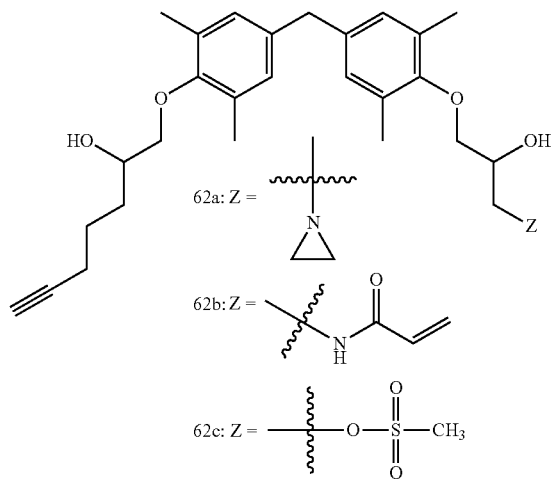
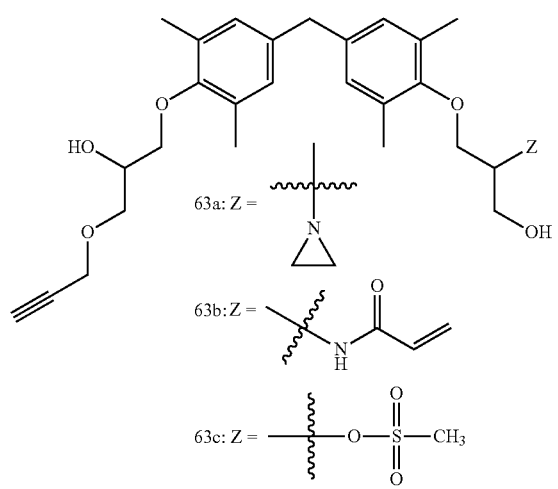
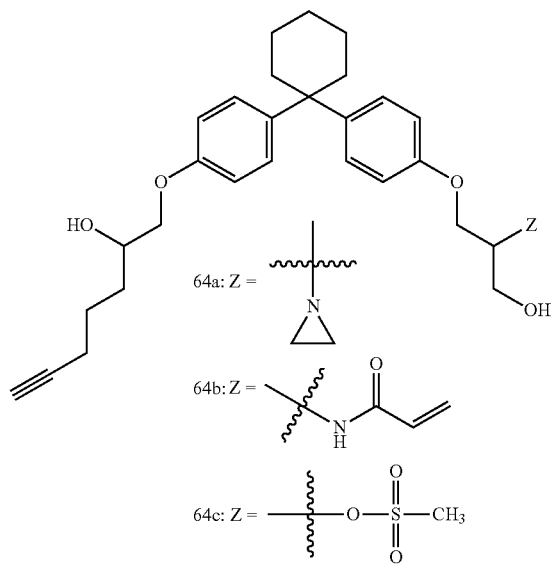

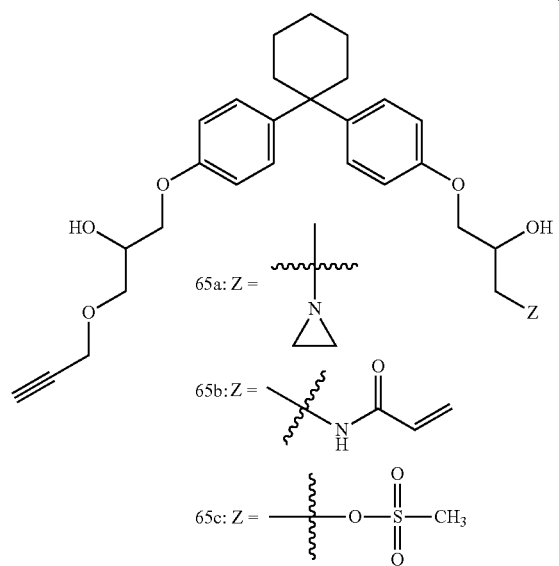
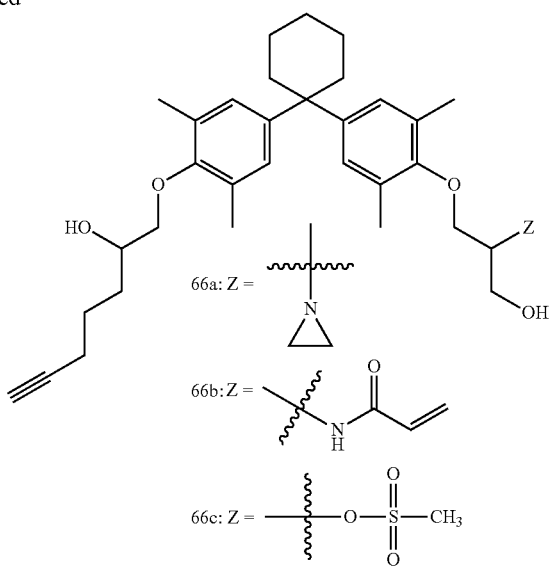
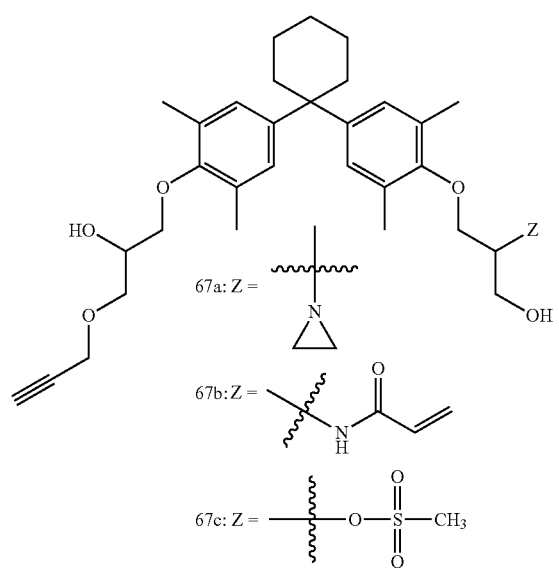
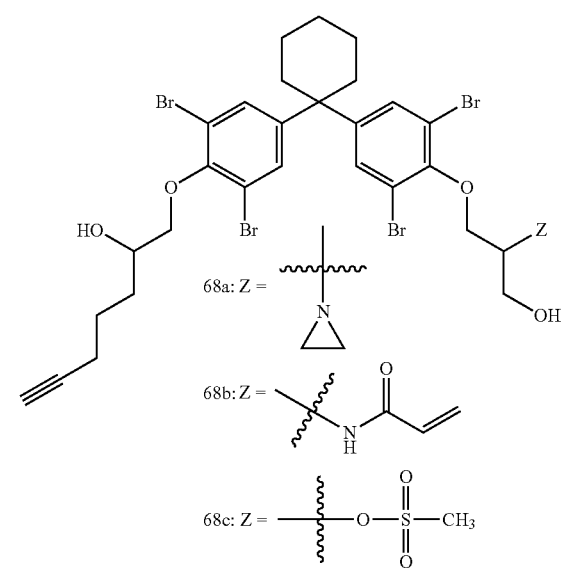
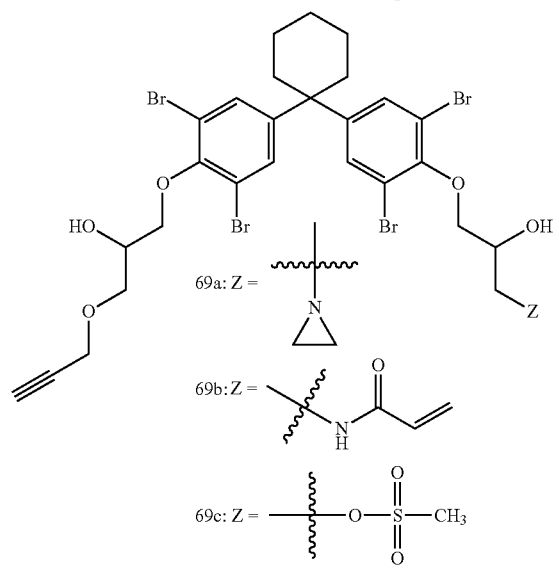
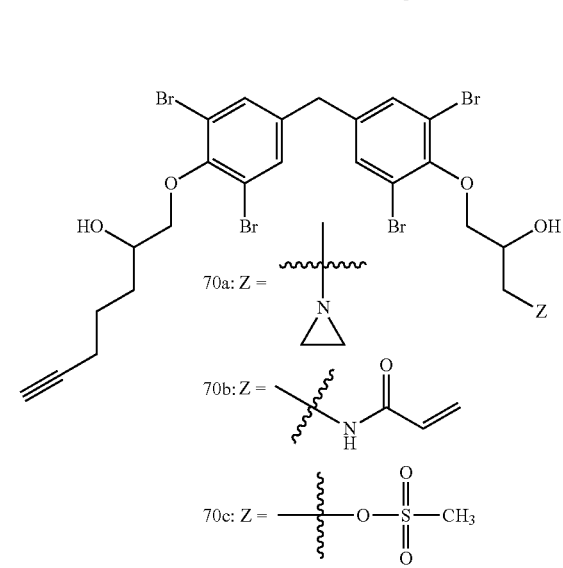

213
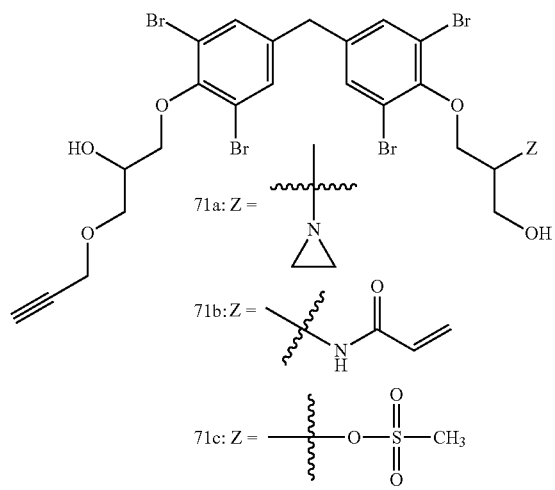
214
-continued
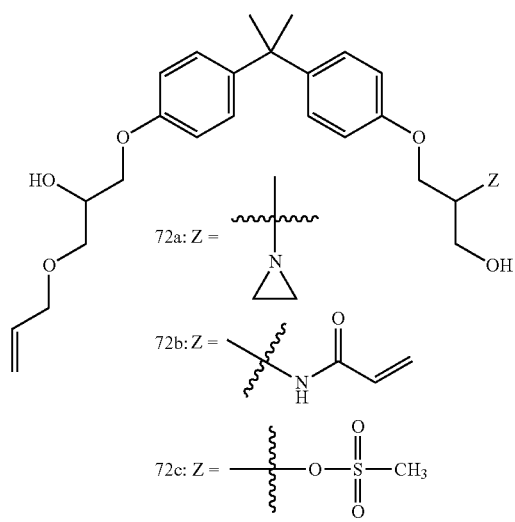
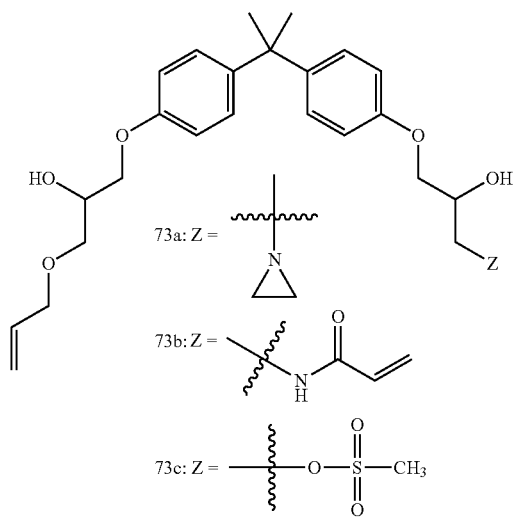
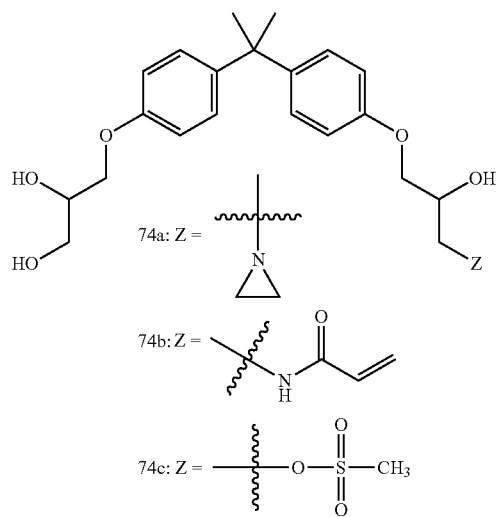
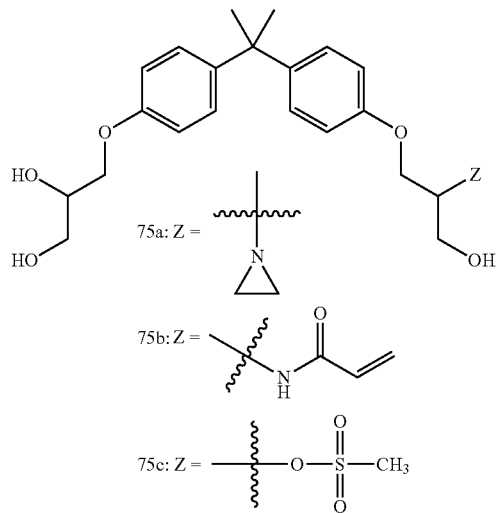
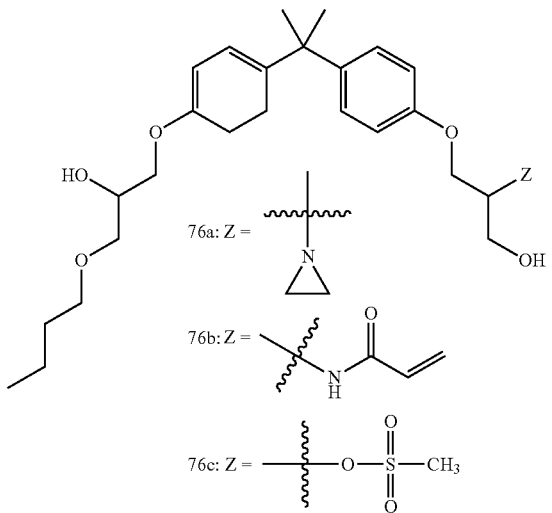

-continued
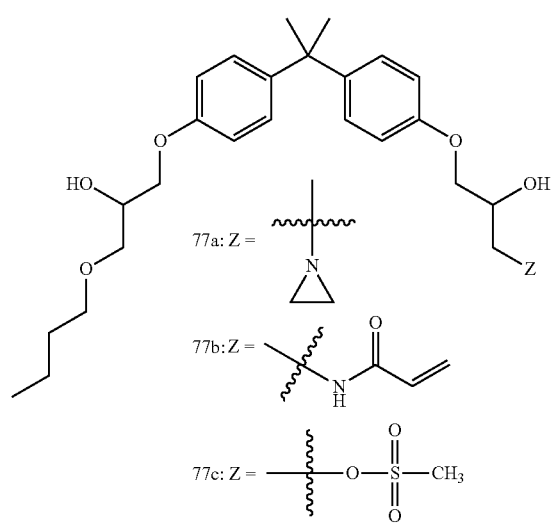
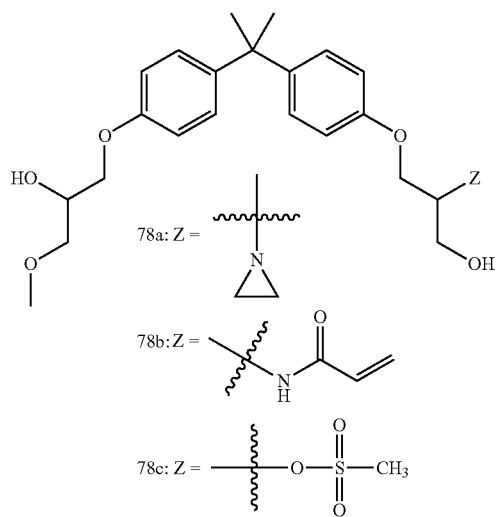
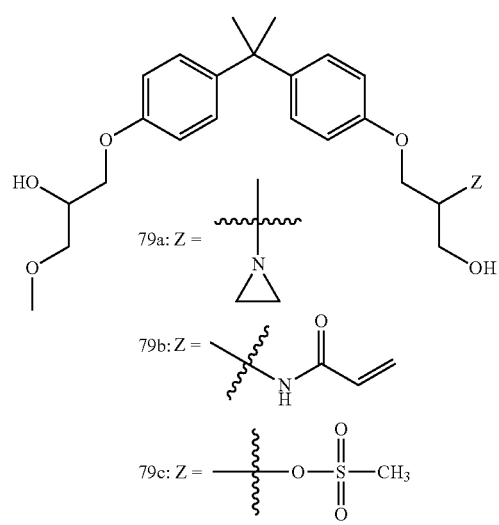
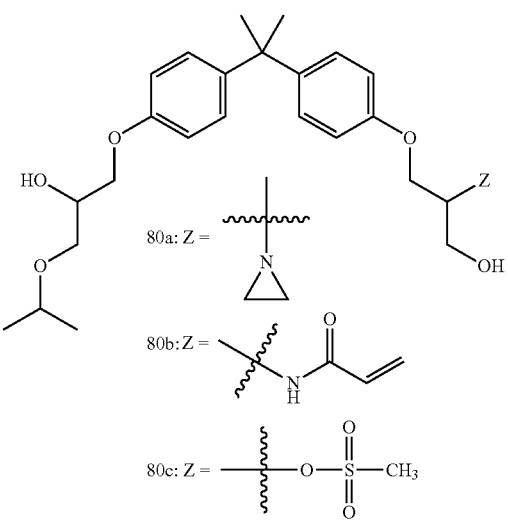
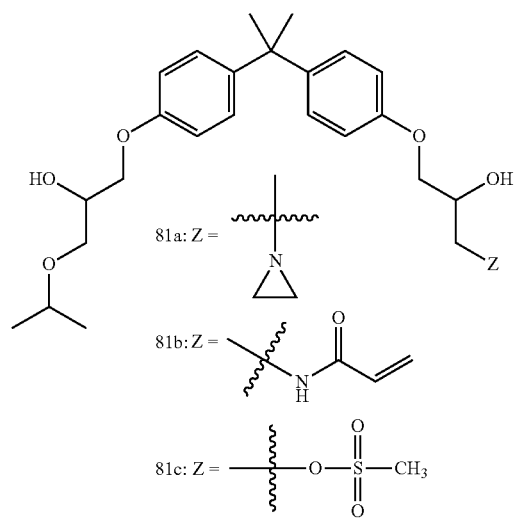
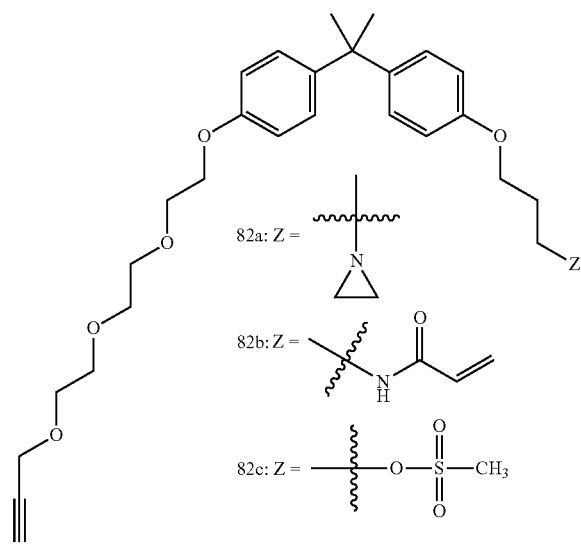

217               218
-continued
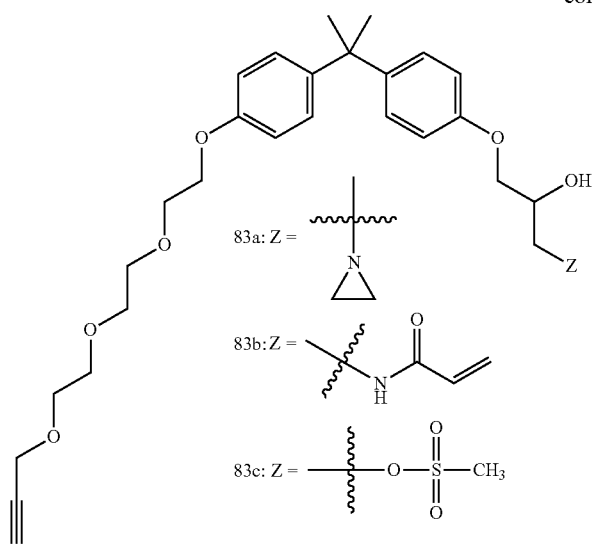
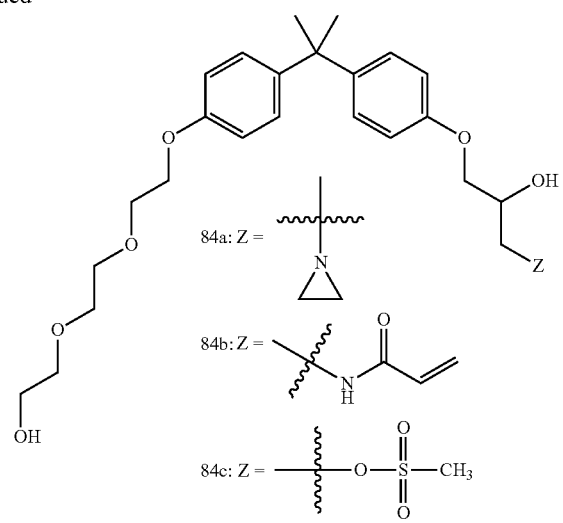
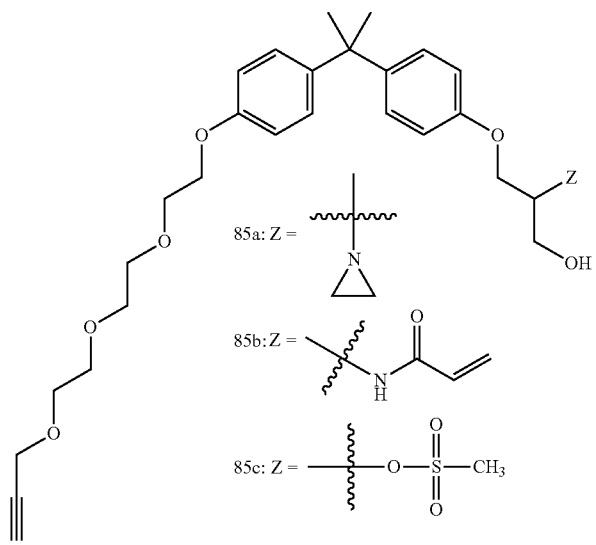
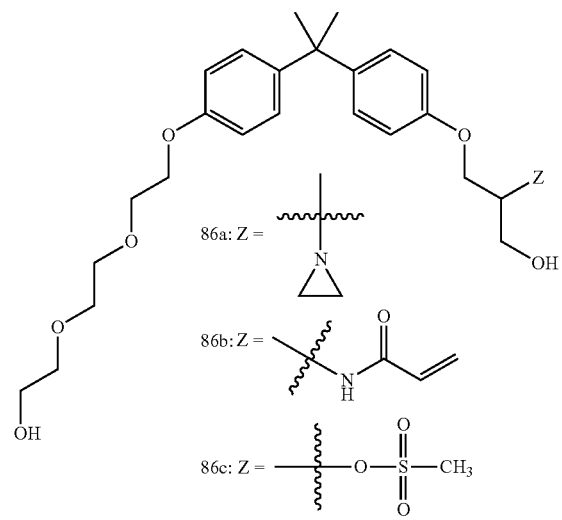
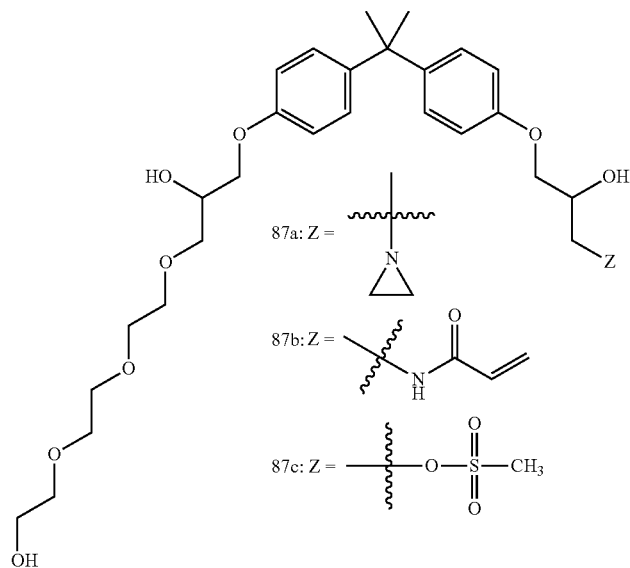

219
220
-continued
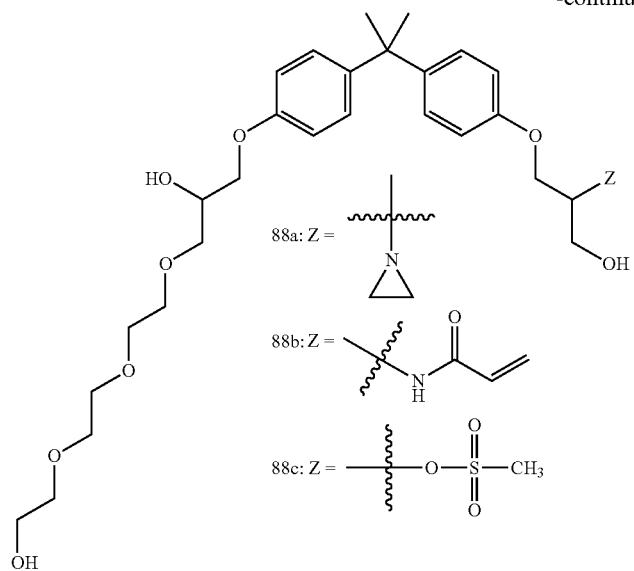
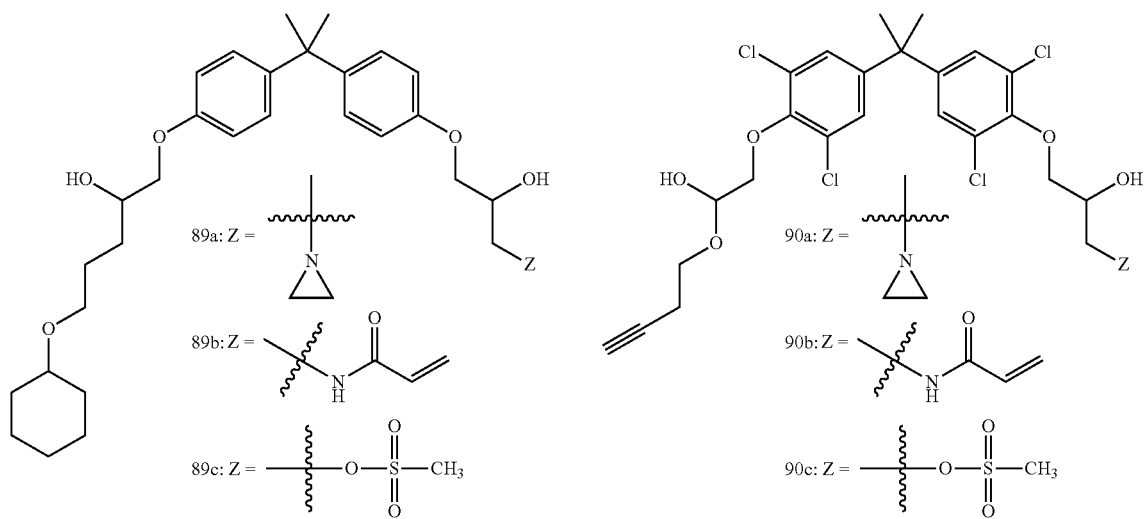
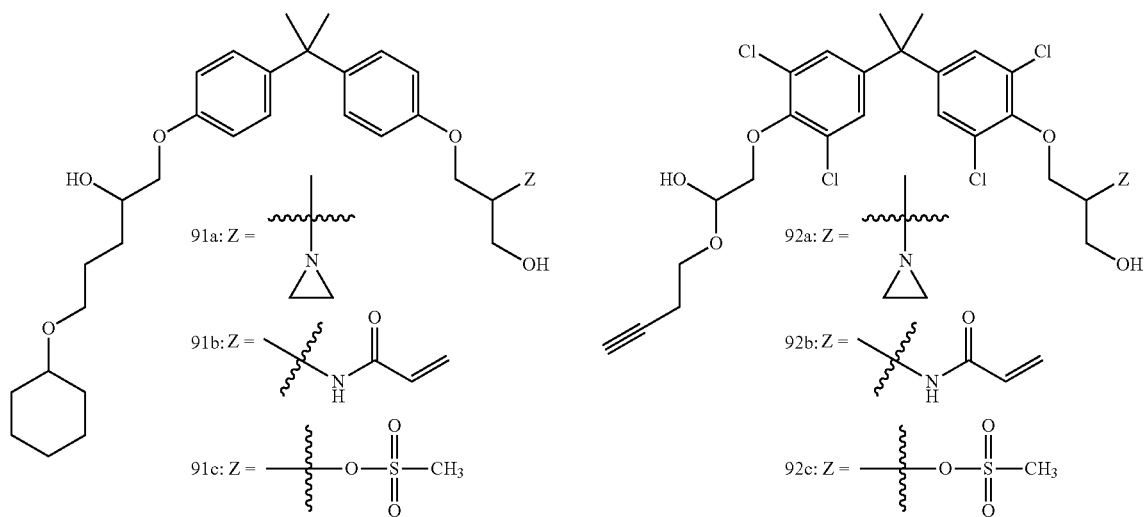

-continued
221
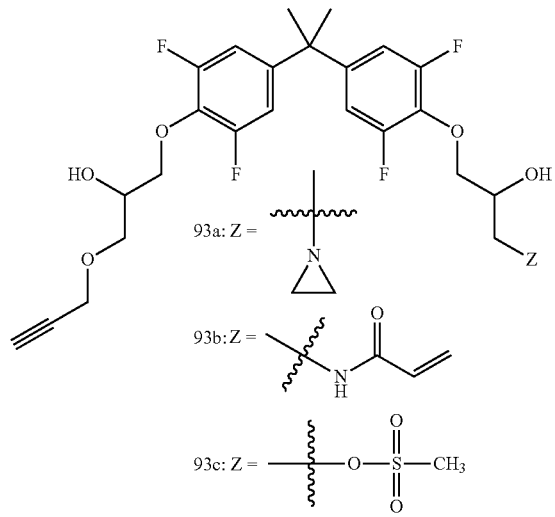
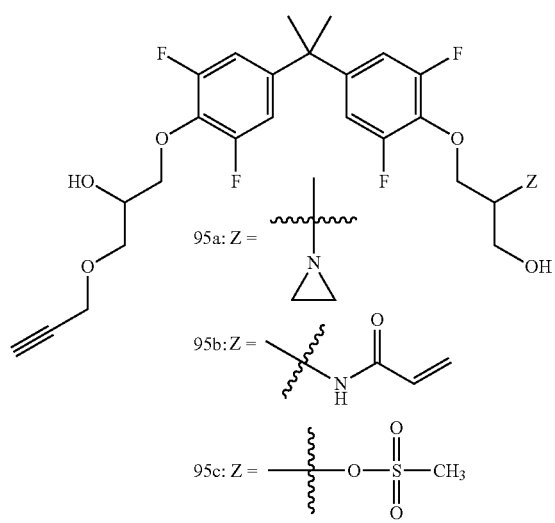
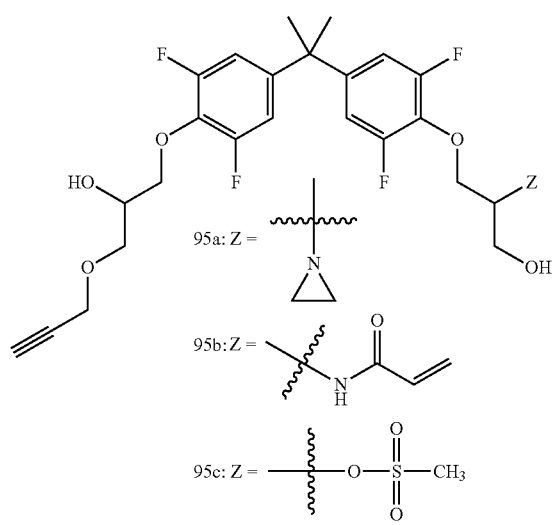
222
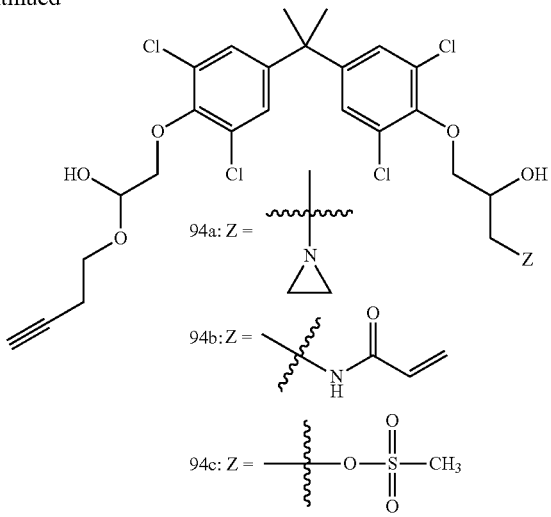
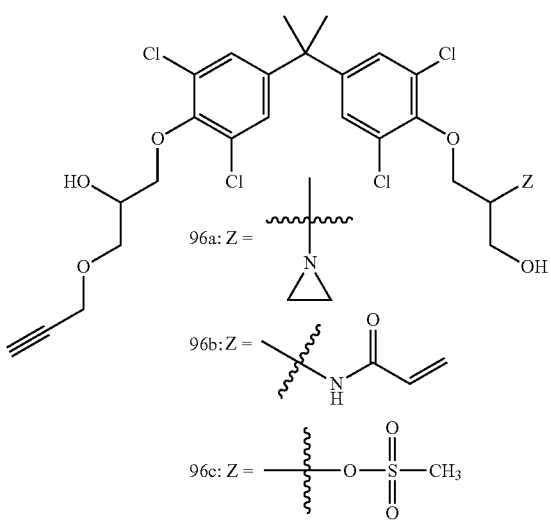
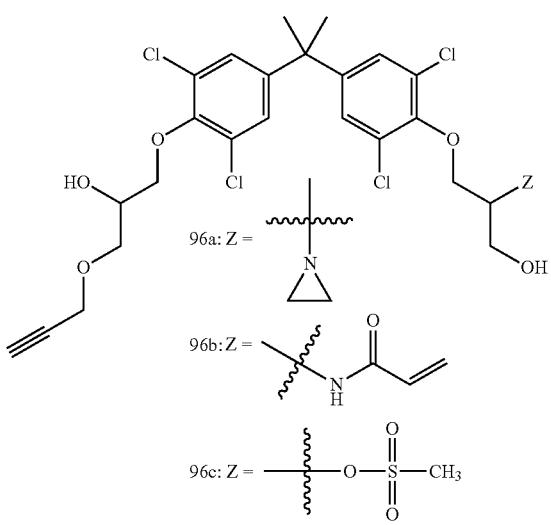

-continued
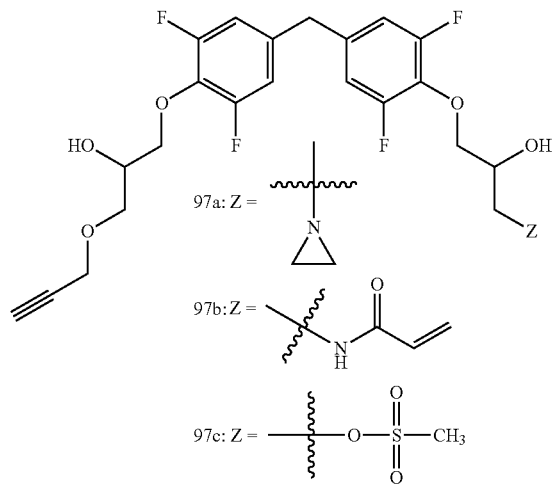
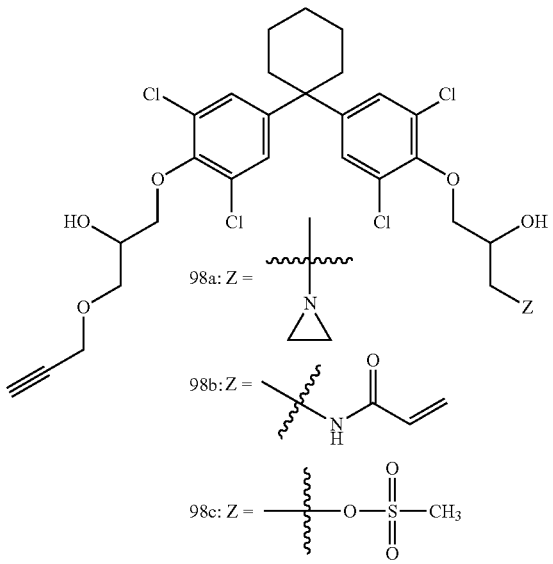
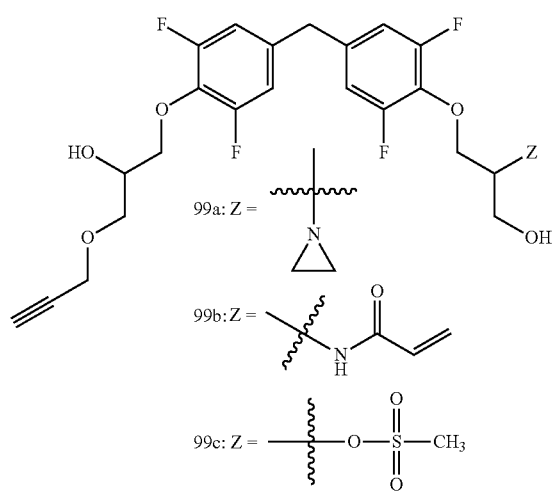
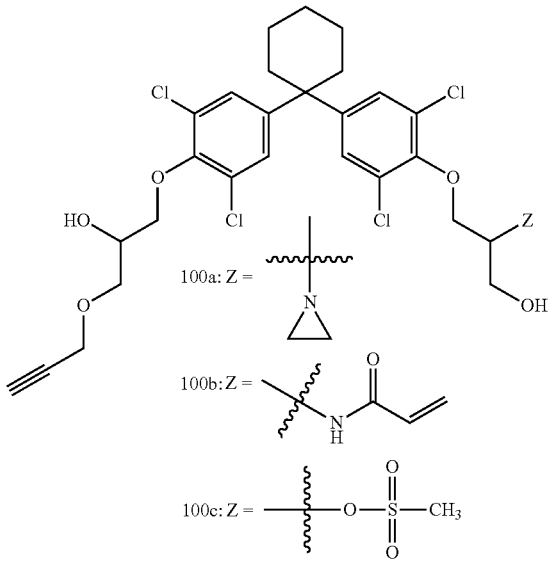
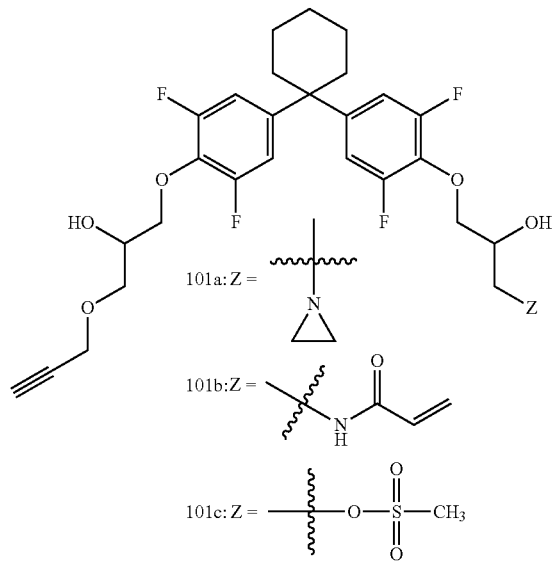
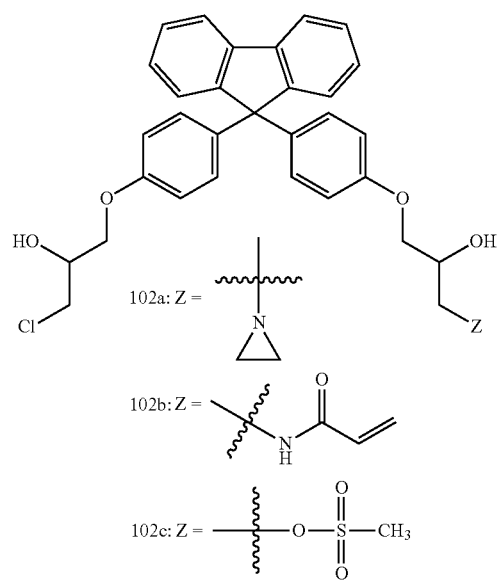

225
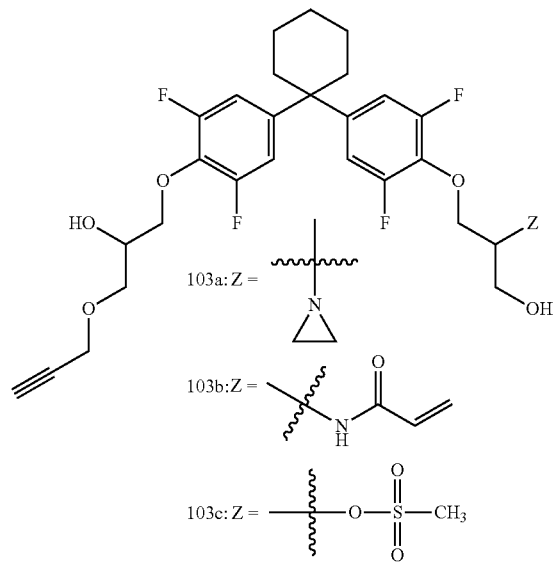
226
-continued
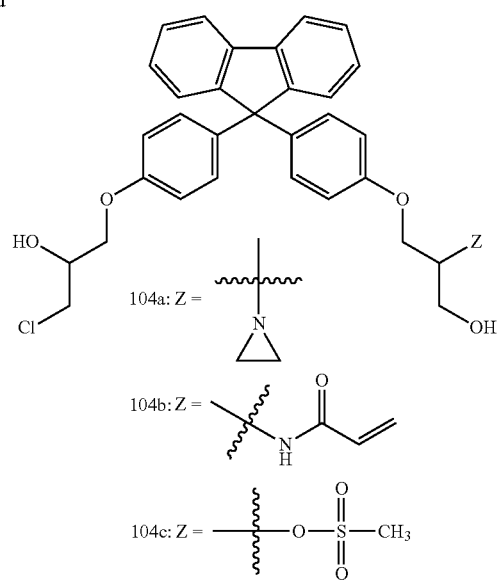
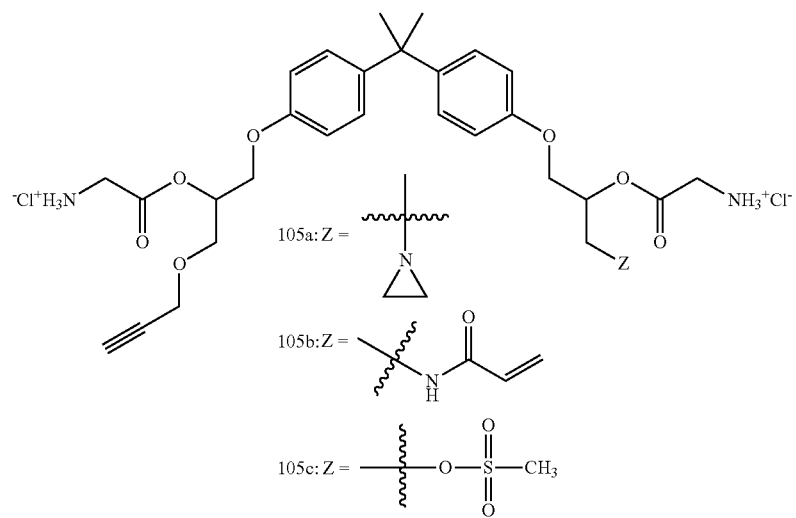
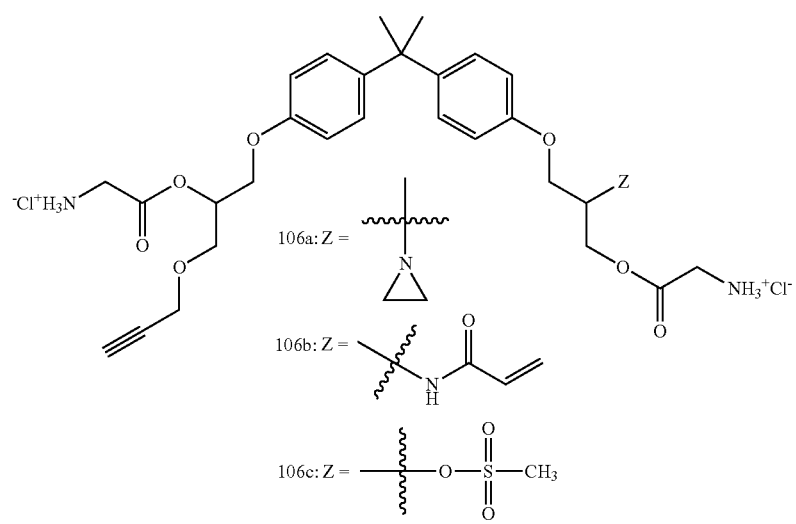

-continued
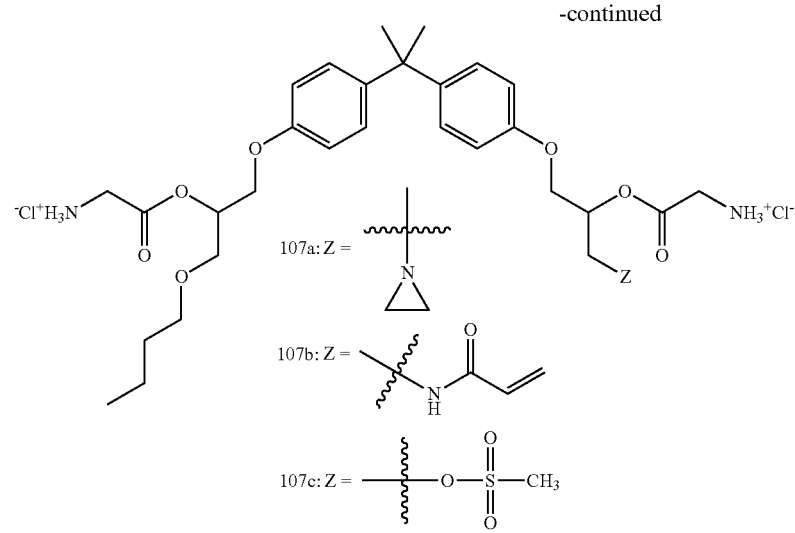
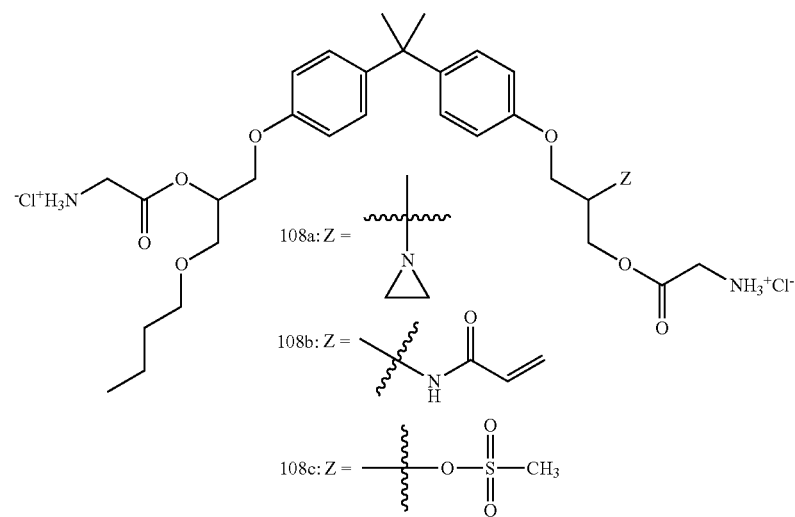
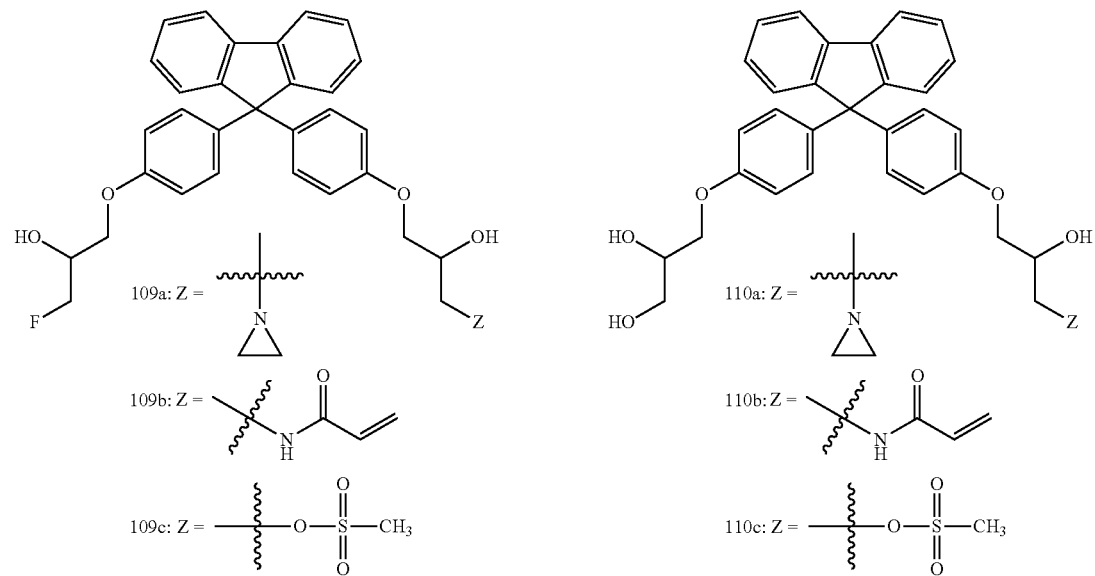

229
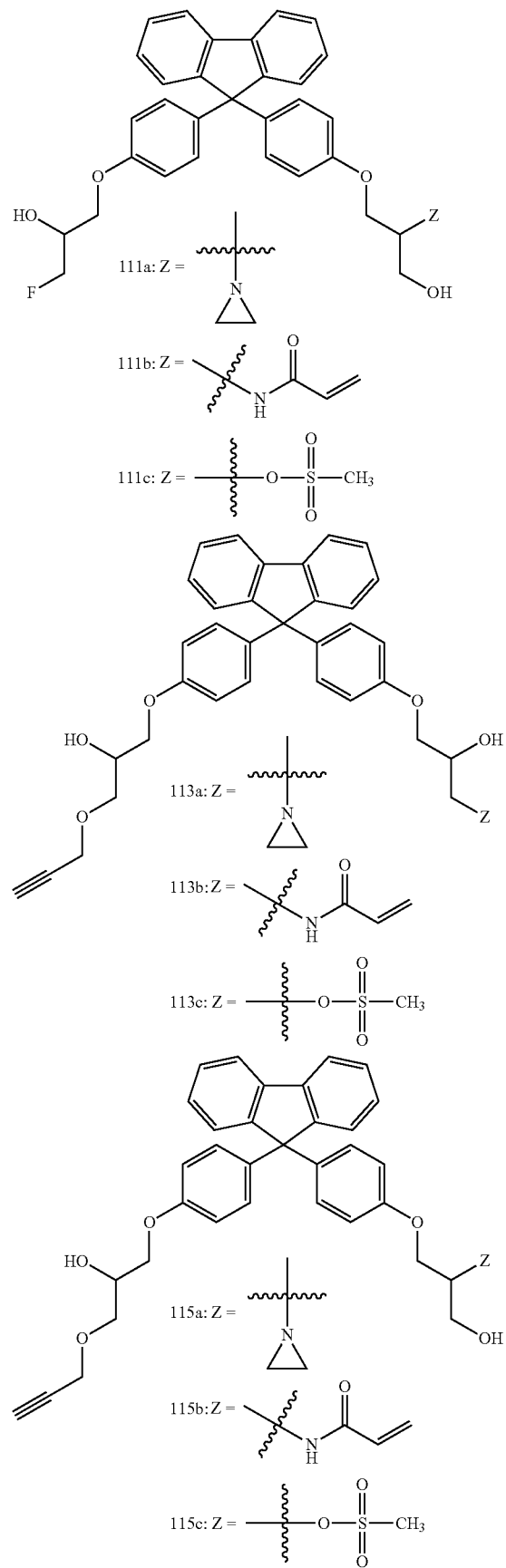
230
-continued
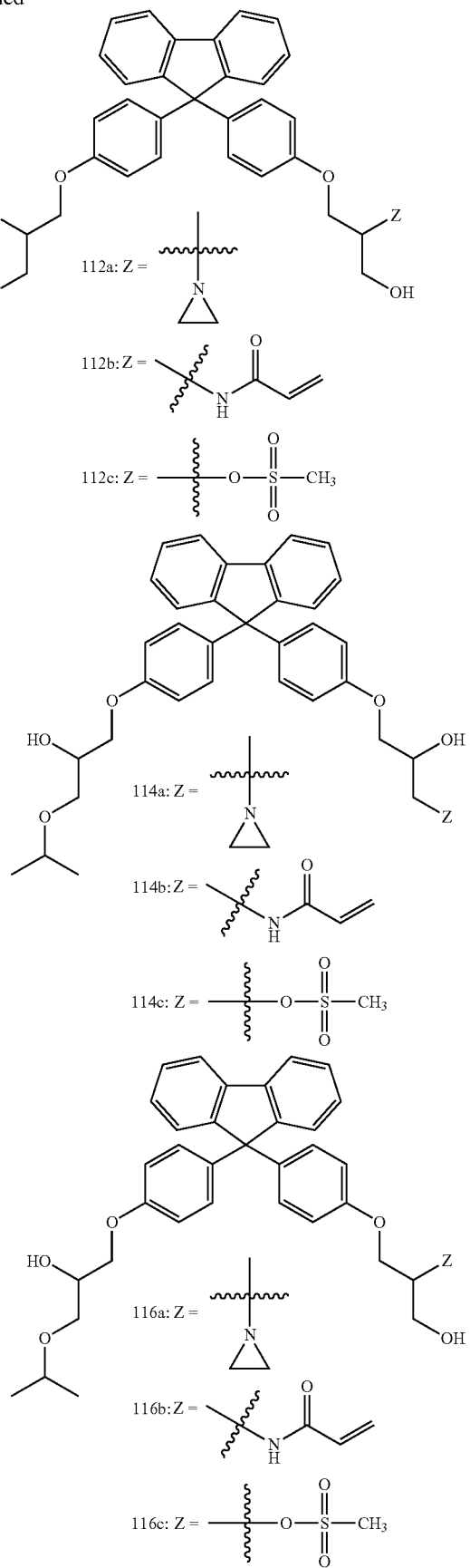

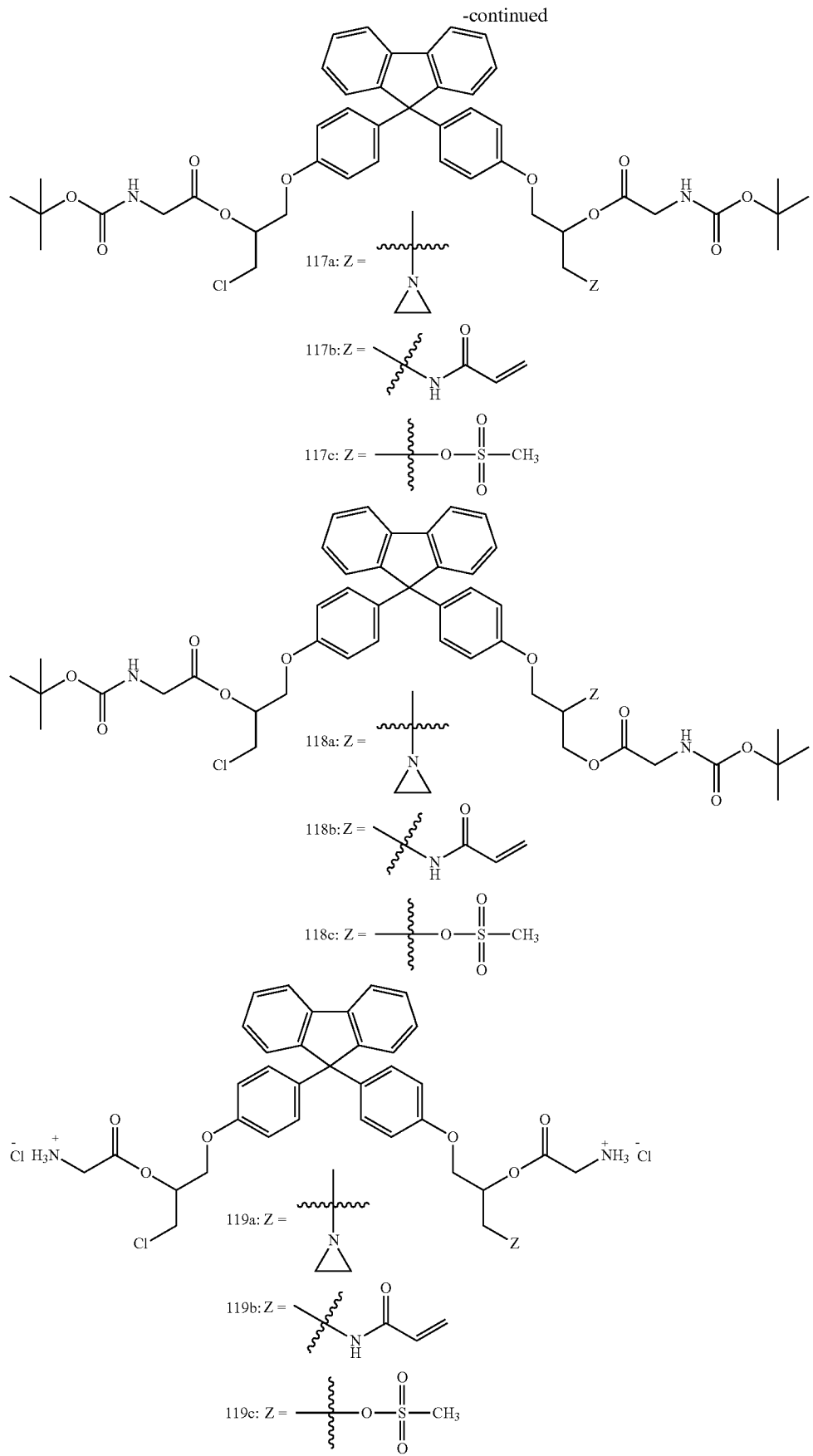

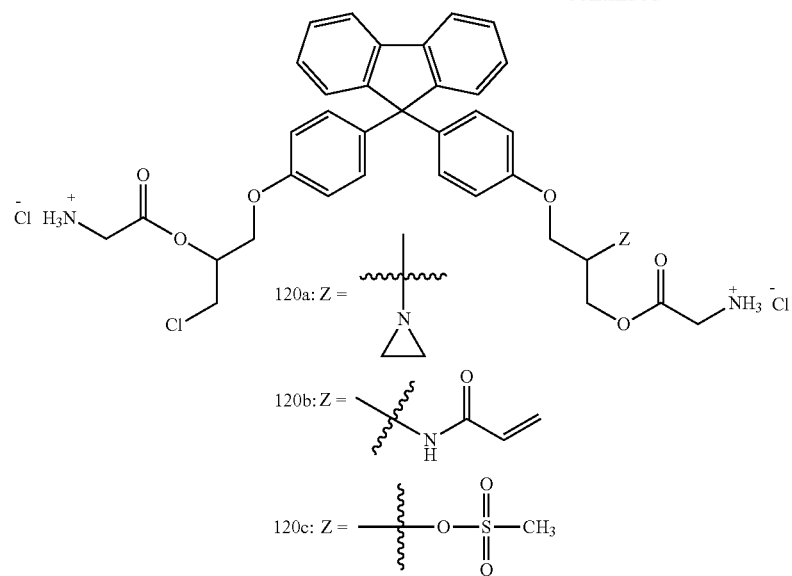
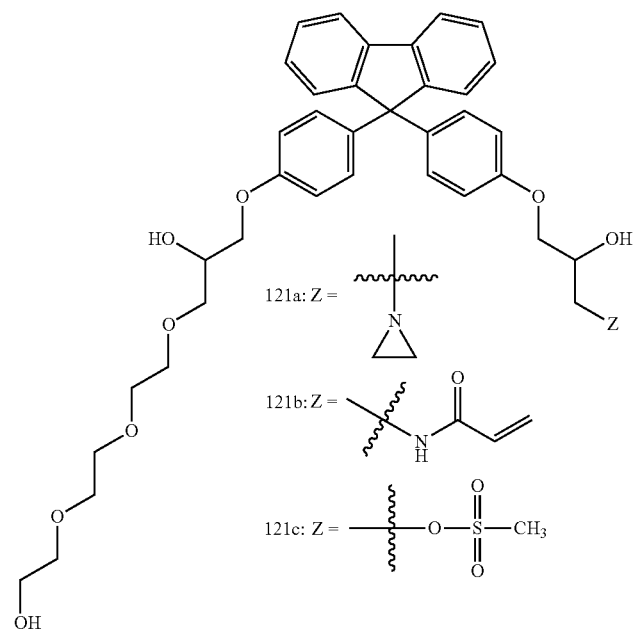

-continued
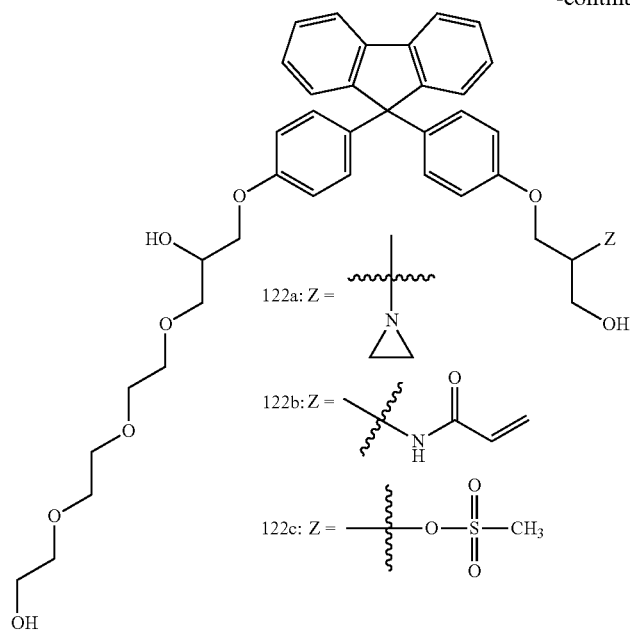
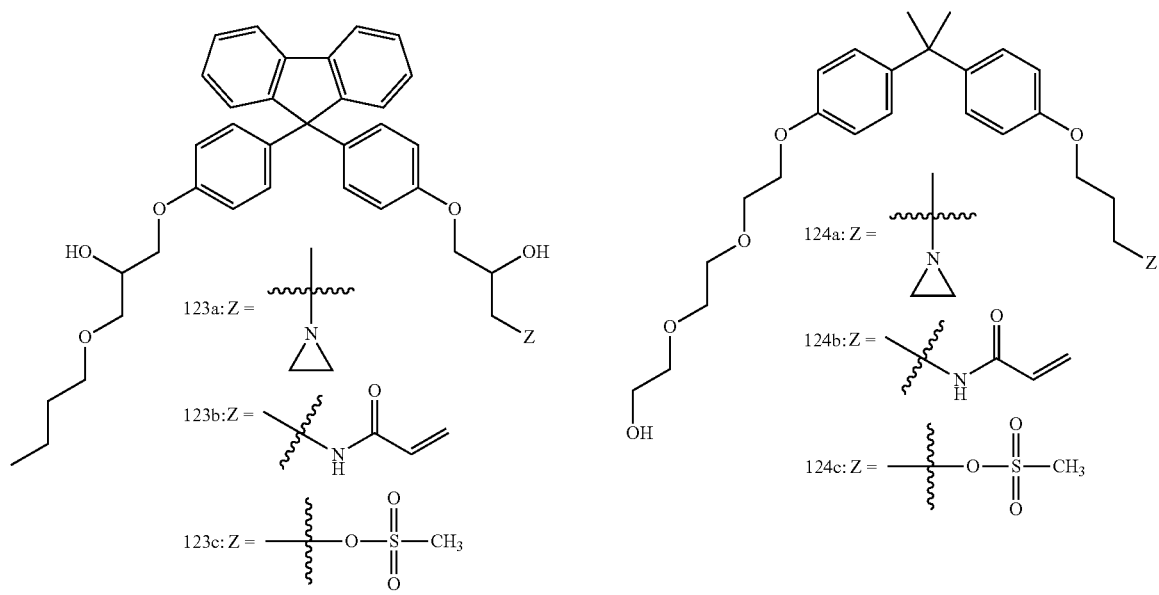

237 238
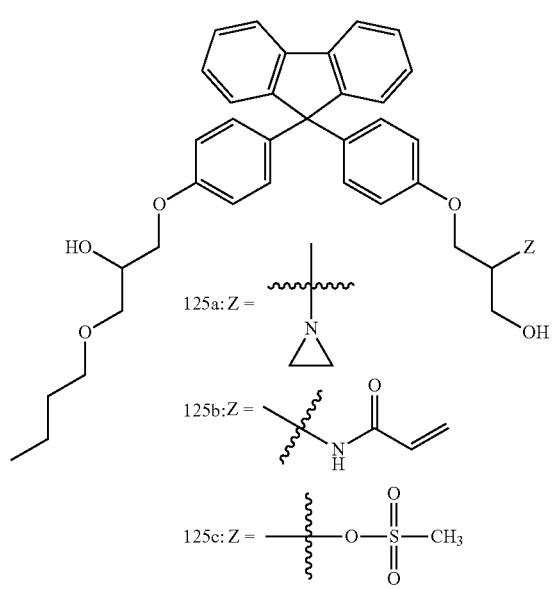 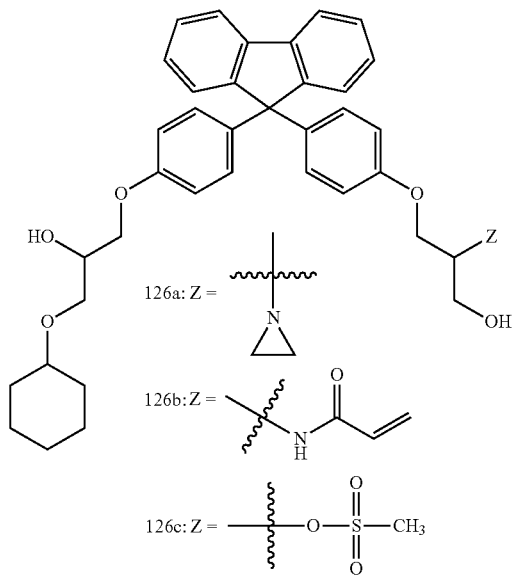
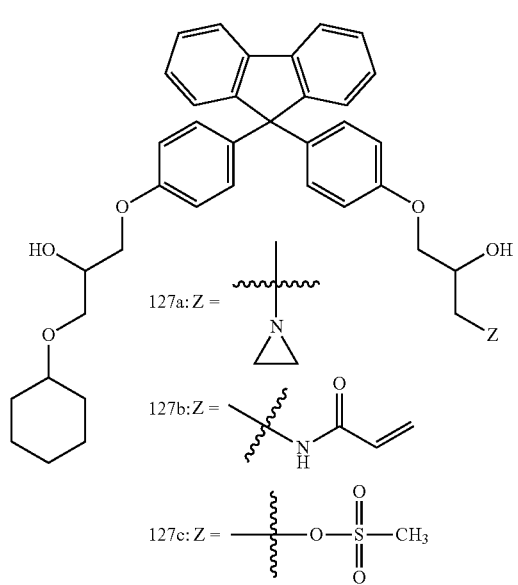 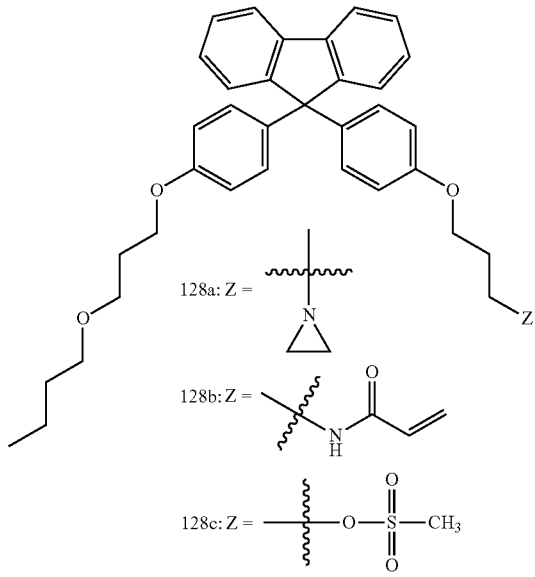

-continued
239
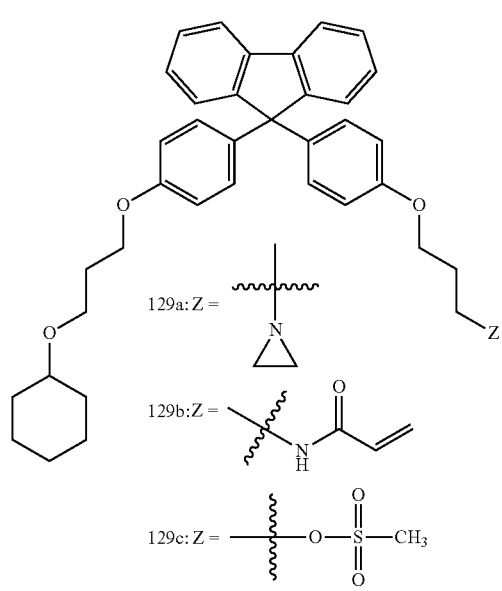
240
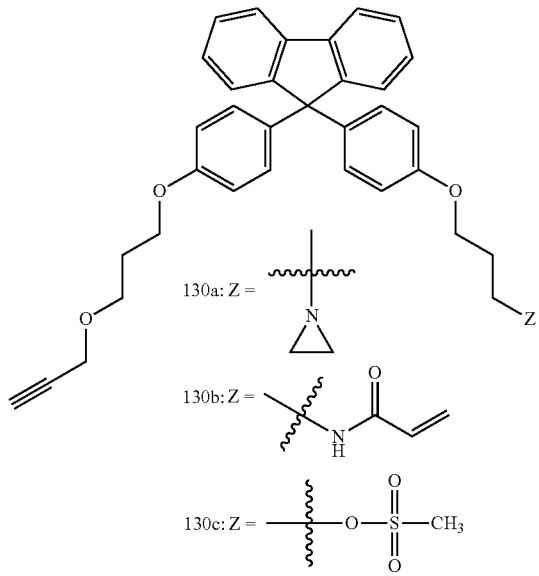
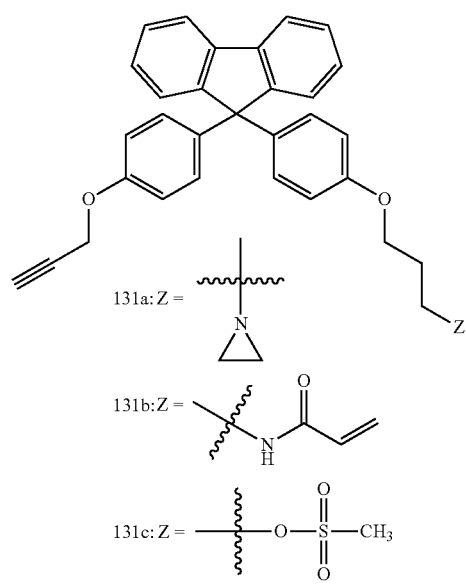
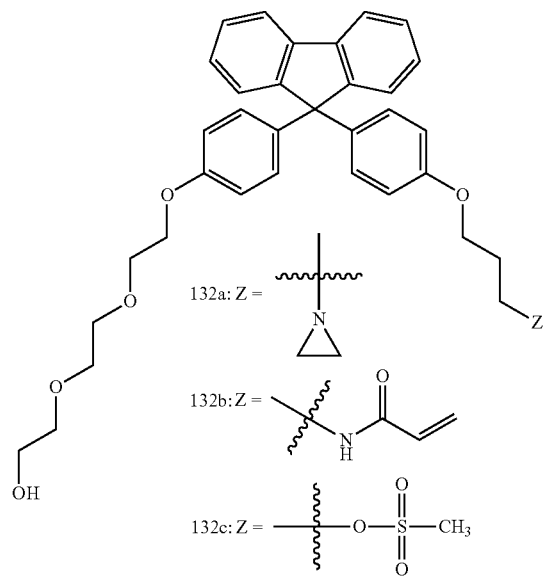

-continued
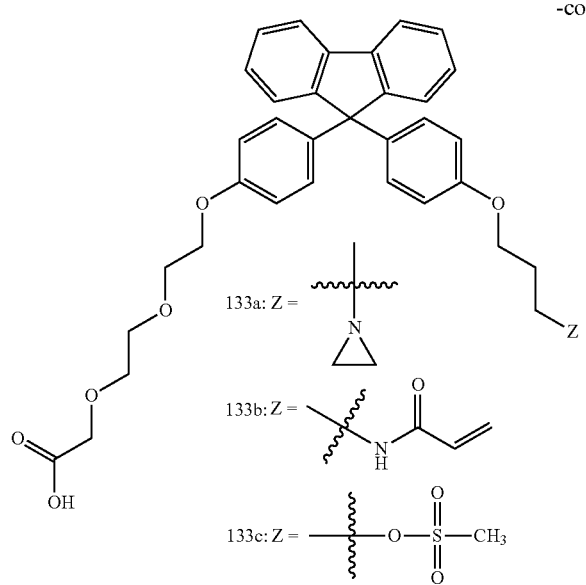
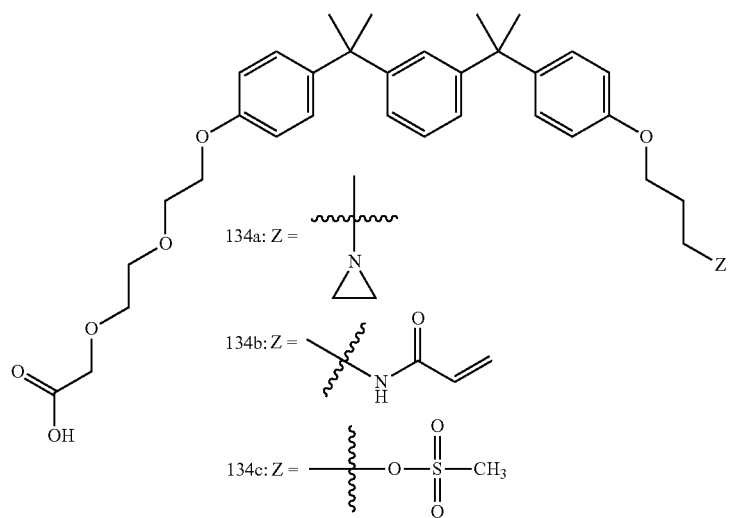
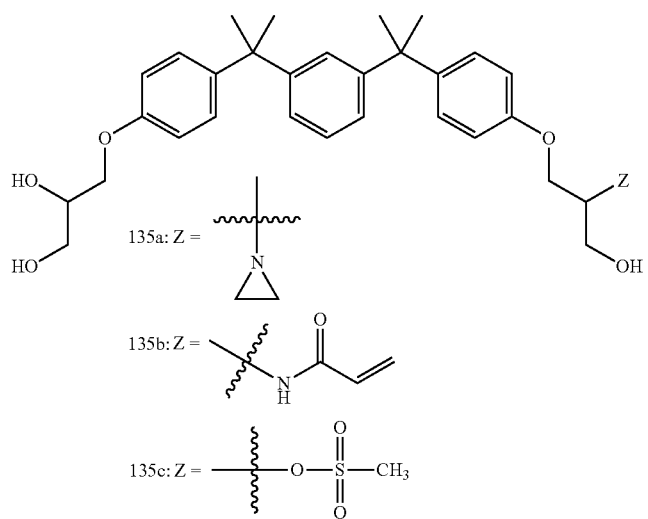

-continued
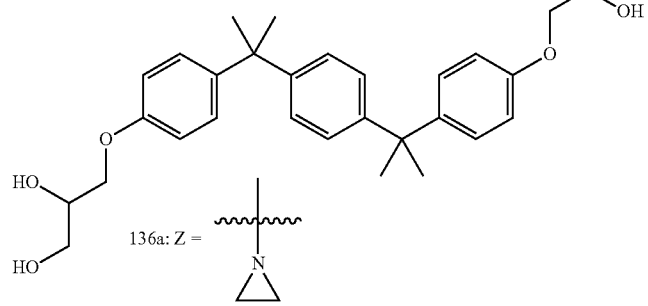
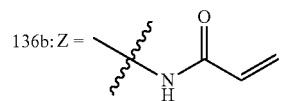
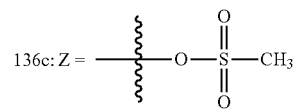
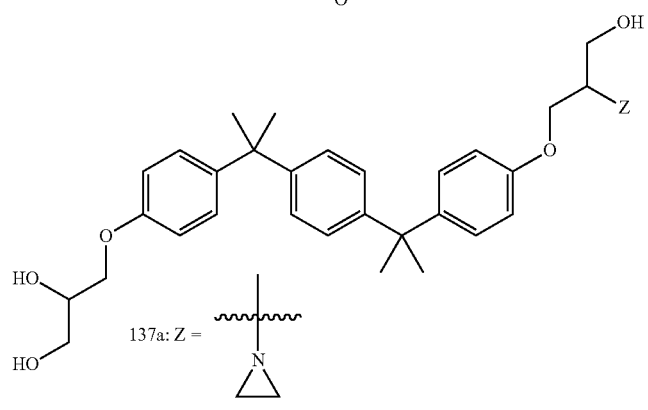
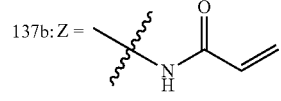
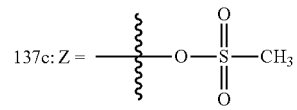
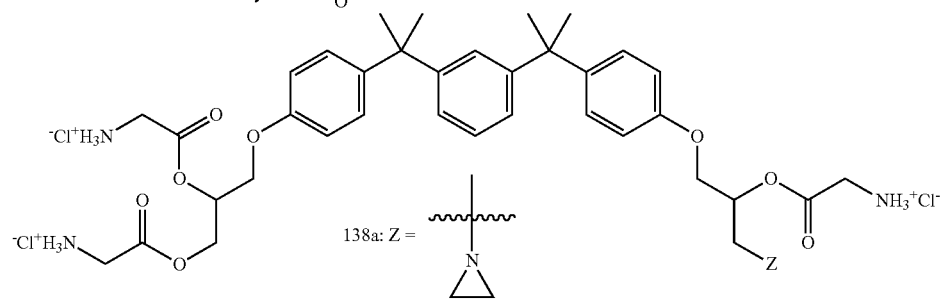
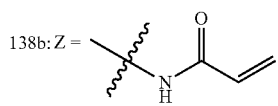
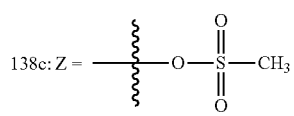

-continued
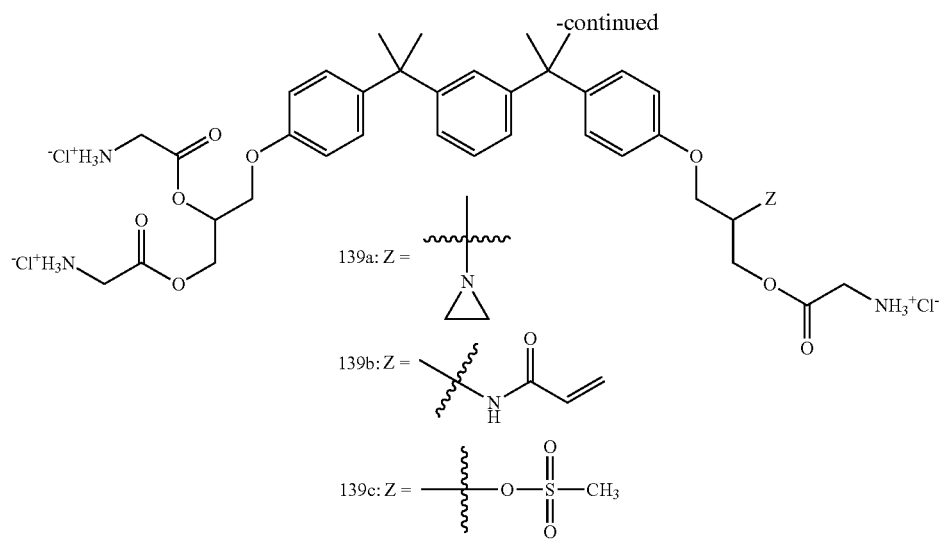
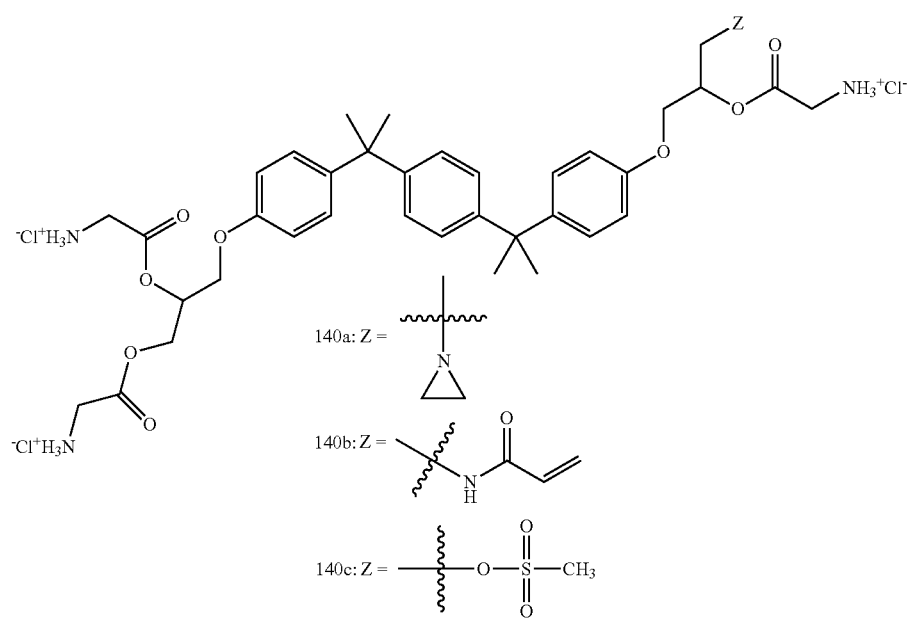

-continued
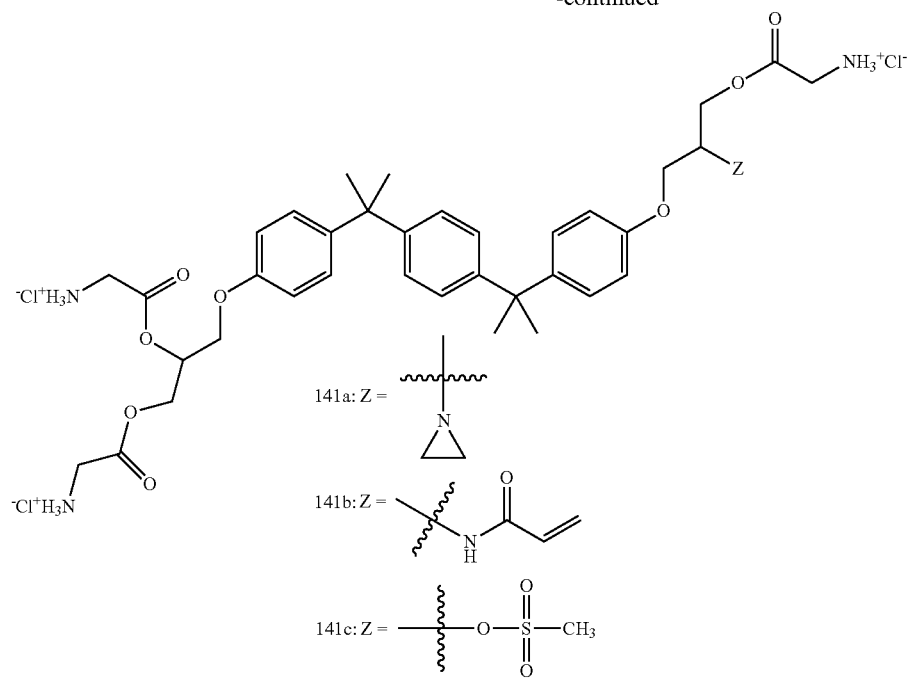
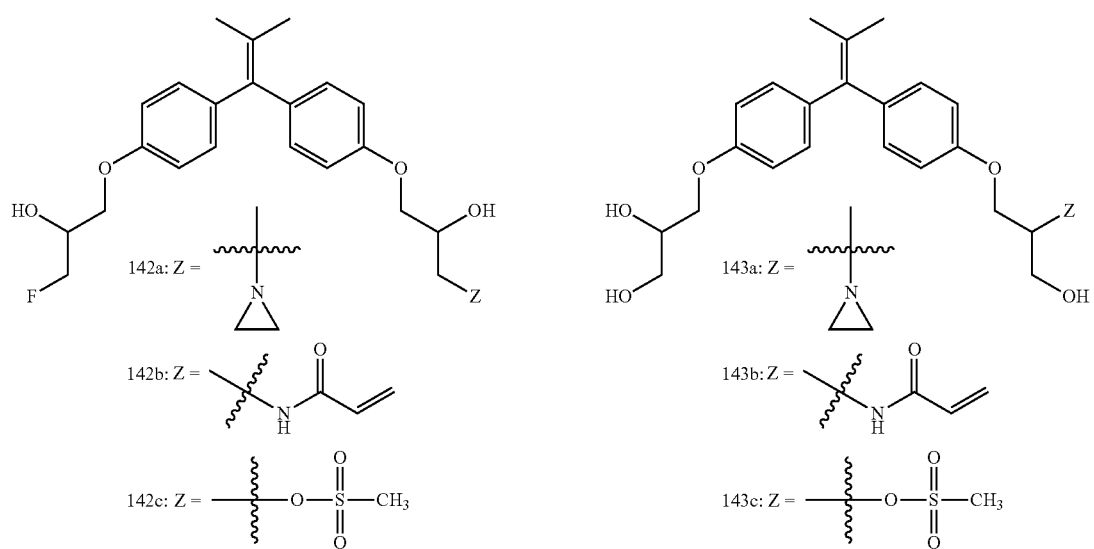

249
-continued
250
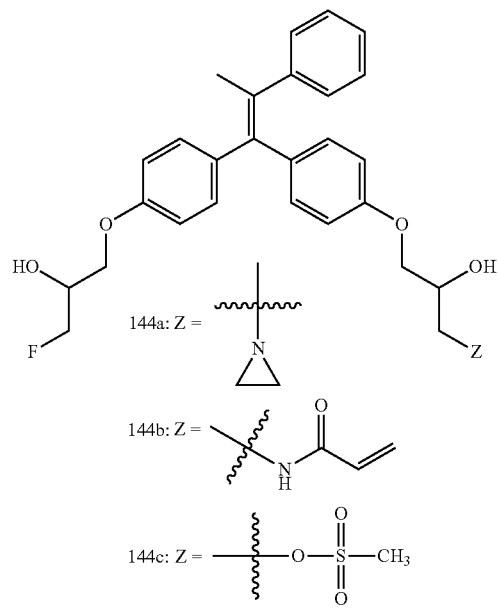
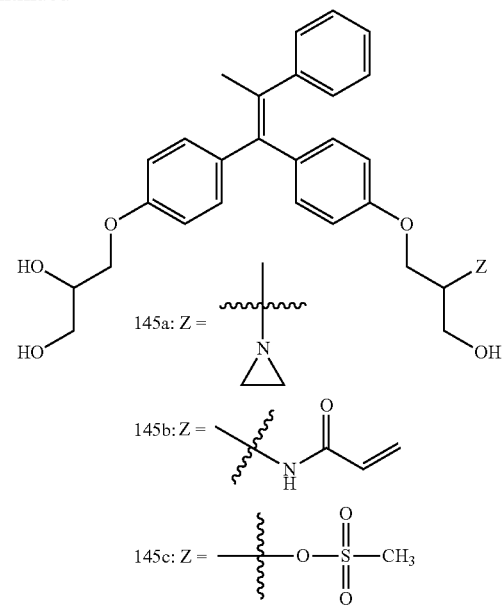
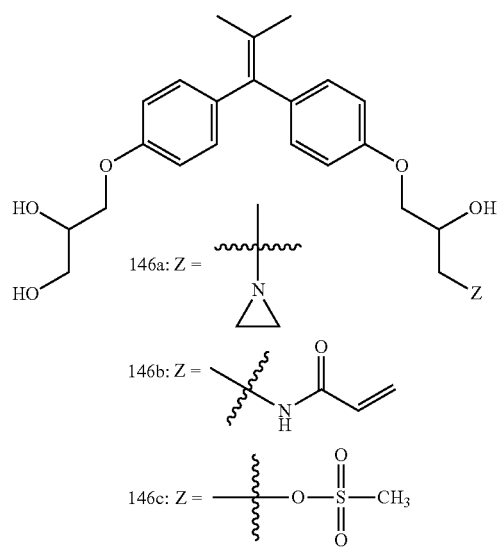
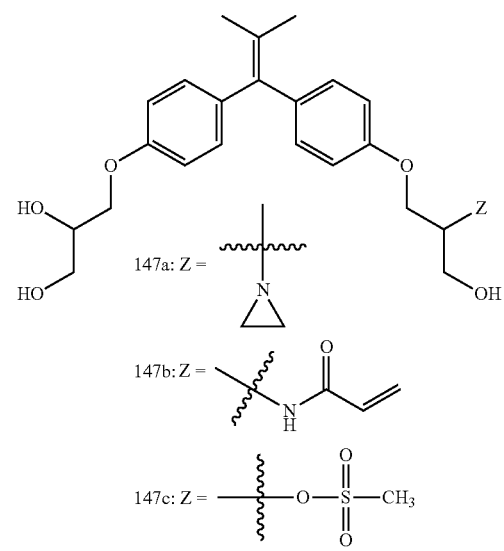

251
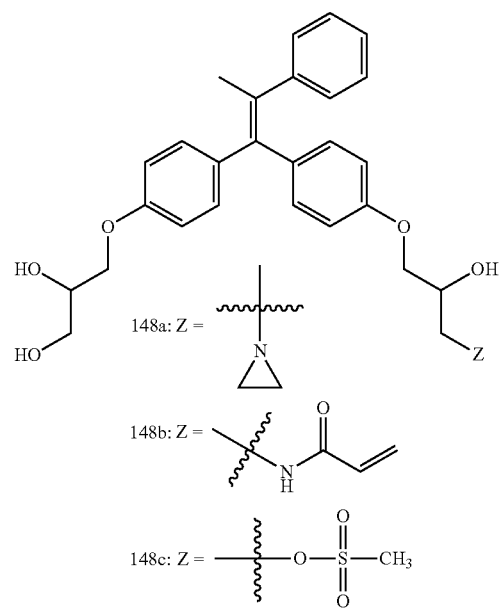
252
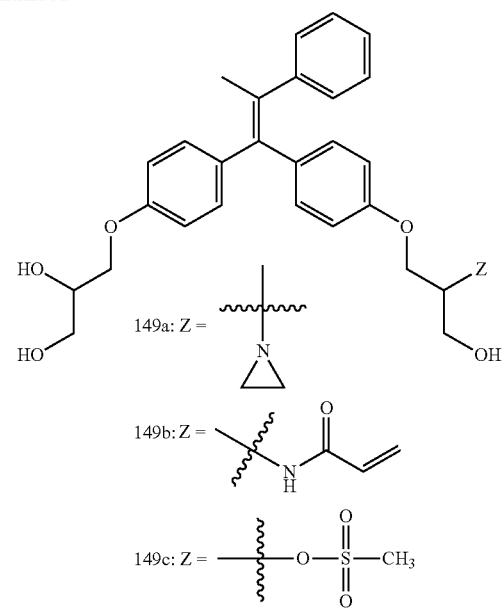
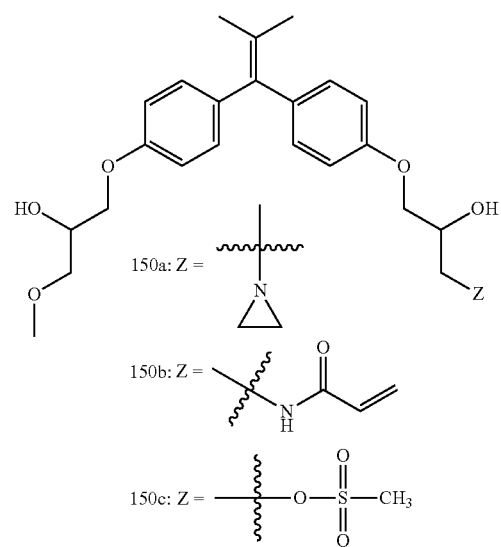
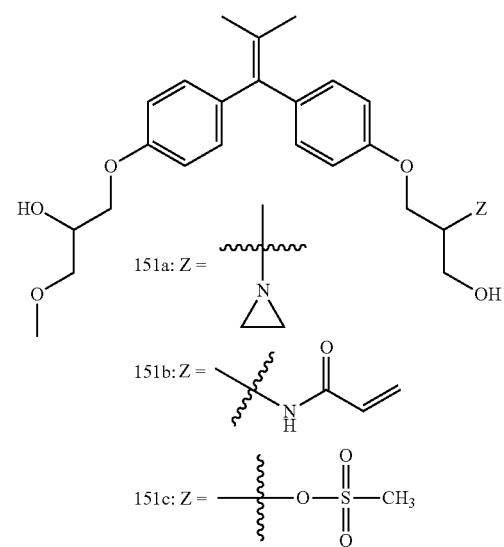

253
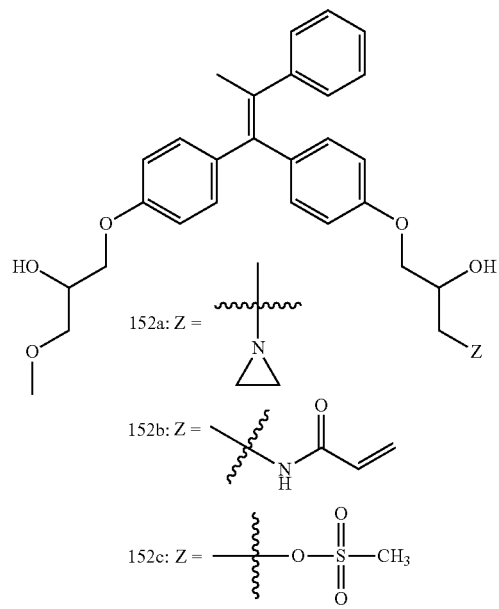
254
-continued
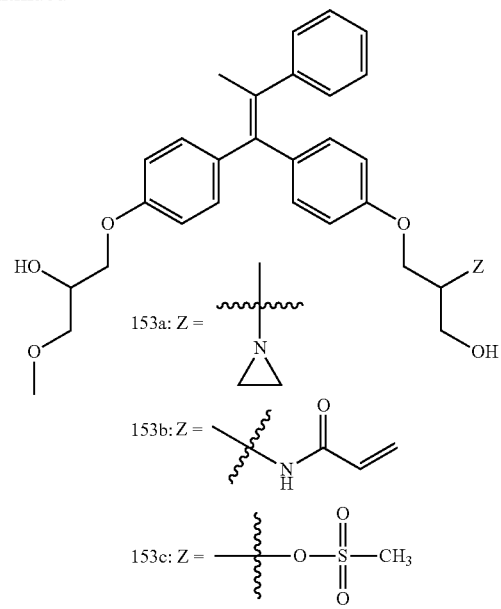
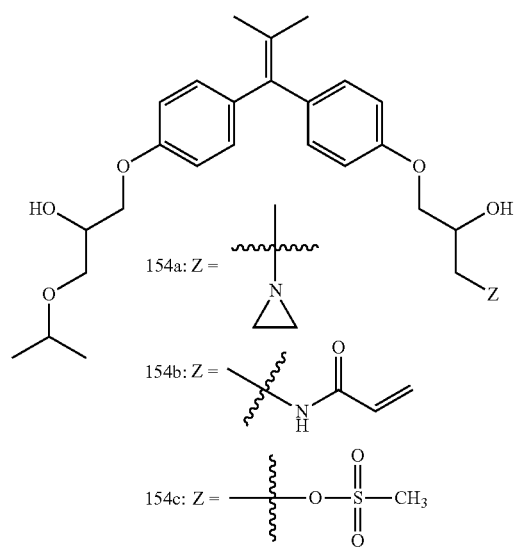
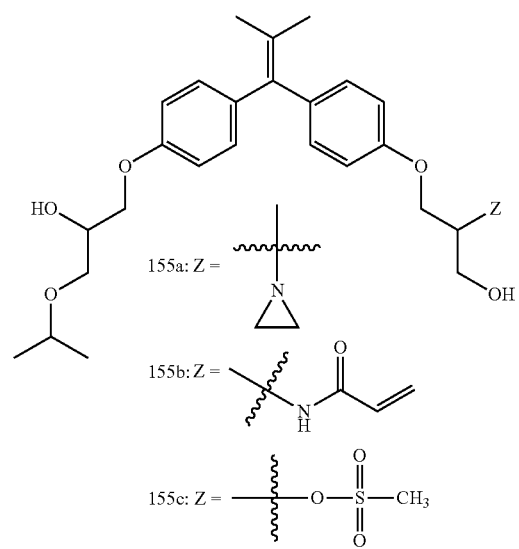

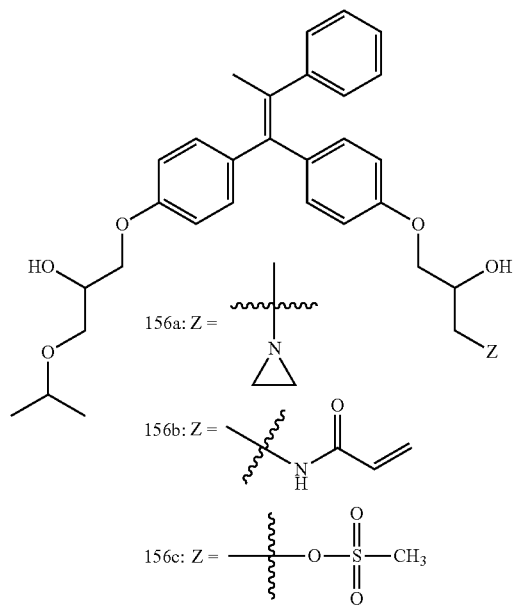
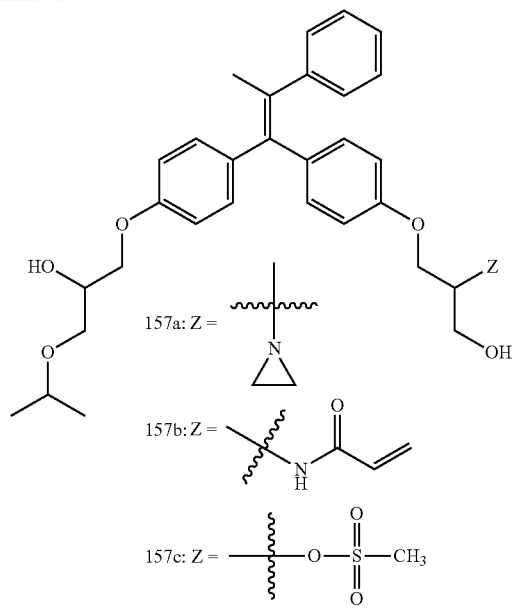
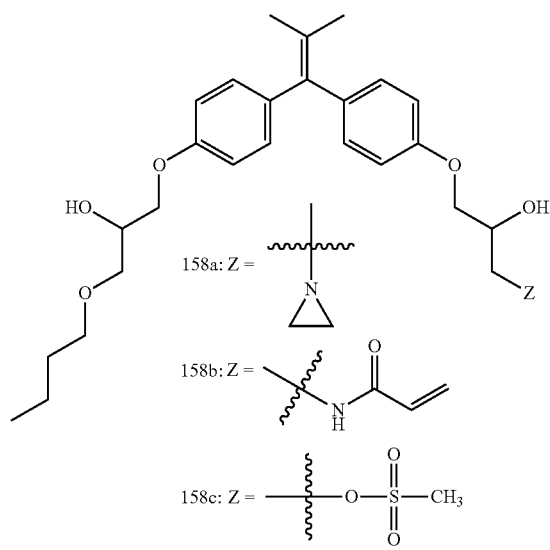
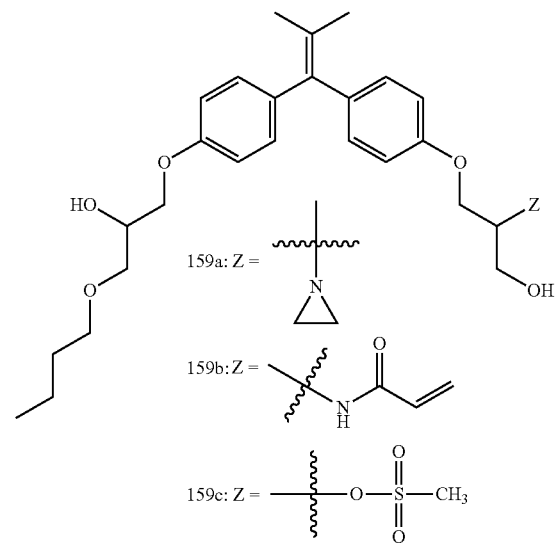

-continued
257
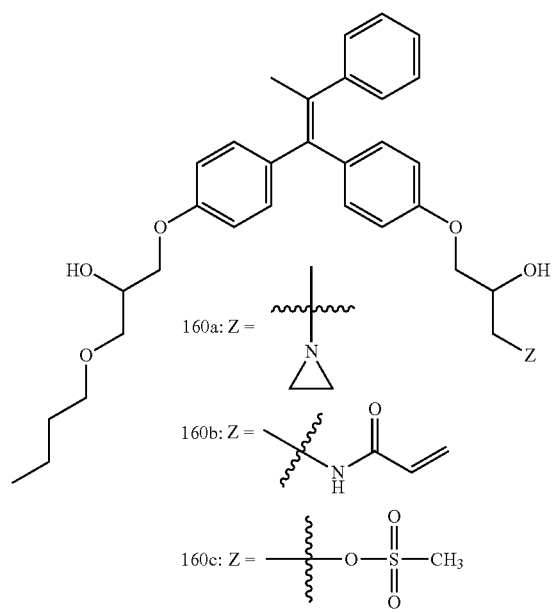
258
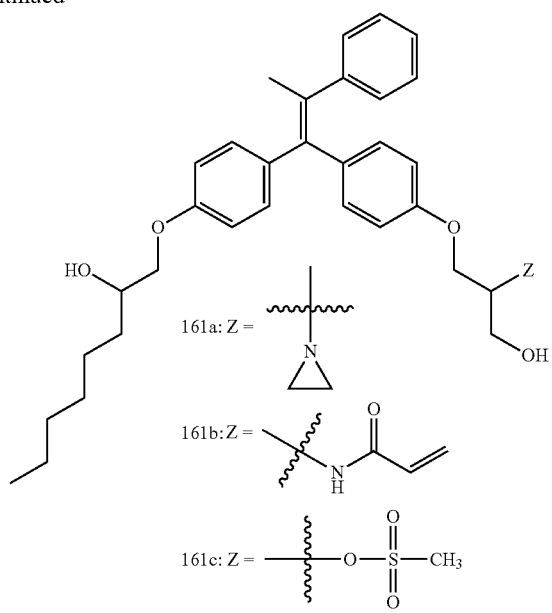
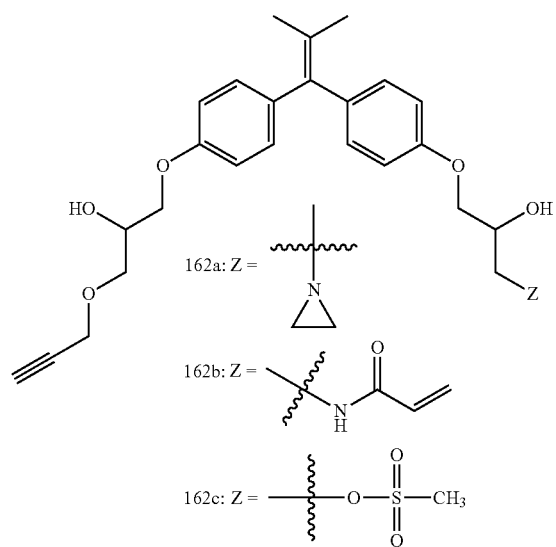
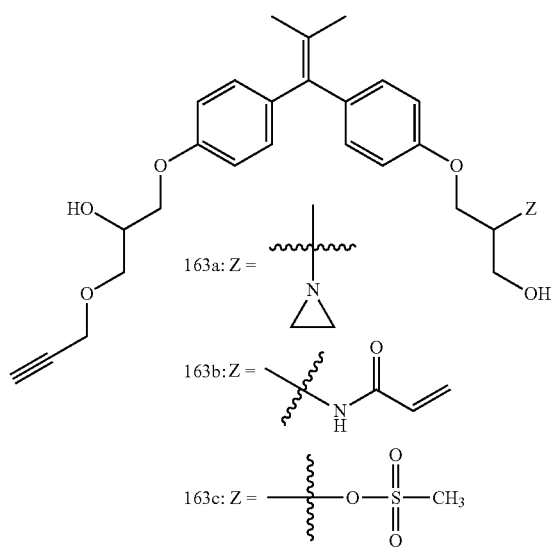

259
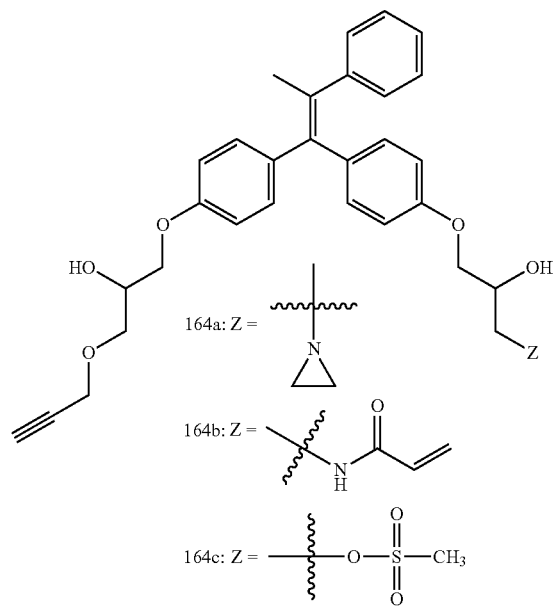
260
-continued
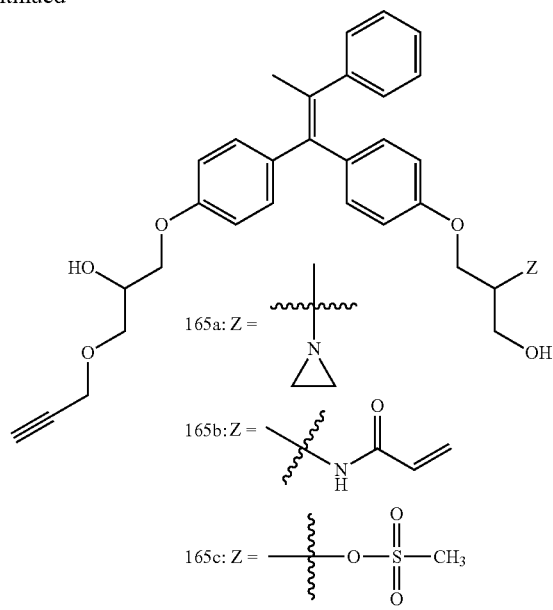
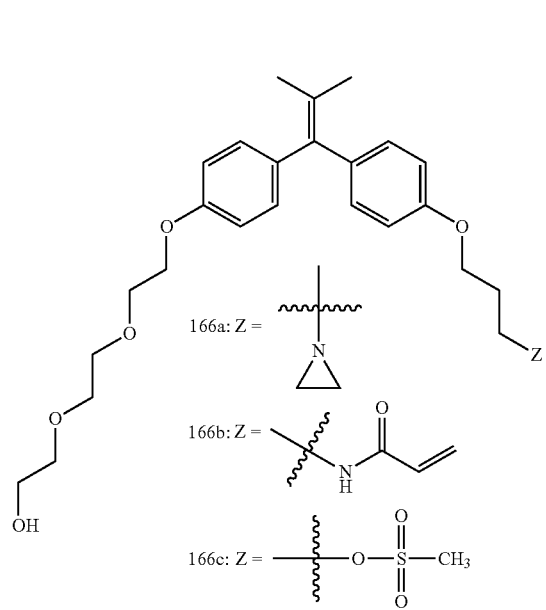
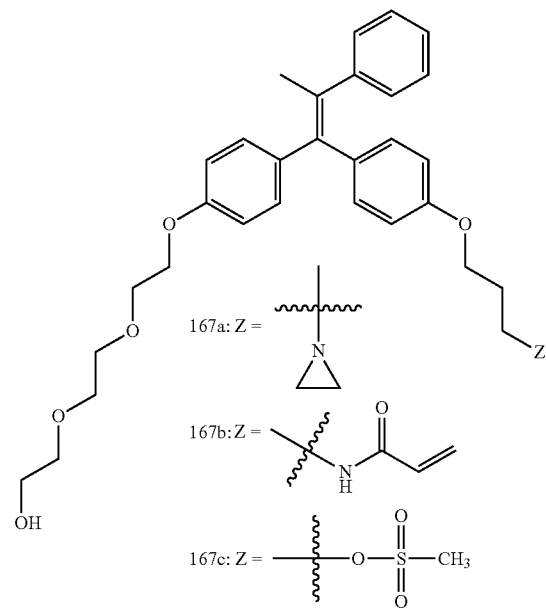

261
-continued
262
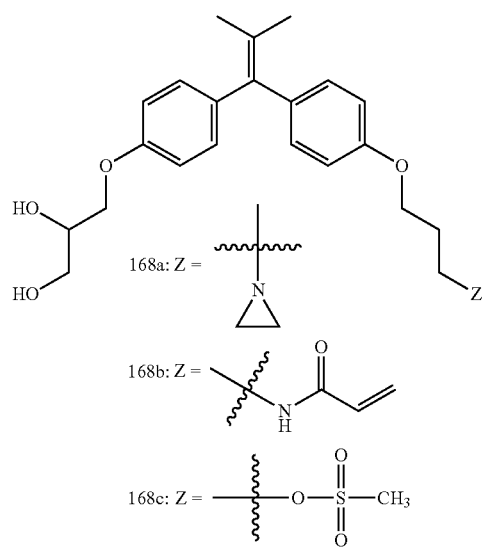
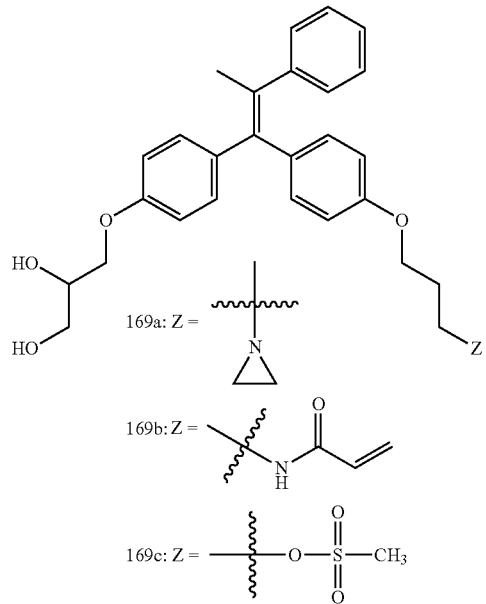
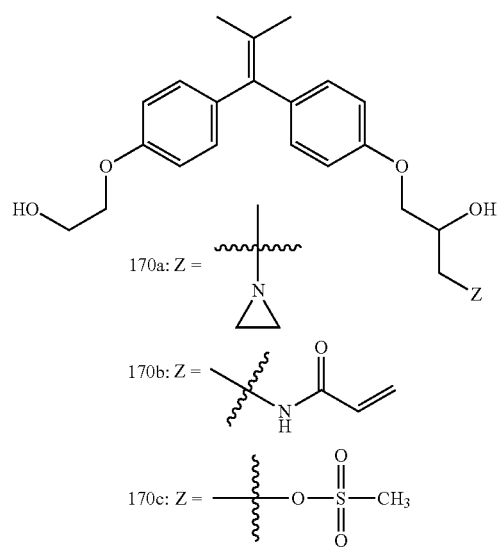
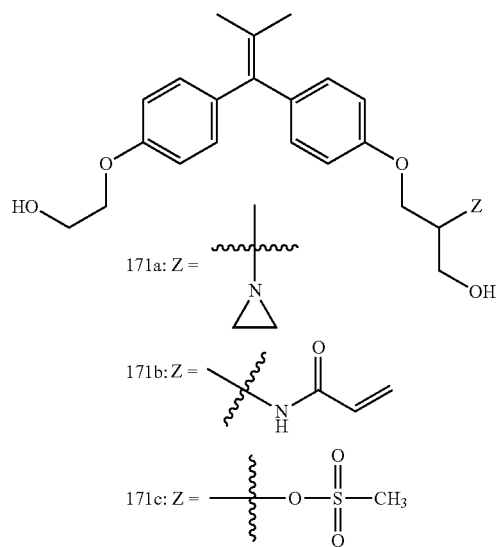

-continued

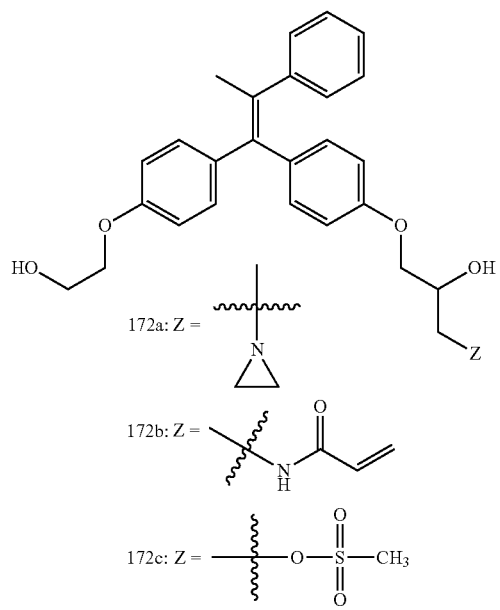

172a: Z = 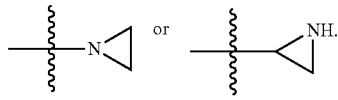

172b: Z = 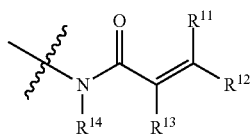

172c: Z = 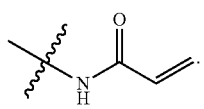 [SMILES: *NC(=O)C=C]

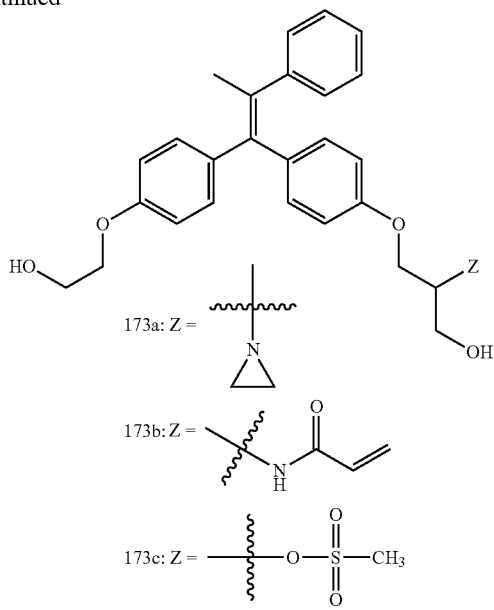

173a: Z =

173b: Z =

173c: Z = 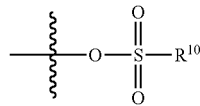

or a pharmaceutically acceptable salt or stereoisomer thereof.

39. The compound of claim 1, wherein Z has one of the following structures:

40. The compound of claim 1, wherein Z has the following structure:

wherein $R^{11}$, $R^{12}$, $R^{13}$ and $R^{14}$ are each independently hydrogen, $C_1$-$C_{10}$ alkyl, aryl or aralkyl.

41. The compound of claim 40, wherein Z has the following structure:

42. The compound of claim 1, wherein Z has the following structure:

wherein $R^{10}$ is $C_1$-$C_{10}$ alkyl, aryl or aralkyl.

43. The compound of claim 42, wherein $R^{10}$ is methyl or 4-methylphenyl.

44. A pharmaceutical composition comprising a compound of claim 1 and a pharmaceutically acceptable carrier.

45. The pharmaceutical composition of claim 44, further comprising an additional therapeutic agent selected from the group consisting of 4-(3-(4-cyano-3-(trifluoromethyl)phenyl)-5,5-dimethyl-4-oxo-2-thioxoimidazolidin-1-yl)-2-fluoro-N-methylbenzamide, ARN-509; abiraterone, bicalutamide, nilutamide, flutamide, cyproterone acetate, docetaxel, Bevacizumab (Avastin), OSU-HDAC42, VITAXIN, sunitumib, ZD-4054, 3β-hydroxy-17-(1H-benz-imidazo-1 -yl)androsta-5,16-diene, Cabazitaxel (XRP-6258), MDX-010(Ipilimumab), OGX 427, OGX 011, finasteride, dutasteride, turosteride, bexlosteride, izonsteride, FCE 28260, SKF105,111 or a related compound thereof.

46. The pharmaceutical composition of claim 45, wherein the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy or age-related macular degeneration.

* * * * *